US010188750B1

(12) United States Patent
Totary-Jain

(10) Patent No.: US 10,188,750 B1
(45) Date of Patent: Jan. 29, 2019

(54) SELF-REPLICATING CELL SELECTIVE GENE DELIVERY COMPOSITIONS, METHODS, AND USES THEREOF

(71) Applicant: Hana Totary-Jain, Wesley Chapel, FL (US)

(72) Inventor: Hana Totary-Jain, Wesley Chapel, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 15/333,074

(22) Filed: Oct. 24, 2016

Related U.S. Application Data

(60) Provisional application No. 62/245,457, filed on Oct. 23, 2015, provisional application No. 62/264,609, filed on Dec. 8, 2015.

(51) Int. Cl.
 *C07H 21/04* (2006.01)
 *A61K 48/00* (2006.01)
 *A61K 38/17* (2006.01)

(52) U.S. Cl.
 CPC ...... *A61K 48/0058* (2013.01); *A61K 38/1709* (2013.01)

(58) Field of Classification Search
 None
 See application file for complete search history.

(56) References Cited

U.S. PATENT DOCUMENTS

| | | | |
|---|---|---|---|
| 4,921,475 A | 5/1990 | Sibalis | |
| 5,008,110 A | 4/1991 | Benecke et al. | |
| 5,087,240 A | 2/1992 | Sibalis | |
| 5,088,977 A | 2/1992 | Sibalis | |
| 5,139,941 A | 8/1992 | Muzyczka et al. | |
| 5,163,899 A | 11/1992 | Sibalis | |
| 5,164,189 A | 11/1992 | Farhadieh et al. | |
| 5,252,479 A | 10/1993 | Srivastava | |
| 5,254,346 A | 10/1993 | Tucker et al. | |
| 5,290,561 A | 3/1994 | Farhadieh et al. | |
| 5,328,470 A | 7/1994 | Nabel et al. | |
| 5,332,213 A | 7/1994 | Klose | |
| 5,336,168 A | 8/1994 | Sibalis | |
| 5,352,456 A | 10/1994 | Fallon et al. | |
| 5,407,713 A | 4/1995 | Wilfong et al. | |
| 5,641,670 A | 6/1997 | Treco et al. | |
| 5,747,469 A | 5/1998 | Roth et al. | |
| 6,017,524 A | 1/2000 | Roth et al. | |
| 6,143,290 A | 11/2000 | Zhang et al. | |
| 6,410,010 B1 | 6/2002 | Zhang et al. | |
| 6,511,847 B1 | 1/2003 | Zhang et al. | |
| 7,232,806 B2 | 6/2007 | Tuschl et al. | |
| 8,398,968 B2 | 3/2013 | Mayall | |
| 8,404,653 B2 | 3/2013 | Zsebo | |
| 2004/0057937 A1 | 3/2004 | Jahoda et al. | |
| 2006/0105360 A1 | 5/2006 | Croce et al. | |
| 2009/0131354 A1* | 5/2009 | Bader | A61K 31/7105 514/44 R |
| 2010/0041737 A1 | 2/2010 | Naldini et al. | |
| 2011/0218234 A1 | 9/2011 | Annoni et al. | |
| 2012/0128643 A1* | 5/2012 | Biffi | C12N 15/111 424/93.21 |
| 2013/0202532 A1 | 8/2013 | Benenson et al. | |
| 2015/0167003 A1 | 6/2015 | Naldini et al. | |
| 2015/0190532 A1 | 7/2015 | Totary-Jain et al. | |
| 2016/0089453 A1* | 3/2016 | Zamore | A61K 48/0058 514/44 R |

FOREIGN PATENT DOCUMENTS

| | | |
|---|---|---|
| WO | 1994013788 A1 | 6/1994 |
| WO | 2001032840 A2 | 5/2001 |
| WO | 2007100870 A2 | 9/2007 |
| WO | 2013152230 A1 | 10/2013 |

OTHER PUBLICATIONS

Brown et al (Nature Medicine. Apr. 23, 2006; 12(5): 585-591).*
Miller et al., 1988. J Virol. 62(11):4337-45.
Shimada et al., 1991. J Clin Invest. 88(3):1043-7.
Helseth et al., 1990. J Virol. 64(12):6314-8.
Page et al., 1990. J Virol. 64(11):5270-6.
Buchschacher & Panganiban, 1992. J Virol. 66(5):2731-9.
Ozau et al., 1993. Trends in Biotechnology J 1:205-2W.
Brower, 1998. Nature Biotechnology, 16:1304-1305.
Chen et al., 1994. Proc. Natl. Acad. Sci. USA 91:3054-3057.
Anderson et al., 1992. Science 256:808-813.
Porter et al., 2011. NEJM 365:725-733.
Kalos et al., 2011 Sci. Transl. Med. 201 3(95): 1-11.
Friedmann, 1989. Science, 244:1275-1281.
Verma, 1990. Scientific American: 68-84.
Kikuchi et al., 2008. J Dermatol Sci. May; 50(2):87-98.
Isaka et al., 2007 Expert Opin Drug Deliv. Sep.; 4(5):561-71.
Waehler et al., 2007 Nat Rev Genet. Aug.; 8(8):573-87.
Jensen et al., 2007. Ann Med.;39(2): 108-15.
Herweijer et al., 2007. Gene Ther. Jan.; 14(2):99-107.
Eliyahu et al., 2005. Molecules, Jan. 31; 10(1):34-64.
Altaras et al., 2005. Adv Biochem Eng Bintechnol.; 99:193-260.
Cleveland et al., 1983. J Immunol Methods, 56(2): 221-234.
Lee et al., 2004. Biomaterials 25:2461-2466.
Peppas et al., 2006. Adv Mater. 18:1345-60.
Hoffman, 2002. Adv Drug Deliv Rev. 43:3-12.
Hoffman, 2001. Ann NY Acad Sci 944:62-73.
Zuker & Stiegler, 1981 Nucleic Acids Res. 9, 133-148.
Carr & Church, 2009. Nature Biotechnol. 27: 1151-1162.

(Continued)

*Primary Examiner* — Kimberly Chong

(74) *Attorney, Agent, or Firm* — Thomas | Horstemeyer, LLP

(57) ABSTRACT

Described herein are cell-selective mRNA constructs that can contain a RNA of interest and one or more miRNA targets. The cell-selective mRNA constructs described herein can be used to express an RNA of interest to a cell in a cell-selective manner.

17 Claims, 34 Drawing Sheets

Specification includes a Sequence Listing.

(56) References Cited

OTHER PUBLICATIONS

Lieber, 2010. Author's Manuscript, 1-24. Published in: Annu. Rev. Biochem. 79: 181-211.
Bleuyard et al., 2006. DNA Repair 5: 1-12.
Kirik et al., 2000. EMBO J. 19: 5562-5566.
Siebert & Puchta, 2002. Plant Cell 14:1121-1131.
Pacher et al., 2007 Genetics 175: 21-29.
Carillo & Lipman, 1988. SIAM J. Applied Math, 48: 1073.
Needelman & Wunsch, 1970. J. Mol. Biol., 48: 443-453.
Konermann et. al., 2015. Author Manuscript, 1-37. Published as: Genome-scale transcriptional activation by an engineered crispr-cas9 complex. Nature. 517:583-588.
Geall, et al., Nonviral delivery of self-amplifying RNA vaccines, PNAS U.S.A. 2012, 109(36): 14604-14609.
Yoshioka, et al., Efficient Generation of Human iPSCs by a Synthetic Self-Replicative RNA, Cell Stem Cell 2013, 13(2):246-254.
Malek et al., 2001. A mouse knock-in model exposes sequential proteolytic pathways that regulate p27Kipl in G1 and S phase, Nature, 413, 323-327.
Fiers et al., 1973. Nature 273: 113-120.
Hager et al., 2002. Curr Opin Genet Dev, 12(2): 137-41.
Zeng et al., 2002. Molecular Cell 9:1327-1333.
Tuschl, 2002. Nat Biotechnol, 20:446-448.
Brummelkamp et al., 2002. Science 296:550-553.
Miyagishi et al., 2002. Nat Biotechnol. 20:497-500.
Paddison et al., 2002. Genes Dev. 16:948-958.
Lee et al., 2002. Nat. Biotechnol. 20:500-505.
Paul et al., 2002. Nat. Biotechnol. 20:505-508.
Rabinowitz et al., 2002. J Virol 76:791-801.
Eglitis, 1988. Biotechniques 6:608-614.
Miller, 1990. Hum. Gene Therap. 1:5-14.
Xia et al., 2002. Nat. Biotech. 20:1006-1010.
Samulski et al., 1987. J. Virol. 61:3096-3101.
Fisher et al., 1996. J. Virol. 70:520-532.
Samulski et al., 1989. J. Virol. 63:3822-3826.
Madzak et al., 1992. J Gen Virol. 73(Pt 6):1533-6.
Berkner, 1992. Curr Top Microbiol Immunol. 158:39-66.
Berkner, 1988. Biotechniques, 6(7):616-29.
Gorziglia & Kapikian, 1992. J Virol. 66(7):4407-12.
Quantin et al., 1992. Proc Natl Acad Sci USA. 89(7):2581-4.
Rosenfeld et al., 1992. Cell. 68(1):143-55.
Wilkinson et al., 1992. Nucleic Acids Res. 20(9):2233-9.
Stratford-Perricaudet et al., 1990. Hum Gene Ther. 1(3):241-56.
Moss, 1992. Curr Opin Biotechnol. 3(5):518-22.
Muzyczka, 1992. Curr Top Microbiol Immunol. 158:97-129.
Ohi et al., 1990. Gene. 89(2):279-82.
Margolskee, 1992. Curr Top Microbiol Immunol. 158:67-95.
Johnson et al., 1992. Brain Res Mol Brain Res. 12(1-3):95-102.
Fink et al., 1992. Hum Gene Ther. 3(1):11-9.
Breakefield & Geller, 1987. Mol Neurobiol. 1(4):339-71.
Freese et al., 1990. Biochem Pharmacol. 40(10):2189-99.
Bandyopadhyay & Temin, 1984. Mol Cell Biol. 4(4):749-54.
Petropoulos et al., 1992. J Virol. 66(6):3391-7.
Miller et al., 1992. Mol Cell Biol. 12(7):3262-72.
Miller et al., 1985. J Virol. 55(3):521-6.
Sorge et al., 1984. Mol Cell Biol. 4(9):1730-7.
Mann & Baltimore, 1985. J Virol. 54(2):401-7.
Bartel, 2009. MicroRNAs: Target Recognition and Regulatory Functions. Cell, 136(2), 215-233.
Brown & Naldini, 2009. Exploiting and antagonizing microRNA regulation for therapeutic and experimental applications. Nature Reviews. Genetics, 10(8), 578-585.
Janssen et al., 2013. Treatment of HCV infection by targeting microRNA. The New England Journal of Medicine, 368, 1685-94.
Karikó et al., 2008. Incorporation of pseudouridine into mRNA yields superior nonimmunogenic vector with increased translational capacity and biological stability. Molecular Therapy : The Journal of the American Society of Gene Therapy, 16(11), 1833-1840.
Krek et al., 2005. Combinatorial microRNA target predictions. Nature Genetics, 37(5), 495-500.
Laursen et al., 2010. Utilization of unlocked nucleic acid (UNA) to enhance siRNA performance in vitro and in vivo. Molecular bioSystems, 6(5), 862-870.
Montgomery et al., 2011. Therapeutic inhibition of miR-208a improves cardiac function and survival during heart failure. Circulation, 124, 1-12 and S1-S19.
Santulli et al., 2014. A selective microRNA-based strategy inhibits restenosis while preserving endothelial function. Journal of Clinical Investigation, 124(9), 4102-4114.
Yeung et al., 2005. siRNA, miRNA and HIV: promises and challenges. Cell Research, 15(11-12), 935-946.
Heron et al., 2009. Deaths: final data for 2006. Natl Vital Stat Rep 57(14), 1-134.
Garg & Serruys, 2010. Journal of the American College of Cardiology 56, S1-42.
Garg & Serruys, 2010. Coronary stents: looking forward. J Am Coll of Cardiol 56(10 Suppl), S43-78.
Jukema et al., 2011. Restenosis after PCI. Part 1: pathophysiology and risk factors. Nat. Rev. Cardiol. Advance Online Publication, 1-10.
Marx et al., 2011. Author Manuscript pp. 1-16. Published as: Vascular smooth muscle cell proliferation in restenosis. Circ Cardiovasc Interv 4(1), 104-111.
Cassese & Kastrati, 2012. JAMA 308, 814-815.
Kotani et al., 2006. Journal of the American College of Cardiology 47, 2108-2111.
Liu et al., 2010. Tex Heart Inst J 37, 194-2010.
Wenaweser et al., 2008. Journal of the American College of Cardiology 52, 1134-1140.
Van Rooij & Olson, 2012. Nat Rev Drug Discov 11, 860-872.
Brown et al., 2006. Nat Med 12, 585-591.
Wang et al., 2008. Dev Cell 15, 261-271.
Hayashi et al., 2009. The American journal of pathology 175, 2226-2234.
Iakovou et al., 2005. JAMA 293, 2126-2130.
Ciccarelli el al., 2008. Endothelial alpha 1-adrenoceptors regulate neoangiogenesis. Br J Pharmacol 153, 936-946.
Santulli et al., 2011. Evaluation of the anti-angiogenic properties of the new selective alphaVbeta3 integrin antagonist RGDechiHCit J Transl Med 9, 7.
Totary-Jain et al., 2012. Author's Manuscript, pp. 1-14. Published as: Rapamycin resistance is linked to defective regulation of Skp2. Cancer Res 72, 1836-1843.
Iaccarino et al., 1999. Targeting Gbeta gamma signaling in arterial vascular smooth muscle proliferation: a novel strategy to limit restenosis. Proc Natl Arad Sci USA 96, 3945-3950.
Iaccarino et al., 2004. AKT participates in endothelial dysfunction in bypertension. Circulation 109, 2587-2593.
Yamaguchi et al., 2011. Local persistent hypercoagulability after sirolimuseluting stent implantation in patients with stable angina. Int J Cardio/153, 272-276.
Vestweber, 2008. VE-cadherin: the major endothelial adhesion molecule controlling cellular junctions and blood vessel formation. Arterioscler Thromb Vase Biol 28, 223-232.
Santulli et al., 2009. In vivo properties of the proangiogenic peptide QK. J Transl Med 7:41, 1-10.
Santulli et al., 2012. CaMK4 Gene Deletion Induces Hypertension. J Am Heart Assoc 1, e001081.
Marks, 2003. Sirolimus for the prevention of in-stent restenosis in a coronary artery. N Engl J Med 349(14), 1307-1309.
Wijns, 2009. Late stent thrombosis after drug-eluting stent: seeing is understanding. Circulation 120(5), 364-365.
Finn et al., 2007. Vascular responses to drug eluting stents: importance of delayed healing. Arterioscler Thromb Vase Biol 27(7), 1500-1510.
Joner et al., 2006. Pathology of drug-eluting stents in humans: delayed healing and late thrombotic risk. J Am Coll Cardiol 48(1), 193-202.
Calin et al., 2002. Proc. Natl. Acad. Sci. USA 99:15524-29.
Landgraf et al., 2007 Cell 129:1401-1414.
Mendell, 2005. Cell Cycle 4(9):1179-84.

(56) References Cited

OTHER PUBLICATIONS

Shivdasani, 2006. Blood 108(12):3646-53.
Hwang & Mendell, 2006. Br J Cancer 94(6):776-80.
Hammond, 2006. Curr Opin Genet Dev. 16(1):4-9.
Osada & Takahashi, 2007. Carcinogenesis 28(1):2-12.
Zhang et al., 2007. Dev Biol. 302(1):1-12.
Ishida et al., 2013. Author's Manuscript 1-14. Published as: miRNA-Based Therapeutic Strategies, Curr Anesthesiol Rep., 1(1):63-70.

\* cited by examiner

| Nucleotide | Catalog Number |
|---|---|
| Pseudouridine | N-1019 |
| N-1-methylpseudouridine | N-1081 |
| 5-methoxyuridine | N-1093 |
| 5-hydroxymethylcytidine | N-1087 |
| Immune Stimulation Reduction Transcription Nucleotide Set | K-1018 |
| ARCA Cap | N-7003 |
| Unmodified dNTP Set | N-2505 |

FIG. 30

SELF-REPLICATING CELL SELECTIVE GENE DELIVERY COMPOSITIONS, METHODS, AND USES THEREOF

CROSS-REFERENCE TO RELATED APPLICATIONS

This application claims the benefit of and priority to U.S. Provisional Patent Application No. 62/245,457, filed on Oct. 23, 2015, entitled "CELL-SELECTIVE GENE EDITING," the contents of which is incorporated by reference herein in its entirety.

This application also claims the benefit of and priority to U.S. Provisional Patent Application No. 62/264,609, filed on Dec. 8, 2015, entitled "SELF-REPLICATING CELL SELECTIVE GENE DELIVERY COMPOSITIONS, METHODS, AND USES THEREOF" the contents of which is incorporated by reference herein in its entirety.

STATEMENT REGARDING FEDERALLY SPONSORED RESEARCH OR DEVELOPMENT

This invention was made with government support under Grant Number HL109133 awarded by National Institutes of Health. The government has certain rights to the invention.

SEQUENCE LISTING

This application contains a sequence listing filed in electronic form as an ASCII.txt file entitled 292105-1040_ST25.txt, created on Oct. 24, 2016. The content of the sequence listing is incorporated herein in its entirety.

BACKGROUND

Despite the remarkable advance in therapeutic strategies over the past decades, the lack of cell selective therapies remains a major hurdle in clinical medicine. As such, there exists a need for improved cell selective therapies.

BRIEF DESCRIPTION OF THE DRAWINGS

Further aspects of the present disclosure will be readily appreciated upon review of the detailed description of its various embodiments, described below, when taken in conjunction with the accompanying drawings.

FIG. 30 shows a table listing modified nucleotides that can be used in the cell-selective RNA molecule.

DETAILED DESCRIPTION

Figure 1:
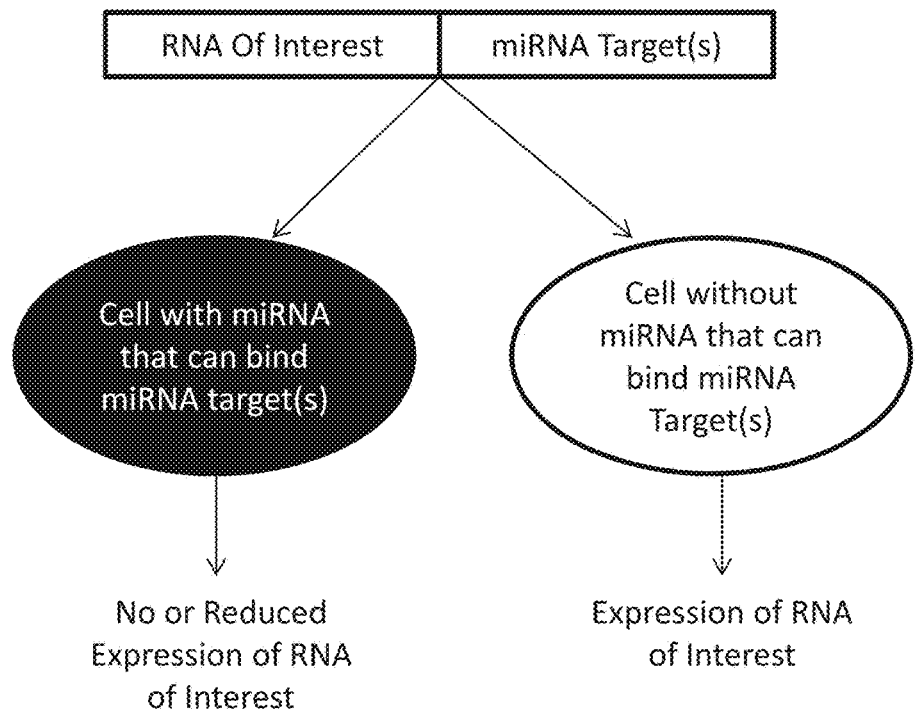
FIG. 1 shows embodiments of a cell-selective RNA molecule and its operation.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, microbiology, nanotechnology, organic chemistry, biochemistry, botany and the like, which are within the skill of the art. Such techniques are explained fully in the literature.

Definitions

As used herein, "control" is an alternative subject or sample used in an experiment for comparison purpose and included to minimize or distinguish the effect of variables other than an independent variable.

As used herein, "biocompatible" or "biocompatibility" refers to the ability of a material to be used by a patient without eliciting an adverse or otherwise inappropriate host response in the patient to the material or a derivative thereof, such as a metabolite, as compared to the host response in a normal or control patient.

As used herein, "biodegradable" refers to the ability of a material or compound to be decomposed by bacteria or other living organisms or organic processes.

As used herein, "about," "approximately," and the like, when used in connection with a numerical variable, generally refers to the value of the variable and to all values of the variable that are within the experimental error (e.g., within the 95% confidence interval for the mean) or within ±10% of the indicated value, whichever is greater.

As used herein, ""effective amount" is an amount sufficient to effect beneficial or desired results. An effective amount can be administered in one or more administrations, applications, or dosages.

As used herein, "administering" can refer to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation, by catheters, stents or via an implanted reservoir or other device that administers, either actively or passively (e.g. by diffusion) a composition the perivascular space and adventitia. For example a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques.

As used herein, "preventative" refers to hindering or stopping a disease or condition before it occurs or while the disease or condition is still in the sub-clinical phase.

As used herein, "therapeutic" can refer to treating or curing a disease or condition.

As used interchangeably herein, "subject," "individual," or "patient," refers to a vertebrate, preferably a mammal, more preferably a human. Mammals include, but are not limited to, murines, simians, humans, farm animals, sport animals, and pets. The term "pet" includes a dog, cat, guinea pig, mouse, rat, rabbit, ferret, and the like. The term farm animal includes a horse, sheep, goat, chicken, pig, cow, donkey, llama, alpaca, turkey, and the like.

As used herein, the terms "cancer," "cancer cells," "neoplastic cells," "neoplasia," "tumor," and "tumor cells" (used interchangeably) refer to cells which exhibit relatively autonomous growth so that they exhibit an aberrant growth phenotype characterized by a significant loss of control of cell proliferation (i.e., de-regulated cell division). Neoplastic cells can be malignant or benign. A metastatic cell or tissue means that the cell can invade and destroy neighboring body structures. The cancer can be selected from astrocytoma, adrenocortical carcinoma, appendix cancer, basal cell carcinoma, bile duct cancer, bladder cancer, bone cancer, brain cancer, brain stem glioma, breast cancer, cervical cancer, colon cancer, colorectal cancer, cutaneous T-cell lymphoma, ductal cancer, endometrial cancer, ependymoma, Ewing sarcoma, esophageal cancer, eye cancer, gallbladder cancer, gastric cancer, gastrointestinal cancer, germ cell tumor, glioma, hepatocellular cancer, histiocytosis, Hodgkin lymphoma, hypopharyngeal cancer, intraocular melanoma, Kaposi sarcoma, kidney cancer, laryngeal cancer, leukemia, liver cancer, lung cancer, lymphoma, macroglobulinemia, melanoma, mesothelioma, mouth cancer, multiple myeloma, nasopharyngeal cancer, neuroblastoma, non-Hodgkin lymphoma, osteosarcoma, ovarian cancer, pancreatic cancer, parathyroid cancer, penile cancer, pharyngeal cancer, pituitary cancer, prostate cancer, rectal cancer, renal cell cancer, retinoblastoma, rhabdomyosarcoma, sarcoma, skin cancer, small cell lung cancer, small intestine cancer, squamous cell carcinoma, stomach cancer, T-cell lymphoma, testicular cancer, throat cancer, thymoma, thyroid cancer, trophoblastic tumor, urethral cancer, uterine cancer, uterine sarcoma, vaginal cancer, vulvar cancer and Wilms tumor. In some embodiments, the cancer is prostate cancer.

The terms "guide polynucleotide," "guide sequence," or "guide RNA" as used herein refers to any polynucleotide sequence having sufficient complementarity with a target polynucleotide sequence to hybridize with the target sequence and direct sequence-specific binding of a CRISPR complex to the target sequence. The degree of complementarity between a guide polynucleotide and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting examples of which include the Smith-Waterman algorithm, the Needleman-Wunsch algorithm, algorithms based on the Burrows-Wheeler Transform (e.g. the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). A guide polynucleotide (also referred to herein as a guide sequence and includes single guide sequences (sgRNA)) can be about or more than about 5, 10, 11, 12, 13, 14, 15, 16, 17, 18, 19, 20, 21, 22, 23, 24, 25, 26, 27, 28, 29, 30, 35, 40, 45, 50, 75, 90, 100, 110, 112, 115, 120, 130, 140, or more nucleotides in length. The guide polynucleotide can include a nucleotide sequence that is complementary to a target DNA sequence. This portion of the guide sequence can be referred to as the complementary region of the guide RNA. In some contexts, the two are distinguished from one another by calling one the complementary region or target region and the rest of the polynucleotide the guide sequence or trans-activating crRNAln (tracrRNA). The guide sequence can also include one or more miRNA target sequences coupled to the 3' end of the guide sequence. The guide sequence can include one or more MS2 RNA aptamers incorporated within the portion of the guide strand that is not the complementary portion. As used herein the term guide sequence can include any specially modified guide sequences, including but not limited to those configured for use in synergistic activation mediator (SAM) implemented CRISPR (*Nature* 517, 583-588 (29 Jan. 2015). A guide polynucleotide can be less than about 150, 125, 75, 50, 45, 40, 35, 30, 25, 20, 15, 12, or fewer nucleotides in length. In some ebodiments, a guide polynucleotide can be 150 nucleotides or more, including, but not limited to 175, 200, 250, 300, 450, 500 or more. It will also be appreciated that the exact number of nucleotides may be any integer bweteen any of the specific numbers given, for example 1, 4, 123, 36, etc. and are all within the spirit and scope of this disclosure. The ability of a guide polynucleotide to direct sequence-specific binding of a CRISPR complex to a target sequence may be assessed by any suitable assay. For example, the components of a CRISPR system sufficient to form a CRISPR complex, including the guide polynucleotide to be tested, may be provided to a host cell having the corresponding target sequence, such as by transfection with vectors encoding the components of the CRISPR sequence, followed by an assessment of preferential cleavage within the target sequence. Similarly, cleavage of a target polynucleotide sequence may be evaluated in a test tube by providing the target sequence, components of a CRISPR complex, including the guide polynucleotide to be tested and a control guide polynucleotide different from the test guide polynucleotide, and comparing binding or rate of cleavage at the target sequence between the test and control guide polynucleotide reactions. Other assays are possible, and will occur to those skilled in the art.

A complementary region of the gRNA can be configured to target any DNA region of interest. The complementary region of the gRNA and the gRNA can be designed using a suitable gRNA design tool. Suitable tools are known in the art and are available to the skilled artisan. As such, the constructs described herein are enabled for any desired target DNA so long as it is CRISPR compatible according to the known requirements for CRISPR activation.

A guide polynucleotide can be selected to reduce the degree of secondary structure within the guide polynucleotide. Secondary structure may be determined by any suitable polynucleotide folding algorithm. Some programs are based on calculating the minimal Gibbs free energy. An example of one such algorithm is mFold, as described by Zuker & Stiegler ((1981) *Nucleic Acids Res.* 9, 133-148). Another example folding algorithm is the online webserver RNAfold, developed at Institute for Theoretical Chemistry at the University of Vienna, using the centroid structure prediction algorithm (see e.g. Gruber et al., (2008) *Cell* 106: 23-24; and Carr & Church (2009) *Nature Biotechnol.* 27: 1151-1162).

Homology-directed repair (HDR) refers to a mechanism in cells to repair double-stranded and single stranded DNA breaks. Homology-directed repair includes homologous recombination (HR) and single-strand annealing (SSA) (Lieber. (2010) *Annu. Rev. Biochem.* 79: 181-211). The most common form of HDR is called homologous recombination (HR), which has the longest sequence homology requirements between the donor and acceptor DNA. Other forms of HDR include single-stranded annealing (SSA) and breakage-induced replication, and these require shorter sequence homology relative to HR. Homology-directed repair at nicks (single-stranded breaks) can occur via a mechanism distinct from HDR at double-strand breaks.

Error-prone DNA repair refers to mechanisms that can produce mutations at double-strand break sites. The Non-Homologous-End-Joining (NHEJ) pathways are the most common repair mechanism to bring the broken ends together (Bleuyard et al., (2006) *DNA Repair* 5: 1-12). The structural integrity of chromosomes is typically preserved by the repair, but deletions, insertions, or other rearrangements are possible. The two ends of one double-strand break are the most prevalent substrates of NHEJ (Kirk et al., (2000) *EMBO J.* 19: 5562-5566), however if two different double-strand breaks occur, the free ends from different breaks can be ligated and result in chromosomal deletions (Siebert & Puchta, (2002) *Plant Cell* 14:1121-1131), or chromosomal translocations between different chromosomes (Pacher et al., (2007) *Genetics* 175: 21-29).

It will also be appreciated that CRISPR can also be used to activate specific genes through CRISPR/synergistic activation mediator procedures. These procedures can utilize a guide polynucleotide that incorporates 2 MS2 RNA aptamers at the tetraloop and the stem-loop of the guide RNA such as that described in, but not limited to (*Nature* 517, 583-588 (29 Jan. 2015).

The term "operatively linked" as used herein can refer to the association of nucleic acid sequences on a single nucleic acid fragment so that the function of one is regulated by the other. For example, a promoter is operatively linked with a coding sequence when it is capable of regulating the expression of that coding sequence (i.e., the coding sequence is under the transcriptional control of the promoter). Coding sequences can be operatively linked to regulatory sequences in a sense or antisense orientation. In one example, the complementary RNA regions can be operatively linked, either directly or indirectly, 5' to the target mRNA, or 3' to the target mRNA, or within the target mRNA, or a first complementary region is 5' and its complement is 3' to the target mRNA. The term "operatively linked" as used herein can also refer to the direct or indirect linkage of any two nucleic acid sequences on a singly nucleic acid fragment such that they are indirectly or directly physically connected on the same nucleic acid fragment. The term "operatively linked" as used herein can also refer to the insertion of a nucleic acid within the 5' and 3' end of another nucleic or the direct coupling of a nucleic acid to the 5' or 3' end of another nucleic acid.

As used herein, "specific binding" can refer to binding which occurs between such paired species as enzyme/substrate, receptor/agonist, antibody/antigen, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody preferably binds to a single epitope and to no other epitope within the family of proteins. As another non-limiting example, a miRNA can specifically bind preferably to a miRNA target and not to a non-specific nucleic acid sequence or if binding to a non-specific nucleic acid sequence occurs that no change in the expression or function of the non-specific nucleic acid can be observed or detected.

As used herein, "differentially expressed," refers to the differential production of RNA, including but not limited to mRNA, tRNA, miRNA, siRNA, snRNA, and piRNA transcribed from a gene or regulatory region of a genome or the protein product encoded by a gene as compared to the level of production of RNA or protein by the same gene or regulator region in a normal or a control cell. In another context, "differentially expressed," also refers to nucleotide sequences or proteins in a cell or tissue which have different temporal and/or spatial expression profiles as compared to a normal or control cell.

As used herein, "polypeptides" or "proteins" are amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

As used herein, "gene" can refer to a hereditary unit corresponding to a sequence of DNA that occupies a specific location on a chromosome and that contains the genetic instruction for a characteristic(s) or trait(s) in an organism. "Gene" also refers to the specific sequence of DNA that is transcribed into an RNA transcript that can be translated into a polypeptide or be a catalytic RNA molecule including but not limited to tRNA, siRNA, piRNA, miRNA, long-non-coding RNA and shRNA.

As used herein, "deoxyribonucleic acid (DNA)" and "ribonucleic acid (RNA)" generally refer to any polyribonucleotide or polydeoxribonucleotide, which can be unmodified RNA or DNA or modified RNA or DNA. RNA can be in the form of non-coding RNA such as tRNA (transfer RNA), snRNA (small nuclear RNA), rRNA (ribosomal RNA), anti-sense RNA, RNAi (RNA interference construct), siRNA (short interfering RNA), microRNA (miRNA), or ribozymes, aptamers or coding mRNA (messenger RNA).

As used herein, "nucleic acid sequence" and "oligonucleotide" also encompasses a nucleic acid and polynucleotide as defined elsewhere herein.

As used herein, "DNA molecule" includes nucleic acids/polynucleotides that are made of DNA.

As used herein, "nucleic acid" and "polynucleotide" generally refer to a string of at least two base-sugar-phosphate combinations and refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that can be single-stranded or, more typically, double-stranded or a mixture of single- and double-stranded regions. In addition, polynucleotide as used herein refers to triple-stranded regions comprising RNA or DNA or both RNA and DNA. The strands in such regions can be from the same molecule or from different molecules. The regions can include all of one or more of the molecules, but more typically involve only a region of some of the molecules. One of the molecules of a triple-helical region often is an oligonucleotide. "Polynucleotide" and "nucleic acids" also encompasses such chemically, enzymatically or metabolically modified forms of polynucleotides, as well as the chemical forms of DNA and RNA characteristic of viruses and cells, including simple and complex cells, inter alia. For instance, the term polynucleotide includes DNAs or RNAs as described above that contain one or more modified bases. Thus, DNAs or RNAs comprising unusual bases, such as inosine, or modified bases, such as tritylated bases, to name just two examples, are polynucleotides as the term is used herein. "Polynucleotide" and "nucleic acids" also includes PNAs (peptide nucleic acids), phosphorothioates, and other variants of the phosphate backbone of native nucleic acids. Natural nucleic acids have a phosphate backbone, artificial nucleic acids can contain other types of backbones, but contain the same bases. Thus, DNAs or RNAs with backbones modified for stability or for other reasons are "nucleic acids" or "polynucleotide" as that term is intended herein.

As used herein, "microRNA" can refer to a small non-coding RNA molecule containing about 21 to about 23 nucleotides found in organisms, which functions in transcriptional and post-transcriptional regulation of transcription and translation of RNA. "MicroRNA" can exist as part of a larger nucleic acid molecule such as a stem-loop structure that can be processed by a cell and yield a microRNA of about 21-23 nucleotides.

As used herein, "pharmaceutically acceptable carrier, diluent, binders, lubricants, glidant, preservative, flavoring agent, coloring agent, and excipient" refers to a carrier, diluent, binder, lubricant, glidant, preservative, flavoring agent, coloring agent, or excipient that is useful in preparing a pharmaceutical formulation that is generally safe, non-toxic, and is neither biologically or otherwise undesirable, and includes a carrier or excipient that is acceptable for veterinary use as well as human pharmaceutical use.

The term "treating", as used herein, can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, "overexpressed" or "overexpression" refers to an increased expression level of an RNA (coding or non-coding RNA) or protein product encoded by a gene as compared to the level of expression of the RNA or protein product in a normal or control cell.

As used herein, "underexpressed" or "underexpression" refers to decreased expression level of an RNA (coding or non-coding RNA) or protein product encoded by a gene as compared to the level of expression of the RNA or protein product in a normal or control cell.

As used herein, "expression" refers to the process by which polynucleotides are transcribed into RNA transcripts. In the context of mRNA and other translated RNA species, "expression" also refers to the process or processes by which the transcribed RNA is subsequently translated into peptides, polypeptides, or proteins.

As used herein "gene editing", "genome editing," "genome modification" can refer to the non-natural manipulation of genomic DNA such that the genomic DNA contains one or more additional nucleotides or has one or more nucleotides removed from the genomic sequence. Such genome editing can be achieved by techniques such as viral integration of a transgene, homologous recombination insertion of a transgene, and CRISPR related methods and techniques, including but not limited to, the self-replicating RNA and self-replicating cell-selective CRISPR methods described herein. "Gene editing" and "genome editing" or "genome modification" can refer to the deletion and/or addition of nucleotides into the genomic DNA.

As used herein with reference to the relationship between DNA, cDNA, cRNA, RNA, and protein/peptides, "corresponding to" can refer to the underlying biological relationship between these different molecules. As such, one of skill in the art would understand that operatively "corresponding to" can direct them to determine the possible underlying and/or resulting sequences of other molecules given the sequence of any other molecule which has a similar biological relationship with these molecules. For example, from a DNA sequence an RNA sequence can be determined and from an RNA sequence a cDNA sequence can be determined.

As used herein, "promoter" can refer to all nucleotide sequences capable of driving or initiating transcription of a coding or a non-coding DNA sequence. The term "promoter" as used herein can refer to a DNA sequence generally described as the 5' regulator region of a gene, located proximal to the start codon. The transcription of an adjacent coding sequence(s) is initiated at the promoter region. The term "promoter" also includes fragments of a promoter that are functional in initiating transcription of the gene.

As used herein, "selectable marker" can refer to a gene whose expression allows one to identify cells that have been transformed or transfected with a vector containing the marker gene. For instance, a recombinant nucleic acid may include a selectable marker operatively linked to a gene of interest and a promoter, such that expression of the selectable marker indicates the successful transformation of the cell with the gene of interest.

As used herein, "constitutive promoter" can refer to a promoter that allows for continual or ubiquitous transcription of its associated gene or polynucleotide. Constitutive promoters are generally are unregulated by cell or tissue type, time, or environment.

As used herein, "inducible promoter" can refer to a promoter that allows transcription of its associated gene or polynucleotide in response to a substance or compound (e.g. an antibiotic, or metal), an environmental condition (e.g.temperature), developmental stage, or tissue type.

As used herein, "electroporation" is a transformation method in which a high concentration of plasmid DNA (containing exogenous DNA) or RNA is added to a suspension of host cell protoplasts, and the mixture shocked with an electrical field of about 200 to 600 V/cm.

As used herein, "plasmid" can refer to a non-chromosomal double-stranded DNA sequence including an intact "replicon" such that the plasmid is replicated in a host cell.

As used herein, the term "vector" can refer to a vehicle used to introduce an exogenous nucleic acid sequence into a cell. A vector can include a DNA molecule, linear or circular (e.g. plasmids), which includes a segment encoding a polypeptide of interest operatively linked to additional segments that provide for its transcription and translation upon introduction into a host cell or host cell organelles. Such additional segments can include promoter and terminator sequences, internal ribosome entry site, and may also include one or more origins of replication, one or more selectable markers, an enhancer, a polyadenylation signal, microRNA target sequences etc. Expression vectors are generally derived from yeast or bacterial genomic or plasmid DNA, or viral DNA, or can contain elements of both.

The term "vector" can also include RNA or circular RNA vectors linked to additional segments that provide for its translation upon introduction into a host cell or host cell organelles. Such additional segments can include 5'Cap, one or more selectable markers, an enhancer, a polyadenylation signal, polyA tail, microRNA target sequences etc.

As used herein, "identity," can refer to a relationship between two or more polypeptide or polynucleotide sequences, as determined by comparing the sequences. In the art, "identity" also refers to the degree of sequence relatedness between polypeptides or polynucleotides as determined by the match between strings of such sequences. "Identity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J. Applied Math. 1988, 48: 1073. Preferred methods to determine identity are designed to give the largest match between the sequences tested. Methods to determine identity are codified in publicly available computer programs. The percent identity between two sequences can be determined by using analysis software (e.g., Sequence Analysis Software Package of the Genetics Computer Group, Madison, Wis.) that incorporates the Needelman and Wunsch, (J. Mol. Biol., 1970, 48: 443-453,) algorithm (e.g., NBLAST, and XBLAST). The default parameters are used to determine the identity for the polypeptides of the present disclosure.

As used herein, the term "transfection" can refer to the introduction of an exogenous and/or recombinant nucleic acid sequence into the interior of a membrane enclosed space of a living cell, including introduction of the nucleic acid sequence into the cytosol of a cell as well as the interior space of a mitochondria, nucleus, or chloroplast. The nucleic acid may be in the form of naked DNA or RNA (unmodified or modified), it may be associated with various proteins or regulatory elements (e.g., a promoter and/or signal element, miRNA target sequences as described herein), or the nucleic acid may be incorporated into a vector or a chromosome. As used herein, "transformation" or "transformed" can refer to the introduction of a nucleic acid (e.g., DNA or RNA) into cells in such a way as to allow expression of the coding or non-coding portions of the introduced nucleic acid.

As used herein a "transformed cell" can refer to a cell transfected with a nucleic acid sequence.

As used herein, a "transgene" can refer to an artificial gene which is used to transform a cell of an organism, such as a bacterium or a plant.

As used herein, "transgenic" can refer to a cell, tissue, or organism that contains a transgene.

As used herein, the term "recombinant" generally refers to a non-naturally occurring nucleic acid, nucleic acid construct, or polypeptide. Such non-naturally occurring nucleic acids can include natural nucleic acids that have been modified, for example that have deletions, substitutions, inversions, insertions, etc., and/or combinations of nucleic acid sequences of different origin that are joined using molecular biology technologies (e.g., a nucleic acid sequences encoding a "fusion protein" (e.g., a protein or polypeptide formed from the combination of two different proteins or protein fragments), the combination of a nucleic acid encoding a polypeptide to a promoter sequence, where the coding sequence and promoter sequence are from different sources or otherwise do not typically occur together naturally (e.g, a nucleic acid and a constitutive promoter etc.). Recombinant also refers to the polypeptide encoded by the recombinant nucleic acid. Non-naturally occurring nucleic acids or polypeptides include nucleic acids and polypeptides modified by man, including but not limited to miRNA target sequences described herein.

As used herein, the term "exogenous DNA" or "exogenous RNA" or exogenous nucleic acid sequence" or "exogenous polynucleotide" can refer to a nucleic acid sequence that was introduced into a cell, organism, or organelle via transfection. Exogenous nucleic acids originate from an external source, for instance, the exogenous nucleic acid may be from another cell or organism and/or it may be synthetic and/or recombinant. While an exogenous nucleic acid sometimes originates from a different organism or species, it may also originate from the same species (e.g., an extra copy or recombinant form of a nucleic acid that is introduced into a cell or organism in addition to or as a replacement for the naturally occurring nucleic acid). Typically, the introduced exogenous sequence is a recombinant sequence.

As used herein "miRNA target" or "miRNA target sequence" can refer to the nucleic acid sequence, typically RNA, that a miRNA specifically binds to. The miRNA target can be or include a sequence that is complementary to the miRNA. As an example, microRNA 126 (miR-126) can specifically bind a miR-126 target. Binding of a miRNA to a miRNA target can result in transcription and/or translation inhibition of the nucleic acid sequence, such as through degradation of the nucleic acid sequence (typically mRNA or other type of RNA), that the miRNA target is part of). A microRNA does not have to have perfect complementarity to a miRNA target for specific binding or transcription inhibition to occur.

As used herein "seed sequence" or "seed region" can refer to the conserved heptametrical sequence of a microRNA that has perfect complementarity to the miRNA target. The seed sequence can be at about positions 2-7 from the miRNA 5'-end.

As used herein, "nonstructural viral protein" and similar phrases can refer to proteins encoded by a virus, but are not incorporated into the viron particle.

As used herein "differentially expressed", "differential expression," and the like can refer to the difference in spatial, temporal, and/or amount of expression of a gene, transcript, and/or protein that can be observed between the same or different genes, transcripts, and/or proteins.

DISCUSSION

Despite the remarkable advance in therapeutic strategies over the past decades, the lack of cell selective therapies remains a major hurdle in clinical medicine. Side effects and reduced efficacy due to poor or no selectivity remains the Achilles' heel in the treatment of many diseases and contributes to the significant morbidity and mortality rates associated with many diseases.

Gene therapy holds significant promise to treat, if not cure, many diseases for which there currently is no effective treatment or cure. However, the benefits of gene therapy still remain illusive. Traditional gene therapy approaches rely on pseudo-viral packaging and delivery of the gene to cells. Off-target effects due to ubiquitous overexpression and oncogenesis due to insertional mutagenesis as a result of poor cell selectivity and insertion control remain issues with virus-based gene therapy. Further, size limitations of currently viral-based systems prevent the use of many viral-based systems for the delivery of many genes of interest.

Wth that said, described herein are cell-selective RNA molecules that can include a gene of interest or guide sequence RNA (gRNA) operatively coupled to one or more miRNA target sites. The cell-selective RNA molecules can be linear or circular, self-replicating, and/or contain one or more chemical modifications that can reduce immunogenecity of the cell-selective RNA molecules. The compositions described herein can be used for the treatment of diseases or symptoms thereof and/or cell selective gene editing. Other compositions, compounds, methods, features, and advantages of the present disclosure will be or become apparent to one having ordinary skill in the art upon examination of the following drawings, detailed description, and examples. It is intended that all such additional compositions, compounds, methods, features, and advantages be included within this description, and be within the scope of the present disclosure.

Cell Selective RNA Molecules

Figure 2:
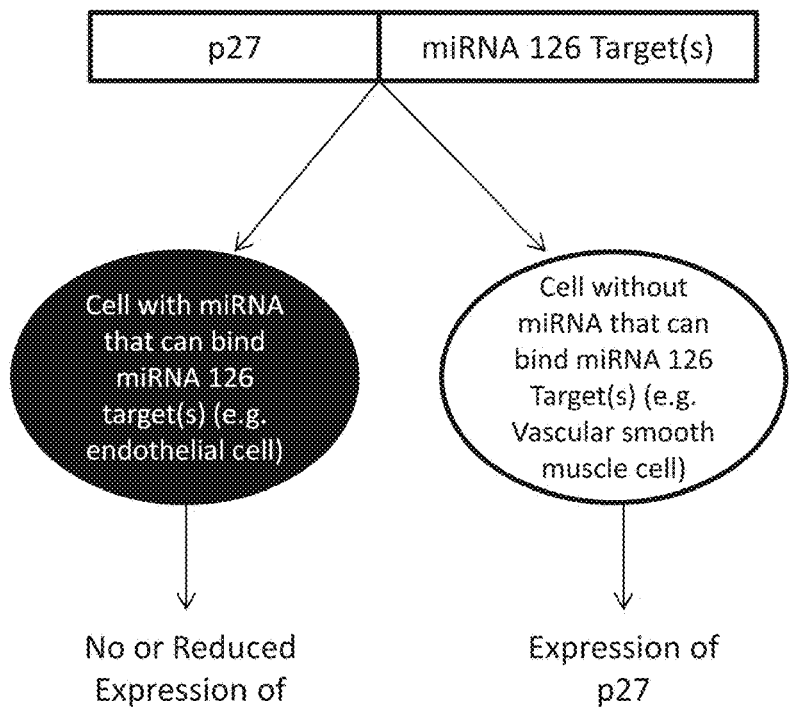
FIG. 2 shows an embodiment of a cell-selective RNA molecule and its operation.
Figure 3:
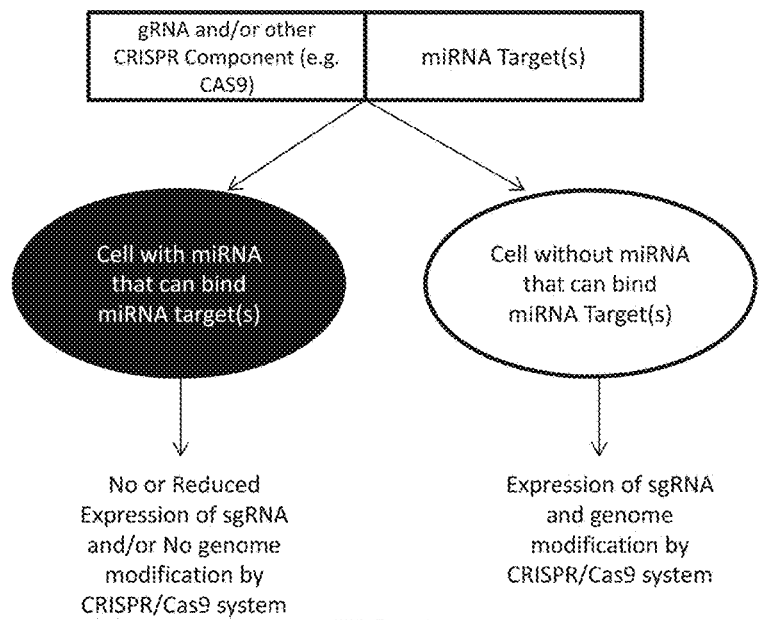
FIG. 3 shows an embodiment of a cell-selective RNA molecule and its operation.

As shown in FIG. 1, the cell-selective RNA molecules can contain one or more RNA molecules of interest. The RNA molecule(s) can be operatively coupled to one or more miRNA target sequences. When introduced to cells that have miRNA that can specifically bind to the miRNA target(s), the miRNA can specifically bind the miRNA target(s) of the cell-selective RNA molecules. This can result in degradation and/or prevent translation of the cell-selective RNA molecules through endogenous pathways (e.g. RISC complex-mediated degradation). Thus, there is no observable expression of the RNA of interest. When introduced into cells that do not express miRNA that can specifically bind to the miRNA target(s) of the cell-selective RNA molecule, the cell-selective RNA molecule can be translated by the cell. It will be appreciated that the same outcome can be realized if a cell expresses the miRNA that can specifically bind the miRNA target(s) at such a low level that binding to the cell-selective RNA does not reduce translation (through degradation or otherwise) of enough cell-selective RNA molecules to inhibit or ablate effective expression of the RNA of interest. In this way expression and/or translation of the RNA of interest can be selective to only cells that do not express miRNA that can bind to the miRNA target(s) in the cell-selective RNA molecule. By way of non-limiting example, FIGS. 2-3 show cell-selective expression of p27, Cas9, and/or gRNA that can be used as part of a CRISPR/Cas9 genome modification system.

In some embodiments, the cell-selective RNA molecule can be a RNA molecule. In other embodiments, the cell-selective molecule can be a DNA molecule that corresponds to (or encodes) cell-selective RNA molecule. The cell-selective RNA molecule or its corresponding DNA molecule can exist as naked RNA or DNA molecule (i.e. not contained in a vector) or contained within a vector.

RNA Molecules of Interest

The cell-selective RNA molecules can contain one or more RNA molecules of interest (ROI). The RNA molecule can correspond to a gene of interest. The ROI can correspond to an untranslated RNA molecule. The ROI can be any RNA molecule, linear or circular. The ROI can contain one or more ROI separated by a self-cleaving 2a peptide sequence. The ROI can contain a sequence corresponding to B18R to mitigate the innate immune response. The B18R can have a sequence that can be 90-100% identical to a sequence that corresponds to SEQ ID NO. 1. ROI can correspond to p27 that can be 90-100% identical to a sequence that corresponds to SEQ ID NO. 2, or any other tumor suppressor gene or suicide gene.

The ROI can be a RNA corresponding to a Cas9 protein. The Casp can have a polypeptide sequence that is identical to or that corresponds to SEQ NO. 3, Cas9n (D10A nickase version of the Cas9 enzyme generates a single-strand DNA break) that correspond to SEQ NO. 4, dCas9 (A catalytically inactive Cas9 or dCas9-repressor peptide fusion can be used to knock-down gene expression by interfering with transcription of the gene) that correspond to SEQ NO. 5 or dCAS9-VP64 activator that corresponds to SEQ NO. 6. The ROI can have or include a sequence 100% identical to any one of SEQ ID NOs: 2-6. The ROI can have or include a sequence that is 90-100% identical to a sequence corresponding to any one of SEQ ID NOs: 2-6. The ROI can be a guide RNA (gRNA).

The ROI can have or include a sequence that is 90-100% identical to SEQ ID NOs: 7. The ROI can be gRNA incorporating two MS2 RNA aptamers gRNA(MS2) cloning backbone include a sequence that is 90-100% identical to SEQ ID NO: 8. The ROI can encode MS2-P65-HSF1 activation helper proteins separated by 2a peptide sequence that have or include a sequence that is 90-100% identical to SEQ ID NO: 9 that can be used as part of a CRISPR/Cas9 genome modification system. The ROI can be self replicating cell-selective RNA molecules (described below).

miRNA Targets

The cell-selective RNA molecules can contain one or more miRNA targets. In some embodiments, the number of miRNA targets can range from 1 to 20 or more. For example, in some embodiments, the cell-selective RNA molecules can contain 1, 2, 3, 4, or 5 miRNA targets. The miRNA target(s) can be operatively linked to the 5' and/or 3' end of the ROI. The miRNA target(s) can be operatively linked to a 5' untranslated region (UTR) of the ROI and/or a 3' UTR of the ROI. In embodiments having one or more miRNA targets, the miRNA targets can be the same miRNA target, they can each be a different miRNA target. In some embodiments at least two of the miRNA targets are the same. In some embodiments, at least two of the miRNA targets are different. The miRNA targets can be operatively linked to each other and/or the ROI of interest. The miRNA target(s) are nucleotide sequences that can specifically bind one or more miRNAs. The miRNA(s) can have differential spatial and temporal expression. As such, effective expression of the ROI can be controlled both spatially and temporally depending on the miRNA target(s) included in the cell-selective RNA molecule as previously described. Some exemplary constructs incorporating various ROIs are demonstrated in FIGS. 4, 5, 17, 18, 19, 20, 22, and 31-42.

Suitable miRNA targets include, but are not limited to, targets for miR-126, miR-145, miR-296, miR-21, miR-22, miR-15a, miR-16, miR-19b, miR-92, miR-93, miR-96, miR-130, miR-130b, miR-128, miR-9, miR-125b, miR-131, miR-178, miR-124a, miR-266, miR-103, miR-9*, miR-125a, miR-132, miR-137, miR-139, miR-7, miR-124b, miR-135, miR-153, miR-149, miR-183, miR-190, miR-219, miR-18, miR-19a, miR-24, miR-32, miR-213, miR-20, miR-141, miR-193, miR-200b, miR99a, miR127, miR142-a, miR-142-s, miR-151, miR-189b, miR-223, miR-142, miR-122a, miR-152, miR-194, miR-199, miR-215, miR-1b, miR-1d, miR-133, miR-206, miR-208, miR-143, miR-30b, miR-30c, miR-26a, miR-27a, let-7a, and miR-7b.

In some embodiments, an miRNA target can have a sequence or include a sequence that is about 20-100% identical to the complement of any one of SEQ ID NOs:

10-135. In some embodiments, an miRNA target can have a sequence or include a sequence that is about 30-100% identical to the complement of a portion of any one of SEQ ID NOs: 10-135, where the portion is at least 5 consecutive nucleotides that corresponds to the seed sequence. The miRNAs that can specifically bind to the miRNA target(s) included in the cell-selective RNA molecule can have or include a sequence or portion thereof that is about 20-100% identical to any of SEQ ID NOs: 10-135, where a portion is at least 6 consecutive nucleotides that corresponds to the seed sequence. Where a stem-loop sequence is provided, those of skill in the art will appreciate, which portions correspond to the mature miRNA sequences that can be produced from the stem-loop sequences.

Self-Replicating Cell-Selective RNA Molecules

The cell-selective RNA molecules can be configured such that they are self-replicating. In other words, the cell-selective RNA molecules can be RNA replicons. The cell-selective RNA molecules can also include one or more viral RNA sequences that confer self-replication functionality once the cell-selective RNA molecule is introduced to a cell. The viral RNA sequence(s) can be alphavirus RNA sequences. The viral RNA sequence(s) can be Venezuelan Equine Encephalitis, Sindbis, and/or Semliki Forest virus sequence(s). Such sequences will be appreciated and determined by those of skill in the art. The sequences can encode one or more nonstrucutrual proteins and/or an RNA replicase. The viral sequences can be operatively linked to the ROI and/or miRNA target(s). Noninfectious self-replicating viral RNA that lacks the genes encoding the viral structural proteins that encodes four nonstructural replication complex proteins (NSPs) as a single open reading frame (ORF) in addition to the ROI. In some embodiments, the cell-selective RNA molecules do not include an RNA replicase. Replicases are generally known in the art. Non-limiting examples include, but are not limited to, those set forth in Geall et al., (2012) PNAS 109(36) 14604-14609 and Yoshioka et al. (2013) Stem Cell. 13(2):246-254, which are incorporated by reference as if expressed in their entirety.

Promoter Sequences and Other Transcription Elements

The cell-selective RNA molecules can contain one or more promoters. The promoter(s) can be operatively linked to the 5' end of the cell selective RNA molecule. The promoter(s) can be operatively linked at any position between the 5' and 3' end of the cell-selective RNA molecules. The promoter(s) can be operatively linked to the 5' end of an ROI. The promoter(s) can be operatively linked to the 5' end of a miRNA target. The promoter(s) can drive in vitro and/or in vivo transcription of the cell-selective RNA molecule or corresponding DNA molecule.

The promoter can be a eukaryotic promoter. The promoter can be a prokaryotic promoter. The promoter can be a Pol I promoter. The promoter can be a Pol II promoter. The promoter can be a Pol III promoter. The promoter can be a T7, Sp6 or T3 polymerase promoter. Example promoters include, but are not limited to 26S subgenomic promoter, CMV, CAG, SV40, EF1a, PGK1, Unc, beta actin promoter, TRE, UAS, Ac5, Polyhedrin, CaMKlla, GAL1, GAL10, TEF1, GDS, GAPDH promoter, ADH1, cAMV35S, Ubi, H1, 7SK, U6, T7, SP6, T7lac. araBAD, trp, lac, Ptac, and pL. The sequences and variants thereof of these promoters as well as other promoters that would be suitable to one of ordinary skill in the art in view of this description are generally known in the art. See also Yoshioka et al. (2013) Stem Cell. 13(2):246-254 and Addgene Plasmid No.: 58976, which are incorporated by reference as if expressed in their entirety.

Markers

The cell-selective RNA molecule can include one or more markers or reporter molecules. Example markers and reporter molecules include, but are not limited to, Examples of selectable markers include, but are not limited to, DNA and/or RNA segments that contain restriction enzyme sites; DNA segments that encode products that provide resistance against otherwise toxic compounds including antibiotics, such as, spectinomycin, ampicillin, kanamycin, tetracycline, Basta, neomycin phosphotransferase II (NEO), hygromycin phosphotransferase (HPT)) and the like; DNA and/or RNA segments that encode products that are otherwise lacking in the recipient cell (e.g., tRNA genes, auxotrophic markers); DNA and/or RNA segments that encode products which can be readily identified (e.g., phenotypic markers such as 8-galactosidase, GUS; fluorescent proteins such as green fluorescent protein (GFP), cyan (CFP), yellow (YFP), red (RFP), luciferase, and cell surface proteins); the generation of new primer sites for PCR (e.g., the juxtaposition of two DNA sequence not previously juxtaposed), the inclusion of DNA sequences not acted upon or acted upon by a restriction endonuclease or other DNA modifying enzyme, chemical, etc.; epitope tags (e.g. FLAG- and His-tags), and, the inclusion of a DNA sequences required for a specific modification (e.g., methylation) that allows its identification. Other suitable markers will be appreciated by those of skill in the art.

The terms "plasmid", "vector" and "cassette" as used herein can refer to an extra chromosomal element often carrying genes that are not part of the central metabolism of the cell, and usually in the form of double-stranded DNA. Such elements may be autonomously replicating sequences, genome integrating sequences, phage, or nucleotide sequences, in linear or circular form, of a single- or double-stranded DNA or RNA, derived from any source, in which a number of nucleotide sequences have been joined or recombined into a unique construction which is capable of introducing a polynucleotide of interest into a cell.

Vectors

Also provided herein are nucleic acid vectors containing a nucleic acid molecule corresponding to a cell-selective RNA molecule described herein. All or part of the vectors can be capable of being transcribed in vitro without a host cell or in a host cell. The vectors can be capable of being replicated by a host cell. All or part of the vector or a RNA molecule produced from the vector template can be capable of being integrated directly or indirectly into a host cell genome. The vectors can be viral vectors, i.e. vectors that are virus based or incorporate viral proteins or nucleic acids corresponding to a viral protein. Suitable viral vectors can include adenoviral, lentiviral, retroviral, and alpha viral vectors.

Synthesis of the Cell-Selective RNA Molecules

The cell-selective RNA molecules can be synthesized using de novo chemical synthesis. The cell-selective RNA molecules can be synthesized using in vitro transcription from a DNA molecule template. In vitro transcription can occur within a host cell or without a host cell. The cell-selective RNA molecules can also be transcribed in vivo after delivery to a subject. The DNA molecule template can be a DNA molecule or DNA vector containing a DNA sequence corresponding to the cell-selective RNA molecules. These DNA molecules and vectors are described elsewhere herein. The cell-selective RNA molecules can be polyadenylated at the 3' end. The cell-selective RNA molecules can be 5' capped in vitro. The cell-selective RNA molecules can be synthesized with an ARCA Cap at the 5' end. The RNA molecule can be expressed in a bacterial, viral, yeast, plant, insect, or mammalian expression system. Suitable systems will be appreciated by those skilled in the art. The RNA molecule produced from transcription can be purified from a solution and/or other cellular components. Methods of RNA purification will be appreciated by those of skill in the art.

In some embodiments, the cell-selective RNA molecules are modified. The modification can occur during or after synthesis (transcription of the RNA molecule). The modification can be a nucleotide modification. As such, the cell-selective RNA molecules can be synthesized with one or more modified nucleotides. Suitable nucleotide modifications include, but are not limited to, pseudouridine (ψU), N-1-methylpseudouridine, 5-methoxyuridine, and 5-hydroxymethylcytidine. In some embodiments 0-100% of the nucleotides are substituted. The modifications can reduce immunogenicity of the cell-selective RNA molecules. The modifications can increase transcription and/or translation of the cell-selective RNA molecules.

Delivery of the Cell-Selective RNA Molecules

The cell-selective RNA molecules, corresponding DNA molecule, vectors, virons, or pseudoviral particles described herein can be delivered to a subject as part of a pharmaceutical formulation as described herein. As described elsewhere herein, the cell-selective RNA molecules can be delivered to a cell by transfection, transduction, or by other suitable method. In other embodiments, a DNA based vector or polynucleotide that encodes a cell-selective RNA molecule as described herein can be configured to be delivered to a cell as being incorporated in a virus, pseudovirus, or virus particle. In these embodiments, the cells can be transduced or infected with a virus, pseudovirus, or other virus particle that can deliver the corresponding DNA molecule to the cell. In other embodiments, the cell-selective RNA molecules and/or corresponding DNA molecule can be delivered to a cell via chemical transfection of a cell. Chemical transfection methods include encapsulating the cell-selective RNA molecules and/or corresponding DNA molecules in a liposome or micelle (e.g. cationic liposome), which can then be taken in by the cell via endocytosis. Suitable transfection reagents will be appreciated by those of skill in the art. In further embodiments, the cell-selective RNA molecules and/or corresponding DNA molecules can be incorporated with mesoporous silica nanoparticles that can include a polycation adjunct or large pore mesoporous silica nanoparticles. The mesoporous silica nanoparticles that include the cell-selective RNA molecules and/or corresponding DNA molecules can be taken up by the cell via endocytosis. In other embodiments, the cell-selective RNA molecules and/or corresponding DNA molecules can couple to organic/inorganic silica hybrid nanoparticleswhich can be taken up by a cell via endocytosis. Other delivery methods include electroporation or chitosan polymers. Other delivery methods will be appreciated by those of ordinary skill in the art.

Pharmaceutical Formulations

Also provided herein are pharmaceutical formulations containing an amount of a cell-selective RNA molecule, corresponding DNA molecule (including vectors), and/or viron particle as described herein. The amount can be an effective amount. Pharmaceutical formulations can be formulated for delivery via a variety of routes and can contain a pharmaceutically acceptable carrier. Techniques and formulations generally can be found in Remmington's Pharmaceutical Sciences, Meade Publishing Co., Easton, Pa. (20th Ed., 2000), the entire disclosure of which is herein incorporated by reference. For systemic administration, an injection is useful, including intramuscular, intravenous, intraperitoneal, and subcutaneous. For injection, the therapeutic compositions of the invention can be formulated in liquid solutions, for example in physiologically compatible buffers such as Hank's solution or Ringer's solution. In addition, the therapeutic compositions can be formulated in solid form and redissolved or suspended immediately prior to use. Lyophilized forms are also included. Pharmaceutical compositions of the present invention are characterized as being at least sterile and pyrogen-free. These pharmaceutical formulations include formulations for human and veterinary use.

Suitable pharmaceutically acceptable carriers include, but are not limited to water, salt solutions, alcohols, gum arabic, vegetable oils, benzyl alcohols, polyethylene glycols, gelatin, carbohydrates such as lactose, amylose or starch, magnesium stearate, talc, silicic acid, viscous paraffin, perfume oil, fatty acid esters, hydroxyl methylcellulose, and polyvinyl pyrrolidone, which do not deleteriously react with the active composition.

The pharmaceutical formulations can be sterilized, and if desired, mixed with auxiliary agents, such as lubricants, preservatives, stabilizers, wetting agents, emulsifiers, salts for influencing osmotic pressure, buffers, coloring, flavoring and/or aromatic substances, and the like which do not deleteriously react with the active composition.

The pharmaceutical formulations can be administered to a subject in need thereof. The subject in need thereof can have a disease, disorder, or a symptom thereof. Example disease or disorder can include, but are not limited to, a cardiovascular disease, a pulmonary disease, a brain disease, a renal disease, a liver disease, a blood disease, a nervous system disease, an intestinal disease, an ocular disease, and cancer. The pharmaceutical formulations can be disposed on or otherwise coupled to or integrated with a medical device, such as, but not limited to, catheters or stents, such that the pharmaceutical formulation is eluted from the medical device over a time period. The pharmaceutical formulation can therefore be delivered to a subject in need thereof during and/or after a procedure such as an angioplasty, vein draft or organ transplant. Other procedures where such a medical device would be useful will be appreciated by those of skill in the art.

A pharmaceutical formulation can be formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. The construct, biologic molecules and pharmaceutical formulations thereof described herein can be disposed on or otherwise integrated with or coupled to a medical device such as, but not limited to, a catheter or stent, such that the construct, biological molecule can be released to the surrounding local area or systemically over a period of time after insertion or implantation into a subject in need thereof. These can also be referred to as drug eluting medical devices.

Pharmaceutical formulations suitable for injectable use can include sterile aqueous solutions (where water soluble) or dispersions and sterile powders for the extemporaneous preparation of sterile injectable solutions or dispersions. For intravenous administration, suitable carriers can include physiological saline, bacteriostatic water, Cremophor EMT™ (BASF, Parsippany, N.J.) or phosphate buffered saline (PBS). Injectable pharmaceutical formulations can be sterile and can be fluid to the extent that easy syringability exists. Injectable pharmaceutical formulations can be stable under the conditions of manufacture and storage and must be preserved against the contaminating action of microorganisms such as bacteria and fungi. The carrier can be a solvent or dispersion medium containing, for example, water, ethanol, a pharmaceutically acceptable polyol like glycerol, propylene glycol, liquid polyetheylene glycol, and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it can be useful to include isotonic agents, for example, sugars, polyalcohols such as mannitol, sorbitol, sodium chloride in the composition. Prolonged absorption of injectable compositions can be brought about by incorporating an agent which delays absorption, for example, aluminum monostearate and gelatin.

Sterile injectable solutions can be prepared by incorporating any of the cell-selective RNA molecules, corresponding DNA molecules, or viron particles as described herein in an amount in an appropriate solvent with one or a combination of ingredients enumerated herein, as required, followed by filtered sterilization. Generally, dispersions can be prepared by incorporating the nucleic acid vectors into a sterile vehicle which contains a basic dispersion medium and the required other ingredients from those enumerated herein. In the case of sterile powders for the preparation of sterile injectable solutions, examples of useful preparation methods are vacuum drying and freeze-drying which yields a powder of the active ingredient plus any additional desired ingredient from a previously sterile-filtered solution thereof.

Systemic administration can also be by transmucosal or transdermal means. For transmucosal or transdermal administration, penetrants appropriate to the barrier to be permeated can be used in the formulation. Such penetrants are generally known in the art, and include, for example, for transmucosal administration, detergents, bile salts, and fluidic acid derivatives. Transmucosal administration can be accomplished through the use of nasal sprays or suppositories. For transdermal administration, the cell-selective RNA molecules, corresponding DNA molecules, and/or viron particles can be formulated into ointments, salves, gels, or creams as generally known in the art. In some embodiments, the cell-selective RNA molecules, corresponding DNA molecules, and/or viron particles can be applied via transdermal delivery systems, which can slowly release the cell-selective RNA, corresponding DNA molecule, and/or viron particles for percutaneous absorption. Permeation enhancers can be used to facilitate transdermal penetration of the active factors in the conditioned media. Transdermal patches are described in for example, U.S. Pat. No. 5,407,713; U.S. Pat. No. 5,352,456; U.S. Pat. No. 5,332,213; U.S. Pat. No. 5,336,168; U.S. Pat. No. 5,290,561; U.S. Pat. No. 5,254,346; U.S. Pat. No. 5,164,189; U.S. Pat. No. 5,163,899; U.S. Pat. No. 5,088,977; U.S. Pat. No. 5,087,240; U.S. Pat. No. 5,008,110; and U.S. Pat. No. 4,921,475.

Administration of the cell-selective RNA molecules, corresponding DNA molecules, and/or viron particles is not restricted to a single route, but may encompass administration by multiple routes. For instance, exemplary administrations by multiple routes include, among others, a combination of intradermal and intramuscular administration, or intradermal and subcutaneous administration. Multiple administrations may be sequential or concurrent. Other modes of application by multiple routes will be apparent to the skilled artisan.

The pharmaceutical formulations can be administered to a subject by any suitable method that allows the agent to exert its effect on the subject in vivo. For example, the formulations or other compositions described herein can be administered to the subject by known procedures including, but not limited to, by oral administration, sublingual or buccal administration, parenteral administration, transdermal administration, via inhalation, via nasal delivery, vaginally, rectally, and intramuscularly. The formulations or other compositions described herein can be administered parenterally, by epifascial, intracapsular, intracutaneous, subcutaneous, intradermal, intrathecal, intramuscular, intraperitoneal, intrasternal, intravascular, intravenous, parenchymatous, and/or sublingual delivery. Delivery can be by injection, infusion, catheter delivery, or some other means, such as by tablet or spray. In some embodiments, the nucleic acid vectors of the invention are administered to the subject by way of delivery directly to the heart tissue, such as by way of a catheter inserted into, or in the proximity of the subject's heart, or by using delivery vehicles capable of targeting the drug to the heart. For example, the cell-selective RNA molecules, corresponding DNA molecules, and/or viron particles described herein can be conjugated to or administered in conjunction with an agent that is targeted to the heart, such as an aptamer, antibody or antibody fragment. The cell-selective RNA molecules, corresponding DNA molecules, and/or viron particles can be administered to the subject by way of delivery directly to the tissue of interest, such as by way of a catheter inserted into, or in the proximity of the subject's tissue of interest, or by using delivery vehicles capable of targeting the nucleic acid vectors to the muscle, such as an antibody or antibody fragment.

For oral administration, a formulation as described herein can be presented as capsules, tablets, powders, granules, or as a suspension or solution. The formulation can contain conventional additives, such as lactose, mannitol, cornstarch or potato starch, binders, crystalline cellulose, cellulose derivatives, acacia, cornstarch, gelatins, disintegrators, potato starch, sodium carboxymethylcellulose, dibasic calcium phosphate, anhydrous or sodium starch glycolate, lubricants, and/or or magnesium stearate.

For parenteral administration (i.e., administration by through a route other than the alimentary canal), the formulations described herein can be combined with a sterile aqueous solution that is isotonic with the blood of the subject. Such a formulation can be prepared by dissolving the active ingredient in water containing physiologically-compatible substances, such as sodium chloride, glycine and the like, and having a buffered pH compatible with physiological conditions, so as to produce an aqueous solution, then rendering the solution sterile. The formulation can be presented in unit or multi-dose containers, such as sealed ampoules or vials. The formulation can be delivered by injection, infusion, or other means known in the art.

For transdermal administration, the formulation described herein can be combined with skin penetration enhancers, such as propylene glycol, polyethylene glycol, isopropanol, ethanol, oleic acid, N-methylpyrrolidone and the like, which increase the permeability of the skin to the nucleic acid vectors of the invention and permit the nucleic acid vectors to penetrate through the skin and into the bloodstream. The formulations and/or compositions described herein can be further combined with a polymeric substance, such as ethylcellulose, hydroxypropyl cellulose, ethylene/vinyl acetate, polyvinyl pyrrolidone, and the like, to provide the composition in gel form, which can be dissolved in a solvent, such as methylene chloride, evaporated to the desired viscosity and then applied to backing material to provide a patch.

Dosage Forms

The pharmaceutical formulations or compositions described herein can be provided in unit dose form such as a tablet, capsule or single-dose injection or infusion vial. Where appropriate, the dosage forms described herein can be microencapsulated. The dosage form can also be prepared to prolong or sustain the release of any ingredient. In some embodiments, the complexed active agent can be the ingredient whose release is delayed. In other embodiments, the release of an auxiliary ingredient is delayed. Suitable methods for delaying the release of an ingredient include, but are not limited to, coating or embedding the ingredients in material in polymers, wax, gels, and the like. Delayed release dosage formulations can be prepared as described in standard references such as "Pharmaceutical dosage form tablets," eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et al., (Media, Pa.: Williams and Wilkins, 1995). These references provide information on excipients, materials, equipment, and processes for preparing tablets and capsules and delayed release dosage forms of tablets and pellets, capsules, and granules. The delayed release can be anywhere from about an hour to about 3 months or more.

Coatings may be formed with a different ratio of water soluble polymer, water insoluble polymers, and/or pH dependent polymers, with or without water insoluble/water soluble non polymeric excipient, to produce the desired release profile. The coating is either performed on the dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Examples of suitable coating materials include, but are not limited to, cellulose polymers such as cellulose acetate phthalate, hydroxypropyl cellulose, hydroxypropyl methylcellulose, hydroxypropyl methylcellulose phthalate, and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

In some embodiments, such as for treatments of plants, the topical formulation of a composition or pharmaceutical formulation described herein can be further formulated as a spray and can include a suitable surfactant, wetting agent, adjuvants/surfactant (stickers, extender, plant penetrant, compatibility agents, buffers, drift control additives, and defoaming agents), or any combination thereof so as to formulated as a spray. The compounds, any optional auxiliary active ingredient, suitable surfactant, wetting agent, adjuvants, or any combination thereof can be formulated as a solution, suspension, or emulsion. The spray dosage from can be administered through a spraying device. In some embodiments, the spraying device can be configured to generate the sprayable formulation as a liquid solution is contacted with the complexed active agent compound or formulation thereof. In other embodiments, the sprayable dosage form is pre-made prior to spraying. As such, the spraying device can act solely as an applicator for these embodiments.

In further embodiments, such as for treatments of plants (e.g. such as a herbicide), the dosage form of composition or pharmaceutical formulation described herein thereof can be further formulated as a dust and can include a suitable dry inert carrier (e.g. talc chalk, clay, nut hull, volcanic ash, or any combination thereof so as to be formulated as a dust. The dust can contain dust particles of varying sizes. In some embodiments, the particle size can be substantially homogenous. In other embodiments, the particle size can be heterogeneous. Dosage forms adapted as a dust can contain one or more adjuvants/surfactants (stickers, extender, plant penetrant, compatibility agents, buffers, drift control additives, and defoaming agents).

In some embodiments, the dosage form can be formulated as a bait. In these embodiments, the complexed active agent compound or other formulation thereof can be further formulated to include a food or other attractive substance that can attract one or more insect or other pest. The bait dosage form can be formulated as a dust, paste, gel, or granule. Dosage forms adapted as baits can contain one or more adjuvants/surfactants (stickers, extender, plant penetrant, compatibility agents, buffers, drift control additives, and defoaming agents).

In additional embodiments, the dosage form can be formulated as granules or pellets that can be applied to the environment. These dosage formulations are similar to dust formulations, but the particles are larger and heavier. The granules can be applied to soil or other environmental area. Dosage forms adapted as granules or pellets can contain one or more adjuvants/surfactants (stickers, extender, plant penetrant, compatibility agents, buffers, drift control additives, and defoaming agents).

The dusts, granules, and pellets described herein can be formulated as wetable dusts, granules, and pellets, soluble dusts granules, and pellets, and/or water-dispersible granules, and/or dry flowables.

The dosage form can be adapted for impregnating (saturating) an object or device, which then can be carried by, worn, or otherwise coupled to an organism in need thereof. In some embodiments, the dosage form can be impregnated onto a collar, bracelet, patch, adhesive tape, livestock ear tags, clothing, blankets, plastics, nets, and paints. The composition or pharmaceutical formulation thereof can be formulated and impregnated in the object or device such that the composition or pharmaceutical formulation evaporates over time, which releases the composition and/or pharmaceutical formulation into the air and/or environment surrounding the organism and/or onto the organism.

The dosage form can be adapted as a fumigant, which is a formulation that forms a gas when utilized or applied. In some embodiments, the composition and/or pharmaceutical formulation thereof can be supplied as a liquid when packaged under pressure and change to a gas when they are released. In other embodiments, the composition and/or pharmaceutical formulation thereof can be supplied as a volatile liquid when enclosed in a container (not under pressure). Others can be formulated as solids that release gases when applied under conditions of high humidity or in the presence of high water vapor. Dosage forms adapted as fumigants can contain one or more adjuvants/surfactants (stickers, extender, plant penetrant, compatibility agents, buffers, drift control additives, and defoaming agents).

Effective Amounts

The pharmaceutical formulations can contain an effective amount of a composition described herein and/or an effective amount of an auxiliary agent. In some embodiments, the effective amount ranges from about 0.001 pg to about 1,000 g or more of the composition described herein. In some embodiments, the effective amount of the composition described herein can range from about 0.001 mg/kg body weight to about 1,000 mg/kg body weight. In yet other embodiments, the effective amount of the composition can range from about 1% w/w to about 99% or more w/w, w/v, or v/v of the total pharmaceutical formulation.

Combination Therapy

The pharmaceutical formulations or other compositions described herein can be administered to a subject either as a single agent, or in combination with one or more other agents. Additional agents include but are not limited to DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics. Multiple cell-selective ROI can be administered simultaneously in a combination treatment.

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepressants, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylate, and sodium salicylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), Hz-receptor antagonists (e.g. cimetidine, famotidine, lafutidine, nizatidine, rafitidine, and roxatidine), tritoqualine, catechin, cromoglicate, nedocromil, and p2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, penicillins (amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxaxillin, dicloxacillin, and nafcillin), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase erwinia chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, and all-trans retinoic acid.

Devices Containing the Cell Selective RNA Molecules

Also described herein are medical devices that can contain a composition or pharmaceutical formulation as described herein. In some embodiments, the composition or pharmaceutical formulation described herein can be encapsulated in one or more polymers. In some embodiments, the polymers are biocompatible polymers. The polymers can be FDA approved polymers. Suitable polymers can include, but are not limited to phosphorylcholine-based polymers, poly lactic-co-glycolic acid (PLGA), polyethylene glycol (PEG), chitosan, cationic nanoemulsion, cationic electrodeposition coating or lipid nanoparticles The composition or pharmaceutical formulations can be encapsulated in the polymer and the polymer can be applied to the medical device. In use, the compositions and/or pharmaceutical formulations described herein can be released from the polymer into the surrounding environment and be utilized by cells in the surrounding environment.

Suitable medical devices include, but are not limited to, stents, spinal plates, pins, screws, replacement joints and components thereof, catheters, coated balloons, cannulas, bone plates, spacers, replacement discs, stabilization rods, and surgical mesh.

Uses of the Cell Selective RNA Molecules and Devices

The compositions and formulations described herein can be used to selectively deliver a translated RNA (e.g. a gene) or untranslated RNA (gRNA) to a cell. In this way, the compositions and formulations described herein can be used to treat and/or prevent a disease, disorder, or symptom thereof by delivering the ROI to a cell. Selective expression of the ROI can increase treatment or preventive efficacy by decreasing side effects.

When the ROI includes a gRNA or sgRNA(MS2), dCas9, dCas9-VP64 fusion or MS2-P65-HSF1 the compositions can be also used for genome editing using the CRISPR/Cas9 system, which includes the addition or deletion of one or more nucleotides to the genome or exon skipping. This can result in gene knock down, knock out, gene repair, gene suppression or gene activation. Thus, in this way genome editing can be cell-selective because the gRNA and/or sgRNA(MS2), Cas9, dCas9, dCas9-VP64 fusion or MS2-P65-HSF1 will only be present in cells lacking the miRNA that can bind the target(s) in the cell-selective RNA molecule.

EXAMPLES

Now having described the embodiments of the present disclosure, in general, the following Examples describe some additional embodiments of the present disclosure. While embodiments of the present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Example 1

Despite the remarkable advances in therapeutic strategies over the past decades the lack of cell selective therapies remain a major overarching problem in clinical medicine. One clear example for this challenge is the deadly consequences of the non-selective agent used on the drug-eluting stents (DES) that were developed to inhibit neointimal overgrowth of vascular smooth muscle cells (VSMCs) following percutaneous intervention.

While DES significantly reduced the occurrence of restenosis compared with a bare-metal stent (BMS), they do not completely eliminate this challenging problem. Moreover, stent thrombosis (ST), reinfarction, and neoatherosclerosis within stent segments have emerged as major safety concerns with DES, all predominantly attributed to the lack of reendothelialization of diseased vessel walls with competent endothelial cells (ECs). DES deployment inevitably traumatizes the normal competent endothelium structure. Compounding this insult, the drugs eluted from the stents, while not delivered systemically, are still universally deleterious to all cell types exposed to the eluted drug, proving toxic to ECs and drastically reducing the quality of regenerating endothelium. This incompetent endothelium, with poorly formed cell-to-cell junctions reduced expression of antithrombotic molecules and endothelial nitric oxide synthase (eNOS), can no longer function normally to maintain vascular tone and fluid-tissue homeostasis. Thus, this requires patients to comply with at least 12 months of dual anti-platelet therapy.

Newer generations of DES, with more sophisticated platforms, thinner struts, and biocompatible polymers have been developed to combat DES-associated risks. Yet, they still deploy the same non-selective drugs (paclitaxel, sirolimus or its analogs, everolimus, zotarolimus and biolimus, with improved pharmacokinetics). Current DES devices with low rates of restenosis and ST translate into a significant number of patients that will suffer from myocardial infarction and death due to the large number of percutaneous coronary intervention (PCI) procedures performed worldwide every year. In fact, percutaneous interventions are among the most performed procedures in Medicine. In the US alone, nearly 1 million patients undergo PCI for symptomatic coronary artery disease (CAD) every year, and non-selective DES are deployed in at least 75% of these cases. In 2010, the DES segment contributed 55%-60% of the global coronary stent market and is expected to reach USD 5.3 billion in 2016 due to the growing aging population and lifestyle changes leading to obesity. The market for DES is growing at 9.0% in the United States, 3.1% in Europe, 10% in Asia-Pacific and 3.1% in the rest of the world. These numbers will potentially expand as DES deployment is used in percutaneous interventions to treat peripheral artery disease (PAD) that affects more than 10 million people in the US, with symptomatic lower-extremity PAD, renal artery stenosis and carotid artery disease.

Although percutaneous transluminal angioplasty (PTA) and stenting achieve a greater lumen diameter, vessel remodeling and restenosis remain its Achilles' heel contributing to significant morbidity and mortality rates in these patients. To date, cell-selective drugs that can discriminate between proliferating VSMCs, inflammatory cells and ECs are not available. Since vascular ECs provide crucial protection against thrombosis, lipid uptake and inflammation, there is a need to develop a cell-selective therapy that can inhibit VSMC proliferation and inhibit infiltration of inflammatory cells, yet spare ECs to carry on their vital functions.

A viral vector approach has been previously developed that contained an EC specific miRNA target sequence (target for miR-126). In that work an adenoviral vector (Ad-p27-126TS) containing target sequences complementary to the mature miR-126-3p strand at the 3'-end of the cyclin-dependent kinase inhibitor p27Kip1 (p27). This approach allowed for exogenous p27 to be selectively overexpressed in VSMCs and infiltrate inflammatory cells, yet preserving the ECs. This therapy achieved results in an established rat model of balloon angioplasty, selectively inhibiting neointimal hyperplasia and inflammation while simultaneously promoting vessel reendothelialization, reducing hypercoagulability and restoring the endothelium-dependent vasodilatory response to levels indistinguishable from uninjured controls. (FIGS. 21-29).

Due to complications with viral gene delivery, this Example describes a messenger RNA based, cell-selective nanotherapy utilizing the mRNA or self-replicating RNA that can be based on an alphavirus genome. This strategy can match the potency of viral vectors yet avoid the serious safety concerns associated with recombinant virus-based therapeutics. This approach can reduce the need for repeated revascularization, reduce the need for prolonged dual anti-platelet drug regimens, and ultimately reduce the morbidity and mortality of CAD and PAD patients. This mRNA based cell-selective nanotherapy could not only replace the use of stents, but potentially treat lesions where DES cannot be deployed or DES is contraindicated, such as in stent restenosis, bifurcations, torturous vessels, small vessels or long calcifications. In addition to its potential benefit in CAD and PAD, this approach can be applied to benefit multiple other stenotic conditions, including transplant vasculopathy, arteriovenous fistulae, and vein graft failure, which all result from VSMC hyperplasia and EC dysfunction. Over 200,000 cardiovascular surgical procedures utilizing venous grafts fail each year in the US, primarily due to restenosis caused by VSMC hyperplasia. This mRNA based cell-selective approach may also inhibit vascular remodeling in deadly diseases such as pulmonary hypertension and pulmonary fibrosis, which still has no cure. The versatile concept of mRNA based, cell-selective nanotherapy can be broadly applied across disciplines and for treating any disease, including but not limited to, liver cirhosis and cancer. This tailored mRNA-based, cell-selective nanotherapy represents an exciting translational and potentially transformative approach in modern clinical medicine.

mRNA-based therapeutics represent a game-changing technology and hold great promise for the treatment of human diseases including genetic disorders, infections, degenerative diseases and cancer. Many are the advantages of these versatile mRNA-based therapies. They can be produced very quickly, cost effectively and in a cell-free system at good manufacturing practice quality. Furthermore, any nucleotide sequence needed can be synthetically produced and stored at room temperature. Importantly, chemically modified mRNA that does not change the amino acid sequence of the corresponding protein not only decreases activation of the innate immune pathway but also improves the stability and enhances the translation levels. mRNA is non-replicative and therefore considered a very safe biomolecule that allows transient protein expression of every protein in virtually all cell types including non-dividing cells. Moreover, no nuclear localization, promoter elements or transcription is required and unlike recombinant virus-vectors the probability of genomic integration is nearly nonexistent. Lastly, chemically modified mRNAs that elude the body's innate immune response make therapeutic gene products and protein replacement therapies possible. However, there still exists the challenge of cell- or tissue-specific delivery that hinders virtually any type of therapeutic agent.

To overcome the deficiencies stated above the miRNA-based cell selective approach can be utilized in a chemically modified self-replicating RNA platform to achieve long lasting cell-selective targeting that can inhibit proliferating VSMCs and infiltration of inflammatory cells while allowing ECs to reendothelialize vessel walls and maintain their crucial function. miR-126 is enriched in ECs and is a pivotal regulator of vascular integrity and angiogenesis. Moreover, miR-126 was observed to be up-regulated following arterial injury and in atherosclerotic plaques. The approach described herein utilizes EC-specific expression of miR-126 to drive cell-specific expression of therapeutic genes of interest.

Figure 22:
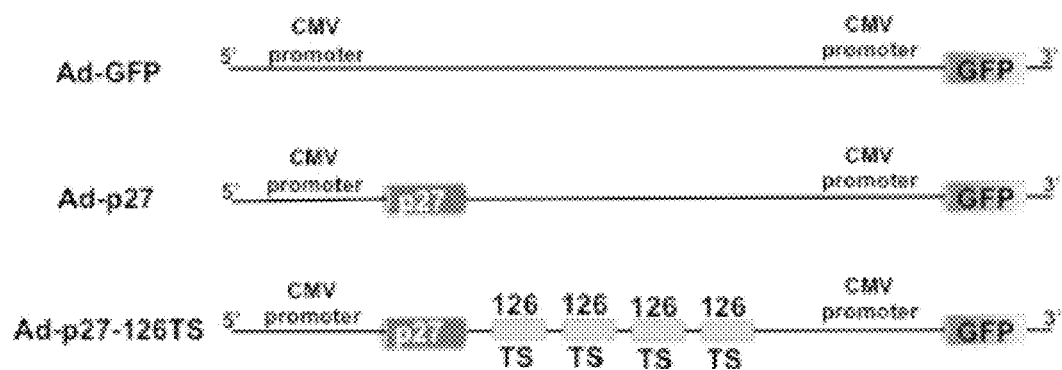
FIG. 22 shows embodiments of adenoviral vector constructs for cell-selective gene delivery.
Figure 23:
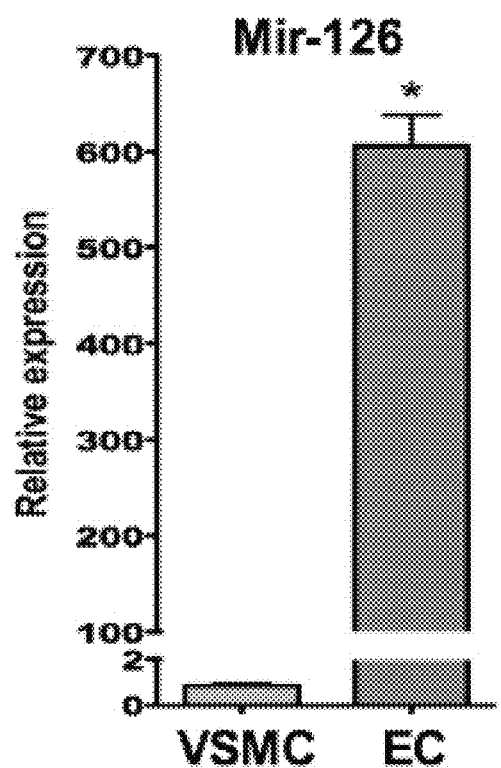
FIG. 23 shows a graph demonstrating high levels of expression of endogenous miR-126-3p in human ECs as determined by RT-qPCR.
Figure 24:
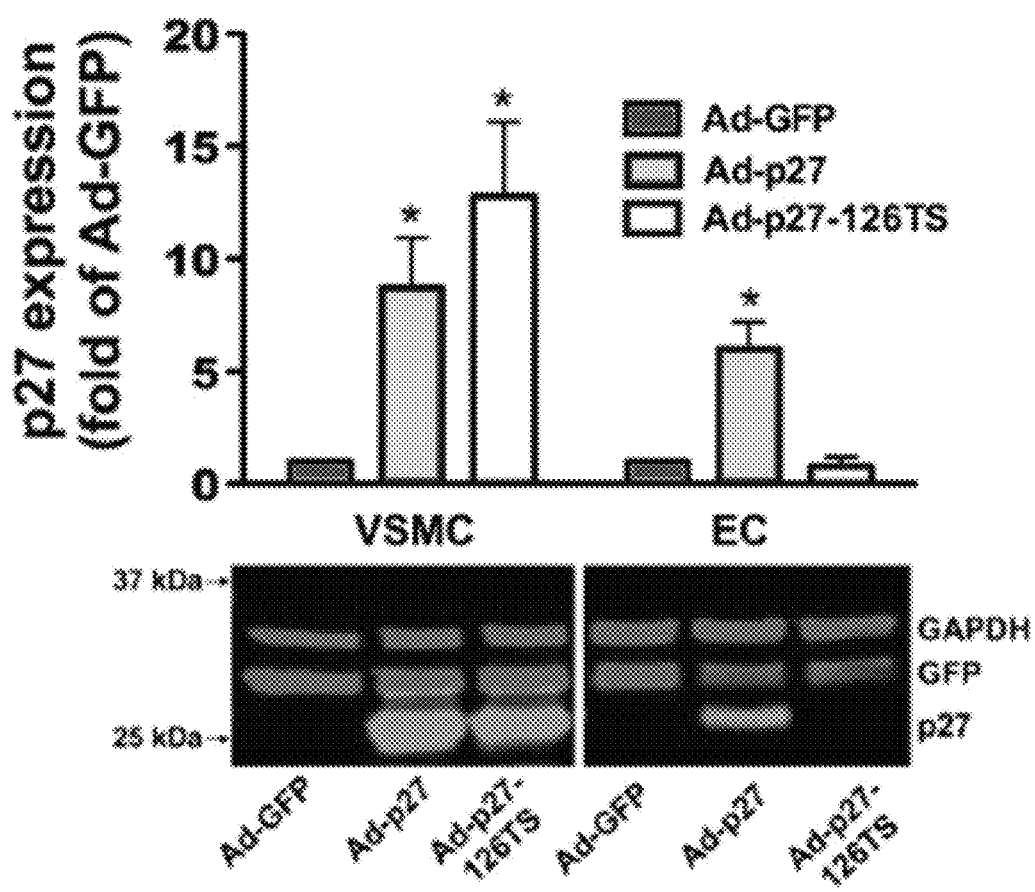
FIG. 24 shows representative immunoblots of p27 expression and corresponding graphs demonstrating densitometric quantification (n=3). Data represent the mean±SEM. Data comparisons were made using 1-way ANOVA with Tukey-Kramer's post hoc test. *P<0.01 versus Ad-GFP.
Figure 25:
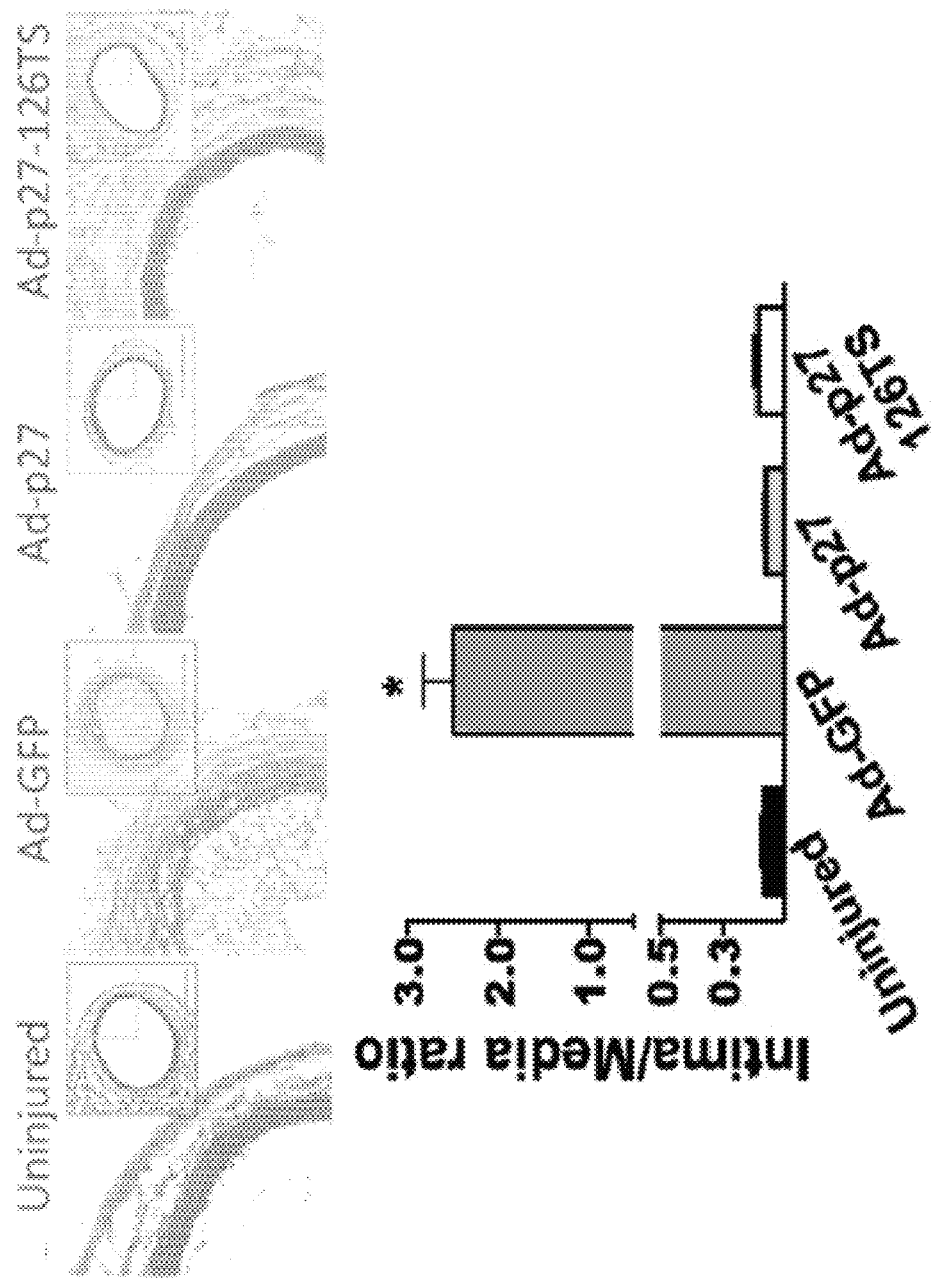
FIG. 25 shows images and corresponding graph demonstrating that treatment with Ad-p27-126TS inhibits neointimal hyperplasia. Representative H&E-stained sections 2 weeks after balloon injury. Scale bars: 500 µm; original magnification, ×10 (insets show the whole arterial section at ×5 original magnification). Intima/media ratios were calculated from at least 6 rats/group. Data represent the mean±SEM and were compared using 1-way repeated measures ANOVA followed by Tukey-Kramer's post hoc test. *P<0.01 versus uninjured arteries.
Figure 26:
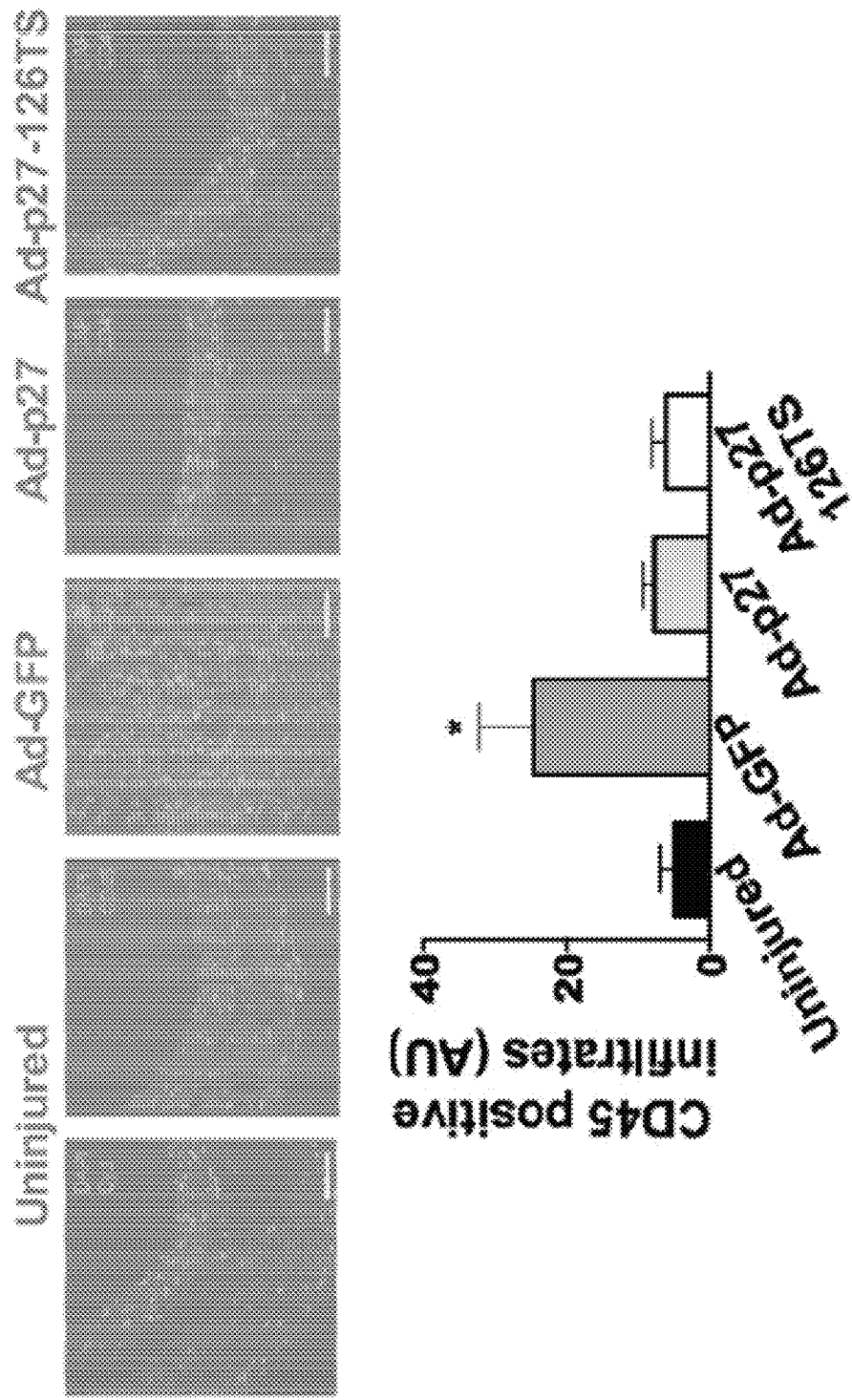
FIG. 26 shows images and corresponding graph demonstrating that treatment with Ad-p27 or Ad-p27-126TS inhibited infiltration of inflammatory cells to the balloon injured vessel. Representative cross-sections of rat carotid arteries immunostained for CD45, 2 weeks after balloon injury. Nuclei were counterstained with DAPI. No positive staining was observed in the negative control sections (Cy3 alone). White scale bars: 100 µm (magnification ×40). CD45 positive cells were quantified by counting the number of CD45 positive cells in the intimal and medial areas from at least 3 sections/group. Data represent the mean±SEM and were compared using 1-way repeated measures ANOVA followed by Tukey-Kramer's post hoc test. *P<0.01 versus uninjured arteries.
Figure 27A:
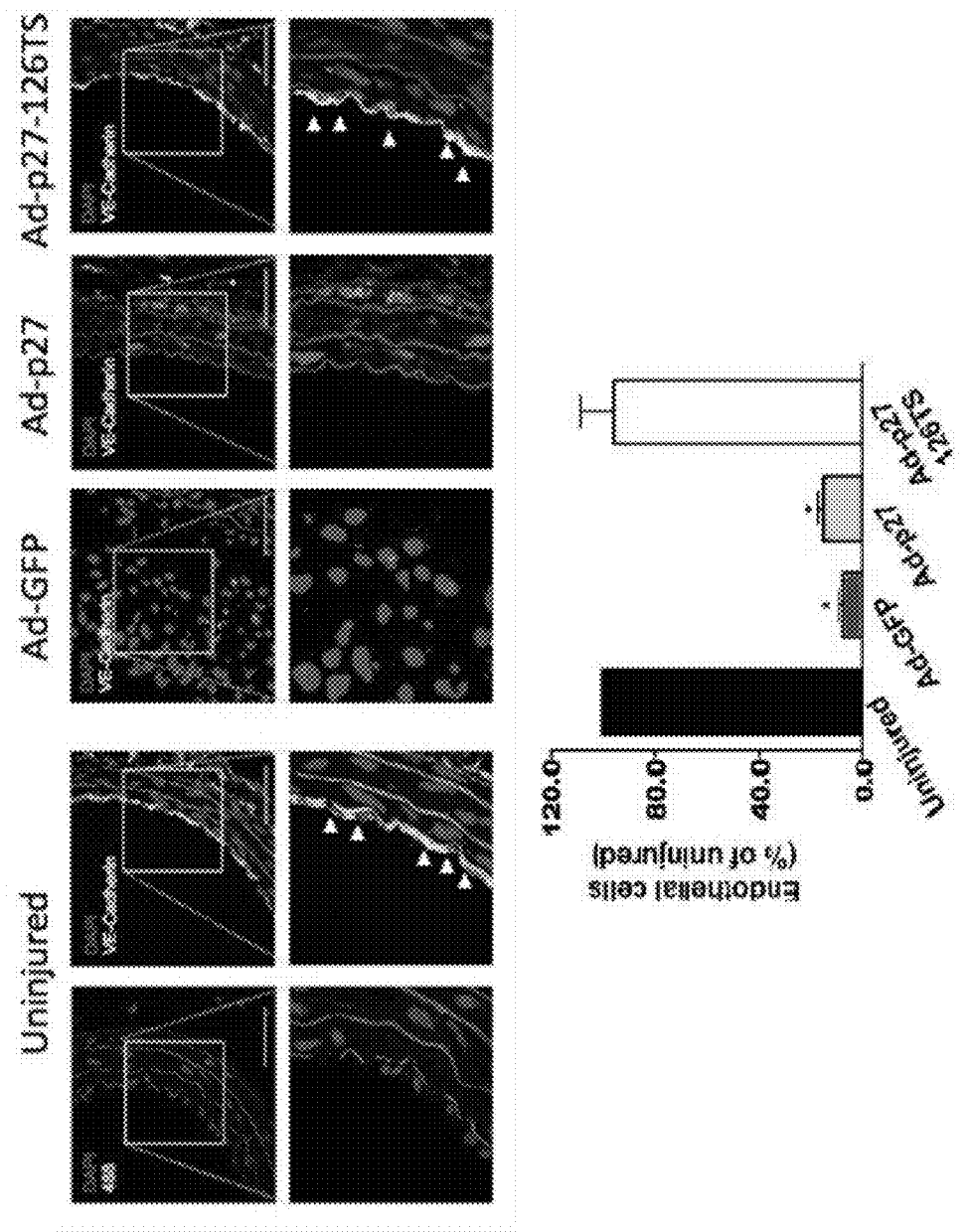
FIGS. 27A-27B show images and graphs demonstrating that treatment with Ad-p27-126TS can allow for rapid and extensive reendothelialization of injured arteries within 2 weeks. Representative confocal images of cross-sections (FIG. 27A) and tridimensional en-face longitudinal arterial preparations (FIG. 27B) of rat carotid arteries immunostained for VE cadherin 2 weeks after injury. Nuclei were counterstained with DAPI. Scale bars: 100 µm; original magnification, ×60 and ×120 (insets). Arrowheads indicate ECs beyond the inner autofluorescent elastic laminae. Endothelial coverage was quantified by counting the number of VEcadherin-positive cells in the circumference of the lumens from at least 6 rats/group. Data represent the mean±SEM and were compared using 1-way repeated measures ANOVA followed by Tukey-Kramer's post hoc test. *P<0.01 versus uninjured arteries.
Figure 27B:
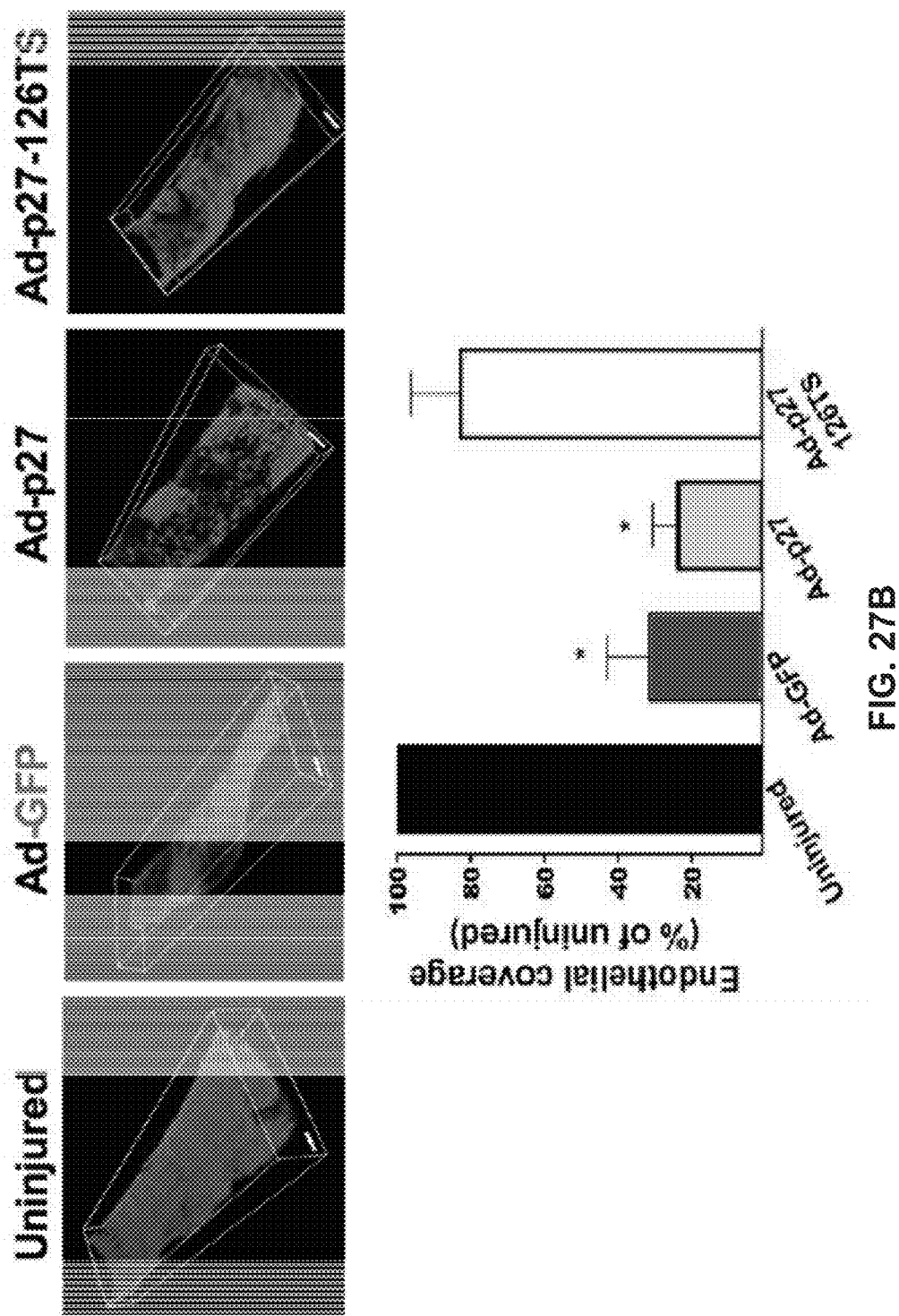
Figure 28:
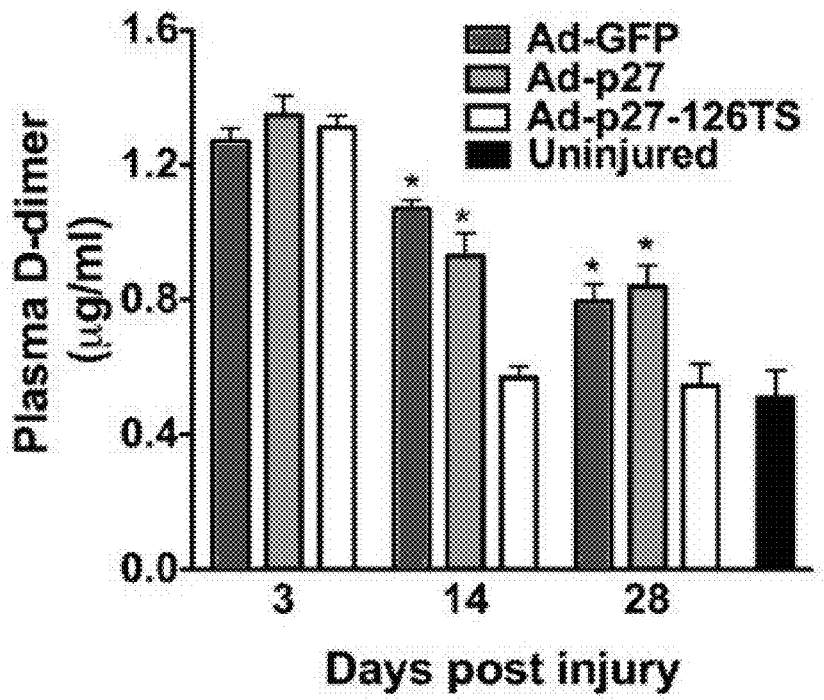
FIG. 28 shows a graph demonstrating that treatment with Ad-p27-126TS can reduce plasma D-Dimer levels of injured arteries. Immunoassay of plasma D-dimer levels before (uninjured) and 3, 14, and 28 days after balloon injury. n=5 rats/group. Data represent the mean±SEM and were compared using 1-way repeated measures ANOVA followed by Tukey-Kramer's post hoc test. *P<0.01 versus uninjured arteries.

As proof of principle, an adenoviral vector (Ad-p27-126TS) containing target sequences complementary to the mature miR-126-3p strand at the 3'-end of the p27 to selectively avoid p27 overexpression in ECs, but not in VSMCs was designed FIG. 22-23. Employing this single comprehensive nanotherapy in a rat carotid balloon injury model we were able to inhibit neointimal hyperplasia, inhibit infiltration of inflammatory cells to the injury site, and at the same time complete reendothelialization of the vessels was achieved as soon as 2 weeks post injury restoring the endothelium-dependent vasodilatory response to levels indistinguishable from uninjured controls and reducing the plasma D-Dimer levels of injured vessels to levels observed in uninjured controls FIG. 25-29.

Incomplete and incompetent endothelial coverage in the vessel when deployed with current DES in PCI procedures greatly increased the risk of potentially catastrophic events such as late ST, primarily caused by the lack of drug specificity. Therefore, a therapy that would selectively inhibit VSMC proliferation, migration and inflammatory cell infiltration without affecting reendothelialization and EC function in the treated vessels would be advantageous. To establish proof of principle for cell-selective inhibition we chose to overexpress p27 in a cells selective manner due to the proven role it plays in the pathophysiology of vascular remodeling. As one of the most potent members of the Cip/Kip family of cyclin-dependent kinase (CDK) inhibitors, p27 binds and modulates cyclin D-, E- and A-dependent kinases, resulting in G1/S transition failure and cell cycle arrest. In healthy arteries, p27 is constitutively expressed in quiescent VSMCs. Upon vascular injury, however, multiple response mechanisms are initiated to conclude with a rapid downregulation of p27, activating and enabling VSMCs to resume cell division. This reentry into the cell cycle triggers intimal hyperplasia, leading to vascular restenosis. p27 knockout mice display a significant increase in VSMC proliferation and develop extensive arterial lesions. In contrast, overexpression of exogenous p27 in VSMCs instigates G1 phase arrest, resulting in VSMC growth inhibition and a significant reduction of neointimal lesion formation in both a porcine femoral arterial injury model as well as a rat carotid model of balloon angioplasty. Moreover, p27 has been shown to play a key role in atherosclerosis. Indeed, p27 deficiency leads to increased atherosclerotic plaque formation in Apoe−/−mice. Lastly, previous reports show that p27 directly regulates the proliferation and migration of bone marrow-derived cells (hematopoietic and non-hematopoietic) to the damaged vessels to reconstitute vascular lesions. Therefore, p27 is a particularly ideal candidate for cell-selective regulation. This approach also takes advantage of the established fact that miR-126 is robustly enriched in EC and is a pivotal regulator of vascular integrity and angiogenesis. Moreover, miR-126 was shown to be up-regulated following arterial injury and in atherosclerotic plaques.

Figure 29:
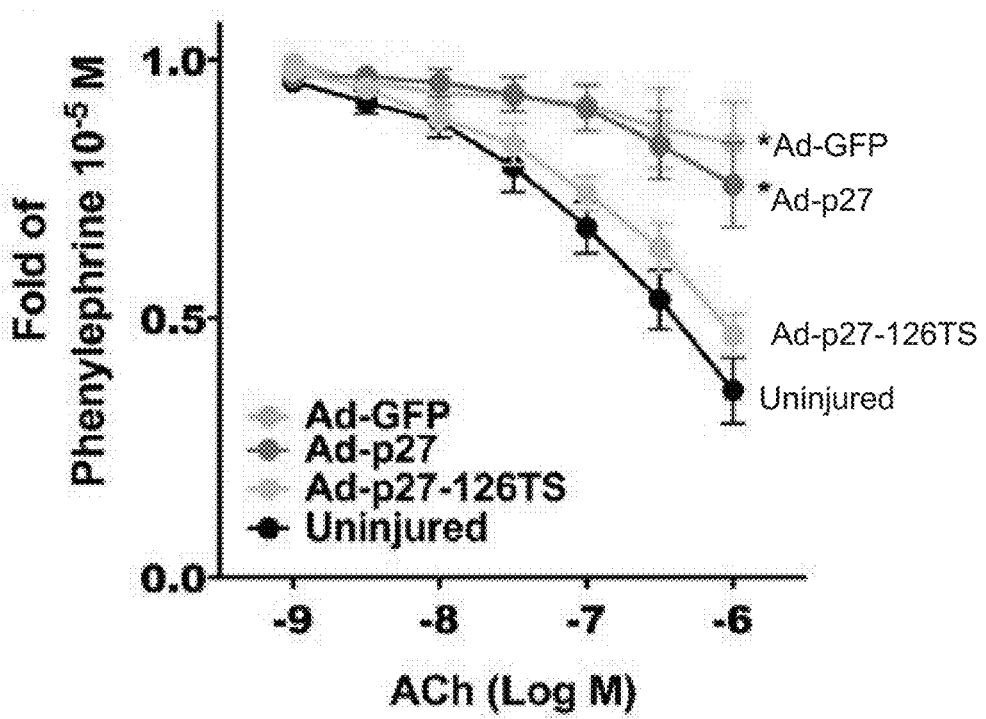
FIG. 29 shows a graph demonstrating that treatment with Ad-p27-126TS can restore the endothelium-dependent vasodilatory response of injured arteries to levels of uninjured controls. Vascular reactivity analysis on carotid rings 2 weeks after balloon injury Ad-p27-126TS treated vessels show vasodilatory in response to acetylcholine (ACh). n=5-6 rats/group. Data represent the mean±SEM and were compared using 2-way repeated measures ANOVA followed by Tukey-Kramer's post hoc test. *P<0.01 versus uninjured arteries.
Figure 31:
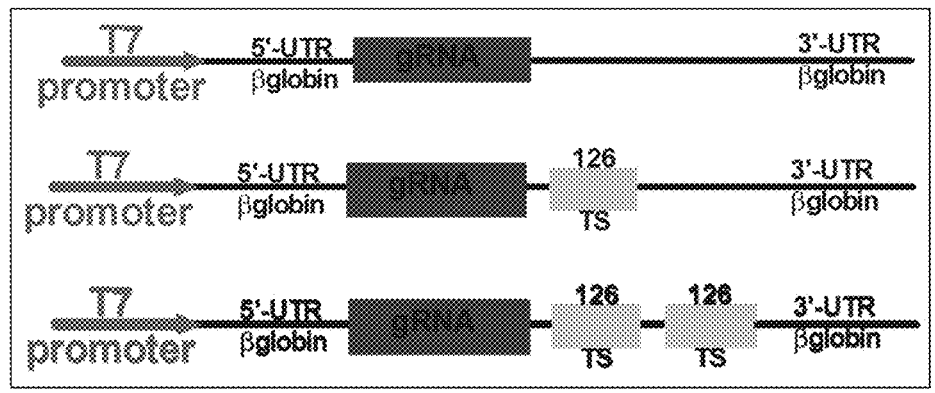
FIG. 31 shows embodiments of a cell-selective gRNA construct.
Figure 32:
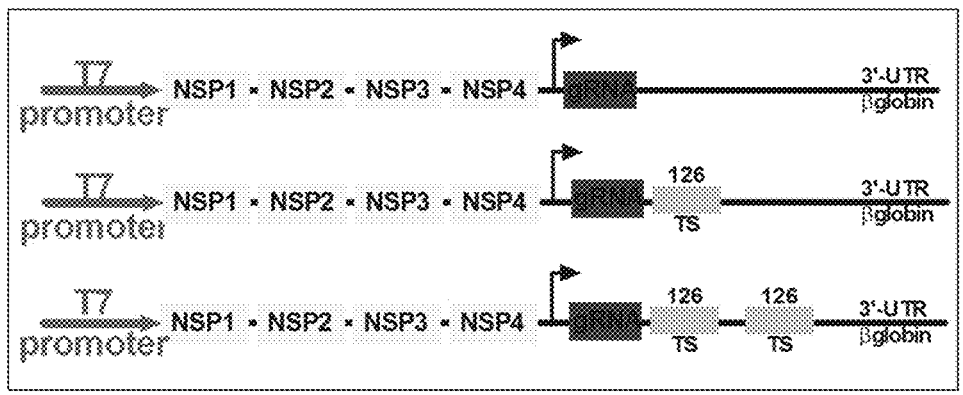
FIG. 32 shows embodiments of a self-replicating, cell-selective gRNA construct.
Figure 33:
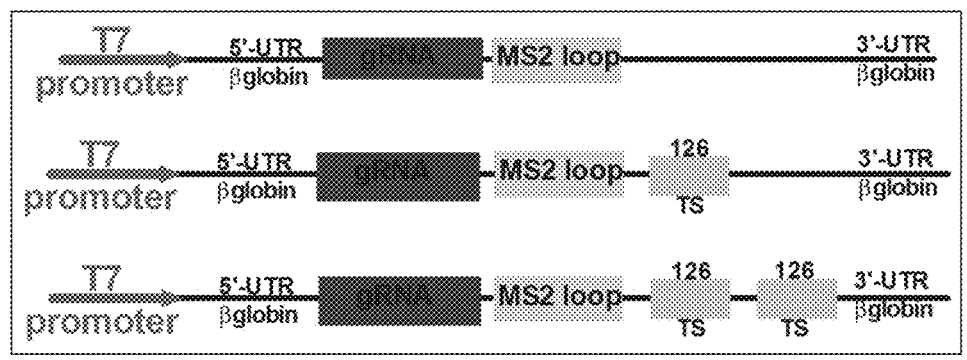
FIG. 33 shows embodiments of a cell-selective gRNA 2.0 construct for CRISPR/Cas9 Synergistic Activation Mediator (SAM) genome editing. *Nature* 517, 583-588 (29 Jan. 2015).
Figure 34:
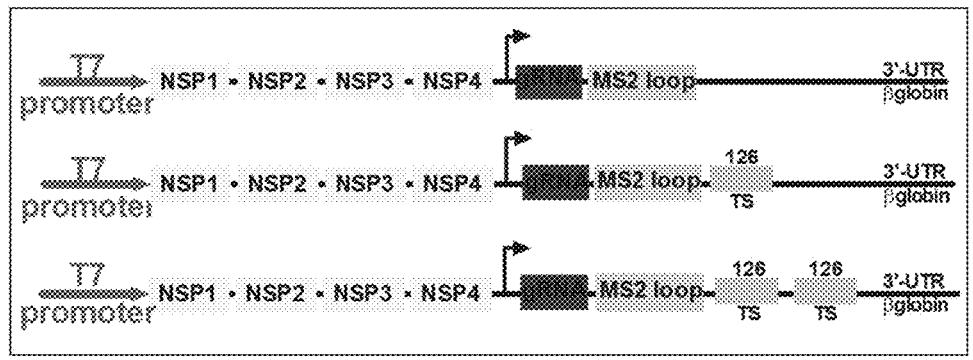
FIG. 34 shows embodiments of a self-replicating, cell-selective gRNA 2.0 construct for CRISPR/Cas9 Synergistic Activation Mediator (SAM) genome editing (*Nature* 517, 583-588 (29 Jan. 2015).
Figure 35:
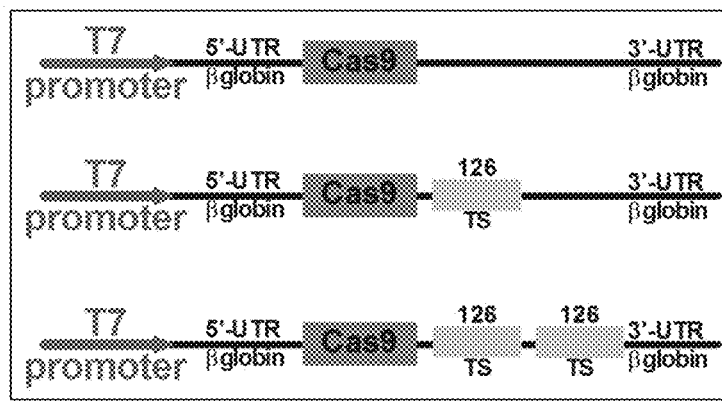
FIG. 35 shows embodiments of a cell-selective Cas9 or dCas9 construct that can be used in CRISPR/Cas9 Synergistic Activation Mediator (SAM) genome editing *Nature* 517, 583-588 (29 Jan. 2015).
Figure 36:
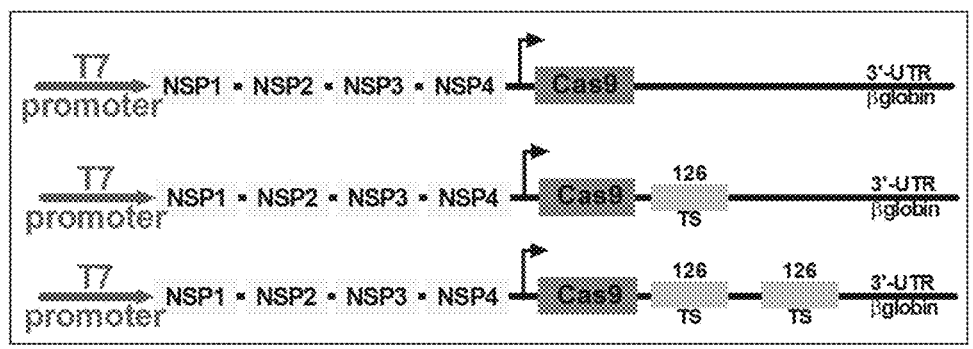
FIG. 36 shows embodiments of a self-replicating, cell-selective Cas9 or dCas9 construct that can be used in CRISPR/Cas9 Synergistic Activation Mediator (SAM) genome editing *Nature* 517, 583-588 (29 Jan. 2015).
Figure 37:
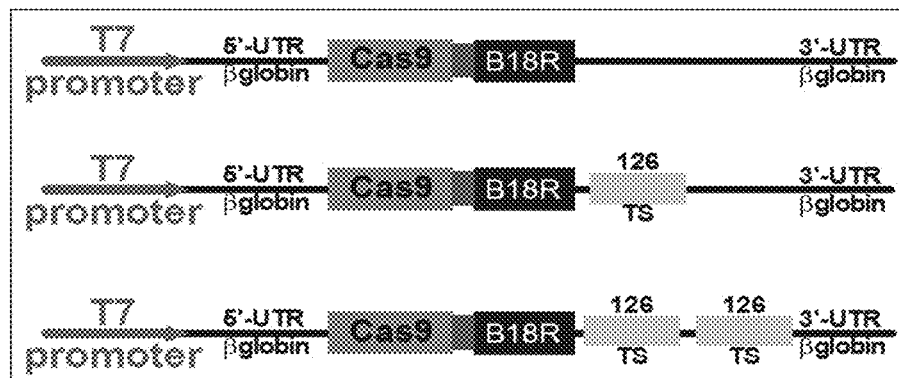
FIG. 37 shows embodiments of a cell selective Cas9 or dCas9 construct that can be used in CRISPR/Cas9 Synergistic Activation Mediator (SAM) genome editing. Embodiments can also include a B18R, separated from the Cas9 or dCas9 by a 2A polypeptide.
Figure 38:
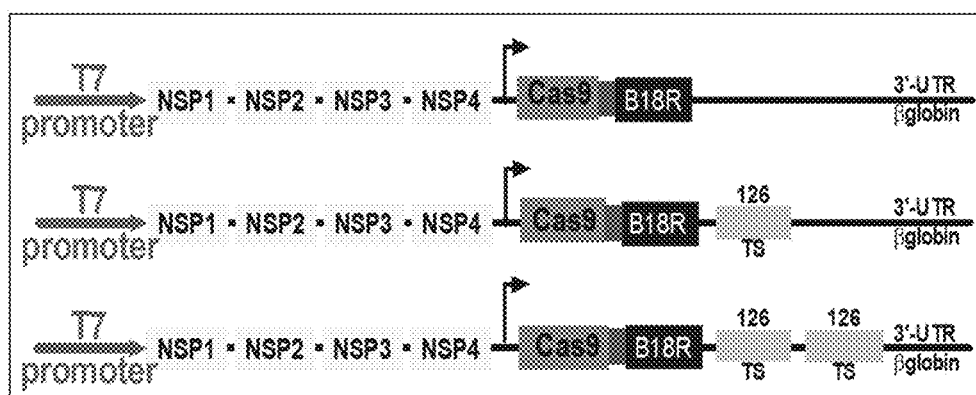
FIG. 38 shows embodiments of a self-replicating, cell-selective Cas9 or dCas9 construct that can be used in CRISPR/Cas9 Synergistic ActivationM (SAM) genome editing. Embodiments can also include a B18R, separated from the Cas9 or dCas9 by a 2A polypeptide.
Figure 39:
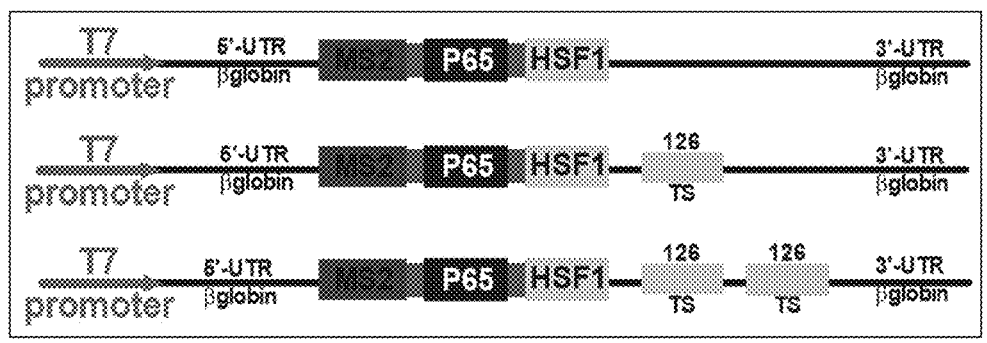
FIG. 39 shows embodiments of a cell-selective construct that can be used in CRISPR/Cas9 Synergistic Activation Mediator (SAM) genome editing. The construct can include a MS2-p65-HSF1 fusion polypeptide.
Figure 40:
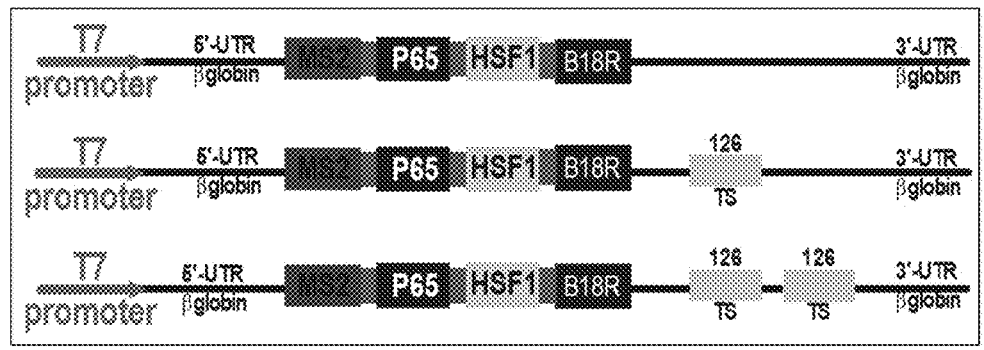
FIG. 40 shows embodiments of a cell-selective construct that can be used in CRISPR/Cas9 Synergistic Activation Mediator (SAM) genome editing. The construct can include a MS2-p65-HSF1 and B18R polypeptide separated by a 2A polypeptide.
Figure 41:
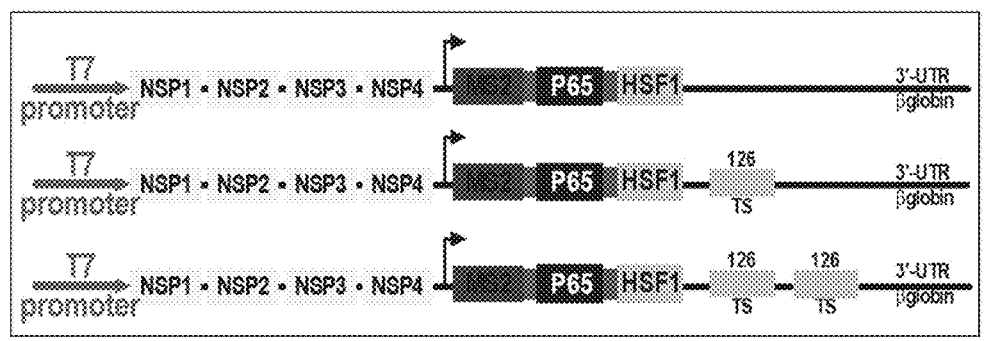
FIG. 41 shows embodiments of a self-replicating, cell-selective construct that can be used in CRISPR/Cas9 Synergistic Activation Mediator (SAM) genome editing. The construct can include a MS2-p65-HSF1 fusion polypeptide.
Figure 42:
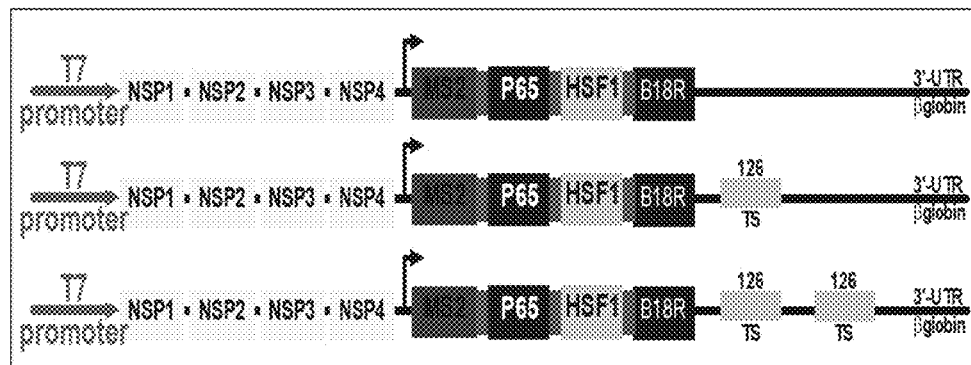
FIG. 42 shows embodiments of a self-replicating, cell-selective construct that can be used in CRISPR/Cas9 Synergistic Activation Mediator (SAM) genome editing. The construct can include a MS2-p65-HSF1 and B18R polypeptide separated by a 2A polypeptide.

An adenoviral (Ad) vector encoding p27 a known cell-cycle inhibitor, and incorporating 4 complementary target sequences for the mature miR-126-3p strand at its 3' end (Ad-p27-126TS) FIGS. 22-23. Our aim was to overexpress exogenous p27, yet effectively regulate its overexpression in a cell-specific manner with the incorporated EC-specific miR-126-3p target sequences FIG. 24. Employing this single comprehensive nanotherapy (Ad-p27-126TS) in a rat carotid balloon injury model the following was achieved: 1) inhibition of neointimal hyperplasia (FIG. 25); 2) inhibition of infiltration of inflammatory cells to the injury site (FIG. 26); 3) reendothelialize vessels rapidly and extensively (FIGS. 27A-B) 4) reduce the plasma D-Dimer levels of injured vessels to levels observed in uninjured controls (FIG. 28); and 5) restore the endothelium-dependent vasodilatory response to levels indistinguishable from uninjured controls (FIG. 29).

These data demonstrate that the simple incorporation of miR-126 target sequences within the Ad-p27-126TS vector provided robust EC protection and at the same time achieved significant inhibition of the neointimal hyperplasia and infiltration of inflammatory cells to the injury site. Although viral delivery systems are very efficient for in vivo transduction and delivery of nucleic acids, they suffer major drawbacks including their possible toxicity, immunogenicity, insertional mutagenicity and oncogenicity. Additionally, viral vectors are difficult and expensive to produce in large quantities. As such the design and engineering of alternative nonviral systems for delivery of therapeutic agents is needed. Presented here are mRNA-based, cell-selective nanotherapies that can self-replicate and can consistently express high levels of exogenous p27 and at the same time retain its cell-selective degradation in a miRNA-controlled fashion, in some cases over multiple cellular divisions.

Figure 4:
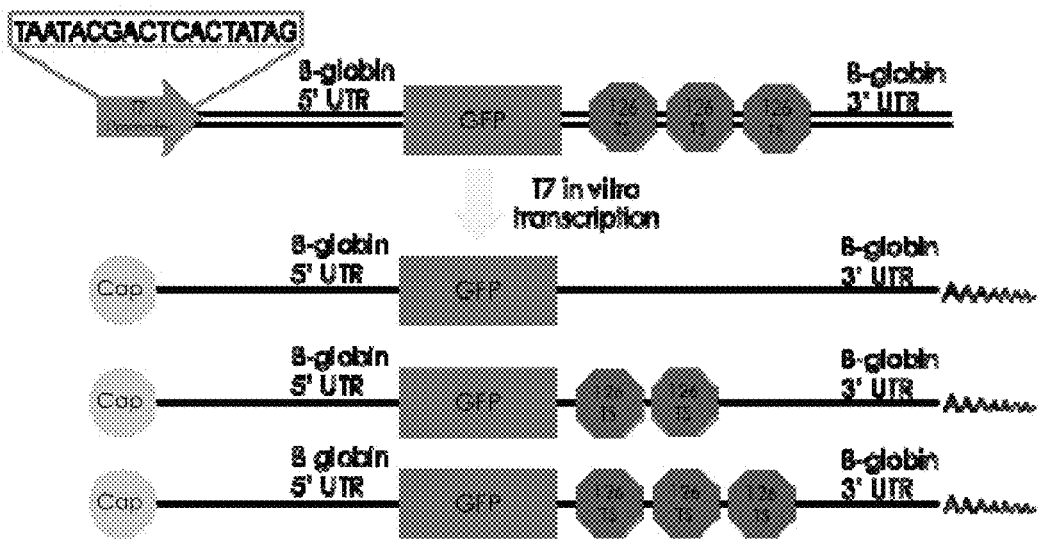
FIG. 4 shows several embodiments of constructs for synthesizing cell-selective mRNA molecules with 0, 2 or 3 microRNA target sites.

To provide proof of concept and to show the feasibility of our cell-selective mRNA approach we constructed the following GFP-encoding plasmids: A) GFP coding sequence placed under the control of the bacteriophage T7 RNA polymerase promoter. To increase the stability of the mRNA we flanked GFP coding sequence with β-globin 5'- and 3'-UTR (FIG. 4); B) GFP-2×126TS, a GFP-coding sequence placed under the control of the bacteriophage T7 RNA polymerase promoter, flanked with β-globin 5'- and 3'-UTR containing 2 or 3 tandem copies of a 22-bp target sequence perfectly complementary to the mature miR-126-3p strand at its 3' end (FIG. 4).

In vitro transcription reaction from the linear plasmid templates described in FIG. 4 was performed using T7 RNA polymerase to produce unmodified (regular nucleotides, NTPs) or modified RNA in which we substituted 100% of the uridine with pseudouridine. After removal of free NTPs, 5' capping and poly(A) tail addition was performed resulting in a high-yield RNA transcript. HEK cells were transfected with miR-126, miR-143 or control mimic and after 24 hr cells were transfected with either unmodified or modified GFP, GFP-2×126TS or GFP-3×126TS mRNAs. The effect of over-expression miR-126, miR-143 or control on GFP protein levels was assessed after 24 hr (FIGS. 6-14). First, a significant increase in GFP expression was observed when uridine was 100% substituted with pseudouridine (FIGS. 7 and 13. In cells transfected with the control unmodified or modified GFP mRNA neither over-expression of miR-126-3p or miR-143 had an effect on GFP expression (FIGS. 6-10 and 13-14). HEK cells transfected with GFP-2×miR-126TS or GFP-3×126TS mRNA, over-expression of miR-126 dramatically inhibited GFP expression of the unmodified or the modified mRNA (FIGS. 6-8 and 11-14). These data demonstrate that pseudouridine modified GFP-2×126TS mRNA is susceptible to argonaute-dependent gene silencing by miR-126. This effect was miR-126 specific since over-expression of miR-143 had no effect on GFP expression in cells transfected with either unmodified or modified GFP-2×miR-126TS or GFP-3×126TS (FIGS. 6-8 and 11-14). The data show that pseudouridine modified mRNA is susceptible to the endogenous miRNA machinery. Adding target sites in the 3'UTR of chemically modified mRNA can affect its expression only when this specific miRNA is expressed.

Example 2

A Flag tagged p27 encoding plasmids can be engineered to facilitate in vitro transcription of p27 encoding mRNA (FIG. 17): A) Flag-tagged p27); B) Flag-tagged p27 followed by two 2 fully complementary target sequences for the mature miR-126-3p strand at its 3'-UTR (p27-2×126TS). A Flag-tag can be incorporated to distinguish between endogenous and exogenous p27 expression.

Figure 17:
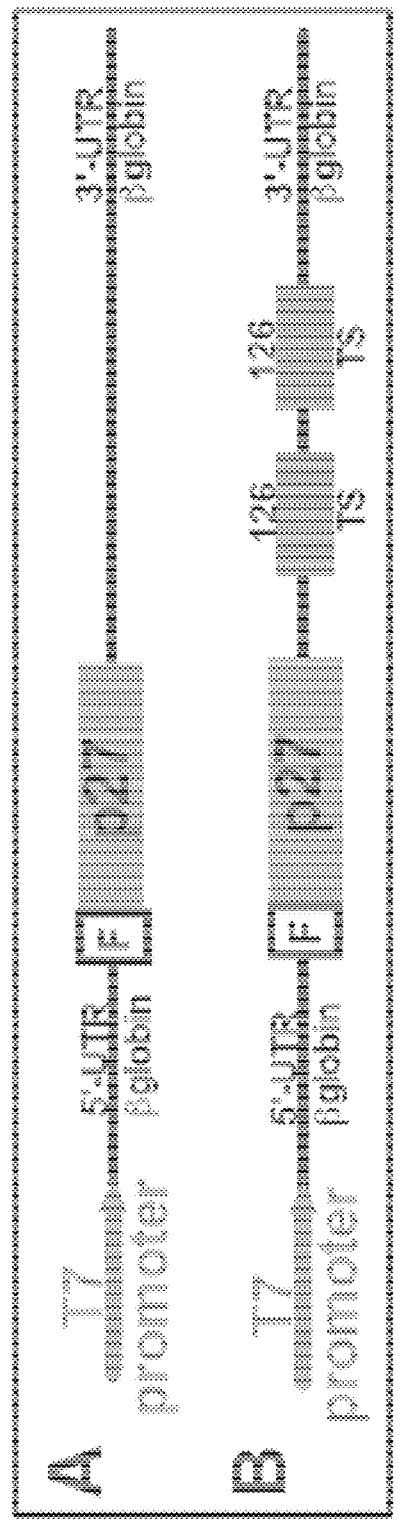
FIG. 17 shows schematics of (A) p27 coding sequence flanked with the 5'- and 3'-UTR of β-globin and placed under the control of the bacteriophage T7 RNA polymerase promoter (p27) and (B) p27 coding sequence flanked with the 5'- and 3'-UTR of β-globin and placed under the control of T7 RNA polymerase promoter, containing 2 fully complementary target sequences for the mature miR-126-3p strand at its 3'-UTR (p27-2×126TS). F, Flag-tag.

To reduce innate immune responses and toxicity and at the same time maximize the efficiency and duration of expression of the mRNA encoding p27 described in FIG. 17, the following modified nucleotide substitutions or combinations thereof can be used: 1) Pseudouridine; 2) N-1-methylpseudouridine; 3) 5-methoxy-U; 4) 5-hydroxymethyl-C; 5) 5-methyl-C and 6) combination of Pseudouridine and 5-methyl-C. mRNAs can be in vitro transcribed using T7 RNA polymerase followed by 5' capping and poly(A) tail addition using a Vaccinia Capping Enzyme and E. coli Poly(A)Polymerase (New England BioLabs Inc.), respectively.

Example 3

Example 1 demonstrates that substitution of uridine with pseudouridine and addition of miR-126 target sequences at the 3'-UTR of GFP mRNA increased the translational efficiently in a cell-selective manner. However, to increase its therapeutic potential, it is desirable that sustained cell selective inhibition matches the potency and the durability of the drugs eluted from the DES. To develop a long-lasting cell-selective mRNA-based therapy, we focused our efforts on an approach that (1) utilizes a single RNA species capable of self-replicating for a limited number of cell divisions; (2) is capable of encoding our gene of interest; (3) consistently expresses the protein at high threshold levels over multiple cellular divisions; and/or (4) can be susceptible to endogenous miRNA degradation in a cell-selective fashion. In this Example, an approach utilizing a noninfectious, self-replicating Venezuelan equine encephalitis (VEE) virus (lacks the genes encoding the viral structural proteins) and mimics cellular mRNA with a 5'-cap and poly(A) tail and does not utilize a DNA intermediate is described. This approach lacks the potential for genomic integration. VEE virus is a positive-stranded RNA that encodes four nonstructural replication complex proteins (NSPs) as a single open reading frame (ORF).

Design of self-replicating, cell-selective mRNA vectors: To ectopically express p27 in a cell-selective manner, a p27-coding sequence can be placed at the 5' end of VEE-structural protein genes. The following VEE10 GFP or Flag tagged p27 encoding plasmids will be engineered: A) VEE-p27, 3'-ORF replaced with flag-tag p27 coding sequence followed by β-globin 3'-UTR (FIG. 19); (B) VEE-p27-2× 126TS, 3'-ORF replaced with flag-tag p27-coding sequence followed by two tandem copies of a 22-bp target sequence perfectly complementary to the mature miR-126-3p at its 3' end (FIG. 19). A Flag-tag can be included to distinguish between endogenous and exogenous p27 expression. More than two miR-126 targets can be incorporated (FIG. 18).

Figure 18:
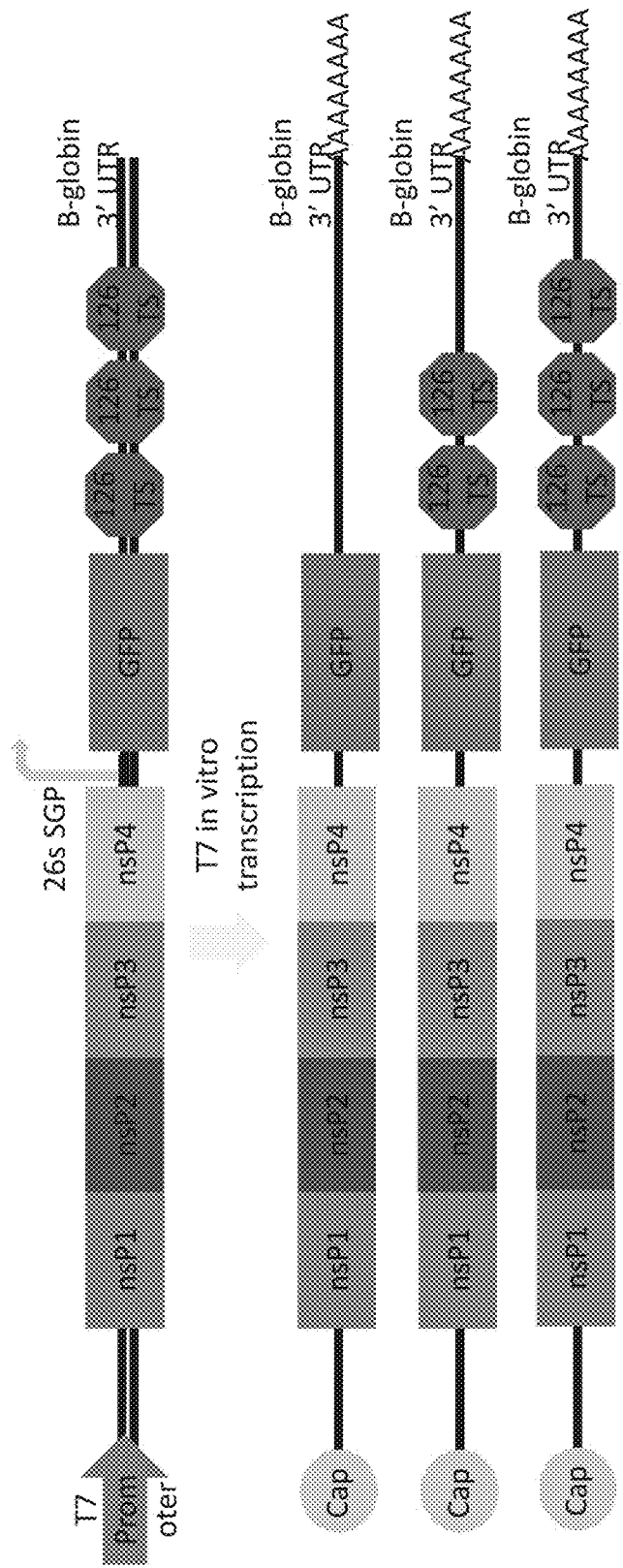
FIG. 18 shows schematics of embodiments of self-replicating VEE based cell-selective mRNA constructs.
Figure 19:
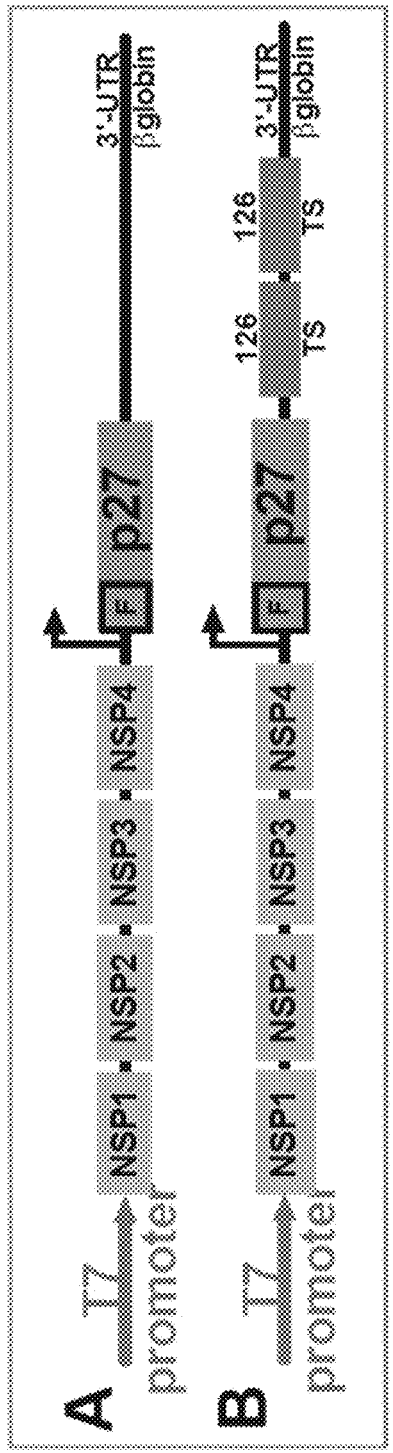
FIG. 19 shows embodiments of a self-replicating mRNA based, cell-selective construct for in vitro transcription. (A) Shows a schematic illustration of a self-replicating RNA derived from an alphavirus contains a 5' T7 RNA polymerase, nonstructural genes (NSP1-4), 26S subgenomic promoter (black arrow), p27 coding sequence followed by β-globin 3'-UTR (VEE-p27); (B) same as in A, p27 coding sequence with 2 fully complementary target sequences for the mature miR-126-3p strand at its 3'-UTR (p27-2×126TS). F, Flag-tag.

Self-replicating mRNA depicted in FIGS. 18-19 can be in vitro transcribed using T7 RNA polymerase in the presence of the unmodified and modified nucleotides (Pseudouridine, N-1-methylpseudouridine, 5-methoxy-U, 5-hydroxymethyl-C, 5-methyl-C or combination of Pseudouridine and 5-methyl-C). mRNAs can be in vitro transcribed using T7 RNA polymerase followed by 5' capping and poly(A) tailing.

Figure 20:
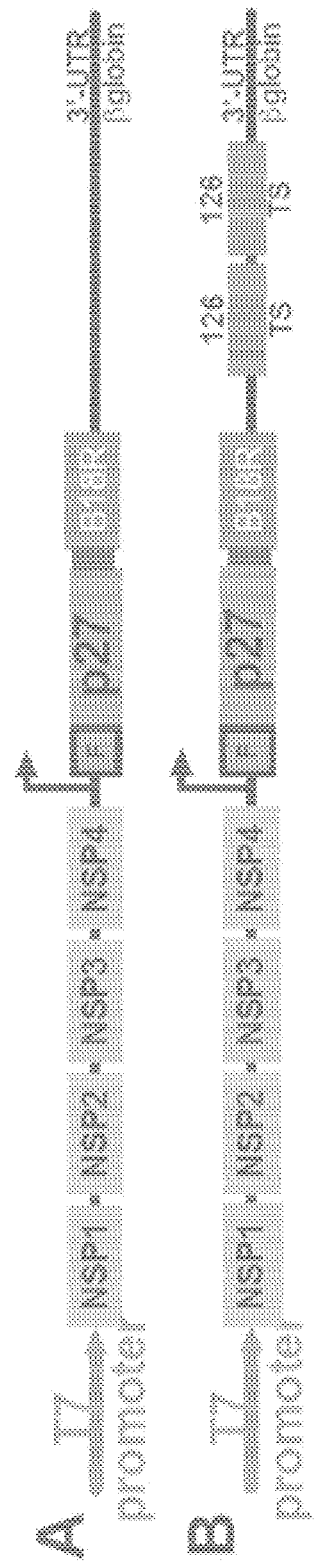
FIG. 20 shows embodiments of a VEE polyprotein constructs. (A) and (B) show constructs that contain a 5' T7 RNA polymerase, nonstructural genes (NSP1-4), 26S subgenomic promoter (black arrow), p27 and B18R polyprotein separated by 2A peptide (in green); 26S subgenomic promoter (black arrow) without (A) or with 2 fully complementary target sequences for the mature miR-126-3p strand at its 3'-UTR (p27-2×126TS) (B).
Figure 21:
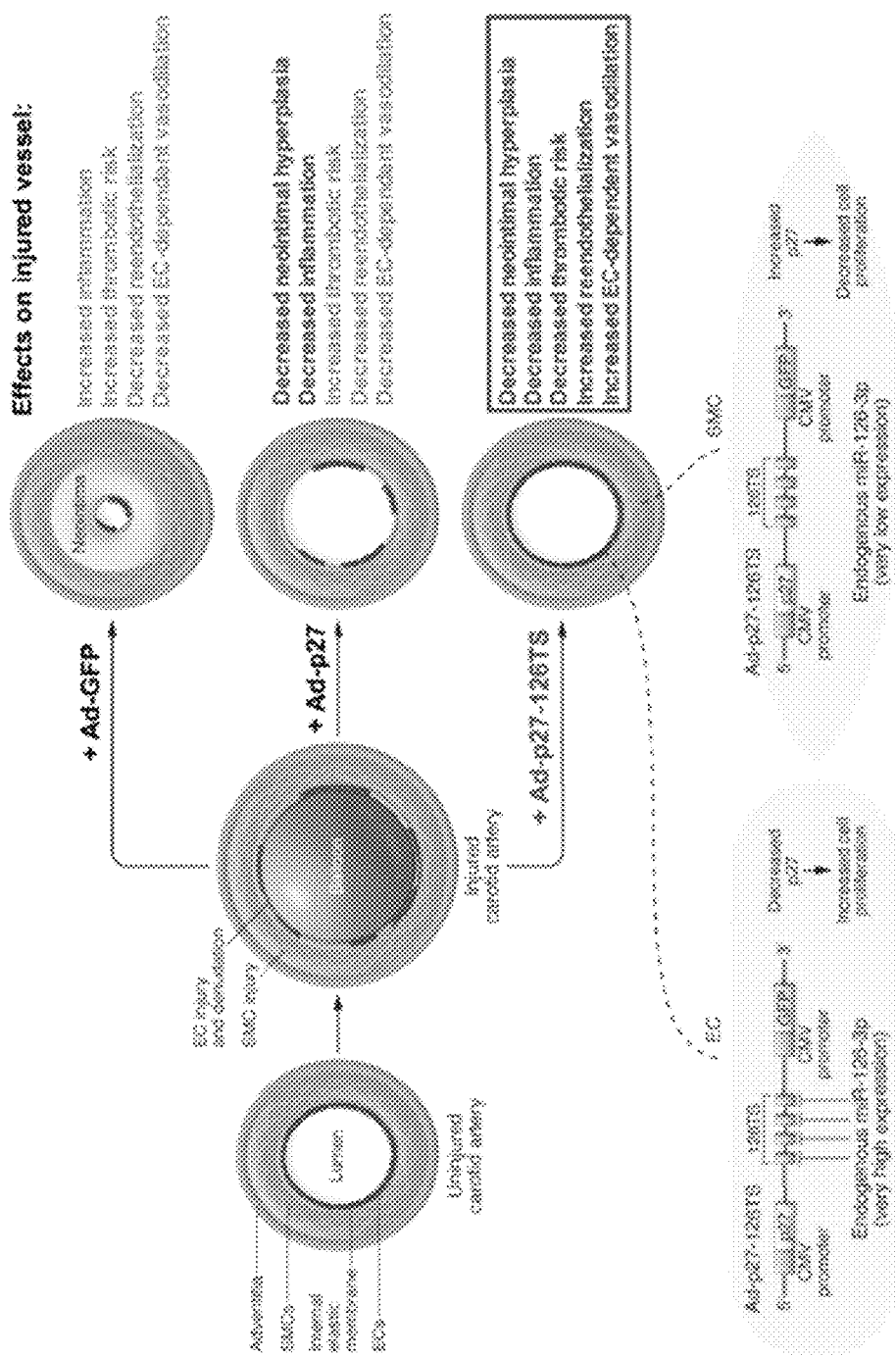
FIG. 21 shows an adenoviral based cell-selective construct for overexpression of exogenous p27 in VSMCs to reduce neointimal hyperplasia while sparing ECs to improve reedothelialization. This figure is a modification from J Clin Invest. 2014 September; 124(9):3694-7. PMID: 25133421, PMCID: PMC4151224.

The self-replicating mRNA can also be designed to include RNA encoding the B18R protein. This can reduce immunogenic reactions (FIG. 20).

The self-replicating mRNA can also incorporate RNA encoding a marker protein such as GFP. FIG. 18.

Example 4

Cell-selective alternatives to the current DES used in percutaneous interventions are needed to inhibit restenosis while promoting reendothelialization. The advantage of such a treatment is the local non-invasive administration of drug in conjunction with balloon angioplasty limiting systemic toxicity. In this Example, an approach using FDA approved polymers to encapsulate the cell-selective mRNA or cell-selective self-replicating mRNA transcripts to facilitate efficient gene delivery in vivo is presented. The cell-selective RNA molecules can be encapsulated with a polymer to form RNA polymer nanoparticles. The RNA polymer nanoparticles can be attached to the stent or other medical device using a suitable method such as surface by dip- or by spray-coating. The following FDA approved polymers can be used:

Phosphorylcholine-based polymers, Poly lactic-co-glycolic acid (PLGA), chitosan, cationic nanoemulsion, cationic electrodeposition coating or lipid nanoparticles.

Example 5

Manipulation of gene expression via the RNAi system is a powerful new tool for the treatment of many diseases, including Hepatitis C and heart failure. The current trend in miRNA therapies focuses on the use of antagomirs, short RNA fragments that block the activity of a specific miRNA. RNAs with numerous target sites for miRNAs, referred to as miRNA sponges, are also able to effectively restore the repressed targeted mRNAs by sequestering the endogenous miRNA. Cell-specific miRNAs can be used to confer cell-protectivity to a gene therapy by incorporating miRNA target sites into the 3' UTR. This strategy prevents expression of the inserted gene in a specific cell type based on the miRNA target sequences.

Figure 15:
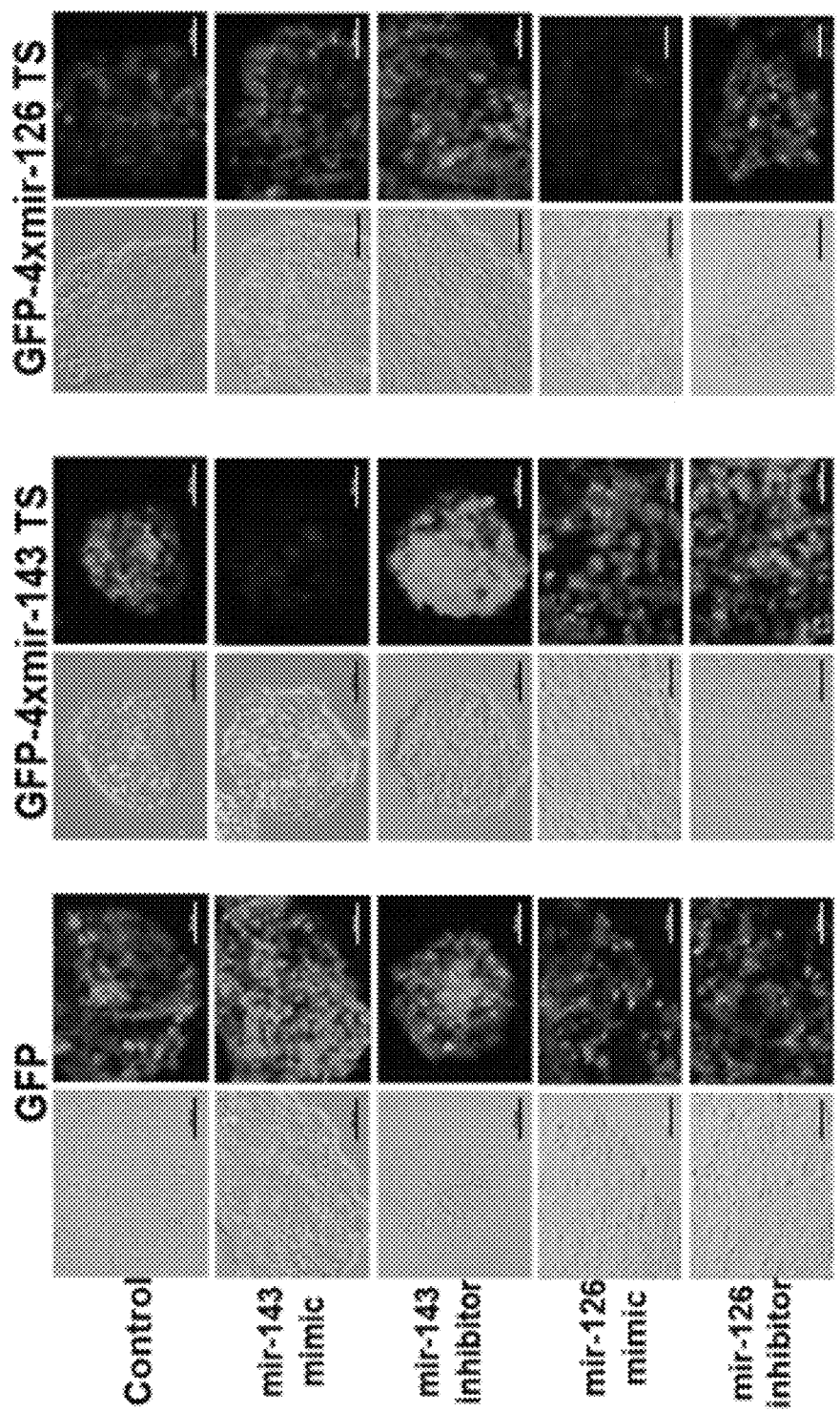
FIG. 15 shows images of HEK cells infected with lentivirus vectors encoding GFP, GFP-4×miR-143TS or GFP-4×miR-126TS ($10^9$ transducing units TU/ml). After 24 h incubation, cells were transfected with 200 nM of the indicated miR-mimic, inhibitor or control and fluorescent images were taken after 72 hrs.

To demonstrate that miRNA can be used to specifically regulate gene of interest a GFP-expressing lentiviral vector was used in which four target sequences for miR-126 were inserted, a vascular endothelial cell (VEC)-specific miRNA, in the GFP 3'UTR (GFP-4×miR-126TS). To control for miRNA specificity, four target sequences for miR-143 (GFP-4×miR-143TS) were inserted, which is vascular smooth muscle cell (VSMC)-specific, or four scramble sequences (GFP) in the GFP-3'UTR region HEK cells were transduced with the different GFP expressing lentiviruses, and the effect of over-expression or inhibition of miR-143, miR-126 or control on GFP expression was assessed. In cells transduced with the control GFP virus, neither over-expression nor inhibition of miR-143 or miR-126 had an effect on GFP expression (FIG. 15, left). However, in HEK cells transduced with GFP-4×miR-143TS virus, only over-expression of miR-143 dramatically inhibited GFP expression (FIG. 15, middle). Similarly, over-expression of miR-143 had no effect on GFP expression in cells transduced with GFP-4×miR-126TS, while over-expression of miR-126 did inhibit GFP expression in these cells (FIG. 15, right).

Figure 16:
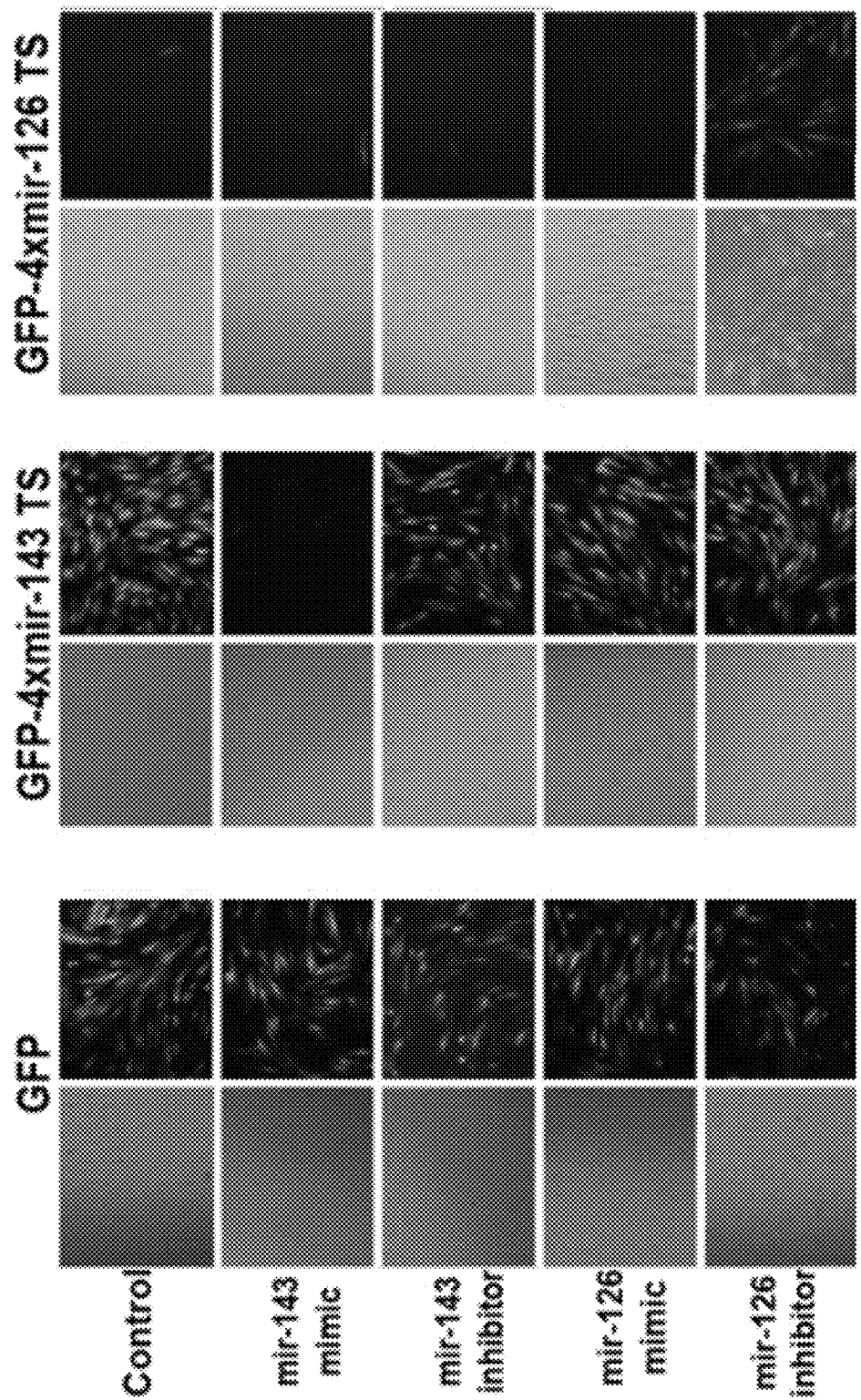
FIG. 16 shows images of VECs infected with lentivirus vectors encoding GFP, GFP-4×miR-143TS or GFP-4×miR-126TS ($10^9$ transducing units TU/ml). After 24 h incubation, cells were transfected with 200 nM of the indicated miR-mimic, inhibitor or control and photographed after 72 hours.

This strategy was used in VEC to ensure that the endogenous miR-126 targets the viral constructs as expected. VEC were transduced with the same lentiviruses. In control GFP virus transduced cells, neither over-expression nor inhibition of miR-143 or miR-126 had an effect on GFP expression (FIG. 16, left). Similarly, over-expression of miR-143 inhibited GFP expression only in GFP-4×miR-143TS transduced cells, while over-expression of miR-126 had no effect (FIG. 16, middle). Interestingly, because miR-126 is highly expressed in VEC, it abolished the expression of GFP in the GFP-4×mir-126TS infected cells. Only inhibition of the endogenous miR-126 with a miR-126 antagomir rescued the expression of GFP (FIG. 16, right).

These results demonstrate the sensitivity and specificity of endogenous miRNA for target sites in the 3' UTR of unmodified mRNAs. Predictable patterns of expression can be observed when using cell-specific miRNA target to regulate expression of the inserted gene.

Example 6

Modified nucleotides can increase the translational efficiency and reduce cellular toxicity caused by the immunogenic response to exogenous mRNA. Here, 4 different representative modified nucleotide compositions (FIG. 30) can be included in the cell-selective mRNA. Each of the modified nucleotides can be used as a complete substitute for the unmodified nucleotides to achieve the maximum effect. Modified and unmodified mRNA can be synthesized with a 5' cap using an ARCA cap analog (TriLink) and PolyA tail using reagents to increase the stability of the mRNAs (TriLink).

Figure 5:
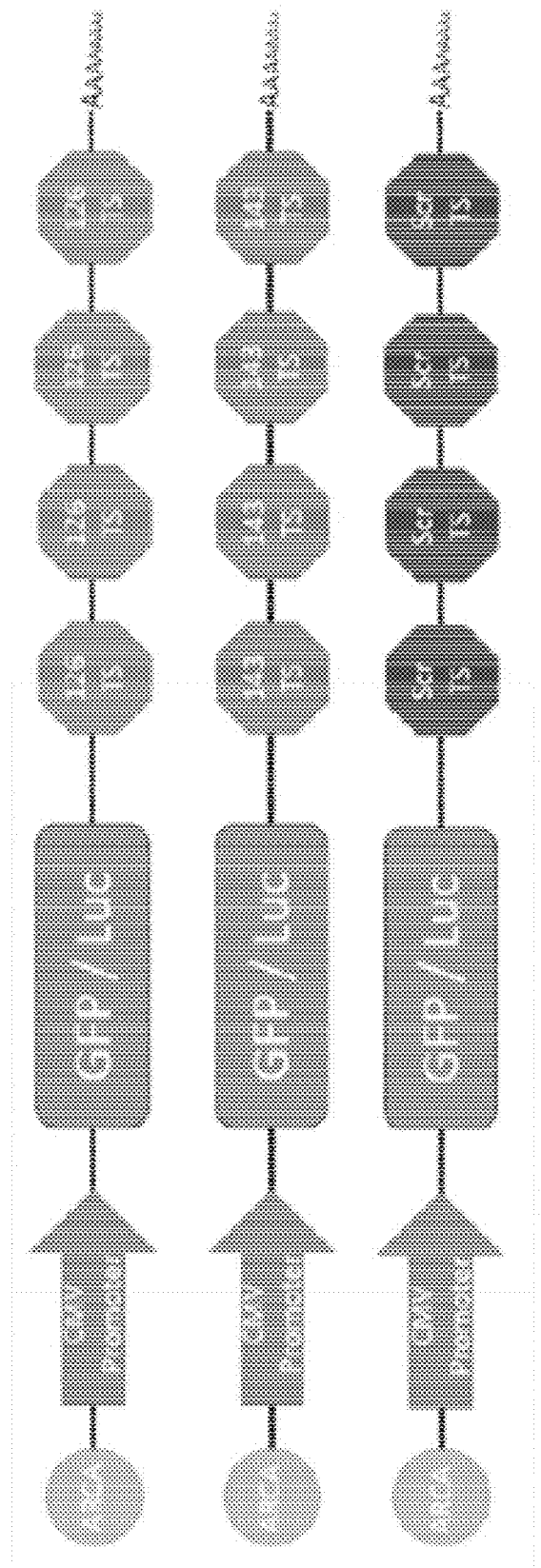
FIG. 5 shows embodiments of in vitro transcription of GFP, Luc or any gene of interest mRNA constructs. All mRNA constructs can be placed under the CMV promoter, capped and polyadenylated. The 3' UTR of each construct can have 4 target sites for miR-126, miR-143 or a scrambled control. The constructs can be used for in vitro transcription of mRNAs that incorporate the selected modified nucleotides.
Figure 6:
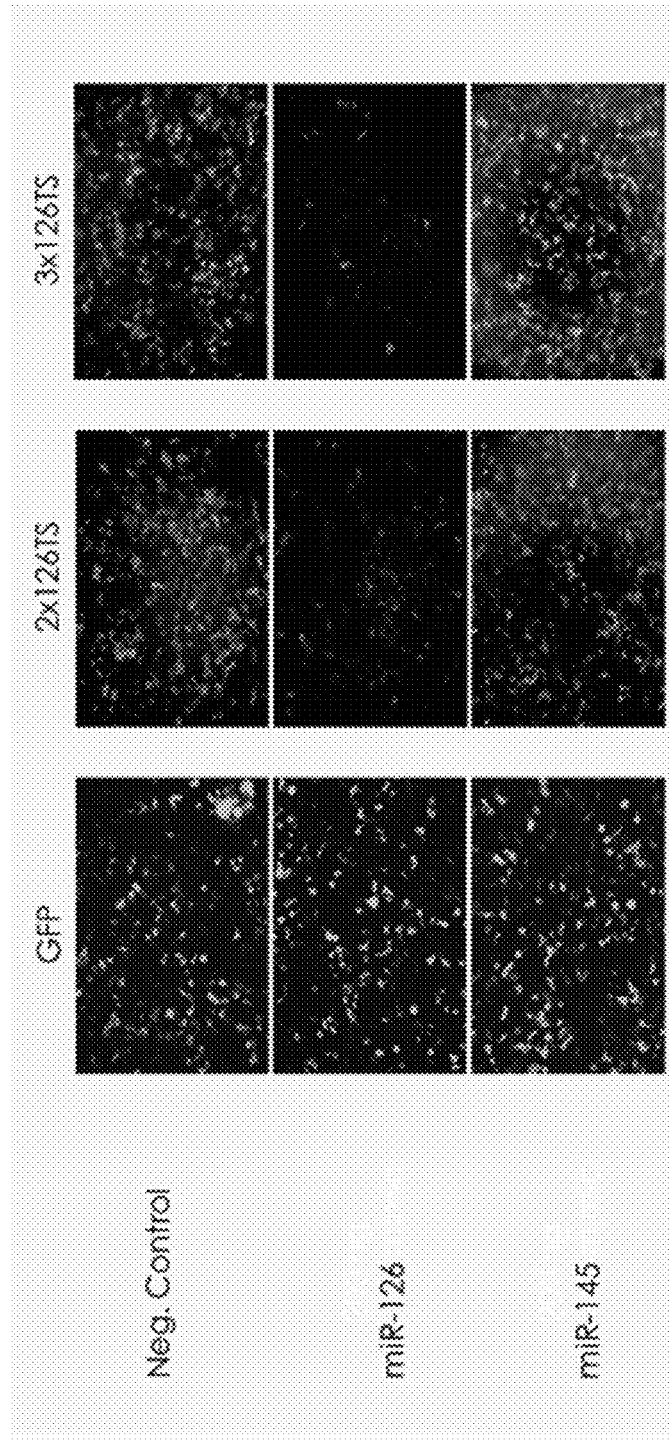
FIG. 6 shows images demonstrating the effect of the number of miR-126 target sites of unmodified mRNA molecule on GFP silencing in HEK cells transfected with miR-126 mimics but not in HEK cells transfected with miR-145 or control mimic.
Figure 7:
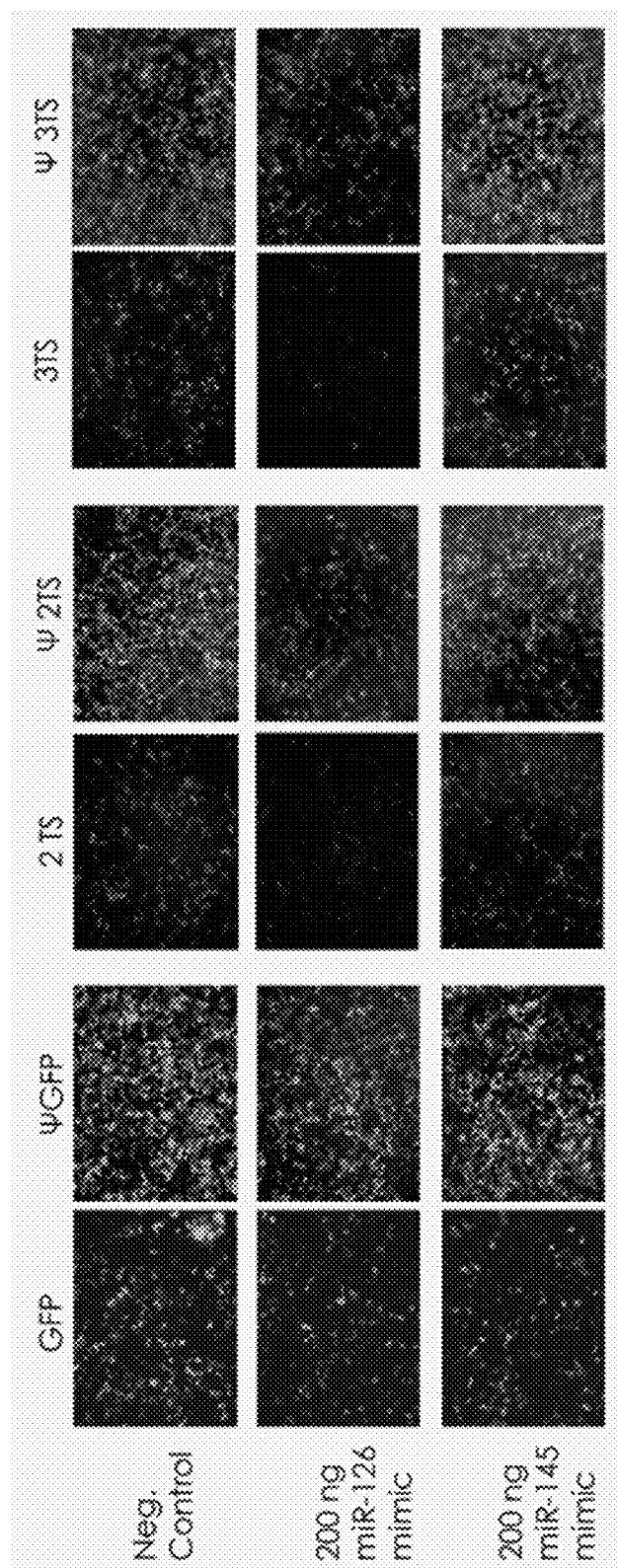
FIG. 7 shows images demonstrating GFP silencing by miR-126 mimics in HEK cells transfected with unmodified or pseudouridine modified mRNA molecule that includes 2 or 3 miR-126 target sites.
Figure 8:
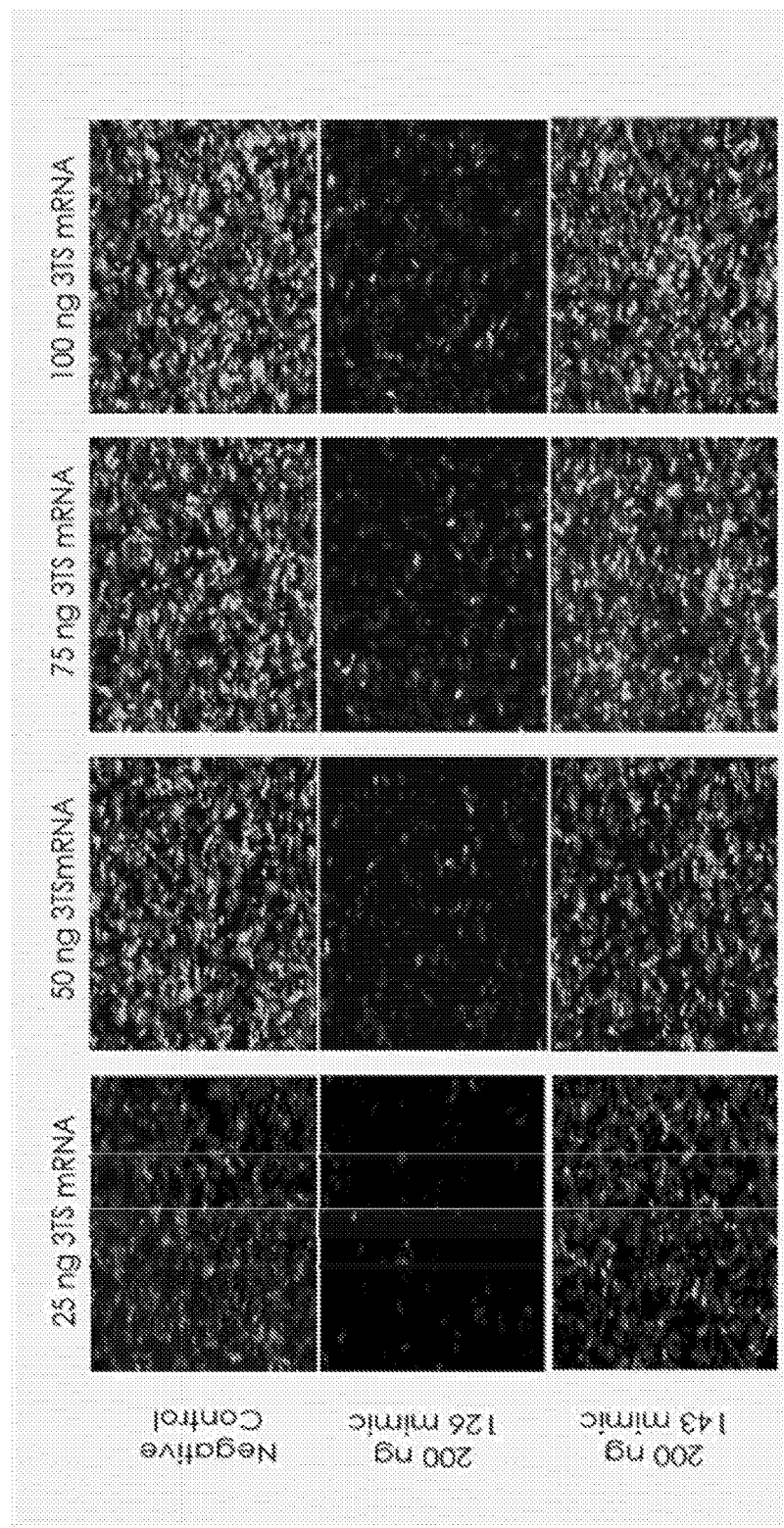
FIG. 8 demonstrates the dose dependency of GFP mRNA silencing of pseudouridine modified cell-selective mRNA by miR-126 mimics but not by miR-143 mimics.
Figure 9:
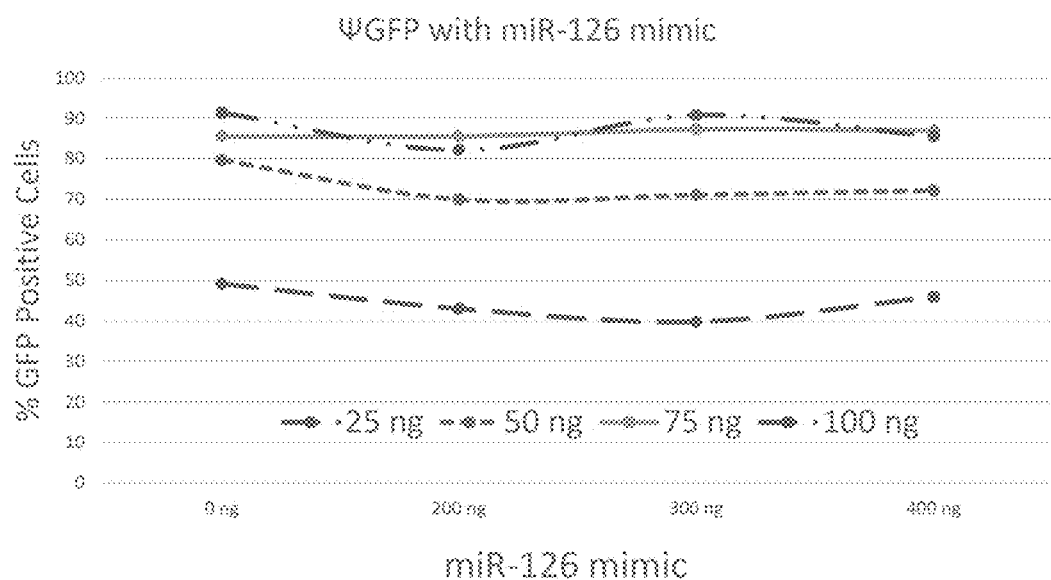
FIG. 9 shows a graph demonstrating flow cytometry analysis of pseudouridune modified GFP expressing mRNA construct with no miR-126 target sites exposed to a miR-126 mimic at varying amounts.
Figure 10:
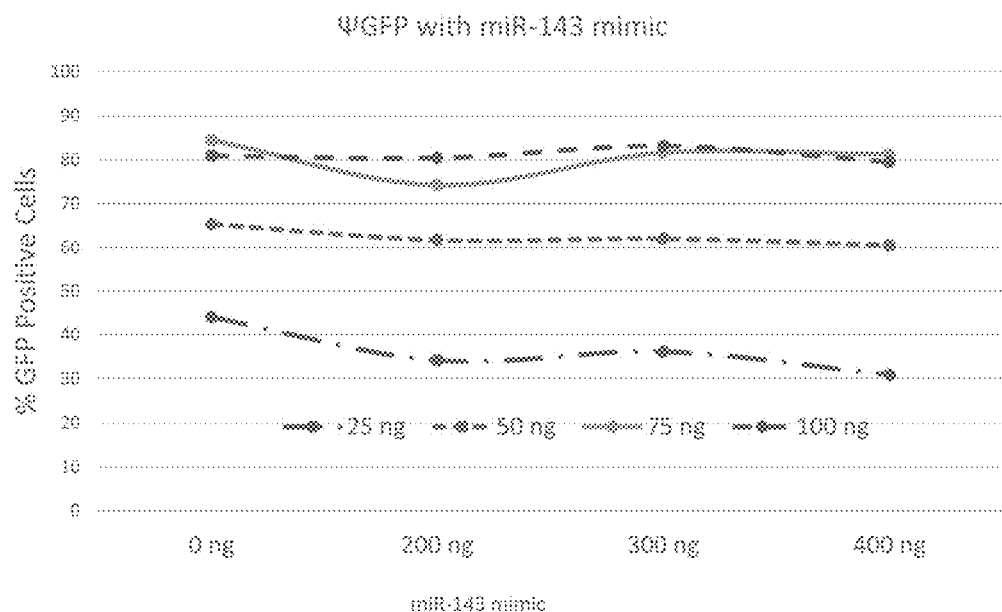
FIG. 10 shows a graph demonstrating flow cytometry analysis of pseudouridine modified GFP expressing mRNA construct with no miR-126 target sites exposed to a miR-143 mimic at varying amounts.
Figure 11:
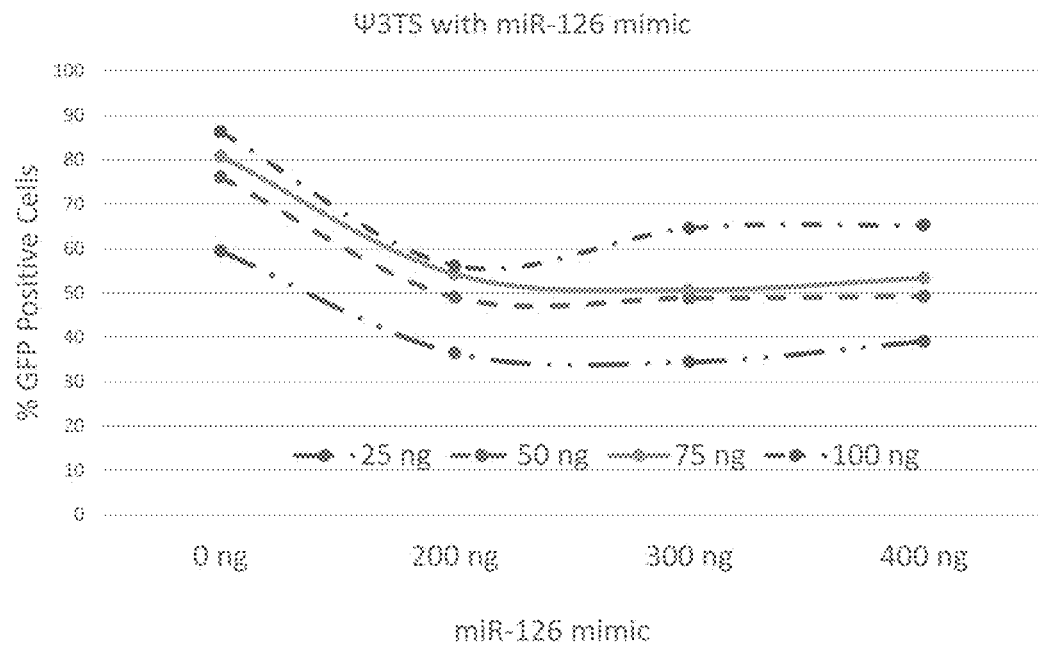
FIG. 11 shows a graph demonstrating flow cytometry analysis of pseudouridine modified GFP expressing mRNA containing 3 miR-126 target sites at its 3'UTR silencing when exposed to miR-126 mimic at varying amounts.
Figure 12:
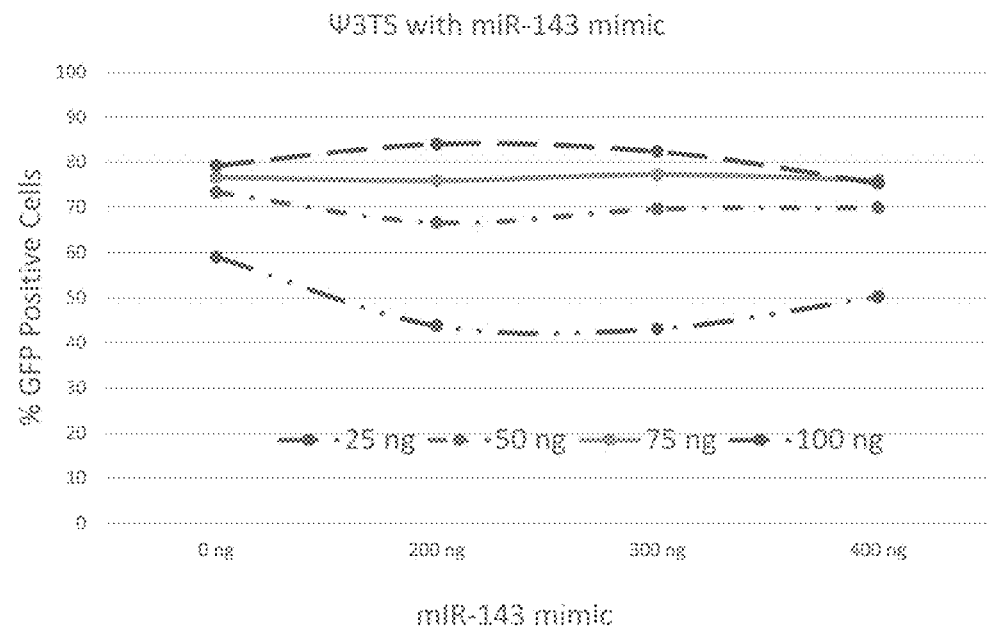
FIG. 12 shows a graph demonstrating flow cytometry analysis of pseudouridune modified GFP expressing mRNA construct containing 3 miR-126 target sites at its 3'UTR exposed to miR-143 mimic at varying amounts.
Figures 13, 14:
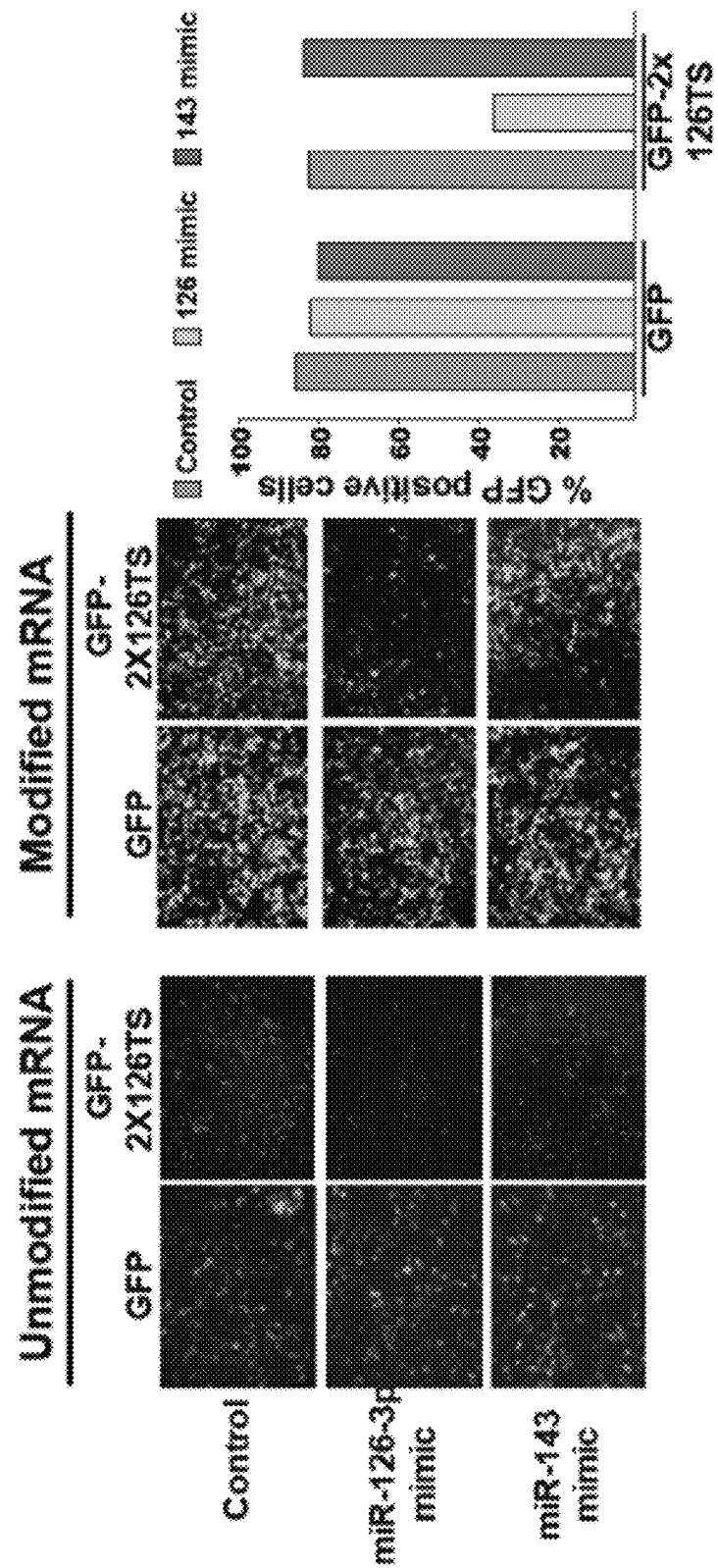
FIG. 13 shows fluorescent images demonstrating GFP expression in HEK cells transfected with 200 nM of the indicated miR-mimic or control. After 24 hr cells were transfection with 100 nM unmodified or pseudouridine modified GFP or GFP-2×miR-126TS and the fluorescent images were taken 24 hr after the second transfection.
FIG. 14 shows a graph demonstrating the percent GFP positive cells transfected with pseudouridine modified mRNAs of FIG. 13 as determined by Flow Cytometry. The total number of cells analyzed was 10,000.

To determine if modified nucleic acids affect target site recognition, modified and unmodified mRNA encoding green fluorescent protein (GFP) or luciferase (Luc) followed by 4 target sequences (TS) for miR-126, miR-143 or control scrambled sequences will be transcribed in vitro by T7 RNA polymerase (FIG. 5).

Example 7

The number of miRNA silencing can be dependent on the number of miRNA target sites present in the construct. As demonstrated in FIGS. 6 and 7, an increase from 0 (GFP) to 2 (2×126TS) to 3 (3×126TS) miRNA target sites within the construct can result in a positively correlated increase in silencing. The data of FIGS. 6 and 7 further demonstrates the specificity of the miRNA target sequences.

Example 8

Figure 43A:
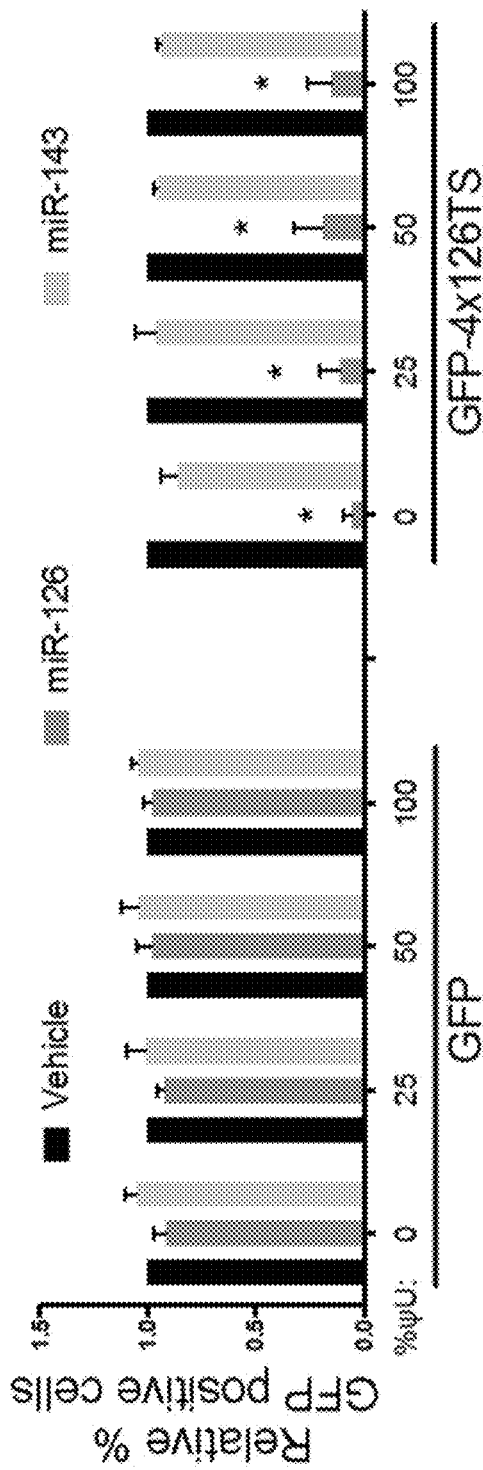
FIGS. 43A-43C show graphs demonstrating and an image of an immunoblot for GFP demonstrating the relative percent of GFP positive cells (FIG. 43A), relative median GFP intensity (FIG. 43B), and relative GFP expression (FIG. 43C) post transfection of HEK cells with GFP or GFP 4×126TS unmodified or with substitutions of uridine with pseudouridine (0%, 25%, 50% or 100%) when exposed to miR-126 or miR-143 mimics.
Figure 43B:
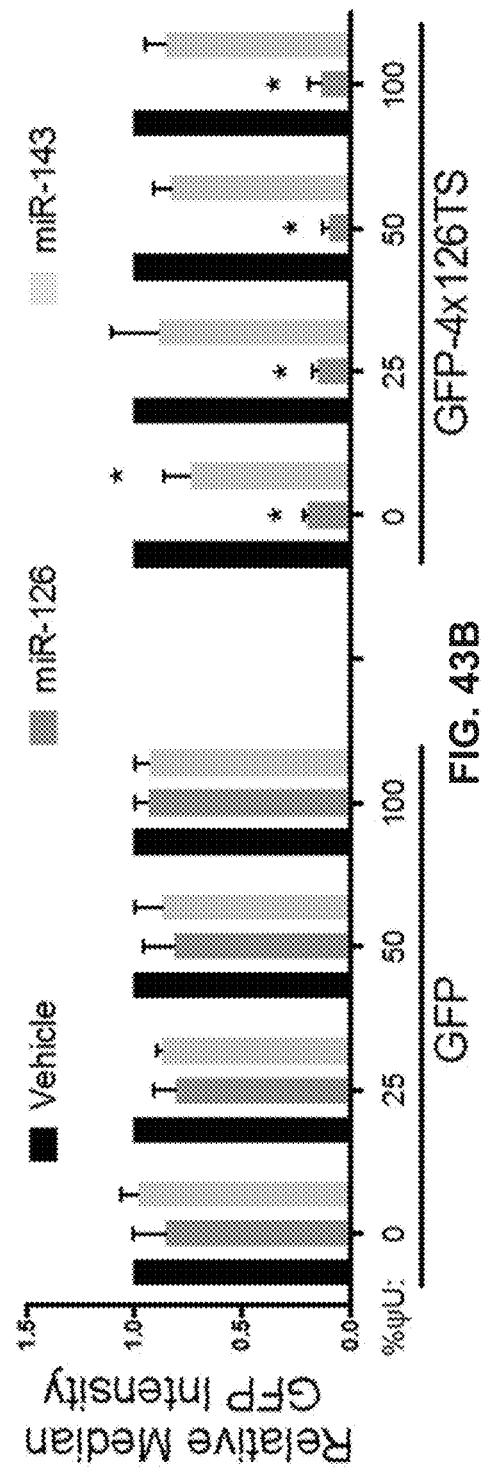
Figure 43C:
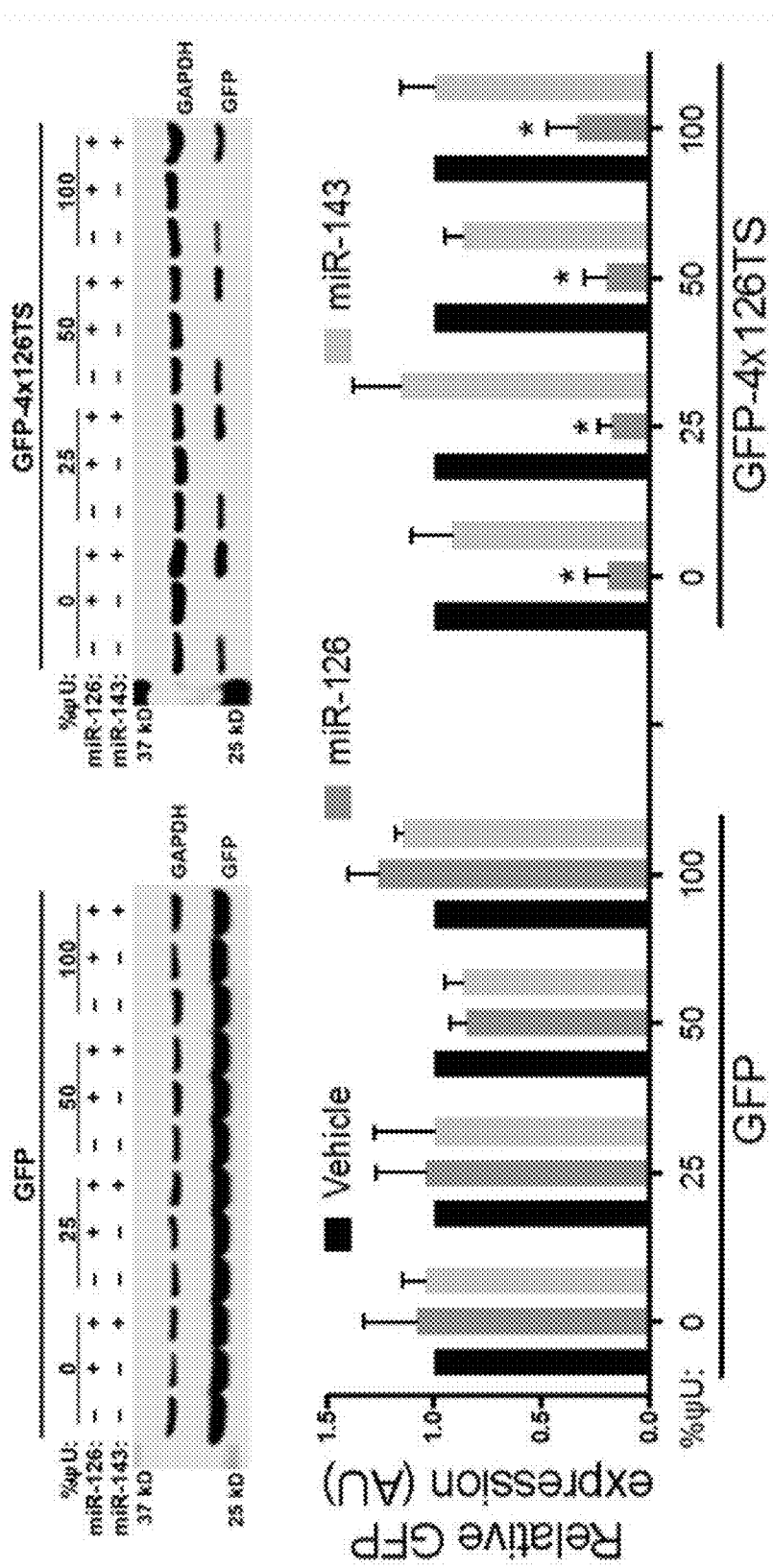

To test whether modified nucleic acids affect the efficiency of miRNA-target site recognition and miRNA-dependent gene silencing, GFP or GFP4×126TS mRNA was in vitro transcribed with substitutions of uridine with pseudouridine (0%, 25%, 50% or 100%). Since ad-HEK293 cells do not express miR-126 or miR-143, we transfected with miR-126 mimic or miR-143 mimic 24 hr prior to transfection with GFP or GFP4×126TS mRNAs to ensure for miRNA/RISC assembly and GFP expression levels were assessed after 24 hr. In the control, unmodified (0% Pseudouridine) GFP transfected cells, the over-expression of miR-126-3p or miR-143 did not have any effect on GFP expression (FIGS. 43A-43C). This was also observed in cells transfected with GFP-mRNA containing increasing percentage of Pseudouridine (FIGS. 43A-43C). However, in cells transfected with GFP4×126TS mRNA, the over-expression of miR-126 and not miR-143 dramatically reduced the percentage of GFP positive cells and inhibited GFP expression. The miR-126-specific inhibition was not affected by increasing the percentage of pseudouridine substitution (FIGS. 43A-43C).

Example 9

Figure 44A:
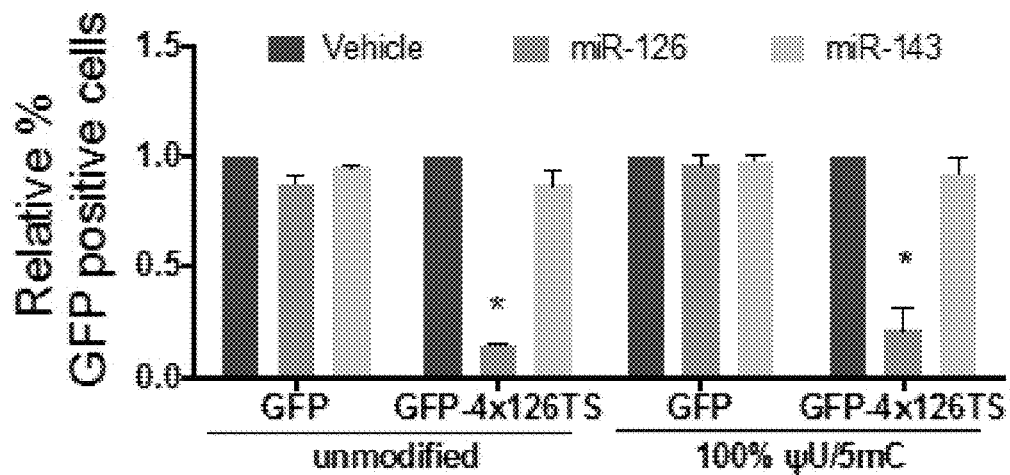
FIGS. 44A-44C show graphs and an image of an immunoblot for GFP demonstrating the relative percent of GFP positive cells (FIG. 44A), relative median GFP intensity (FIG. 44B), and relative GFP expression (FIG. 44C) post transfection with unmodified GFP or GFP 4×126TS or with 100% of uridines and cytosines substituted with pseudouridineand 5-methylcystidine when exposed to miR-126 or miR-143 mimics.
Figure 44B:
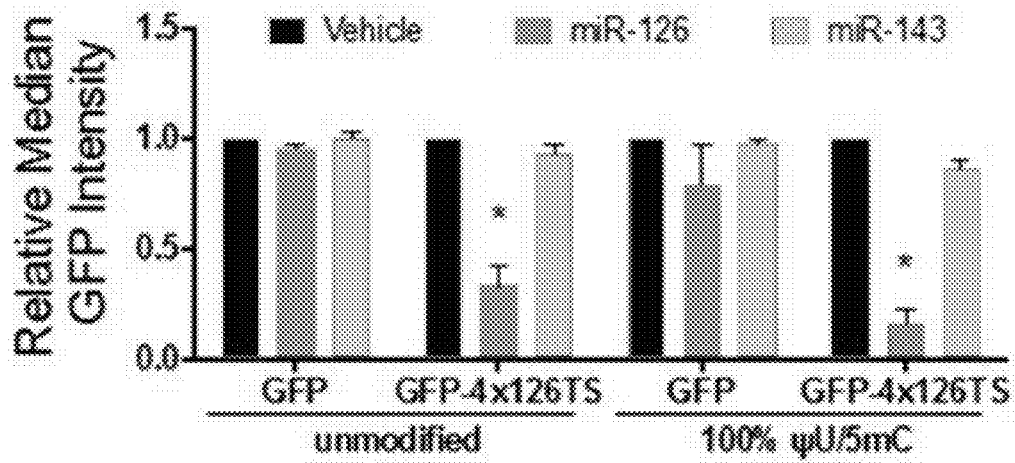
Figure 44C:
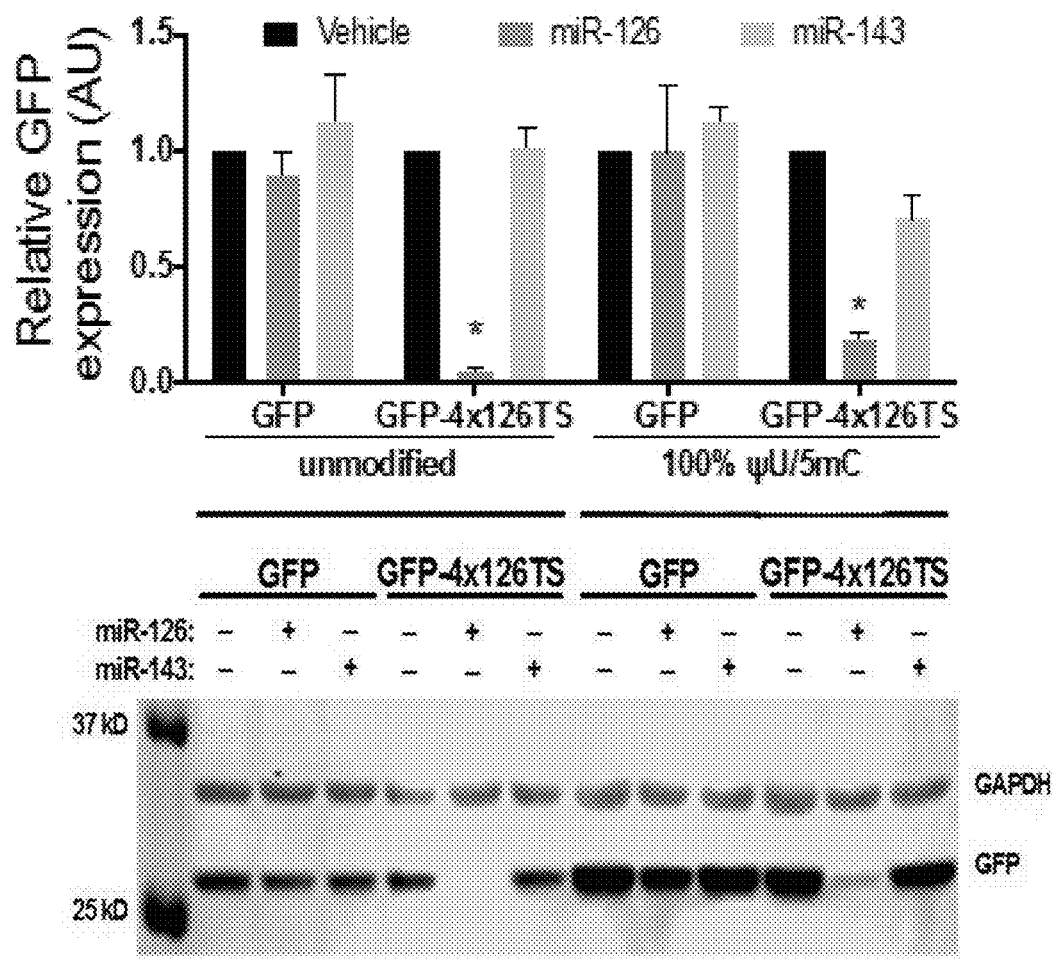

It was also tested whether 100% substitution of both uridine and cytosine with pseudouridine and 5-methylcystidine nucleotides would affect miRNA-dependent gene silencing. To that end, GFP or GFP-4×126TS mRNA were in vitro transcribed with 100% pseudouridine and 100% 5-methylcystidine and transfected into Ad-HEK293 cells that were priory (24 hr) transfected with miR-126 or miR-143 mimics. The inhibitory effect of miR-126 on the expression of the double-modified GFP-4×126TS mRNA were compared to the unmodified mRNA after 24 hr. Cells transfected with pseudouridine and 5-methylcystidine modified mRNA, miR-126 and not miR-143 reduced the percentage of GFP positive cells and inhibited GFP expression to the same extent as the unmodified mRNA (FIGS. 44A-44C). Thus, our data show that complete substitution of pseudouridine, or combination of pseudouridine and 5-methylcystidine modified mRNA, can still be targeted by microRNA-dependent silencing.

Example 10

Figure 45A:
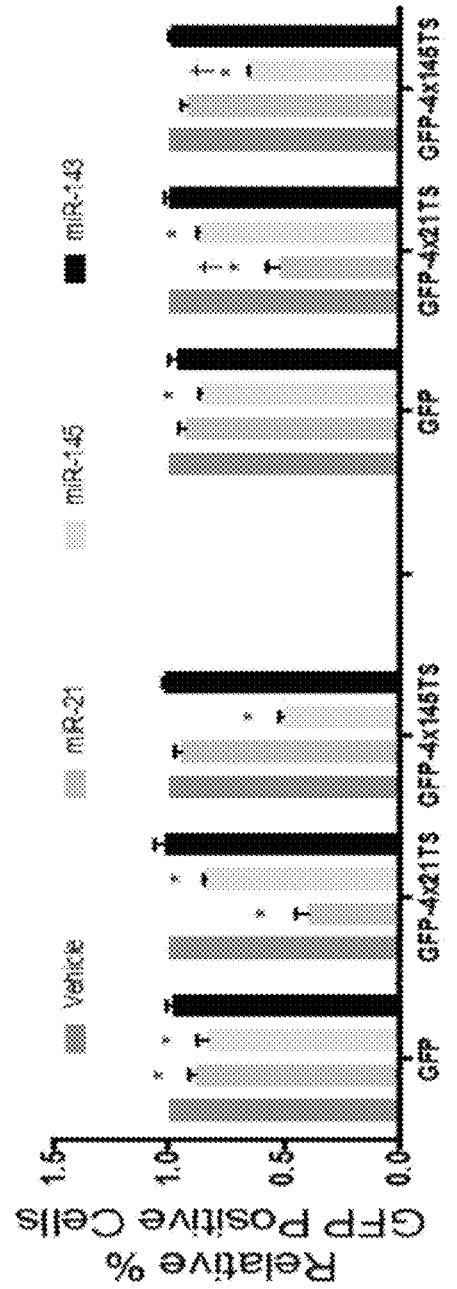
FIGS. 45A-45C show graphs and an image of an immunoblot for GFP demonstrating the relative percent of GFP positive cells (FIG. 45A), relative median GFP intensity (FIG. 45B), and relative GFP expression (FIG. 45C) post transfection with unmodified GFP, GFP 4×21TS, or GFP4× 145TS or with 100% of uridines and cytosines substituted with pseudouridineand 5-methylcystidine when exposed to miR-21 or miR-145, miR143 mimics
Figure 45B:
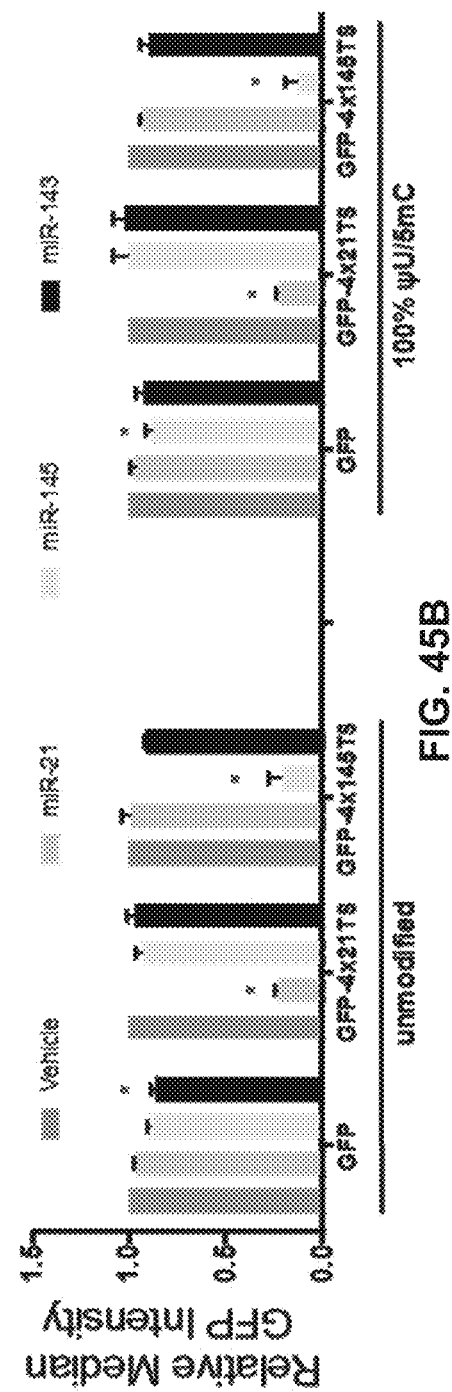
Figure 45C:
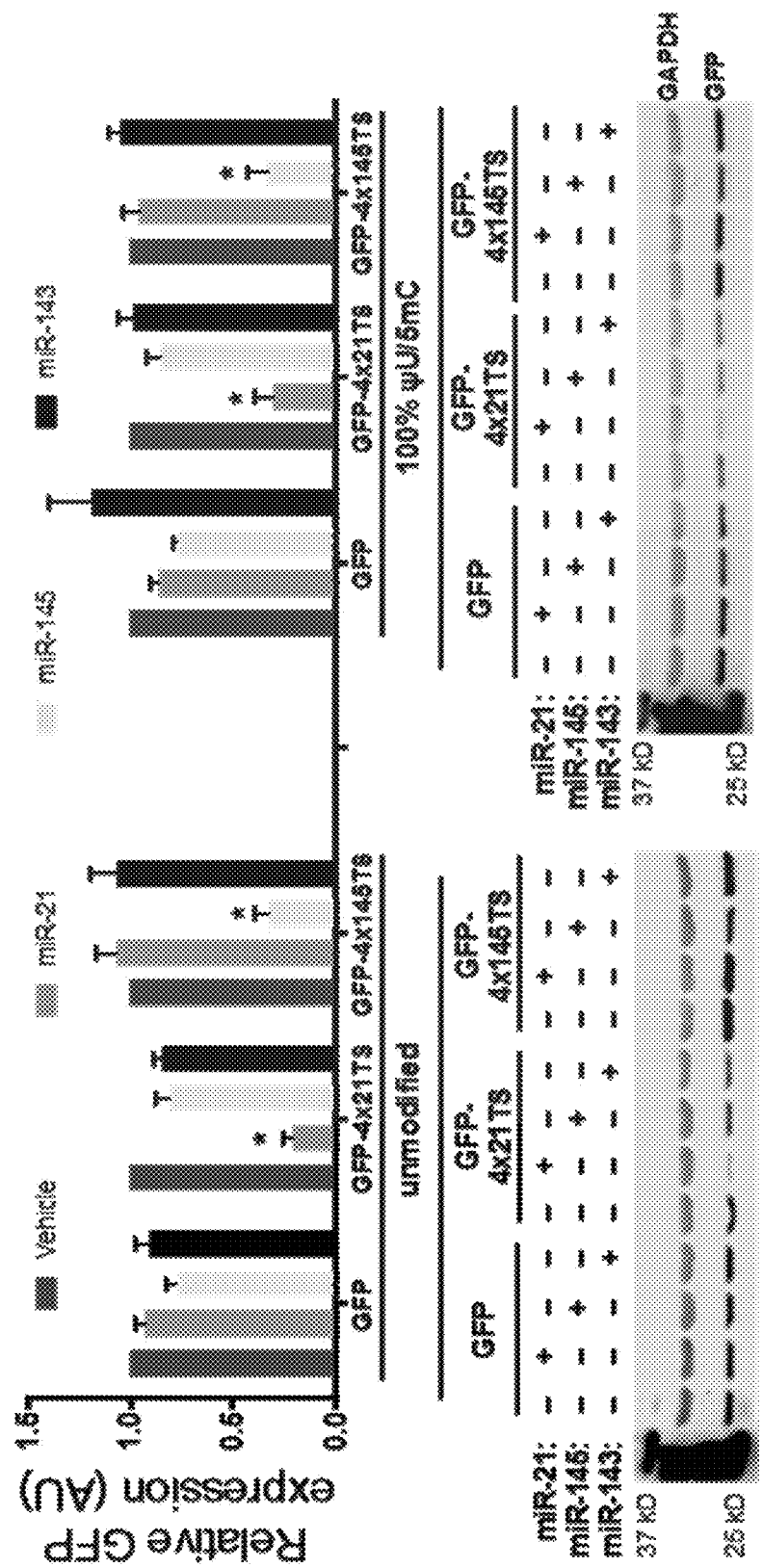

To test whether this miRNA dependent silencing of modified mRNAs is not limited to miR-126, GFP coding mRNA containing target sites for miR-21 or miR-145 was designed. Ad-HEH293 cells were transfected with miR-21, miR-145 or miR-143 mimics 24 hr prior to transfection with unmodified or pseudouridine and 5-methylcystidine modified GFP, GFP4×21TS or GFP4×145TS mRNAs to ensure for RISC assembly and the GFP expression levels were assessed after 24 hr. Cells transfected with 100% Pseudouridine and 5-methylcystidine substituted GFP4×21TS mRNA, the over-expression of miR-21 and not miR-145, miR-21 or moR-143 reduced the expression GFP to the same extent as cells transfected with unmodified GFP4×21TS mRNA (FIGS. 45A-45C). Cells transfected with 100% Pseudouridine and 5-methylcystidine substituted GFP4×154TS mRNA, showed the same reduction in GFP expression as unmodified mRNA when miR-145 mimic was added and not when miR-21, miR-126 or miR-143 mimics were added (FIGS. 45A-45C). In the control transfected cells with unmofdified or 100% substitution with Pseudouridine and 5-methylcystidine GFP mRNA (with no miRNA target sites), the over-expression of miR-21, miR-145 or miR-143 did not have an effect on GFP expression (FIGS. 45A-45C).

Example 11

Figure 46:
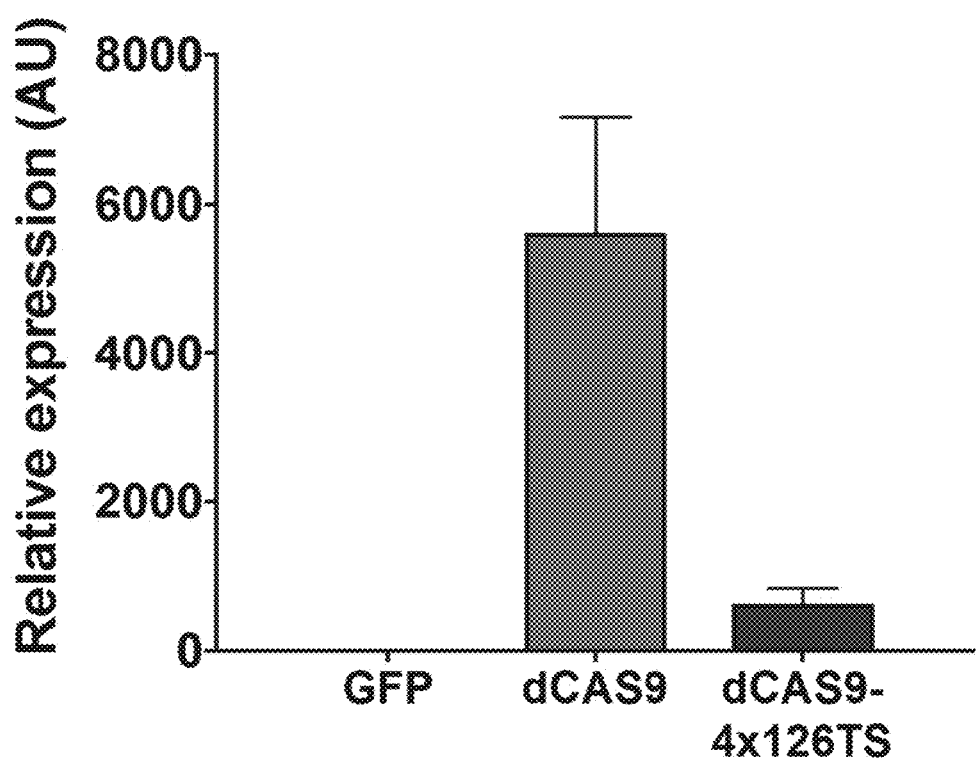
FIG. 46 shows a graph demonstrating the relative expression levels of LIN28A in cells transfected with miR-126 mimic about 24 hours prior to transfection with CRISPR-SAM components containing dCas9 or dCas9-4×126TS.

Cell-Selective Gene Activation Using CRISPR/CAS9 Synergistic Activation Mediator (SAM) System As proof of principle the modified CRISPR/dCas 9 Synergistic Activation Mediator (SAM) system (Konermann et al. 2015. Nature, 517:583-588) was employed that included the sgRNA2.0, MS2-p65-HSF1 and NLS-dCas9-VP64. To activate LIN28A in a cell selective manner, we added four tandem copies of a 22-bp target sequence perfectly complementary to the mature miR-126-3p strand at dCas9 3'UTR (dCas9-4×126TS). Ad-HEK293 cells were transfected with miR-126 mimic 24 hours prior to transfection with CRISPR-SAM components containing dCas9 or dCas9-4×126TS and the expression levels of LIN28A was assessed after 72 hours after. Transient transfected adHEK293 cells transfected with CRISPR-SAM components with dCas9 activated the transcription of LIN28A by >5000 fold while adHEK293 cells transfected with CRISPR-SAM and dCas9-4×126TS showed only 600-fold in LIN28A (FIG. 46).

I claim:

1. A polyribonucleotide comprising:
   a RNA molecule of interest (ROI), wherein the ROI is an RNA capable of being translated into p27;
   a microRNA (miRNA) target sequence, wherein the miRNA target sequence is a target for miR-126, and wherein the miRNA target sequence is operatively linked to the ROI; and
   a RNA molecule capable of being translated into a viral RNA replicase, wherein the RNA molecule capable of being translated into a viral RNA replicase is operatively linked to the ROI, the miRNA target sequence, or both the ROI and miRNA target sequence.

2. The polyribonucleotide of claim 1, wherein the viral replicase is a Venezuelan Equine Encephalitis viral replicase, a Sindbis viral replicase, or a Semliki Forest virus replicase.

3. The polyribonucleotide of claim 1, further comprising a RNA molecule capable of being translated into one or more additional nonstructural viral proteins, wherein the RNA molecule capable of being translated into one or more additional nonstructural viral proteins is operatively linked to the ROI, the miRNA target sequence, or both the ROI and miRNA target sequence.

4. The polyribonucleotide of claim 1, wherein the polyribonucleotide is a linear polyribonucleotide or a circular polyribonucleotide.

5. The polyribonucleotide of claim 1, wherein one or more ribonucleotides of the polyribonucleotide is modified.

6. The polyribonucleotide of claim 5, wherein the modification is a Pseudouridine, N-1-methylpseudouridineridine, 5-methoxy-Uridine, a 5-hydroxymethyl-C, a 5-methyl-C, or a combination thereof.

7. The polyribonucleotide of claim 1, wherein p27 is differentially expressed.

8. The polyribonucleotide of claim 1, wherein the ROI has a sequence that is 85-100% identical to or corresponds to a sequence that is 85% to 100% identical to SEQ ID NO: 2.

9. The polyribonucleotide of claim 1, wherein the miRNA target has a sequence that is complementary to a sequence that is 20-100% SEQ ID NO: 10.

10. The polyribonucleotide of claim 1, wherein the miRNA target has a sequence that is complementary to a sequence that is 90-100% identical to SEQ ID NO: 10, where the portion is 5 or more consecutive nucleotides.

11. A pharmaceutical formulation comprising:
    a polyribonucleotide comprising:
      a RNA molecule of interest (ROI), wherein the ROI is an RNA capable of being translated into p27;
      a microRNA (miRNA) target sequence, wherein the miRNA target sequence is a target for miR-126, and wherein the miRNA target sequence is operatively linked to the ROI; and
      a RNA molecule capable of being translated into a viral RNA replicase, wherein the RNA molecule capable of being translated into a viral RNA replicase is operatively linked to the ROI, the miRNA target sequence, or both the ROI and miRNA target sequence; and
    a pharmaceutically acceptable carrier.

12. The pharmaceutical formulation of claim 11, wherein the viral replicase is a Venezuelan Equine Encephalitis viral replicase, a Sindbis viral replicase, or a Semliki Forest virus replicase.

13. A method comprising:
    administering a polyribonucleotide to subject, wherein the polyribonucleotide comprises
    a RNA molecule of interest (ROI), wherein the ROI is an RNA capable of being translated into p27;
      a microRNA (miRNA) target sequence, wherein the miRNA target sequence is a target for miR-126, and wherein the miRNA target sequence is operatively linked to the ROI; and
    a RNA molecule capable of being translated into a viral RNA replicase, wherein the RNA molecule capable of being translated into a viral RNA replicase is operatively linked to the ROI, the miRNA target sequence, or both the ROI and miRNA target sequence.

14. The method of claim 13, wherein the viral replicase is a Venezuelan Equine Encephalitis viral replicase, a Sindbis viral replicase, or a Semliki Forest virus replicase.

15. The pharmaceutical formulation of claim 11, wherein the polynucleotide is present in the pharmaceutical formulation at an amount effective to inhibit neointimal hyperplasia, inhibit inflammatory cell infiltration to a site of vascular injury, or inhibit neointimal hyperplasia and inhibit inflammatory cell infiltration to a site of vascular injury while not adversely affecting endothelial cells.

16. The pharmaceutical formulation of claim 11, wherein the polynucleotide is present in the pharmaceutical formulation at an amount effective to inhibit proliferation of vascular smooth muscle cells while not adversely affecting endothelial cells.

17. The pharmaceutical formulation of claim 11, wherein the polynucleotide is present in the pharmaceutical formulation at an amount effective to overexpress p27 in a vascular smooth muscle cell but not overexpress p27 in a vascular endothelial cell.

* * * * *

SEQUENCE LISTING

```
<160> NUMBER OF SEQ ID NOS: 135

<210> SEQ ID NO 1
<211> LENGTH: 1725
<212> TYPE: DNA
<213> ORGANISM: Artificial Sequence
<220> FEATURE:
<223> OTHER INFORMATION: ACCESSION NC_006998 REGION:
      177306..179030;VERSION NC_006998.1 GI:66275797; gene1..1725;Gene
      ID 3707576,CDS 1..1725/gene="B18R"/locus_tag="VACWR199"
      /codon_start=1/product="ankyrin-like

<400> SEQUENCE: 1
atgagtcgtc gtctgattta tgttttaaat atcaaccgcg aatcaactca taaaatacaa      60
gagaatgaaa tatatacata ttttagtcat tgcaatatag accatacttc tacagaactt     120
gattttgtag ttaaaaacta tgatctaaac agacgacaac ctgtaactgg gtatactgca     180
ctacactgct atttgtataa taattacttt acaaacgatg tactgaagat attattaaat     240
catggagtgg atgtaacgat gaaaaccagt agcggacgta tgcctgttta tatattgctt     300
actagatgtt gcaatatttc acatgatgta gtgatagata tgatagacaa agataaaaac     360
cacttattac atagagacta ttccaaccta ttactagagt atataaaatc tcgttacatg     420
ttattaaagg aagaggatat cgatgagaac atagtatcca ctttattaga taagggaatc     480
gatcctaact ttaaacaaga cggatataca gcgttacatt attattattt gtgtctcgca     540
cacgtttata aaccaggtga gtgtagaaaa ccgataacga taaaaaaggc caagcgaatt     600
atttctttgt ttatacaaca tggagctaat ctaaacgcgt tagataattg tggtaataca     660
ccattccatt tgtatcttag tattgaaatg tgtaataata ttcatatgac taaaatgctg     720
ttgactttta atccgaattt cgaaatatgt aataatcatg gattaacgcc tatactatgt     780
tatataactt ccgactacat acaacacgat attcttgtta tgttaataca tcactatgaa     840
acaaatgttg gagaaatgcc gatagatgag cgtcgtataa tcgtattcga gtttatcaaa     900
acatattcta cacgtcctgc agattcgata acttatttga tgaataggtt taaaaatata     960
gatatttata cccgctatga aggaaagaca ttattacacg tagcatgtga atataataat    1020
acacacgtaa tagattatct tatacgtatc aacggagata taaatgcgtt aaccgacaat    1080
aacaaacacg ctacacaact cattatagat aacaaagaaa attccccata taccattaat    1140
tgtttactgt atatacttag atatattgta gataagaatg tgataagatc gttggtggat    1200
caacttccat ctctacctat cttcgatata aaatcatttg agaaattcat atcctactgt    1260 atactttag atgacacatt ttacaataga cacgttagga atcgcgattc taaaacgtat      1320
cgatacgcat tttcaaaata catgtcgttt gataaatacg atggtataat aactaaatgt    1380
cataaagaaa caatattgct caaactatcc actgttctag acactacact atatgcagtt    1440
ttaagatgcc ataattcgaa aaagttaaga agatacctca ccgagttaaa aaaatataat    1500
aacgataagt cctttaaaat atattctaat attatgaatg agagatacct taatgtatat    1560
tataaagata tgtacgtgtc aaaggtatat gataaactat ttcctgtttt cacagataaa    1620
```

| aattgtctac taacattact accttcagaa attatatacg aaatattata catgctgaca | 1680 |
| attaacgatc tttataatat atcgtatcca cctaccaaag tatag | 1725 |

<210> SEQ ID NO 2
<211> LENGTH: 2535
<212> TYPE: DNA
<213> ORGANISM: Artificial Sequence
<220> FEATURE:
<223> OTHER INFORMATION: Accession No.: NM_004064; NCBI Ref. Seq.
    NM_004064.4: Homo sapiens cyclin-dependent kinase inhibitor 1B
    (p27, Kip1) (CDKN1B), mRNA

<400> SEQUENCE: 2

| ttaaggccgc gctcgccagc ctcggcgggg cggctcccgc cgccgcaacc aatggatctc | 60 |
| ctcctctgtt taaatagact cgccgtgtca atcattttct tcttcgtcag cctcccttcc | 120 |
| accgccatat tgggccacta aaaaagggg gctcgtcttt cggggtgtt tttctccccc | 180 |
| tccctgtcc ccgcttgctc acggctctgc gactccgacg ccggcaaggt ttggagagcg | 240 |
| gctgggttcg cggacccgc gggcttgcac ccgcccagac tcggacgggc tttgccaccc | 300 |
| tctccgcttg cctggtcccc tctcctctcc gccctcccgc tcgccagtcc atttgatcag | 360 |
| cggagactcg gcggccgggc cggggcttcc ccgcagcccc tgcgcgctcc tagagctcgg | 420 |
| gccgtggctc gtcggggtct gtgtcttttg gctccgaggg cagtcgctgg gcttccgaga | 480 |
| ggggttcggg ctgcgtaggg gcgctttgtt ttgttcggtt ttgttttttt gagagtgcga | 540 |
| gagaggcggt cgtgcagacc cgggagaaag atgtcaaacg tgcgagtgtc taacgggagc | 600 |
| cctagcctgg agcggatgga cgccaggcag gcggagcacc ccaagccctc ggcctgcagg | 660 |
| aacctcttcg gcccggtgga ccacgaagag ttaacccggg acttggagaa gcactgcaga | 720 |
| gacatggaag aggcgagcca gcgcaagtgg aatttcgatt ttcagaatca aaaccccta | 780 |
| gagggcaagt acgagtggca agaggtggag aagggcagct gcccgagtt ctactacaga | 840 |
| cccccgcggc cccccaaagg tgcctgcaag gtgccggcgc aggagagcca ggatgtcagc | 900 |
| gggagccgcc cggcggcgcc tttaattggg gctccggcta actctgagga cacgcatttg | 960 |
| gtggacccaa agactgatcc gtcggacagc cagacgggt tagcggagca atgcgcagga | 1020 |
| ataaggaagc gacctgcaac cgacgattct tctactcaaa acaaaagagc caacagaaca | 1080 |
| gaagaaaatg tttcagacgg ttccccaaat gccggttctg tggagcagac gcccaagaag | 1140 |
| cctggcctca gaagacgtca aacgtaaaca gctcgaatta agaatatgtt tccttgttta | 1200 |
| tcagatacat cactgcttga tgaagcaagg aagatataca tgaaaatttt aaaaatacat | 1260 |
| atcgctgact tcatggaatg acatcctgt ataagcactg aaaaacaaca acacaataac | 1320 |
| actaaaattt taggcactct taaatgatct gcctctaaaa gcgttggatg tagcattatg | 1380 |
| caattaggtt tttccttatt tgcttcattg tactacctgt gtatatagtt tttacctttt | 1440 |
| atgtagcaca taaactttgg ggaagggagg gcagggtggg gctgaggaac tgacgtggag | 1500 |
| cggggtatga agagcttgct ttgatttaca gcaagtagat aaatatttga cttgcatgaa | 1560 |
| gagaagcaat tttggggaag ggtttgaatt gttttctttta aagatgtaat gtcccttttca | 1620 |
| gagacagctg atacttcatt taaaaaaatc acaaaaattt gaacactggc taaagataat | 1680 |
| tgctatttat ttttacaaga agtttattct catttgggag atctggtgat ctcccaagct | 1740 |
| atctaaagtt tgttagatag ctgcatgtgg cttttttaaa aaagcaacag aaacctatcc | 1800 |
| tcactgccct ccccagtctc tcttaaagtt ggaatttacc agttaattac tcagcagaat | 1860 |
| ggtgatcact ccaggtagtt tggggcaaaa atccgaggtg cttgggagtt ttgaatgtta | 1920 |

-continued

| | |
|---|---|
| agaattgacc atctgctttt attaaatttg ttgacaaaat tttctcattt tcttttcact | 1980 |
| tcgggctgtg taaacacagt caaaataatt ctaaatccct cgatattttt aaagatctgt | 2040 |
| aagtaacttc acattaaaaa atgaaatatt ttttaattta aagcttactc tgtccattta | 2100 |
| tccacaggaa agtgttattt ttcaaggaag gttcatgtag agaaaagcac acttgtagga | 2160 |
| taagtgaaat ggatactaca tctttaaaca gtatttcatt gcctgtgtat ggaaaaacca | 2220 |
| tttgaagtgt acctgtgtac ataactctgt aaaaacactg aaaaattata ctaacttatt | 2280 |
| tatgttaaaa gattttttt aatctagaca atatacaagc caaagtggca tgttttgtgc | 2340 |
| atttgtaaat gctgtgttgg gtagaatagg ttttcccctc ttttgttaaa taatatggct | 2400 |
| atgcttaaaa ggttgcatac tgagccaagt ataatttttt gtaatgtgtg aaaaagatgc | 2460 |
| caattattgt tacacattaa gtaatcaata agaaaacttt ccatagctat tcattgagtc | 2520 |
| aaaaaaaaaa aaaaa | 2535 |

<210> SEQ ID NO 3
<211> LENGTH: 11878
<212> TYPE: DNA
<213> ORGANISM: Artificial Sequence
<220> FEATURE:
<223> OTHER INFORMATION: . Cas9 endonuclease: KM099231

<400> SEQUENCE: 3

| | |
|---|---|
| gcctcactga ttaagcattg gtaactgtca gaccaagttt actcatatat actttagatt | 60 |
| gatttaaaac ttcatttta atttaaaagg atctaggtga agatccttt tgataatctc | 120 |
| atgaccaaaa tcccttaacg tgagttttcg ttccactgag cgtcagaccc cgtagaaaag | 180 |
| atcaaaggat cttcttgaga tccttttttt ctgcgcgtaa tctgctgctt gcaaacaaaa | 240 |
| aaaccaccgc taccagcggt ggtttgtttg ccggatcaag agctaccaac tcttttttccg | 300 |
| aaggtaactg gcttcagcag agcgcagata ccaaatactg ttcttctagt gtagccgtag | 360 |
| ttaggccacc acttcaagaa ctctgtagca ccgcctacat acctcgctct gctaatcctg | 420 |
| ttaccagtgg ctgctgccag tggcgataag tcgtgtctta ccgggttgga ctcaagacga | 480 |
| tagttaccgg ataaggcgca gcggtcgggc tgaacggggg gttcgtgcac acagcccagc | 540 |
| ttggagcgaa cgacctacac cgaactgaga tacctacagc gtgagctatg agaaagcgcc | 600 |
| acgcttcccg aagggagaaa ggcggacagg tatccggtaa gcggcagggt cggaacagga | 660 |
| gagcgcacga gggagcttcc agggggaaac gcctggtatc tttatagtcc tgtcgggttt | 720 |
| cgccacctct gacttgagcg tcgatttttg tgatgctcgt caggggggcg gagcctatgg | 780 |
| aaaaacgcca gcaacgcggc cttttacgg ttcctggcct tttgctggcc ttttgctcac | 840 |
| atgttctttc ctgcgttatc ccctgattct gtggataacc gtattaccgc ctttgagtga | 900 |
| gctgataccg ctcgccgcag ccgaacgacc gagcgcagcg agtcagtgag cgaggaagcg | 960 |
| gaagagcgcc caatacgcaa accgcctctc ccgcgcgtt ggccgattca ttaatgcagc | 1020 |
| tggcacgaca ggtttcccga ctggaaagcg ggcagtgagc gcaacgcaat taatgtgagt | 1080 |
| tagctcactc attaggcacc ccaggcttta cactttatgc ttccggctcg tatgttgtgt | 1140 |
| ggaattgtga gcggataaca atttcacaca ggaaacagct atgaccatga ttacgccaag | 1200 |
| ctatttaggt gacactatag aatactcaag cttgggggga tcctctagag tcgacctgca | 1260 |
| ggcatgctat ttgatgaatt aactacactt aaaataatac aattattatt aaattttttt | 1320 |
| ttgatttatt tattaatttt taaacttaat catttgtatt tgggaggaat tatatatatc | 1380 |

```
tttataatta ttttattttt ttttattttt ttatttttt attattatta ttttttttta   1440
tttttttttt ttactgtatc aaagaaaaac ctttaaaaaa aaaattataa tttccccatc   1500
ttactatatt tttaatacat acgttttaag gaattaaatt agacaaaagc tatattatgc   1560
tttacatata attagaattt ataaacgttt ggttattaga tatttcatgt ctcagtaaag   1620
tctttcaata catatgtaaa aaaatatata tgaatacaca taagttgtta atatattta   1680
tatgcataaa tgtataaata tatatatata tatatatata tgtatgtatg tatatgtgtg   1740
tatatgaaat tatttcaatg tttaattttt taaattttaa ttttttttt tttttttttt   1800
tttattatgt atattgatct ttattattta aatattactt ttttcgtttt ttcttctttt   1860
tattatttt ttttttttt atattttata caaatggtaa ttcaaataaa aggtataaat   1920
ttatatttaa ttttctttta tggataaata aaagaaaaat ataaatatat aaaaatataa   1980
aaatatatat atgtatattg gggtgatgat aaaatgaaag ataatatata tatatatata   2040
tctttatttt ttttttttg tagaccccat tgtgagtaca taaatatatt ataaactcg   2100
ggagcatcag tcatggaatt cttatttctt tttcttttt gcctggccgg cctttttcgt   2160
ggccgccggc cttttgtcgc ctcccagctg agacaggtcg atccgtgtct cgtacaggcc   2220
ggtgatgctc tggtggatca gggtggcgtc cagcacctct ttggtgctgg tgtacctctt   2280
ccggtcgatg gtggtgtcaa agtacttgaa ggcggcaggg gctcccagat tggtcagggt   2340
aaacaggtgg atgatattct cggcctgctc tctgatgggc ttatcccggt gcttgttgta   2400
ggcggacagc actttgtcca gattagcgtc ggccaggatc actctcttgg agaactcgct   2460
gatctgctcg atgatctcgt ccaggtagtg cttgtgctgt tccacaaaca gctgtttctg   2520
ctcattatcc tcggggagc ccttcagctt ctcatagtgg ctggccaggt acaggaagtt   2580
cacatatttg gagggcaggg ccagttcgtt tcccttctgc agttcgccgg cagaggccag   2640
cattctcttc cggccgtttt ccagctcgaa cagggagtac ttaggcagct tgatgatcag   2700
gtccttttc acttctttgt agcccttggc ttccagaaag tcgatgggat tcttctcgaa   2760
gctgcttctt tccatgatgg tgatccccag cagctctttc acactcttca gtttcttgga   2820
cttgcccttt tccactttgg ccaccaccag cacagaatag gccacggtgg ggctgtcgaa   2880
gccgccgtac ttcttagggt cccagtcctt ctttctggcg atcagcttat cgctgttcct   2940
cttgggcagg atagactctt tgctgaagcc gcctgtctgc acctcggtct ttttcacgat   3000
attcacttgg ggcatgctca gcactttccg cacggtggca aaatcccggc ccttatccca   3060
cacgatctcc ccggtttcgc cgtttgtctc gatcagaggc cgcttccgga tctcgccgtt   3120
ggccagggta atctcggtct tgaaaaagtt catgatgttg ctgtagaaga agtacttggc   3180
ggtagccttg ccgatttcct gctcgctctt ggcgatcatc ttccgcacgt cgtacacctt   3240
gtagtcgccg tacacgaact cgctttccag cttagggtac ttttttgatca gggcggttcc   3300
cacgacggcg ttcaggtagg cgtcgtgggc gtggtggtag ttgttgatct cgcgcacttt   3360
gtaaaactgg aaatccttcc ggaaatcgga caccagcttg gacttcaggg tgatcacttt   3420
cacttcccgg atcagcttgt cattctcgtc gtacttagtg ttcatccggg agtccaggat   3480
ctgtgccacg tgctttgtga tctgccgggt ttccaccagc tgtctcttga tgaagccggc   3540
cttatccagt tcgctcaggc cgcctctctc ggccttggtc agattgtcga actttctctg   3600
ggtaatcagc ttggcgttca gcagctgccg ccagtagttc ttcatcttct tcacgacctc   3660
ttcggagggc acgttgtcgc tcttgccccg gttcttgtcg cttctggtca gcaccttgtt   3720
gtcgatggag tcgtccttca gaaagctctg aggcacgata tggtccacat cgtagtcgga   3780
```

```
cagccggttg atgtccagtt cctggtccac gtacatatcc cgcccattct gcaggtagta    3840
caggtacagc ttctcgttct gcagctgggt gttttccacg gggtgttctt tcaggatctg    3900
gctgcccagc tctttgatgc cctcttcgat ccgcttcatt ctctcgcggc tgttcttctg    3960
tcccttctgg gtggtctggt tctctctggc catttcgatc acgatgttct cgggcttgtg    4020
ccggcccatc actttcacga gctcgtccac caccttcact gtctgcagga tgcccttctt    4080
aatggcgggg ctgccggcca gattggcaat gtgctcgtgc aggctatcgc cctggccgga    4140
cacctgggct ttctggatgt cctctttaaa ggtcaggctg tcgtcgtgga tcagctgcat    4200
gaagtttctg ttggcgaagc cgtcggactt caggaaatcc aggattgtct gccggactg    4260 cttgtcccgg atgccgttga tcagcttccg gctcagcctg ccccagccgg tgtatctccg    4320
ccgcttcagc tgcttcatca ctttgtcgtc gaacaggtgg gcataggttt tcagccgttc    4380
ctcgatcatc tctctgtcct caaacagtgt cagggtcagc acgatatctt ccagaatgtc    4440
ctcgttttcc tcattgtcca ggaagtcctt gtccttgata ttttcagca gatcgtggta    4500 tgtgcccagg gaggcgttga accgatcttc cacgccggag atttccacgg agtcgaagca    4560
ctcgattttc ttgaagtagt cctctttcag ctgcttcacg gtcactttcc ggttggtctt    4620
gaacagcagg tccacgatgg ccttttttctg ctcgccgctc aggaaggcgg gctttctcat    4680
tccctcggtc acgtatttca ctttggtcag ctcgttatac acggtgaagt actcgtacag    4740
caggctgtgc ttgggcagca ccttctcgtt gggcaggttc ttatcgaagt tggtcatccg    4800
ctcgatgaag ctctgggcgg aagcgcccct gtccaccact cctcgaagt tccaggggt    4860 gatggtttcc tcgctctttc tggtcatcca ggcgaatctg ctgtttcccc tggccagagg    4920
gcccacgtag taggggatgc ggaaggtcag gatcttctcg atcttttccc ggttgtcctt    4980
caggaatggg taaaaatctt cctgccgccg cagaatggcg tgcagctctc ccaggtggat    5040
ctggtggggg atgctgccgt tgtcgaaggt ccgctgcttc cgcagcaggt cctctctgtt    5100
cagcttcacg agcagttcct cggtgccgtc catcttttcc aggatgggct tgatgaactt    5160
gtagaactct tcctggctgg ctccgccgtc aatgtagccg gcgtagccgt tcttgctctg    5220
gtcgaagaaa atctctttgt acttctcagg cagctgctgc cgcacgagag ctttcagcag    5280
ggtcaggtcc tggtggtgct cgtcgtatct cttgatcata gaggcgctca ggggggcctt    5340
ggtgatctcg gtgttcactc tcaggatgtc gctcagcagg atggcgtcgg acaggttctt    5400
ggcggccaga acaggtcgg cgtactggtc gccgatctgg gccagcaggt tgtccaggtc    5460
gtcgtcgtag gtgtccttgc tcagctgcag tttggcatcc tcggccaggt cgaagttgct    5520
cttgaagttg ggggtcaggc ccaggctcag ggcaatcagg tttccgaaca ggccattctt    5580
cttctcgccg ggcagctggg cgatcagatt ttccagccgt ctgctcttgc tcagtctggc    5640
agacaggatg gccttggcgt ccacgccgct ggcgttgatg gggttttcct cgaacagctg    5700
gttgtaggtc tgcaccagct ggatgaacag cttgtccacg tcgctgttgt cggggttcag    5760
gtcgccctcg atcaggaagt ggccccggaa cttgatcatg tgggccaggg ccagatagat    5820
cagccgcagg tcggccttgt cggtgctgtc caccagtttc tttctcaggt ggtagatggt    5880
ggggtacttc tcgtggtagg ccacctcgtc cacgatgttg ccgaagatgg ggtgccgctc    5940
gtgcttctta tcctcttcca ccaggaagga ctcttccagt ctgtggaaga agctgtcgtc    6000
caccttggcc atctcgttgc tgaagatctc ttgcagatag cagatccggt tcttccgtct    6060
ggtgtatctt cttctggcgg ttctcttcag ccgggtggcc tcggctgttt cgccgctgtc    6120
```

```
gaacagcagg gctccgatca ggttcttctt gatgctgtgc cggtcggtgt tgcccagcac    6180
cttgaatttc ttgctgggca ccttgtactc gtcggtgatc acggcccagc ccacagagtt    6240
ggtgccgatg tccaggccga tgctgtactt cttgtcggct gctgggactc cgtggatacc    6300
gaccttccgc ttcttctttg gggccatctt atcgtcatcg tctttgtaat caatatcatg    6360
atccttgtag tctccgtcgt ggtccttata gtccattttt ctcgagggat cctgatatat    6420
ttctattagg tatttattat tataaaatat aaatcttgaa tgataataaa taaaatatta    6480
gttattcctt ttctagttta aaatatacat attataaata tatatatata tatatatatt    6540
tttattgtga caagaatata taattataaa ttatattatt tattttttgta ttttttttt     6600 tttttttttt ttttctttt tttgttttat ttttcttttt tttataaat attattttt       6660 tcttttatca tgcacattgg aataatacat taatatatat atatatatta tattatacat    6720
atattgaata atgtttataa aaatgcata acttatatga ataatttt ttttaaatat       6780 gacaaaaga aaaaaaaaa aaaccaaaaa aaattaaaat tgaaatgaaa tatataaata       6840
tattatttat atatattata cattgtttaa tactactaca tgtatatata tatattatat    6900
atatatatat atcaatttt tttcaaaaat aaattaatat aaaaagaggg gaaaaaaaaa     6960
aaaaaaaaaa aaaaagata attaagtaag catttaaaaa tatataaatt gataatatat     7020
aaaattaatc acatataaaa gcttataaac actaggttag ctaattcgct tgtaagaggt    7080
actctcgttt atgcaaaact atttgatata gcattttaac aagtacacat atatatatgt    7140
aatatatata ctatatatat ctattgcatg tgtactaagc atgtgcatgg catccccttt    7200
ttctcgtgtt taaaacagtt tgtatgataa aatataaagg atttgaaaaa gagaaaaaaa    7260
tatatgatct catcctatat agcgccataa ttttatttg ggttgaataa aattttctac     7320
taaatttagg tgtaagtaaa ataatggaat atatataagt acaataaaaa agtgcataaa    7380
ttaaaaaatt tttataataa atattttttt taaaaaagtc aataataata ttaaatatat    7440
ataacacagg attatatatg ttcactacaa tttttttatt tataatataa attcttttca    7500
attttcattt tatttttacat acactttcct tttttgtcac tatattttaa tattcacata   7560
tttagtttaa atactggcta tttctttcta catttgctag taacaattgt gtagtgctta    7620
aatatataca cacacctaaa acttacaaag tatcctagga ccatggccaa gcctttgtct    7680
caagaagaat ccaccctcat tgaaagagca acggctacaa tcaacagcat ccccatctct    7740
gaagactaca gcgtcgccag cgcagctctc tctagcgacg gccgcatctt cactggtgtc    7800
aatgtatatc attttactgg gggaccttgt gcagaactcg tggtgctggg cactgctgct    7860
gctgcggcag ctggcaacct gacttgtatc gtcgcgatcg gaaatgagaa caggggcatc    7920
ttgagcccct gcggacggtg ccgacaggtg cttctcgatc tgcatcctgg gatcaaagcc    7980
atagtgaagg acagtgatgg acagccgacg gcagttggga ttcgtgaatt gctgccctct    8040
ggttatgtgt gggagggcta accgcgggta ccccattaaa tttatttaat aatagattaa    8100
aaatattata aaataaaaaa cataaacaca gaaattacaa aaaaaataca tatgaatttt    8160 tttttttgtaa tcttccttat aaatatagaa taatgaatca tataaaacat atcattattc   8220
atttatttac atttaaaatt attgtttcag tatcttaat ttattatgta tatataaaaa     8280
taacttacaa ttttattaat aaacaatata tgtttattaa ttcatgttt gtaatttatg     8340 ggatagcgat ttttttttact gtctgtattt tcttttttaa ttatgtttta attgtattta   8400 tttttatttttt attattgttc tttttatagt attatttaa aacaaatgt attttctaag    8460 aacttataat aataataata taaattttaa taaaaattat atttatctttt tacaatatga   8520
```

```
acataaagta caacattaat atatagcttt taatatttt attcctaatc atgtaaatct      8580
taaatttttc tttttaaaca tatgttaaat atttatttct cattatatat aagaacatat      8640
ttattacatc tagaggtacc gagctcgttt tcgacactgg atggcggcgt tagtatcgaa      8700
tcgacagcag tatagcgacc agcattcaca tacgattgac gcatgatatt actttctgcg      8760
cacttaactt cgcatctggg cagatgatgt cgaggcgaaa aaaatataa atcacgctaa       8820
catttgatta aaatagaaca actacaatat aaaaaaacta tacaaatgac aagttcttga      8880
aaacaagaat cttttttattg tcagtactga ttagaaaaac tcatcgagca tcaaatgaaa     8940
ctgcaattta ttcatatcag gattatcaat accatatttt tgaaaaagcc gtttctgtaa     9000
tgaaggagaa aactcaccga ggcagttcca taggatggca agatcctggt atcggtctgc     9060
gattccgact cgtccaacat caatacaacc tattaatttc ccctcgtcaa aaataaggtt     9120
atcaagtgag aaatcaccat gagtgacgac tgaatccggt gagaatggca aaagcttatg     9180
catttctttc cagacttgtt caacaggcca gccattacgc tcgtcatcaa aatcactcgc     9240
atcaaccaaa ccgttattca ttcgtgattg cgcctgagcg agacgaaata cgcgatcgct     9300
gttaaaagga caattacaaa caggaatcga atgcaaccgg cgcaggaaca ctgccagcgc     9360
atcaacaata ttttcacctg aatcaggata ttcttctaat acctggaatg ctgttttgcc     9420
ggggatcgca gtggtgagta accatgcatc atcaggagta cggataaaat gcttgatggt     9480
cggaagaggc ataaattccg tcagccagtt tagtctgacc atctcatctg taacatcatt     9540
ggcaacgcta cctttgccat gtttcagaaa caactctggc gcatcgggct tcccatacaa     9600
tcgatagatt gtcgcacctg attgcccgac attatcgcga gcccatttat acccatataa     9660
atcagcatcc atgttggaat ttaatcgcgg cctcgaaacg tgagtctttt ccttacccat     9720
ggttgtttat gttcggatgt gatgtgagaa ctgtatccta gcaagatttt aaaaggaagt     9780
atatgaaaga agaacctcag tggcaaatcc taacctttta tatttctcta caggggcgcg     9840
gcgtggggac aattcaacgc gtctgtgagg ggagcgtttc cctgctcgca ggtctgcagc     9900
gaggagccgt aattttttgct tcgcgccgtg cggccatcaa aatgtatgga tgcaaatgat     9960
tatacatggg gatgtatggg ctaaatgtac gggcgacagt cacatcatgc ccctgagctg    10020
cgcacgtcaa gactgtcaag gagggtattc tgggcctcca tgtcgctggc ctaacattag    10080
taatgtaggt ctgactttca ctcatataag tcttatggta actaaactaa ggtcttacct    10140
ttactgatat atgtcttact ttcactaact taggtattac ttttactaac ttaggtctta    10200
aattcagtaa ctaaggtcat acttcgacta actaaggtct tacattcact gatataggtc    10260
ttatgattac taacttaggt cctaatttga ctaacataag tcctaacatt agtaatgtag    10320
gtcttaactt aactaactta ggtcttacct tcactaatat aggtcttaat attactgact    10380
taagtaatta aggtactaac ttaggtcgta aggtaactaa tatataggtc ttaaggtaac    10440
taatttaggt cttgacttaa taaatatagg tcctaacata aatagtatag gtcctaatat    10500
aagtactata ggccttaact taaccaacat aggtcctaac ataagttata taggtcttaa    10560
cgtaactaac ataagtcatt aaggtactaa gtttggtctt aatttaacaa taacatgtcg    10620
ctggcctaac attagtaatg taggtctgac tttcactcat ataagtctta tggtaactaa    10680
actaaggtct tacctttact gatatatgtc ttactttcac taacttaggt attacttttta    10740
ctaacttagg tcttaaattc agtaactaag gtcatacttc gactaactaa ggtcttacat    10800
tcactgatat aggtcttatg attactaact taggtcctaa tttgactaac ataagtccta    10860
```

```
acattagtaa tgtaggtctt aacttaacta acttaggtct taccttcact aatataggtc    10920
ttaatattac tgacttaagt aattaaggta ctaacttagg tcgtaaggta actaatatat    10980
aggtcttaag gtaactaatt taggtcttga cttaataaat ataggtccta acataaatag    11040
tataggtcct aatataagta ctataggcct taacttaacc aacataggtc ctaacataag    11100
ttatataggt cttaacgtaa ctaacataag tcattaaggt actaagtttg gtcttaattt    11160
aacaataacc atgtcgctgg ccgggtggtc ttaatttaac aaatatagac catgtcgctg    11220
gccgggtgac ccggcgggga cgaggcaagc taaacagatc ctcgtgatac gcctattttt    11280
ataggttaat gtcatgataa taatggtttc ttaggacgga tcgcttgcct gtaacttaca    11340
cgcgcctcgt atcttttaat gatggaataa tttgggaatt tactctgtgt ttatttattt    11400
ttatgttttg tatttggatt ttagaaagta aataaagaag gtagaagagt tacggaatga    11460
agaaaaaaaa ataaacaaag gtttaaaaaa tttcaacaaa aagcgtactt tacatatata    11520
tttattagac aagaaaagca gattaaatag atatacattc gattaacgat aagtaaaatg    11580
taaaatcaca ggattttcgt gtgtggtctt ctacacagac aagatgaaac aattcggcat    11640
taatacctga gagcaggaag agcaagataa aaggtagtat tgttggcga tccccctaga    11700 gtcttttaca tcttcggaaa acaaaaacta ttttttcttt aatttctttt tttactttct    11760
atttttaatt tatatattta tattaaaaaa tttaaattat aattattttt atagcacgtg    11820
atgaaaagga cccaggtggc acttttcggg gaaatctcga cctgcagcgt acgaagct      11878
```

<210> SEQ ID NO 4
<211> LENGTH: 12860
<212> TYPE: DNA
<213> ORGANISM: Artificial Sequence
<220> FEATURE:
<223> OTHER INFORMATION: Cas9n (D10A nickase version of the Cas9 enzyme
      generates a single-strand DNA break) Addgene # 63593

<400> SEQUENCE: 4

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg     360
acccccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
```

```
gcccgaacag ggacttgaaa gcgaaaggga aaccagagga gctctctcga cgcaggactc    1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc aggggggaaag aaaaaatata    1260 aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctgggggatt    1920 tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggctgtatt catccacaat tttaaaagaa aagggggat    2460 tgggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta agctagctag gtcttgaaag gagtgggaat tggctccggt    2640
gcccgtcagt gggcagagcg cacatcgccc acagtccccg agaagttggg gggaggggtc    2700
ggcaattgat ccggtgccta gagaaggtgg cgcggggtaa actgggaaag tgatgtcgtg    2760
tactggctcc gcctttttcc cgagggtggg ggagaaccgt atataagtgc agtagtcgcc    2820
gtgaacgttc tttttcgcaa cgggtttgcc gccagaacac aggaccggtt ctagagcgct    2880
gccaccatgg acaagaagta cagcatcggc ctggccatcg gcaccaactc tgtgggctgg    2940
gccgtgatca ccgacgagta caaggtgccc agcaagaaat tcaaggtgct gggcaacacc    3000
gaccggcaca gcatcaagaa gaacctgatc ggagccctgc tgttcgacag cggcgaaaca    3060
gccgaggcca cccggctgaa gagaaccgcc agaagaagat acaccagacg gaagaaccgg    3120
atctgctatc tgcaagagat cttcagcaac gagatggcca aggtggacga cagcttcttc    3180
cacagactgg aagagtcctt cctggtggaa gaggataaga agcacgagcg gcaccccatc    3240
ttcggcaaca tcgtggacga ggtggcctac cacgagaagt accccaccat ctaccacctg    3300
agaaagaaac tggtggacag caccgacaag gccgacctgc ggctgatcta tctggccctg    3360
gcccacatga tcaagttccg gggccacttc ctgatcgagg gcgacctgaa ccccgacaac    3420
```

```
agcgacgtgg acaagctgtt catccagctg gtgcagacct acaaccagct gttcgaggaa   3480
aaccccatca acgccagcgg cgtggacgcc aaggccatcc tgtctgccag actgagcaag   3540
agcagacggc tggaaaatct gatcgcccag ctgcccggcg agaagaagaa tggcctgttc   3600
ggcaacctga ttgccctgag cctgggcctg acccccaact tcaagagcaa cttcgacctg   3660
gccgaggatg ccaaactgca gctgagcaag gacacctacg acgacgacct ggacaacctg   3720
ctggcccaga tcggcgacca gtacgccgac ctgtttctgg ccgccaagaa cctgtccgac   3780
gccatcctgc tgagcgacat cctgagagtg aacaccgaga tcaccaaggc cccctgagc   3840 gcctctatga tcaagagata cgacgagcac caccaggacc tgaccctgct gaaagctctc   3900
gtgcggcagc agctgcctga agtacaaa gagattttct tcgaccagag caagaacggc   3960
tacgccggct acattgacgg cggagccagc caggaagagt tctacaagtt catcaagccc   4020
atcctggaaa agatggacgg caccgaggaa ctgctcgtga gctgaacag agaggacctg   4080 ctgcggaagc agcggaccct tcgacaacgg agcatccccc accagatcca cctgggagag   4140
ctgcacgcca ttctgcggcg gcaggaagat ttttacccat cctgaagga caaccgggaa   4200 aagatcgaga agatcctgac cttccgcatc ccctactacg tgggccctct ggccagggga   4260
aacagcagat tcgcctggat gaccagaaag agcgaggaaa ccatcacccc ctggaacttc   4320
gaggaagtgg tggacaaggg cgcttccgcc cagagcttca tcgagcggat gaccaacttc   4380
gataagaacc tgcccaacga aaggtgctg cccaagcaca gcctgctgta cgagtacttc   4440
accgtgtata acgagctgac caaagtgaaa tacgtgaccg agggaatgag aaagcccgcc   4500
ttcctgagcg gcgagcagaa aaaggccatc gtggacctgc tgttcaagac caaccggaaa   4560
gtgaccgtga agcagctgaa agaggactac ttcaagaaaa tcgagtgctt cgactccgtg   4620
gaaatctccg gcgtggaaga tcggttcaac gcctccctgg gcacatacca cgatctgctg   4680
aaaattatca aggacaagga cttcctggac aatgaggaaa acgaggacat tctggaagat   4740
atcgtgctga ccctgacact gtttgaggac agagagatga tcgaggaacg gctgaaaacc   4800
tatgcccacc tgttcgacga caaagtgatg aagcagctga gcggcggag atacaccggc   4860 tggggcaggc tgagccggaa gctgatcaac ggcatccggg acaagcagtc cggcaagaca   4920
atcctggatt tcctgaagtc cgacggcttc gccaacagaa acttcatgca gctgatccac   4980
gacgacagcc tgacctttaa agaggacatc cagaaagccc aggtgtccgg ccagggcgat   5040
agcctgcacg agcacattgc caatctggcc ggcagccccg ccattaagaa gggcatcctg   5100
cagacagtga aggtggtgga cgagctcgtg aaagtgatgg gccggcacaa gcccgagaac   5160
atcgtgatcg aaatggccag agagaaccag accacccaga agggacagaa gaacagccgc   5220
gagagaatga agcggatcga agagggcatc aaagagctgg gcagccagat cctgaaagaa   5280 cacccccgtgg aaaacaccca gctgcagaac gagaagctgt acctgtacta cctgcagaat   5340
gggcgggata tgtacgtgga ccaggaactg gacatcaacc ggctgtccga ctacgatgtg   5400
gaccatatcg tgcctcagag cttcctgaag gacgactcca tcgacaacaa ggtgctgacc   5460
agaagcgaca agaaccgggg caagagcgac aacgtgccct ccgaagaggt cgtgaagaag   5520
atgaagaact actggcggca gctgctgaac gccaagctga ttacccagag aaagttcgac   5580
aatctgacca aggccgagag aggcggcctg agcgaactgg ataaggccgg cttcatcaag   5640
agacagctgt ggaaacccgc gcagatcaca aagcacgtgg cacagatcct ggactcccgg   5700
atgaacacta agtacgacga gaatgacaag ctgatccggg aagtgaaagt gatcaccctg   5760
```

```
aagtccaagc tggtgtccga tttccggaag gatttccagt tttacaaagt gcgcgagatc   5820
aacaactacc accacgccca cgacgcctac ctgaacgccg tcgtgggaac cgccctgatc   5880
aaaaagtacc ctaagctgga agcgagttc gtgtacggcg actacaaggt gtacgacgtg   5940
cggaagatga tcgccaagag cgagcaggaa atcggcaagg ctaccgccaa gtacttcttc   6000
tacagcaaca tcatgaactt tttcaagacc gagattaccc tggccaacgg cgagatccgg   6060
aagcggcctc tgatcgagac aaacggcgaa accggggaga tcgtgtggga taagggccgg   6120
gattttgcca ccgtgcggaa agtgctgagc atgccccaag tgaatatcgt gaaaaagacc   6180
gaggtgcaga caggcggctt cagcaaagag tctatcctgc caagaggaa cagcgataag   6240 ctgatcgcca gaaagaagga ctgggaccct aagaagtacg gcggcttcga cagccccacc   6300
gtggcctatt ctgtgctggt ggtggccaaa gtggaaaagg gcaagtccaa gaaactgaag   6360
agtgtgaaag agctgctggg gatcaccatc atggaaagaa gcagcttcga aagaatccc   6420 atcgactttc tggaagccaa gggctacaaa gaagtgaaaa aggacctgat catcaagctg   6480
cctaagtact ccctgttcga gctggaaaac ggccggaaga gaatgctggc ctctgccggc   6540
gaactgcaga agggaaacga actggccctg ccctccaaat atgtgaactt cctgtacctg   6600
gccagccact atgagaagct gaagggctcc cccgaggata tgagcagaa acagctgttt   6660 gtggaacagc acaagcacta cctggacgag atcatcgagc agatcagcga gttctccaag   6720
agagtgatcc tggccgacgc taatctggac aaagtgctgt ccgcctacaa caagcaccgg   6780
gataagccca tcagagagca ggccgagaat atcatccacc tgtttaccct gaccaatctg   6840
ggagcccctg ccgccttcaa gtactttgac accaccatcg accggaagag gtacaccagc   6900
accaaagagg tgctggacgc caccctgatc caccagagca tcaccggcct gtacgagaca   6960
cggatcgacc tgtctcagct gggaggcgac aagcgacctg ccgccacaaa gaaggctgga   7020
caggctaaga gaagaaaga ttacaaagac gatgacgata agggatccgg cgcaacaaac   7080
ttctctctgc tgaaacaagc cggagatgtc gaagagaatc ctggaccgat ggccaagcct   7140
ttgtctcaag aagaatccac cctcattgaa agagcaacgg ctacaatcaa cagcatcccc   7200
atctctgaag actacagcgt cgccagcgca gctctctcta cgacggccg catcttcact   7260 ggtgtcaatg tatatcattt tactgggga ccttgtgcag aactcgtggt gctgggcact   7320
gctgctgctg cggcagctgg caacctgact tgtatcgtcg cgatcggaaa tgagaacagg   7380
ggcatcttga gccctgcgg acggtgccga caggtgcttc tcgatctgca tcctgggatc   7440
aaagccatag tgaaggacag tgatggacag ccgacggcag ttgggattcg tgaattgctg   7500
ccctctggtt atgtgtggga gggctaagaa ttcgatatca agcttatcga taatcaacct   7560
ctggattaca aaatttgtga agatttgact ggtattctta actatgttgc tccttttacg   7620
ctatgtggat acgctgcttt aatgcctttg tatcatgcta ttgcttcccg tatggctttc   7680
attttctcct ccttgtataa atcctggttg ctgtctcttt atgaggagtt gtggcccgtt   7740
gtcaggcaac gtggcgtggt gtgcactgtg tttgctgacg caaccccac tggttggggc   7800 attgccacca cctgtcagct cctttccggg actttcgctt tccccctccc tattgccacg   7860
gcggaactca tcgccgcctg ccttgcccgc tgctggacag ggctcggct gttgggcact   7920 gacaattccg tggtgttgtc ggggaaatca tcgtcctttc cttggctgct cgcctgtgtt   7980
gccacctgga ttctgcgcgg gacgtccttc tgctacgtcc cttcggccct caatccagcg   8040
gaccttcctt cccgcggcct gctgccggct ctgcggcctc ttccgcgtct tcgccttcgc   8100
cctcagacga gtcggatctc cctttgggcc gcctccccgc atcgataccg tcgacctcga   8160
```

```
gacctagaaa aacatggagc aatcacaagt agcaatacag cagctaccaa tgctgattgt    8220
gcctggctag aagcacaaga ggaggaggag gtgggttttc cagtcacacc tcaggtacct    8280
ttaagaccaa tgacttacaa ggcagctgta gatcttagcc acttttaaa agaaaagggg    8340 ggactggaag ggctaattca ctcccaacga agacaagata tccttgatct gtggatctac    8400
cacacacaag gctacttccc tgattggcag aactacacac cagggccagg atcagatat    8460 ccactgacct ttggatggtg ctacaagcta gtaccagttg agcaagagaa ggtagaagaa    8520
gccaatgaag gagagaacac ccgcttgtta caccctgtga gcctgcatgg gatggatgac    8580
ccggagagag aagtattaga gtggaggttt gacagccgcc tagcatttca tcacatggcc    8640
cgagagctgc atccggactg tactgggtct ctctggttag accagatctg agcctgggag    8700
ctctctggct aactagggaa cccactgctt aagcctcaat aaagcttgcc ttgagtgctt    8760
caagtagtgt gtgcccgtct gttgtgtgac tctggtaact agagatccct cagacccttt    8820
tagtcagtgt ggaaaatctc tagcagggcc cgtttaaacc cgctgatcag cctcgactgt    8880
gccttctagt tgccagccat ctgttgtttg cccctccccc gtgccttcct tgaccctgga    8940
aggtgccact cccactgtcc tttcctaata aaatgaggaa attgcatcgc attgtctgag    9000
taggtgtcat tctattctgg ggggtggggt ggggcaggac agcaaggggg aggattggga    9060
agacaatagc aggcatgctg gggatgcggt gggctctatg gcttctgagg cggaaagaac    9120
cagctggggc tctaggggt atccccacgc gccctgtagc ggcgcattaa gcgcggcggg    9180
tgtggtggtt acgcgcagcg tgaccgctac acttgccagc gccctagcgc ccgctccttt    9240
cgctttcttc ccttcctttc tcgccacgtt cgccggcttt ccccgtcaag ctctaaatcg    9300
ggggctccct ttagggttcc gatttagtgc tttacggcac ctcgaccca aaaaacttga    9360 ttagggtgat ggttcacgta gtgggccatc gccctgatag acggtttttc gccctttgac    9420
gttggagtcc acgttcttta atagtggact cttgttccaa actggaacaa cactcaaccc    9480
tatctcggtc tattcttttg atttataagg gattttgccg atttcggcct attggttaaa    9540
aaatgagctg atttaacaaa aatttaacgc gaattaattc tgtggaatgt gtgtcagtta    9600
gggtgtggaa agtccccagg ctccccagca ggcagaagta tgcaaagcat gcatctcaat    9660
tagtcagcaa ccaggtgtgg aaagtcccca ggctccccag caggcagaag tatgcaaagc    9720
atgcatctca attagtcagc aaccatagtc ccgcccctaa ctccgcccat cccgcccta    9780 actccgccca gttccgccca ttctccgccc catggctgac taatttttt tatttatgca    9840 gaggccgagg ccgcctctgc ctctgagcta ttccagaagt agtgaggagg cttttttgga    9900
ggcctaggct tttgcaaaaa gctcccggga gcttgtatat ccattttcgg atctgatcag    9960
cacgtgttga caattaatca tcggcatagt atatcggcat agtataatac gacaaggtga   10020
ggaactaaac catggccaag ttgaccagtg ccgttccggt gctcaccgcg cgcgacgtcg   10080
ccggagcggt cgagttctgg accgaccggc tcgggttctc cgggacttc gtggaggacg   10140 acttcgccgg tgtggtccgg gacgacgtga ccctgttcat cagcgcggtc caggaccagg   10200
tggtgccgga caacccctg gcctgggtgt gggtgcgcgg cctggacgag ctgtacgccg   10260
agtggtcgga ggtcgtgtcc acgaacttcc gggacgcctc cggccggcc atgaccgaga   10320 tcggcgagca gccgtggggg cgggagttcg ccctgcgcga cccggccggc aactgcgtgc   10380
acttcgtggc cgaggagcag gactgacacg tgctacgaga tttcgattcc accgccgcct   10440
tctatgaaag gttgggcttc ggaatcgttt tccgggacgc cggctggatg atcctccagc   10500
```

-continued

```
gcggggatct catgctggag ttcttcgccc accccaactt gtttattgca gcttataatg    10560
gttacaaata aagcaatagc atcacaaatt tcacaaataa agcattttt tcactgcatt     10620
ctagttgtgg tttgtccaaa ctcatcaatg tatcttatca tgtctgtata ccgtcgacct    10680
ctagctagag cttggcgtaa tcatggtcat agctgtttcc tgtgtgaaat tgttatccgc    10740
tcacaattcc acacaacata cgagccggaa gcataaagtg taaagcctgg ggtgcctaat    10800
gagtgagcta actcacatta attgcgttgc gctcactgcc cgctttccag tcgggaaacc    10860
tgtcgtgcca gctgcattaa tgaatcggcc aacgcgcggg gagaggcggt ttgcgtattg    10920
ggcgctcttc cgcttcctcg ctcactgact cgctgcgctc ggtcgttcgg ctgcggcgag    10980
cggtatcagc tcactcaaag gcggtaatac ggttatccac agaatcaggg gataacgcag    11040
gaaagaacat gtgagcaaaa ggccagcaaa aggccaggaa ccgtaaaaag gccgcgttgc    11100
tggcgttttt ccataggctc cgcccccctg acgagcatca caaaaatcga cgctcaagtc    11160
agaggtggcg aaacccgaca ggactataaa gataccaggc gtttccccct ggaagctccc    11220
tcgtgcgctc tcctgttccg accctgccgc ttaccggata cctgtccgcc tttctccctt    11280
cgggaagcgt ggcgctttct catagctcac gctgtaggta tctcagttcg gtgtaggtcg    11340
ttcgctccaa gctgggctgt gtgcacgaac cccccgttca gcccgaccgc tgcgccttat    11400
ccggtaacta tcgtcttgag tccaacccgg taagacacga cttatcgcca ctggcagcag    11460
ccactggtaa caggattagc agagcgaggt atgtaggcgg tgctacagag ttcttgaagt    11520
ggtggcctaa ctacggctac actagaagaa cagtatttgg tatctgcgct ctgctgaagc    11580
cagttacctt cggaaaaaga gttggtagct cttgatccgg caaacaaacc accgctggta    11640
gcggtggttt ttttgtttgc aagcagcaga ttacgcgcag aaaaaaagga tctcaagaag    11700
atcctttgat cttttctacg gggtctgacg ctcagtggaa cgaaaactca cgttaaggga    11760
ttttggtcat gagattatca aaaaggatct tcacctagat ccttttaaat taaaaatgaa    11820
gttttaaatc aatctaaagt atatatgagt aaacttggtc tgacagttac caatgcttaa    11880
tcagtgaggc acctatctca gcgatctgtc tatttcgttc atccatagtt gcctgactcc    11940
ccgtcgtgta gataactacg atacgggagg gcttaccatc tggccccagt gctgcaatga    12000
taccgcgaga cccacgctca ccggctccag atttatcagc aataaaccag ccagccggaa    12060
gggccgagcg cagaagtggt cctgcaactt tatccgcctc catccagtct attaattgtt    12120
gccgggaagc tagagtaagt agttcgccag ttaatagttt gcgcaacgtt gttgccattg    12180
ctacaggcat cgtggtgtca cgctcgtcgt ttggtatggc ttcattcagc tccggttccc    12240
aacgatcaag gcgagttaca tgatccccca tgttgtgcaa aaaagcggtt agctccttcg    12300
gtcctccgat cgttgtcaga agtaagttgg ccgcagtgtt atcactcatg gttatggcag    12360
cactgcataa ttctcttact gtcatgccat ccgtaagatg cttttctgtg actggtgagt    12420
actcaaccaa gtcattctga atagtgta tgcggcgacc gagttgctct tgcccggcgt      12480
caatacggga taataccgcg ccacatagca gaactttaaa agtgctcatc attggaaaac    12540
gttcttcggg gcgaaaactc tcaaggatct taccgctgtt gagatccagt tcgatgtaac    12600
ccactcgtgc acccaactga tcttcagcat cttttacttt caccagcgtt tctgggtgag    12660
caaaaacagg aaggcaaaat gccgcaaaaa agggaataag ggcgacacgg aaatgttgaa    12720
tactcatact cttcctttt caatattatt gaagcattta tcagggttat tgtctcatga    12780
gcggatacat atttgaatgt atttagaaaa ataaacaaat aggggttccg cgcacatttc    12840
cccgaaaagt gccacctgac                                                12860
```

<210> SEQ ID NO 5
<211> LENGTH: 10477
<212> TYPE: DNA
<213> ORGANISM: Artificial Sequence
<220> FEATURE:
<223> OTHER INFORMATION: dCas9 (A catalytically inactive Cas9 or dCas9-repressor peptide fusion can be used to knock-down gene expression by interfering with transcription of the gene). Addgene #44246

<400> SEQUENCE: 5

| | | | | | |
|---|---|---|---|---|---|
| tgaaagaccc | cacctgtagg | tttggcaagc | tagcttaagt | aacgccattt tgcaaggcat | 60 |
| ggaaaataca | taactgagaa | tagagaagtt | cagatcaagg | ttaggaacag agagacagca | 120 |
| gaatatgggc | caaacaggat | atctgtggta | agcagttcct | gccccggctc agggccaaga | 180 |
| acagatggtc | cccagatgcg | gtcccgccct | cagcagtttc | tagagaacca tcagatgttt | 240 |
| ccagggtgcc | ccaaggacct | gaaatgaccc | tgtgccttat | ttgaactaac caatcagttc | 300 |
| gcttctcgct | tctgttcgcg | cgcttctgct | ccccgagctc | aataaaagag cccacaaccc | 360 |
| ctcactcggc | gcgccagtcc | tccgatagac | tgcgtcgccc | gggtacccgt attcccaata | 420 |
| aagcctcttg | ctgtttgcat | ccgaatcgtg | gactcgctga | tccttgggag gtctcctca | 480 |
| gattgattga | ctgcccacct | cgggggtctt | tcatttggag | gttccaccga gatttggaga | 540 |
| ccctgccca | gggaccaccg | acccccccgc | cgggaggtaa | gctggccagc ggtcgtttcg | 600 |
| tgtctgtctc | tgtctttgtg | cgtgtttgtg | ccggcatcta | atgtttgcgc ctgcgtctgt | 660 |
| actagttagc | taactagctc | tgtatctggc | ggacccgtgg | tggaactgac gagttctgaa | 720 |
| cacccggccg | caaccctggg | agacgtccca | gggactttgg | gggccgtttt tgtggcccga | 780 |
| cctgaggaag | ggagtcgatg | tggaatccga | ccccgtcagg | atatgtggtt ctggtaggag | 840 |
| acgagaacct | aaaacagttc | ccgcctccgt | ctgaattttt | gctttcggtt tggaaccgaa | 900 |
| gccgcgcgtc | ttgtctgctg | cagcgctgca | gcatcgttct | gtgttgtctc tgtctgactg | 960 |
| tgtttctgta | tttgtctgaa | aattagggcc | agactgttac | cactcccctta agtttgacct | 1020 |
| taggtcactg | gaaagatgtc | gagcggatcg | ctcacaacca | gtcggtagat gtcaagaaga | 1080 |
| gacgttgggt | taccttctgc | tctgcagaat | ggccaacctt | taacgtcgga tggccgcgag | 1140 |
| acggcacctt | taaccgagac | ctcatcaccc | aggttaagat | caaggtcttt tcacctggcc | 1200 |
| cgcatggaca | cccagaccag | gtcccctaca | tcgtgacctg | ggaagccttg gcttttgacc | 1260 |
| cccctccctg | ggtcaagccc | tttgtacacc | ctaagcctcc gcctcctctt cctccatccg | 1320 |
| ccccgtctct | cccccttgaa | cctcctcgtt | cgacccccgcc | tcgatcctcc ctttatccag | 1380 |
| ccctcactcc | ttctctaggc | gccggaatta | gatctcgcca | ccatggacaa gaagtattct | 1440 |
| atcggactgg | ccatcgggac | taatagcgtc | gggtgggccg | tgatcactga cgagtacaag | 1500 |
| gtgccctcta | agaagttcaa | ggtgctcggg | aacaccgacc | ggcattccat caagaaaaat | 1560 |
| ctgatcggag | ctctcctctt | tgattcaggg | gagaccgctg | aagcaacccg cctcaagcgg | 1620 |
| actgctagac | ggcggtacac | caggaggaag | aaccggattt | gttaccttca agagatattc | 1680 |
| tccaacgaaa | tggcaaaggt | cgacgacagc | ttcttccata | ggctgaagga atcattcctc | 1740 |
| gtggaagagg | ataagaagca | tgaacggcat | cccatcttcg | gtaatatcgt cgacgaggtg | 1800 |
| gcctatcacg | agaaataccc | aaccatctac | catcttcgca | aaaagctggt ggactcaacc | 1860 |
| gacaaggcag | acctccggct | tatctacctg | gccctggccc | acatgatcaa gttcagaggc | 1920 |
| cacttcctga | tcgagggcga | cctcaatcct | gacaatagcg | atgtggataa actgttcatc | 1980 |

```
cagctggtgc agacttacaa ccagctcttt gaagagaacc ccatcaatgc aagcggagtc    2040
gatgccaagg ccattctgtc agcccggctg tcaaagagcc gcagacttga gaatcttatc    2100
gctcagctgc cgggtgaaaa gaaaaatgga ctgttcggga acctgattgc tctttcactt    2160
gggctgactc ccaatttcaa gtctaatttc gacctggcag aggatgccaa gctgcaactg    2220
tccaaggaca cctatgatga cgatctcgac aacctcctgg cccagatcgg tgaccaatac    2280
gccgaccttt tccttgctgc taagaatctt tctgacgcca cctgctgtc tgacattctc    2340 cgcgtgaaca ctgaaatcac caaggcccct ctttcagctt caatgattaa gcggtatgat    2400
gagcaccacc aggacctgac cctgcttaag gcactcgtcc ggcagcagct tccggagaag    2460
tacaaggaaa tcttctttga ccagtcaaag aatggatacg ccggctacat cgacggaggt    2520
gcctcccaag aggaatttta taagtttatc aaacctatcc ttgagaagat ggacggcacc    2580
gaagagctcc tcgtgaaact gaatcgggag gatctgctgc ggaagcagcg cactttcgac    2640
aatgggagca ttccccacca gatccatctt ggggagcttc acgccatcct tcggcgccaa    2700
gaggacttct accccttcct taaggacaac agggagaaga ttgagaaaat tctcactttc    2760
cgcatcccct actacgtggg acccctcgcc agaggaaata gccggtttgc ttggatgacc    2820
agaaagtcag aagaaactat cactccctgg aacttcgaag aggtggtgga caagggagcc    2880
agcgctcagt cattcatcga acggatgact aacttcgata agaacctccc caatgagaag    2940
gtcctgccga acattccct gctctacgag tactttaccg tgtacaacga gctgaccaag    3000
gtgaaatatg tcaccgaagg gatgaggaag cccgcattcc tgtcaggcga acaaaagaag    3060
gcaattgtgg accttctgtt caagaccaat agaaaggtga ccgtgaagca gctgaaggag    3120
gactatttca gaaaaattga atgcttcgac tctgtggaga ttagcgggt cgaagatcgg    3180 ttcaacgcaa gcctgggtac ctaccatgat ctgcttaaga tcatcaagga caaggatttt    3240
ctggacaatg aggagaacga ggacatcctt gaggacattg tcctgactct cactctgttc    3300
gaggaccggg aaatgatcga ggagaggctt aagacctacg cccatctgtt cgacgataaa    3360
gtgatgaagc aacttaaacg gagaagatat accggatggg gacgccttag ccgcaaactc    3420
atcaacggaa tccgggacaa acagagcgga aagaccattc ttgatttcct taagagcgac    3480
ggattcgcta atcgcaactt catgcaactt atccatgatg attccctgac ctttaaggag    3540
gacatccaga aggcccaagt gtctggacaa ggtgactcac tgcacgagca tatcgcaaat    3600
ctggctggtt cacccgctat taagaagggt attctccaga ccgtgaaagt cgtggacgag    3660
ctggtcaagg tgatgggtcg ccataaacca gagaacattg tcatcgagat ggccagggaa    3720
aaccagacta cccagaaggg acagaagaac agcagggagc ggatgaaaag aattgaggaa    3780
gggattaagg agctcgggtc acagatcctt aaagagcacc cggtggaaaa cacccagctt    3840
cagaatgaga agctctatct gtactacctt caaaatggac gcgatatgta tgtggaccaa    3900
gagcttgata tcaacaggct ctcagactac gacgtggacg ccatcgtccc tcagagcttc    3960
ctcaaagacg actcaattga caataaggtg ctgactcgct cagacaagaa ccggggaaag    4020
tcagataacg tgccctcaga ggaagtcgtg aaaaagatga aaaactattg gcgccagctt    4080
ctgaacgcaa agctgatcac tcagcggaag ttcgacaatc tcactaaggc tgagagggc    4140 ggactgagcg aactggacaa agcaggattc attaaacggc aacttgtgga gactcggcag    4200
attactaaac atgtcgccca aatccttgac tcacgcatga ataccaagta cgacgaaaac    4260
gacaaactta tccgcgaggt gaaggtgatt accctgaagt ccaagctggt cagcgatttc    4320
```

```
agaaaggact ttcaattcta caaagtgcgg gagatcaata actatcatca tgctcatgac    4380
gcatatctga atgccgtggt gggaaccgcc ctgatcaaga agtacccaaa gctggaaagc    4440
gagttcgtgt acggagacta caaggtctac gacgtgcgca agatgattgc caaatctgag    4500
caggagatcg gaaaggccac cgcaaagtac ttcttctaca gcaacatcat gaatttcttc    4560
aagaccgaaa tcacccttgc aaacggtgag atccggaaga ggccgctcat cgagactaat    4620
ggggagactg gcgaaatcgt gtgggacaag ggcagagatt tcgctaccgt gcgcaaagtg    4680
ctttctatgc ctcaagtgaa catcgtgaag aaaaccgagg tgcaaaccgg aggcttttct    4740
aaggaatcaa tcctccccaa gcgcaactcc gacaagctca ttgcaaggaa gaaggattgg    4800
gaccctaaga agtacggcgg attcgattca ccaactgtgg cttattctgt cctggtcgtg    4860
gctaaggtgg aaaaaggaaa gtctaagaag ctcaagagcg tgaaggaact gctgggtatc    4920
accattatgg agcgcagctc cttcgagaag aacccaattg actttctcga agccaaaggt    4980
tacaaggaag tcaagaagga ccttatcatc aagctcccaa agtatagcct gttcgaactg    5040
gagaatgggc ggaagcggat gctcgcctcc gctggcgaac ttcagaaggg taatgagctg    5100
gctctcccct ccaagtacgt gaatttcctc taccttgcaa gccattacga gaagctgaag    5160
gggagccccg aggacaacga gcaaaagcaa ctgtttgtgg agcagcataa gcattatctg    5220
gacgagatca ttgagcagat ttccgagttt tctaaacgcg tcattctcgc tgatgccaac    5280
ctcgataaag tccttagcgc atacaataag cacagagaca aaccaattcg ggagcaggct    5340
gagaatatca tccacctgtt caccctcacc aatcttggtg cccctgccgc attcaagtac    5400
ttcgacacca ccatcgaccg gaaacgctat acctccacca agaagtgct ggacgccacc     5460 ctcatccacc agagcatcac cggactttac gaaactcgga ttgacctctc acagctcgga    5520
ggggatgagg gagctgatcc aaaaaagaag agaaaggtag atccaaaaaa gaagagaaag    5580
gtagatccaa aaagaagag aaaggtatag aattctaccg ggtaggggag gcgcttttcc     5640
caaggcagtc tggagcatgc gctttagcag ccccgctggg cacttggcgc tacacaagtg    5700
gcctctggcc tcgcacacat tccacatcca ccggtaggcg ccaaccggct ccgttctttg    5760
gtggcccctt cgcgccacct tctactcctc ccctagtcag gaagttcccc cccgccccgc    5820
agctcgcgtc gtgcaggacg tgacaaatgg aagtagcacg tctcactagt ctcgtgcaga    5880
tggacagcac cgctgagcaa tggaagcggg taggcctttg gggcagcggc caatagcagc    5940
tttgctcctt cgctttctgg gctcagaggc tgggaagggg tgggtccggg ggcgggctca    6000
ggggcgggct caggggcggg gcgggcgccc gaaggtcctc cggaggcccg gcattctgca    6060
cgcttcaaaa gcgcacgtct gccgcgctgt tctcctcttc ctcatctccg ggcctttcga    6120
cctgcagccc aagcttacca tgaccgagta caagcccacg gtgcgcctcg ccacccgcga    6180
cgacgtcccc agggccgtac gcaccctcgc cgccgcgttc gccgactacc ccgccacgcg    6240
ccacaccgtc gatccggacc gccacatcga gcgggtcacc gagctgcaag aactcttcct    6300
cacgcgcgtc gggctcgaca tcggcaaggt gtgggtcgcg gacgacggcg ccgcggtggc    6360
ggtctggacc acgccggaga gcgtcgaagc gggggcggtg ttcgccgaga tcggcccgcg    6420
catggccgag ttgagcggtt ccggctggcc gcgcagcaa cagatggaag gcctcctggc     6480
gccgcaccgg cccaaggagc ccgcgtggtt cctggccacc gtcggcgtct cgcccgacca    6540
ccagggcaag gtctgggcag gcgccgtcgt gctccccgga gtggaggcgg ccagcgcgc     6600 cggggtgccc gccttcctgg agacctccgc gccccgcaac ctccccttct acgagcggct    6660
cggcttcacc gtcaccgccg acgtcgaggt gcccgaagga ccgcgcacct ggtgcatgac    6720
```

```
ccgcaagccc ggtgcctgac gcccgcccca cgacccgcag cgcccgaccg aaaggagcgc    6780
acgaccccat gcatcgataa aataaaagat tttatttagt ctccagaaaa aggggggaat    6840
gaaagacccc acctgtaggt ttggcaagct agcttaagta acgccatttt gcaaggcatg    6900
gaaaatacat aactgagaat agagaagttc agatcaaggt taggaacaga gagacagcag    6960
aatatgggcc aaacaggata tctgtggtaa gcagttcctg ccccggctca gggccaagaa    7020
cagatggtcc ccagatgcgg tcccgccctc agcagtttct agagaaccat cagatgtttc    7080
cagggtgccc caaggacctg aaatgaccct gtgccttatt tgaactaacc aatcagttcg    7140
cttctcgctt ctgttcgcgc gcttctgctc cccgagctca ataaaagagc ccacaacccc    7200
tcactcggcg cgccagtcct ccgatagact gcgtcgcccg ggtacccgtg tatccaataa    7260
accctcttgc agttgcatcc gacttgtggt ctcgctgttc cttgggaggg tctcctctga    7320
gtgattgact acccgtcagc gggggtcttt catgggtaac agtttcttga agttggagaa    7380
caacattctg agggtaggag tcgaatatta agtaatcctg actcaattag ccactgtttt    7440
gaatccacat actccaatac tcctgaaata gttcattatg gacagcgcag aagagctggg    7500
gagaattaat tcgtaatcat ggtcatagct gtttcctgtg tgaaattgtt atccgctcac    7560
aattccacac aacatacgag ccggaagcat aaagtgtaaa gcctggggtg cctaatgagt    7620
gagctaactc acattaattg cgttgcgctc actgcccgct ttccagtcgg gaaacctgtc    7680
gtgccagctg cattaatgaa tcggccaacg cgcggggaga ggcggtttgc gtattgggcg    7740
ctcttccgct tcctcgctca ctgactcgct gcgctcggtc gttcggctgc ggcgagcggt    7800
atcagctcac tcaaaggcgg taatacggtt atccacagaa tcaggggata acgcaggaaa    7860
gaacatgtga gcaaaaggcc agcaaaaggc caggaaccgt aaaaaggccg cgttgctggc    7920 gttttccat aggctccgcc cccctgacga gcatcacaaa aatcgacgct caagtcagag    7980
gtggcgaaac ccgacaggac tataaagata ccaggcgttt ccccctggaa gctccctcgt    8040
gcgctctcct gttccgaccc tgccgcttac cggatacctg tccgcctttc tcccttcggg    8100
aagcgtggcg ctttctcata gctcacgctg taggtatctc agttcggtgt aggtcgttcg    8160
ctccaagctg ggctgtgtgc acgaaccccc cgttcagccc gaccgctgcg ccttatccgg    8220
taactatcgt cttgagtcca acccggtaag acacgactta tcgccactgg cagcagccac    8280
tggtaacagg attagcagag cgaggtatgt aggcggtgct acagagttct tgaagtggtg    8340
gcctaactac ggctacacta aggacagt atttggtatc tgcgctctgc tgaagccagt     8400
taccttcgga aaaagagttg gtagctcttg atccggcaaa caaaccaccg ctggtagcgg    8460 tggtttttt gtttgcaagc agcagattac gcgcagaaaa aaaggatctc aagaagatcc     8520
tttgatcttt tctacggggt ctgacgctca gtggaacgaa aactcacgtt aagggatttt    8580
ggtcatgaga ttatcaaaaa ggatcttcac ctagatcctt ttaaattaaa aatgaagttt    8640
taaatcaatc taaagtatat atgagtaaac ttggtctgac agttaccaat gcttaatcag    8700
tgaggcacct atctcagcga tctgtctatt tcgttcatcc atagttgcct gactccccgt    8760
cgtgtagata actacgatac gggagggctt accatctggc cccagtgctg caatgatacc    8820
gcgagaccca cgctcaccgg ctccagattt atcagcaata aaccagccag ccggaagggc    8880
cgagcgcaga agtggtcctg caactttatc cgcctccatc cagtctatta attgttgccg    8940
ggaagctaga gtaagtagtt cgccagttaa tagtttcgc aacgttgttg ccattgctac     9000
aggcatcgtg gtgtcacgct cgtcgtttgg tatggcttca ttcagctccg gttcccaacg    9060
```

```
atcaaggcga gttacatgat cccccatgtt gtgcaaaaaa gcggttagct ccttcggtcc    9120
tccgatcgtt gtcagaagta agttggccgc agtgttatca ctcatggtta tggcagcact    9180
gcataattct cttactgtca tgccatccgt aagatgcttt tctgtgactg gtgagtactc    9240
aaccaagtca ttctgagaat agtgtatgcg gcgaccgagt tgctcttgcc cggcgtcaat    9300
acgggataat accgcgccac atagcagaac tttaaaagtg ctcatcattg gaaaacgttc    9360
ttcggggcga aaactctcaa ggatcttacc gctgttgaga tccagttcga tgtaacccac    9420
tcgtgcaccc aactgatctt cagcatcttt tactttcacc agcgtttctg ggtgagcaaa    9480
aacaggaagg caaaatgccg caaaaaaggg aataagggcg acacggaaat gttgaatact    9540
catactcttc ctttttcaat attattgaag catttatcag ggttattgtc tcatgagcgg    9600
atacatattt gaatgtattt agaaaaataa acaaataggg gttccgcgca catttccccg    9660
aaaagtgcca cctgacgtct aagaaaccat tattatcatg acattaacct ataaaaatag    9720
gcgtatcacg aggccctttc gtctcgcgcg tttcggtgat gacggtgaaa acctctgaca    9780
catgcagctc ccggagacgg tcacagcttg tctgtaagcg gatgccggga gcagacaagc    9840
ccgtcagggc gcgtcagcgg gtgttggcgg gtgtcggggc tggcttaact atgcggcatc    9900
agagcagatt gtactgagag tgcaccatat gcggtgtgaa ataccgcaca gatgcgtaag    9960
gagaaaatac cgcatcaggc gccattcgcc attcaggctg cgcaactgtt gggaagggcg   10020
atcggtgcgg gcctcttcgc tattacgcca gctggcgaaa gggggatgtg ctgcaaggcg   10080
attaagttgg gtaacgccag ggttttccca gtcacgacgt tgtaaaacga cggcgcaagg   10140
aatggtgcat gcaaggagat ggcgcccaac agtcccccgg ccacgggcc tgccaccata    10200 cccacgccga acaagcgct catgagcccg aagtggcgag cccgatcttc cccatcggtg    10260
atgtcggcga tataggcgcc agcaaccgca cctgtggcgc cggtgatgcc ggccacgatg   10320
cgtccggcgt agaggcgatt agtccaattt gttaaagaca ggatatcagt ggtccaggct   10380
ctagttttga ctcaacaata tcaccagctg aagcctatag agtacgagcc atagataaaa   10440
taaaagattt tatttagtct ccagaaaaag gggggaa                            10477
```

<210> SEQ ID NO 6
<211> LENGTH: 14382
<212> TYPE: DNA
<213> ORGANISM: Artificial Sequence
<220> FEATURE:
<223> OTHER INFORMATION: dCAS9-VP64 activator, Addgene #61422

<400> SEQUENCE: 6

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg     360 accccgccc attgacgtca ataatgacgt atgttcccat agtaacgcca atagggactt     420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
```

```
ttgactcacg gggatttcca agtctccacc ccattgacgt caatgggagt ttgttttggc    720
accaaaatca acgggacttt ccaaaatgtc gtaacaactc cgccccattg acgcaaatgg    780
gcggtaggcg tgtacggtgg gaggtctata taagcagcgc gttttgcctg tactgggtct    840
ctctggttag accagatctg agcctggagc tctctggcta actagggaac ccactgctt    900
aagcctcaat aaagcttgcc ttgagtgctt caagtagtgt gtgcccgtct gttgtgtgac    960
tctggtaact agagatccct cagacccttt tagtcagtgt ggaaaatctc tagcagtggc   1020
gcccgaacag ggacttgaaa gcgaaaggga accagagga gctctctcga cgcaggactc   1080
ggcttgctga agcgcgcacg gcaagaggcg aggggcggcg actggtgagt acgccaaaaa   1140
ttttgactag cggaggctag aaggagagag atgggtgcga gagcgtcagt attaagcggg   1200
ggagaattag atcgcgatgg gaaaaaattc ggttaaggcc agggggaaag aaaaaatata   1260
aattaaaaca tatagtatgg gcaagcaggg agctagaacg attcgcagtt aatcctggcc   1320
tgttagaaac atcagaaggc tgtagacaaa tactgggaca gctacaacca tcccttcaga   1380
caggatcaga agaacttaga tcattatata atacagtagc aaccctctat tgtgtgcatc   1440
aaaggataga gataaaagac accaaggaag ctttagacaa gatagaggaa gagcaaaaca   1500
aaagtaagac caccgcacag caagcggccg ctgatcttca gacctggagg aggagatatg   1560
agggacaatt ggagaagtga attatataaa tataaagtag taaaaattga accattagga   1620
gtagcaccca ccaaggcaaa gagaagagtg gtgcagagag aaaaaagagc agtgggaata   1680
ggagcttttgt tccttgggtt cttgggagca gcaggaagca ctatgggcgc agcgtcaatg   1740
acgctgacgg tacaggccag acaattattg tctggtatag tgcagcagca gaacaatttg   1800
ctgagggcta ttgaggcgca acagcatctg ttgcaactca cagtctgggg catcaagcag   1860
ctccaggcaa gaatcctggc tgtggaaaga tacctaaagg atcaacagct cctggggatt   1920
tggggttgct ctggaaaact catttgcacc actgctgtgc cttggaatgc tagttggagt   1980
aataaatctc tggaacagat ttggaatcac acgacctgga tggagtggga cagagaaatt   2040
aacaattaca caagcttaat acactcctta attgaagaat cgcaaaacca gcaagaaaag   2100
aatgaacaag aattattgga attagataaa tgggcaagtt tgtggaattg gtttaacata   2160
acaaattggc tgtggtatat aaaattattc ataatgatag taggaggctt ggtaggttta   2220
agaatagttt ttgctgtact ttctatagtg aatagagtta ggcagggata ttcaccatta   2280
tcgtttcaga cccacctccc aaccccgagg ggacccgaca ggcccgaagg aatagaagaa   2340
gaaggtggag agagagacag agacagatcc attcgattag tgaacggatc ggcactgcgt   2400
gcgccaattc tgcagacaaa tggcagtatt catccacaat tttaaaagaa aagggggga t   2460
tgggggggtac agtgcagggg aaagaatagt agacataata gcaacagaca tacaaactaa   2520
agaattacaa aaacaaatta caaaaattca aaattttcgg gtttattaca gggacagcag   2580
agatccagtt tggttaatta atgcaaagat ggataaagtt ttaaacagag aggaatcttt   2640
gcagctaatg gaccttctag gtcttgaaag gagtgggaat tggctccggt gcccgtcagt   2700
gggcagagcg cacatcgccc acagtccccg agaagttggg gggaggggtc ggcaattgaa   2760
ccggtgccta gagaaggtgg cgcggggtaa actgggaaag tgatgtcgtg tactggctcc   2820
gcctttttcc cgagggtggg ggagaaccgt atataagtgc agtagtcgcc gtgaacgttc   2880
ttttcgcaa cgggtttgcc gccagaacac aggtaagtgc cgtgtgtggt tcccgcgggc   2940
ctggcctctt tacgggttat ggcccttgcg tgccttgaat tacttccact ggctgcagta   3000
```

```
cgtgattctt gatcccgagc ttcgggttgg aagtgggtgg gagagttcga ggccttgcgc    3060
ttaaggagcc ccttcgcctc gtgcttgagt tgaggcctgg cctgggcgct ggggccgccg    3120
cgtgcgaatc tggtggcacc ttcgcgcctg tctcgctgct ttcgataagt ctctagccat    3180
ttaaaatttt tgatgacctg ctgcgacgct ttttttctgg caagatagtc ttgtaaatgc    3240
gggccaagat ctgcacactg gtatttcggt ttttggggcc gcgggcggcg acggggcccg    3300
tgcgtcccag cgcacatgtt cggcgaggcg gggcctgcga gcgcggccac cgagaatcgg    3360 acggggtag  tctcaagctg gccggcctgc tctggtgcct ggcctcgcgc cgccgtgtat    3420
cgccccgccc tgggcggcaa ggctggcccg gtcggcacca gttgcgtgag cggaaagatg    3480
gccgcttccc ggccctgctg cagggagctc aaaatggagg acgcggcgct cgggagagcg    3540
ggcgggtgag tcacccacac aaaggaaaag ggcctttccg tcctcagccg tcgcttcatg    3600
tgactccacg gagtaccggg cgccgtccag gcacctcgat tagttctcga gcttttggag    3660
tacgtcgtct ttaggttggg gggaggggtt ttatgcgatg gagtttcccc acactgagtg    3720
ggtggagact gaagttaggc cagcttggca cttgatgtaa ttctccttgg aatttgccct    3780
ttttgagttt ggatcttggt tcattctcaa gcctcagaca gtggttcaaa gttttttct    3840 tccatttcag gtgtcgtgac gtacggccac catgagcccc aagaagaaga gaaggtgga    3900 ggccagcgac aagaagtaca gcatcggcct ggccatcggc accaactctg tgggctgggc    3960
cgtgatcacc gacgagtaca aggtgcccag caagaaattc aaggtgctgg gcaacaccga    4020
ccggcacagc atcaagaaga acctgatcgg agccctgctg ttcgacagcg gcgaaacagc    4080
cgaggccacc cggctgaaga gaaccgccag aagaagatac accagacgga gaaccggat    4140 ctgctatctg caagagatct tcagcaacga gatggccaag gtggacgaca gcttcttcca    4200
cagactggaa gagtccttcc tggtggaaga ggataagaag cacgagcggc acccccatctt    4260 cggcaacatc gtggacgagg tggcctacca cgagaagtac cccaccatct accacctgag    4320
aaagaaactg gtggacagca ccgacaaggc cgacctgcgg ctgatctatc tggccctggc    4380
ccacatgatc aagttccggg gccacttcct gatcgagggc gacctgaacc ccgacaacag    4440
cgacgtggac aagctgttca tccagctggt gcagacctac aaccagctgt tcgaggaaaa    4500
ccccatcaac gccagcggcg tggacgccaa ggccatcctg tctgccagac tgagcaagag    4560
cagacgactg gaaaatctga tcgcccagct gcccggcgag aagaagaatg gcctgttcgg    4620
caacctgatt gccctgagcc tgggcctgac ccccaacttc aagagcaact tcgacctggc    4680
cgaggatgcc aaactgcagc tgagcaagga cacctacgac gacgacctgg acaacctgct    4740
ggcccagatc ggcgaccagt acgccgacct gtttctggcc gccaagaacc tgtccgacgc    4800
catcctgctg agcgacatcc tgagagtgaa caccgagatc accaaggccc ccctgagcgc    4860
ctctatgatc aagagatacg acgagcacca ccaggacctg accctgctga agctctcgt    4920 gcggcagcag ctgcctgaga agtacaaaga gatttttctc gaccagagca agaacggcta    4980
cgccggctac attgacggcg gagccagcca ggaagagttc tacaagttca tcaagcccat    5040
cctggaaaag atggacggca ccgaggaact gctcgtgaag ctgaacagag aggacctgct    5100
gcggaagcag cggaccttcg acaacggcag catcccccac cagatccacc tgggagagct    5160
gcacgccatt ctgcggcggc aggaagattt ttacccattc ctgaaggaca ccgggaaaa    5220 gatcgagaag atcctgacct tccgcatccc ctactacgtg ggccctctgg ccaggggaaa    5280
cagcagattc gcctgatga ccagaaagag cgaggaaacc atcacccct ggaacttcga    5340 ggaagtggtg gacaagggcg cttccgccca gagcttcatc gagcggatga ccaacttcga    5400
```

```
taagaacctg cccaacgaga aggtgctgcc caagcacagc ctgctgtacg agtacttcac   5460
cgtgtataac gagctgacca aagtgaaata cgtgaccgag ggaatgagaa agcccgcctt   5520
cctgagcggc gagcagaaaa aggccatcgt ggacctgctg ttcaagacca accggaaagt   5580
gaccgtgaag cagctgaaag aggactactt caagaaaatc gagtgcttcg actccgtgga   5640
aatctccggc gtggaagatc ggttcaacgc ctccctgggc acataccacg atctgctgaa   5700
aattatcaag gacaaggact tcctggacaa tgaggaaaac gaggacattc tggaagatat   5760
cgtgctgacc ctgacactgt tgaggacag agagatgatc gaggaacggc tgaaaaccta   5820
tgcccacctg ttcgacgaca aagtgatgaa gcagctgaag cggcggagat acaccggctg   5880
gggcaggctg agccggaagc tgatcaacgg catccgggac aagcagtccg gcaagacaat   5940
cctggatttc ctgaagtccg acggcttcgc caacagaaac ttcatgcagc tgatccacga   6000
cgacagcctg accttttaaag aggacatcca gaaagcccag gtgtccggcc agggcgatag   6060
cctgcacgag cacattgcca atctggccgg cagccccgcc attaagaagg gcatcctgca   6120
gacagtgaag gtggtggacg agctcgtgaa agtgatgggc cggcacaagc ccgagaacat   6180
cgtgatcgaa atggccagag agaaccgac cacccagaag ggacagaaga acagccgcga   6240
gagaatgaag cggatcgaag agggcatcaa agagctgggc agccagatcc tgaaagaaca   6300
ccccgtggaa acacccagc tgcagaacga gaagctgtac ctgtactacc tgcagaatgg   6360
gcgggatatg tacgtggacc aggaactgga catcaaccgg ctgtccgact acgatgtgga   6420
cgctatcgtg cctcagagct ttctgaagga cgactccatc gacaacaagg tgctgaccag   6480
aagcgacaag aaccggggca gagcgacaa cgtgccctcc aagaggtcg tgaagaagat   6540 gaagaactac tggcggcagc tgctgaacgc caagctgatt acccagagaa agttcgacaa   6600
tctgaccaag gccgagagag cggcctgag cgaactggat aaggccggct tcatcaagag   6660
acagctggtg gaaaccccggc agatcacaaa gcacgtggca cagatcctgg actcccggat   6720
gaacactaag tacgacgaga atgacaagct gatccgggaa gtgaaagtga tcaccctgaa   6780
gtccaagctg gtgtccgatt ccggaaggga tttccagttt tacaaagtgc gcgagatcaa   6840
caactaccac cacgcccacg acgcctacct gaacgccgtc gtgggaaccg ccctgatcaa   6900
aaagtaccct aagctggaaa gcgagttcgt gtacggcgac tacaaggtgt acgacgtgcg   6960
gaagatgatc gccaagagcg agcaggaaat cggcaaggct accgccaagt acttcttcta   7020
cagcaacatc atgaactttt tcaagaccga gattaccctg gccaacggcg agatccggaa   7080
gcggcctctg atcgagacaa acggcgaaac cggggagatc gtgtgggata agggccggga   7140
ttttgccacc gtgcggaaag tgctgagcat gccccaagtg aatatcgtga aaaagaccga   7200
ggtgcagaca ggcggcttca gcaaagagtc tatcctgccc aagaggaaca gcgataagct   7260
gatcgccaga aagaaggact gggaccctaa gaagtacggc ggcttcgaca gccccaccgt   7320
ggcctattct gtgctggtgg tggccaaagt ggaaaagggc aagtccaaga actgaagag   7380 tgtgaaagag ctgctgggga tcaccatcat ggaaagaagc agcttcgaga gaatcccat   7440 cgactttctg gaagccaagg gctacaaaga agtgaaaaag gacctgatca tcaagctgcc   7500
taagtactcc ctgttcgagc tggaaaacgg ccggaagaga atgctggcct ctgcggcga   7560 actgcagaag ggaaacgaac tggccctgcc ctccaaatat gtgaacttcc tgtacctggc   7620
cagccactat gagaagctga agggctcccc cgaggataat gagcagaaac agctgtttgt   7680
ggaacagcac aagcactacc tggacgagat catcgagcag atcagcgagt ctccaagag   7740
```

```
agtgatcctg gccgacgcta atctggacaa agtgctgtcc gcctacaaca agcaccggga    7800
taagcccatc agagagcagg ccgagaatat catccacctg tttaccctga ccaatctggg    7860
agcccctgcc gccttcaagt actttgacac caccatcgac cggaagaggt acaccagcac    7920
caaagaggtg ctggacgcca ccctgatcca ccagagcatc accggcctgt acgagacacg    7980
gatcgacctg tctcagctgg aggcgacag cgctggagga ggtggaagcg gaggaggagg    8040
aagcggagga ggaggtagcg gacctaagaa aaagaggaag gtggcggccg ctggatccgg    8100
acgggctgac gcattggacg attttgatct ggatatgctg ggaagtgacg ccctcgatga    8160
ttttgacctt gacatgcttg gttcggatgc ccttgatgac tttgacctcg acatgctcgg    8220
cagtgacgcc cttgatgatt tcgacctgga catgctgatt aacgctagcg gcagtggaga    8280
gggcagagga agtctgctaa catgcggtga cgtcgaggag aatcctggcc cagtgagcaa    8340
gggcgaggag ctgttcaccg gggtggtgcc catcctggtc gagctggacg gcgacgtaaa    8400
cggccacaag ttcagcgtgt ccggcgaggg cgagggcgat gccacctacg gcaagctgac    8460
cctgaagttc atctgcacca ccggcaagct gcccgtgccc tggcccaccc tcgtgaccac    8520
cctgacctac ggcgtgcagt gcttcagccg ctaccccgac cacatgaagc agcacgactt    8580
cttcaagtcc gccatgcccg aaggctacgt ccaggagcgc accatcttct tcaaggacga    8640
cggcaactac aagacccgcg ccgaggtgaa gttcgagggc gacaccctgg tgaaccgcat    8700
cgagctgaag ggcatcgact tcaaggagga cggcaacatc ctggggcaca gctggagta    8760 caactacaac agccacaacg tctatatcat ggccgacaag cagaagaacg gcatcaaggt    8820
gaacttcaag atccgccaca acatcgagga cggcagcgtg cagctcgccg accactacca    8880
gcagaacacc cccatcggcg acggccccgt gctgctgccc gacaaccact acctgagcac    8940
ccagtccgcc ctgagcaaag accccaacga gaagcgcgat cacatggtcc tgctggagtt    9000
cgtgaccgcc gccgggatca ctctcggcat ggacgagctg tacaagtaag aattcgatat    9060
caagcttatc gataatcaac ctctggatta caaaatttgt gaaagattga ctggtattct    9120
taactatgtt gctcctttta cgctatgtgg atacgctgct ttaatgcctt tgtatcatgc    9180
tattgcttcc cgtatggctt tcattttctc ctccttgtat aaatcctggt tgctgtctct    9240
ttatgaggag ttgtggcccg ttgtcaggca acgtggcgtg gtgtgcactg tgtttgctga    9300 cgcaacccc actggttggg gcattgccac cacctgtcag ctcctttccg ggactttcgc    9360
tttccccctc cctattgcca cggcggaact catcgccgcc tgccttgccc gctgctggac    9420
aggggctcgg ctgttgggca ctgacaattc cgtggtgttg tcggggaaat catcgtcctt    9480
tccttggctg ctcgcctgtg ttgccacctg gattctgcgc gggacgtcct tctgctacgt    9540
cccttcggcc ctcaatccag cggaccttcc ttcccgcggc ctgctgccgg ctctgcggcc    9600
tcttccgcgt cttcgccttc gccctcagac gagtcggatc tccctttggg ccgcctcccc    9660
gcatcgatac cgtcgacctc gagacctaga aaaacatgga gcaatcacaa gtagcaatac    9720
agcagctacc aatgctgatt gtgcctggct agaagcacaa gaggaggagg aggtgggttt    9780
tccagtcaca cctcaggtac ctttaagacc aatgacttac aaggcagctg tagatcttag    9840
ccacttttta aaagaaaagg ggggactgga agggctaatt cactcccaac gaagacaaga    9900
tatccttgat ctgtggatct accacacaca aggctacttc cctgattggc agaactacac    9960
accagggcca gggatcagat atccactgac ctttggatgg tgctacaagc tagtaccagt   10020
tgagcaagag aaggtagaag aagccaatga aggagagaac acccgcttgt tacaccctgt   10080
gagcctgcat gggatggatg acccggagag agaagtatta gagtggaggt ttgacagccg   10140
```

```
cctagcattt catcacatgg cccgagagct gcatccggac tgtactgggt ctctctggtt    10200
agaccagatc tgagcctggg agctctctgg ctaactaggg aacccactgc ttaagcctca    10260
ataaagcttg ccttgagtgc ttcaagtagt gtgtgcccgt ctgttgtgtg actctggtaa    10320
ctagagatcc ctcagaccct tttagtcagt gtggaaaatc tctagcaggg cccgtttaaa    10380
cccgctgatc agcctcgact gtgccttcta gttgccagcc atctgttgtt tgcccctccc    10440
ccgtgccttc cttgaccctg gaaggtgcca ctcccactgt cctttcctaa taaaatgagg    10500
aaattgcatc gcattgtctg agtaggtgtc attctattct gggggtgggg gtggggcagg    10560
acagcaaggg ggaggattgg gaagacaata gcaggcatgc tggggatgcg gtgggctcta    10620
tggcttctga ggcggaaaga accagctggg gctctagggg gtatccccac gcgccctgta    10680
gcggcgcatt aagcgcggcg ggtgtggtgg ttacgcgcag cgtgaccgct acacttgcca    10740
gcgccctagc gcccgctcct ttcgctttct tcccttcctt tctcgccacg ttcgccggct    10800
ttccccgtca agctctaaat cggggggctcc ctttagggtt ccgatttagt gctttacggc    10860
acctcgaccc caaaaaactt gattagggtg atggttcacg tagtgggcca tcgccctgat    10920
agacggtttt tcgccctttg acgttggagt ccacgttctt taatagtgga ctcttgttcc    10980
aaactggaac aacactcaac cctatctcgg tctattcttt tgatttataa gggattttgc    11040
cgatttcggc ctattggtta aaaaatgagc tgatttaaca aaaatttaac gcgaattaat    11100
tctgtggaat gtgtgtcagt tagggtgtgg aaagtcccca ggctcccag caggcagaag    11160 tatgcaaagc atgcatctca attagtcagc aaccaggtgt ggaaagtccc caggctcccc    11220
agcaggcaga agtatgcaaa gcatgcatct caattagtca gcaaccatag tcccgcccct    11280
aactccgccc atcccgcccc taactccgcc cagttccgcc cattctccgc cccatggctg    11340
actaattttt tttatttatg cagaggccga ggccgcctct gcctctgagc tattccagaa    11400
gtagtgagga ggcttttttg gaggcctagg cttttgcaaa aagctcccgg gagcttgtat    11460
atccattttc ggatctgatc agcacgtgtt gacaattaat catcggcata gtatatcggc    11520
atagtataat acgacaaggt gaggaactaa accatggcca agttgaccag tgccgttccg    11580
gtgctcaccg cgcgcgacgt cgccggagcg gtcgagttct ggaccgaccg gctcgggttc    11640
tcccgggact tcgtggagga cgacttcgcc ggtgtggtcc gggacgacgt gaccctgttc    11700
atcagcgcgg tccaggacca ggtggtgccg gacaacaccc tggcctgggt gtgggtgcgc    11760
ggcctggacg agctgtacgc cgagtggtcg gaggtcgtgt ccacgaactt ccgggacgcc    11820
tccgggccgg ccatgaccga gatcggcgag cagccgtggg ggcgggagtt cgccctgcgc    11880
gacccggccg gcaactgcgt gcacttcgtg gccgaggagc aggactgaca cgtgctacga    11940
gatttcgatt ccaccgccgc cttctatgaa aggttgggct tcggaatcgt tttccgggac    12000
gccggctgga tgatcctcca gcgcggggat ctcatgctgg agttcttcgc ccaccccaac    12060
ttgtttattg cagcttataa tggttacaaa taaagcaata gcatcacaaa tttcacaaat    12120
aaagcatttt tttcactgca ttctagttgt ggtttgtcca aactcatcaa tgtatcttat    12180
catgtctgta taccgtcgac ctctagctag agcttggcgt aatcatggtc atagctgttt    12240
cctgtgtgaa attgttatcc gctcacaatt ccacacaaca tacgagccgg aagcataaag    12300
tgtaaagcct ggggtgccta atgagtgagc taactcacat taattgcgtt gcgctcactg    12360
cccgctttcc agtcgggaaa cctgtcgtgc cagctgcatt aatgaatcgg ccaacgcgcg    12420
gggagaggcg gtttgcgtat tgggcgctct tccgcttcct cgctcactga ctcgctgcgc    12480
```

```
tcggtcgttc ggctgcggcg agcggtatca gctcactcaa aggcggtaat acggttatcc   12540
acagaatcag gggataacgc aggaaagaac atgtgagcaa aaggccagca aaaggccagg   12600
aaccgtaaaa aggccgcgtt gctggcgttt ttccataggc tccgcccccc tgacgagcat   12660
cacaaaaatc gacgctcaag tcagaggtgg cgaaacccga caggactata agataccagg   12720
cgtttccccc ctggaagctc cctcgtgcgc tctcctgttc cgaccctgcc gcttaccgga   12780
tacctgtccg cctttctccc ttcgggaagc gtggcgcttt ctcatagctc acgctgtagg   12840
tatctcagtt cggtgtaggt cgttcgctcc aagctgggct gtgtgcacga accccccgtt   12900
cagcccgacc gctgcgcctt atccggtaac tatcgtcttg agtccaaccc ggtaagacac   12960
gacttatcgc cactggcagc agccactggt aacaggatta gcagagcgag gtatgtaggc   13020
ggtgctacag agttcttgaa gtggtggcct aactacggct acactagaag aacagtattt   13080
ggtatctgcg ctctgctgaa gccagttacc ttcggaaaaa gagttggtag ctcttgatcc   13140
ggcaaacaaa ccaccgctgg tagcggtggt ttttttgttt gcaagcagca gattacgcgc   13200
agaaaaaaag gatctcaaga agatcctttg atcttttcta cggggtctga cgctcagtgg   13260
aacgaaaact cacgttaagg gattttggtc atgagattat caaaaaggat cttcacctag   13320
atccttttaa attaaaaatg aagttttaaa tcaatctaaa gtatatatga gtaaacttgg   13380
tctgacagtt accaatgctt aatcagtgag gcacctatct cagcgatctg tctatttcgt   13440
tcatccatag ttgcctgact ccccgtcgtg tagataacta cgatacggga gggcttacca   13500
tctggcccca gtgctgcaat gataccgcga gacccacgct caccggctcc agatttatca   13560
gcaataaacc agccagccgg aagggccgag cgcagaagtg gtcctgcaac tttatccgcc   13620
tccatccagt ctattaattg ttgccgggaa gctagagtaa gtagttcgcc agttaatagt   13680
ttgcgcaacg ttgttgccat tgctacaggc atcgtggtgt cacgctcgtc gtttggtatg   13740
gcttcattca gctccggttc ccaacgatca aggcgagtta catgatcccc catgttgtgc   13800
aaaaaagcgg ttagctcctt cggtcctccg atcgttgtca gaagtaagtt ggccgcagtg   13860
ttatcactca tggttatggc agcactgcat aattctctta ctgtcatgcc atccgtaaga   13920
tgcttttctg tgactggtga gtactcaacc aagtcattct gagaatagtg tatgcggcga   13980
ccgagttgct cttgcccggc gtcaatacgg gataataccg cgccacatag cagaacttta   14040
aaagtgctca tcattggaaa acgttcttcg gggcgaaaac tctcaaggat cttaccgctg   14100
ttgagatcca gttcgatgta acccactcgt gcacccaact gatcttcagc atcttttact   14160
ttcaccagcg tttctgggtg agcaaaaaca ggaaggcaaa atgccgcaaa aaagggaata   14220
agggcgacac ggaaatgttg aatactcata ctcttccttt ttcaatatta ttgaagcatt   14280
tatcagggtt attgtctcat gagcggatac atatttgaat gtatttagaa aaataaacaa   14340
ataggggttc cgcgcacatt tccccgaaaa gtgccacctg ac                       14382

<210> SEQ ID NO 7
<211> LENGTH: 4952
<212> TYPE: DNA
<213> ORGANISM: Artificial Sequence
<220> FEATURE:
<223> OTHER INFORMATION: gRNA Addgene #51133

<400> SEQUENCE: 7
ggtaccgatt agtgaacgga tctcgacggt atcgatcacg agactagcct cgagcggccg     60 ccccccttcac cgagggccta tttcccatga ttccttcata tttgcatata cgatacaagg   120
ctgttagaga gataattgga attaatttga ctgtaaacac aaagatatta gtacaaaata   180
```

-continued

```
cgtgacgtag aaagtaataa tttcttgggt agtttgcagt tttaaaatta tgtttaaaa      240 tggactatca tatgcttacc gtaacttgaa agtatttcga tttcttggct ttatatatct      300
tgtggaaagg acgaaacacc ggtgagaccg agagagggtc tcagttttag agctagaaat      360
agcaagttaa aataaggcta gtccgttatc aacttgaaaa agtggcaccg agtcggtgct      420 tttttttaaag aattctcgac ctcgagacaa atggcagtat tcatccacaa ttttaaaaga    480
aaagggggga ttggggggta cagtgcaggg gaaagaatag tagacataat agcaacagac    540
atacaaacta aagaattaca aaaacaaatt acaaaaattc aaaattttcg ggtttattac    600
agggacagca gagatccact ttggccgcgg ctcgaggggg ttggggttgc gccttttcca    660
aggcagccct gggtttgcgc agggacgcgg ctgctctggg cgtggttccg ggaaacgcag    720
cggcgccgac cctgggactc gcacattctt cacgtccgtt cgcagcgtca cccgatctt    780 cgccgctacc cttgtgggcc cccggcgac gcttcctgct ccgcccctaa gtcgggaagg    840
ttccttgcgg ttcgcggcgt gccggacgtg acaaacggaa gccgcacgtc tcactagtac    900
cctcgcagac ggacagcgcc agggagcaat ggcagcgcgc cgaccgcgat gggctgtggc    960
caatagcggt tgctcagcag ggcgcgccga gagcagcggc cggaaggggg cggtgcggga    1020
ggcggggtgt ggggcggtag tgtgggccct gttcctgccc gcgcggtgtt ccgcattctg    1080
caagcctccg gagcgcacgt cggcagtcgg ctccctcgtt gaccgaatca ccgacctctc    1140
tccccagggg gatccaccgg agcttaccat gaccgagtac aagcccacgg tgcgcctcgc    1200
cacccgcgac gacgtcccca gggccgtacg caccctcgcc gccgcgttcg ccgactaccc    1260
cgccacgcgc cacaccgtcg atccggaccg ccacatcgag cgggtcaccg agctgcaaga    1320
actcttcctc acgcgcgtcg ggctcgacat cggcaaggtg tgggtcgcgg acgacggcgc    1380
cgcggtggcg gtctggacca cgccggagag cgtcgaagcg ggggcggtgt cgccgagat    1440 cggcccgcgc atggccgagt tgagcggttc ccggctggcc gcgcagcaac agatggaagg    1500
cctcctggcg ccgcaccggc ccaaggagcc cgcgtggttc ctggccaccg tcggcgtctc    1560
gcccgaccac cagggcaagg gtctgggcag cgccgtcgtg ctccccggag tggaggcggc    1620
cgagcgcgcc ggggtgcccg ccttcctgga aacctccgcg ccccgcaacc tcccttcta    1680 cgagcggctc ggcttcaccg tcaccgccga cgtcgaggtg cccgaaggac gcgcacctg    1740 gtgcatgacc cgcaagcccg tgcctgacg cccgccccac gacccgcagc gcccgaccga    1800
aaggagcgca cgaccccatg catcggtacc tttaagacca atgacttaca aggcagctgt    1860
agatcttagc cactttctag agtcggggcg gccggccgct tcgagcagac atgataagat    1920
acattgatga gtttggacaa accacaacta gaatgcagtg aaaaaaatgc tttatttgtg    1980
aaatttgtga tgctattgct ttatttgtaa ccattataag ctgcaataaa caagttaaca    2040
acaacaattg cattcatttt atgtttcagg ttcaggggga ggtgtgggag gttttttaaa    2100
gcaagtaaaa cctctacaaa tgtggtaaaa tcgataagga tccgtcgacc gatgcccttg    2160
agagccttca acccagtcag ctccttccgg tgggcgcggg gcatgactat cgtcgccgca    2220
cttatgactg tcttctttat catgcaactc gtaggacagg tgccggcagc gctcttccgc    2280
ttcctcgctc actgactcgc tgcgctcggt cgttcggctg cggcgagcgg tatcagctca    2340
ctcaaaggcg gtaatacggt tatccacaga atcagggat aacgcaggaa agaacatgtg    2400
agcaaaaggc cagcaaaagg ccaggaaccg taaaaaggcc gcgttgctgg cgttttccca    2460
taggctccgc ccccctgacg agcatcacaa aaatcgacgc tcaagtcaga ggtggcgaaa    2520
```

```
cccgacagga ctataaagat accaggcgtt tccccctgga agctccctcg tgcgctctcc    2580
tgttccgacc ctgccgctta ccggatacct gtccgccttt ctcccttcgg aagcgtggc    2640 gctttctcaa tgctcacgct gtaggtatct cagttcggtg taggtcgttc gctccaagct    2700
gggctgtgtg cacgaacccc ccgttcagcc cgaccgctgc gccttatccg gtaactatcg    2760
tcttgagtcc aacccggtaa gacacgactt atcgccactg gcagcagcca ctggtaacag    2820
gattagcaga gcgaggtatg taggcggtgc tacagagttc ttgaagtggt ggcctaacta    2880
cggctacact agaaggacag tatttggtat ctgcgctctg ctgaagccag ttaccttcgg    2940
aaaaagagtt ggtagctctt gatccggcaa acaaaccacc gctggtagcg gtggtttttt    3000
tgtttgcaag cagcagatta cgcgcagaaa aaaggatct caagaagatc ctttgatctt    3060
ttctacgggg tctgacgctc agtggaacga aaactcacgt taagggattt tggtcatgag    3120
attatcaaaa aggatcttca cctagatcct tttaaattaa aaatgaagtt ttaaatcaat    3180
ctaaagtata tatgagtaaa cttggtctga cagttaccaa tgcttaatca gtgaggcacc    3240
tatctcagcg atctgtctat ttcgttcatc catagttgcc tgactccccg tcgtgtagat    3300
aactacgata cgggagggct taccatctgg ccccagtgct gcaatgatac cgcgggaccc    3360
acgctcaccg gctccagatt tatcagcaat aaaccagcca gccggaaggg ccgagcgcag    3420
aagtggtcct gcaactttat ccgcctccat ccagtctatt aattgttgcc gggaagctag    3480
agtaagtagt tcgccagtta atagtttgcg caacgttgtt gccattgcta caggcatcgt    3540
ggtgtcacgc tcgtcgtttg gtatggcttc attcagctcc ggttcccaac gatcaaggcg    3600
agttacatga tcccccatgt tgtgcaaaaa agcggttagc tccttcggtc ctccgatcgt    3660
tgtcagaagt aagttggccg cagtgttatc actcatggtt atggcagcac tgcataattc    3720
tcttactgtc atgccatccg taagatgctt ttctgtgact ggtgagtact caaccaagtc    3780
attctgagaa tagtgtatgc ggcgaccgag ttgctcttgc ccggcgtcaa tacgggataa    3840
taccgcgcca catagcagaa ctttaaaagt gctcatcatt ggaaaacgtt cttcggggcg    3900
aaaactctca aggatcttac cgctgttgag atccagttcg atgtaaccca ctcgtgcacc    3960
caactgatct tcagcatctt ttactttcac cagcgtttct gggtgagcaa aaacaggaag    4020
gcaaaatgcc gcaaaaaagg aataagggc gacacggaaa tgttgaatac tcatactctt    4080
cctttttcaa tattattgaa gcatttatca gggttattgt ctcatgagcg gatacatatt    4140
tgaatgtatt tagaaaaata aacaataggg gttccgcgc acatttcccc gaaaagtgcc    4200
acctgacgcg ccctgtagcg gcgcattaag cgcggcgggt gtggtggtta cgcgcagcgt    4260
gaccgctaca cttgccagcg ccctagcgcc cgctcctttc gctttcttcc cttcctttct    4320
cgccacgttc gccggctttc cccgtcaagc tctaaatcgg gggctccctt tagggttccg    4380
atttagtgct ttacggcacc tcgaccccaa aaaacttgat tagggtgatg gttcacgtag    4440
tgggccatcg ccctgataga cggtttttcg ccctttgacg ttggagtcca cgttctttaa    4500
tagtggactc ttgttccaaa ctggaacaac actcaaccct atctcggtct attctttga    4560 tttataaggg attttgccga tttcggccta ttggttaaaa aatgagctga tttaacaaaa    4620
atttaacgcg aattttaaca aaatattaac gtttacaatt tcccattcgc cattcaggct    4680
gcgcaactgt tgggaagggc gatcggtgcg ggcctcttcg ctattacgcc agcccaagct    4740
accatgataa gtaagtaata ttaaggtacg gaggtactt ggagcggccg caataaaata    4800
tctttatttt cattacatct gtgtgttggt ttttgtgtg aatcgatagt actaacatac    4860
gctctccatc aaaacaaaac gaaacaaaac aaactagcaa aataggctgt ccccagtgca    4920
```

```
agtgcaggtg ccagaacatt tctctatcga ta                                   4952
```

<210> SEQ ID NO 8
<211> LENGTH: 9996
<212> TYPE: DNA
<213> ORGANISM: Artificial Sequence
<220> FEATURE:
<223> OTHER INFORMATION: gRNA-MS2 sequence. Addgene #61427

<400> SEQUENCE: 8

```
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg     360
accccgccc attgacgtca ataatgacgt atgttcccat agtaacgcca atagggactt      420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc      1080
ggcttgctga agcgcgcacg gcaagaggcg aggggcggcg actggtgagt acgccaaaaa    1140
ttttgactag cggaggctag aaggagagag atgggtgcga gagcgtcagt attaagcggg    1200
ggagaattag atcgcgatgg gaaaaaattc ggttaaggcc agggggaaag aaaaaatata    1260
aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctgggattt    1920
tggggttgct ctggaaaact catttgcacc actgctgtgc cttggaatgc tagttggagt    1980
```

```
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta gctagcgagg gcctatttcc catgattcct tcatatttgc    2640
atatacgata caaggctgtt agagagataa ttgaattaa tttgactgta aacacaaaga    2700
tattagtaca aaatacgtga cgtagaaagt aataatttct tgggtagttt gcagttttaa    2760
aattatgttt taaaatggac tatcatatgc ttaccgtaac ttgaaagtat ttcgatttct    2820
tggctttata tatcttgtgg aaaggacgaa acaccgagga cgggataccg tctctgtttt    2880
agagctaggc caacatgagg atcacccatg tctgcagggc ctagcaagtt aaaataaggc    2940
tagtccgtta tcaacttggc caacatgagg atcacccatg tctgcagggc caagtggcac    3000
cgagtcggtg cttttttttgg atcctgcaaa gatggataaa gttttaaaca gagaggaatc    3060
tttgcagcta atggaccttc taggtcttga aaggagtggg aattggctcc ggtgcccgtc    3120
agtgggcaga gcgcacatcg cccacagtcc ccgagaagtt gggggggaggg gtcggcaatt    3180 gatccggtgc ctagagaagg tggcgcgggg taaactggga aagtgatgtc gtgtactggc    3240
tccgcctttt tcccgagggt gggggagaac cgtatataag tgcagtagtc gccgtgaacg    3300 ttcttttttcg caacgggttt gccgccagaa cacaggtaag tgccgtgtgt ggttcccgcg    3360
ggcctggcct ctttacgggt tatggccctt gcgtgccttg aattacttcc actggctgca    3420
gtacgtgatt cttgatcccg agcttcgggt tggaagtggg tgggagagtt cgaggccttg    3480
cgcttaagga gccccttcgc ctcgtgcttg agttgaggcc tggcctgggc gctggggccg    3540
ccgcgtgcga atctggtggc accttcgcgc ctgtctcgct gctttcgata agtctctagc    3600
catttaaaat ttttgatgac ctgctgcgac gcttttttc tggcaagata gtcttgtaaa    3660
tgcgggccaa gatctgcaca ctggtatttc ggttttttggg gccgcgggcg gcgacggggc    3720
ccgtgcgtcc cagcgcacat gttcggcgag gcggggcctg cgagcgcggc caccgagaat    3780
cggacggggg tagtctcaag ctggccggcc tgctctggtg cctggcctcg cgccgccgtg    3840
tatcgccccg ccctgggcgg caaggctggc ccggtcggca ccagttgcgt gagcggaaag    3900
atggccgctt cccggccctg ctgcaggag ctcaaaatgg aggacgcggc gctcgggaga    3960
gcgggcgggt gagtcaccca cacaaaggaa aagggccttt ccgtcctcag ccgtcgcttc    4020
atgtgactcc acggagtacc gggcgccgtc caggcacctc gattagttct cgagcttttg    4080
gagtacgtcg tctttaggtt ggggggaggg gttttatgcg atggagtttc cccacactga    4140
gtgggtggag actgaagtta ggccagcttg gcacttgatg taattctcct tggaatttgc    4200 ccttttttgag tttggatctt ggttcattct caagcctcag acagtggttc aaagtttttt    4260
tcttccattt caggtgtcgt gatgtacaat ggccaagttg accagtgccg ttccggtgct    4320
caccgcgcgc gacgtcgccg gagcggtcga gttctggacc gaccggctcg ggttctcccg    4380
```

```
ggacttcgtg gaggacgact tcgccggtgt ggtccgggac gacgtgaccc tgttcatcag    4440
cgcggtccag gaccaggtgg tgccggacaa caccctggcc tgggtgtggg tgcgcggcct    4500
ggacgagctg tacgccgagt ggtcggaggt cgtgtccacg aacttccggg acgcctccgg    4560
gccggccatg accgagatcg gcgagcagcc gtggggcgg gagttcgccc tgcgcgaccc    4620
ggccggcaac tgcgtgcact tcgtggccga ggagcaggac tgagaattcg atatcaagct    4680
tatcggtaat caacctctgg attacaaaat ttgtgaaaga ttgactggta ttcttaacta    4740
tgttgctcct tttacgctat gtggatacgc tgctttaatg cctttgtatc atgctattgc    4800
ttcccgtatg gctttcattt tctcctcctt gtataaatcc tggttgctgt ctctttatga    4860
ggagttgtgg cccgttgtca ggcaacgtgg cgtggtgtgc actgtgtttg ctgacgcaac    4920
ccccactggt tggggcattg ccaccacctg tcagctcctt ccgggacttt cgctttccc    4980 cctccctatt gccacggcgg aactcatcgc cgcctgcctt gcccgctgct ggacaggggc    5040
tcggctgttg ggcactgaca attccgtggt gttgtcgggg aaatcatcgt cctttccttg    5100
gctgctcgcc tgtgttgcca cctggattct gcgcgggacg tccttctgct acgtcccttc    5160
ggccctcaat ccagcggacc ttccttcccg cggcctgctg ccggctctgc ggcctcttcc    5220
gcgtcttcgc cttcgccctc agacgagtcg gatctccctt gggccgcct ccccgcatcg    5280 ataccgtcga cctcgagacc tagaaaaaca tggagcaatc acaagtagca atacagcagc    5340
taccaatgct gattgtgcct ggctagaagc acaagaggag gaggaggtgg ttttccagt    5400 cacacctcag gtacctttaa gaccaatgac ttacaaggca gctgtagatc ttagccactt    5460
tttaaaagaa aaggggggac tggaagggct aattcactcc caacgaagac aagatatcct    5520
tgatctgtgg atctaccaca cacaaggcta cttccctgat tggcagaact acacaccagg    5580
gccagggatc agatatccac tgacctttgg atggtgctac aagctagtac cagttgagca    5640
agagaaggta gaagaagcca atgaaggaga gaacacccgc ttgttacacc ctgtgagcct    5700
gcatgggatg gatgacccgg agagagaagt attagagtgg aggtttgaca gccgcctagc    5760
atttcatcac atggcccgag agctgcatcc ggactgtact gggtctctct ggttagacca    5820
gatctgagcc tgggagctct ctggctaact agggaaccca ctgcttaagc ctcaataaag    5880
cttgccttga gtgcttcaag tagtgtgtgc ccgtctgttg tgtgactctg gtaactagag    5940
atccctcaga cccttttagt cagtgtggaa atctctagc agggcccgtt taaacccgct    6000
gatcagcctc gactgtgcct tctagttgcc agccatctgt tgtttgcccc tcccccgtgc    6060
cttccttgac cctggaaggt gccactccca ctgtcctttc ctaataaaat gaggaaattg    6120
catcgcattg tctgagtagg tgtcattcta ttctgggggg tggggtgggg caggacagca    6180
agggggagga ttgggaagac aatagcaggc atgctgggga tgcggtgggc tctatggctt    6240
ctgaggcgga agaaccagc tggggctcta ggggggtatcc ccacgcgccc tgtagcggcg    6300
cattaagcgc ggcgggtgtg gtggttacgc gcagcgtgac cgctacactt gccagcgccc    6360
tagcgcccgc tcctttcgct ttcttccctt cctttctcgc cacgttcgcc ggctttcccc    6420
gtcaagctct aaatcggggg ctccctttag ggttccgatt tagtgcttta cggcacctcg    6480
accccaaaaa acttgattag ggtgatggtt cacgtagtgg gccatcgccc tgatagacgg    6540
tttttcgccc tttgacgttg gagtccacgt tctttaatag tggactcttg ttccaaactg    6600
gaacaacact caaccctatc tcggtctatt cttttgattt ataagggatt ttgccgattt    6660
cggcctattg gttaaaaaat gagctgattt aacaaaaatt taacgcgaat taattctgtg    6720
```

```
gaatgtgtgt cagttagggt gtggaaagtc cccaggctcc ccagcaggca gaagtatgca    6780
aagcatgcat ctcaattagt cagcaaccag gtgtggaaag tccccaggct ccccagcagg    6840
cagaagtatg caaagcatgc atctcaatta gtcagcaacc atagtcccgc ccctaactcc    6900
gcccatcccg cccctaactc cgcccagttc cgcccattct ccgcccatg gctgactaat    6960 ttttttatt tatgcagagg ccgaggccgc ctctgcctct gagctattcc agaagtagtg    7020
aggaggcttt tttggaggcc taggcttttg caaaaagctc ccgggagctt gtatatccat    7080
tttcggatct gatcagcacg tgttgacaat taatcatcgg catagtatat cggcatagta    7140
taatacgaca aggtgaggaa ctaaaccatg gccaagttga ccagtgccgt tccggtgctc    7200
accgcgcgcg acgtcgccgg agcggtcgag ttctggaccg accggctcgg gttctcccgg    7260
gacttcgtgg aggacgactt cgccggtgtg gtccgggacg acgtgaccct gttcatcagc    7320
gcggtccagg accaggtggt gccggacaac accctggcct gggtgtgggt gcgcggcctg    7380
gacgagctgt acgccgagtg gtcggaggtc gtgtccacga acttccggga cgcctccggg    7440
ccggccatga ccgagatcgg cgagcagccg tgggggcggg agttcgccct gcgcgacccg    7500
gccggcaact gcgtgcactt cgtggccgag gagcaggact gacacgtgct acgagatttc    7560
gattccaccg ccgccttcta tgaaaggttg ggcttcggaa tcgttttccg ggacgccggc    7620
tggatgatcc tccagcgcgg ggatctcatg ctggagttct tcgcccaccc caacttgttt    7680
attgcagctt ataatggtta caaataaagc aatagcatca caaatttcac aaataaagca    7740
tttttttcac tgcattctag ttgtggtttg tccaaactca tcaatgtatc ttatcatgtc    7800
tgtataccgt cgacctctag ctagagcttg gcgtaatcat ggtcatagct gtttcctgtg    7860
tgaaattgtt atccgctcac aattccacac aacatacgag ccggaagcat aaagtgtaaa    7920
gcctggggtg cctaatgagt gagctaactc acattaattg cgttgcgctc actgcccgct    7980
ttccagtcgg gaaacctgtc gtgccagctg cattaatgaa tcggccaacg cgcggggaga    8040
ggcggtttgc gtattgggcg ctcttccgct tcctcgctca ctgactcgct gcgctcggtc    8100
gttcggctgc ggcgagcggt atcagctcac tcaaaggcgg taatacggtt atccacagaa    8160 tcagggggata cgcaggaaa gaacatgtga gcaaaaggcc agcaaaaggc caggaaccgt    8220
aaaaaggccg cgttgctggc gtttttccat aggctccgcc ccctgacga gcatcacaaa    8280 aatcgacgct caagtcagag gtggcgaaac ccgacaggac tataaagata ccaggcgttt    8340
ccccctggaa gctccctcgt gcgctctcct gttccgaccc tgccgcttac cggatacctg    8400
tccgcctttc tcccttcggg aagcgtggcg ctttctcata gctcacgctg taggtatctc    8460
agttcggtgt aggtcgttcg ctccaagctg ggctgtgtgc acgaaccccc cgttcagccc    8520
gaccgctgcg ccttatccgg taactatcgt cttgagtcca acccggtaag acacgactta    8580
tcgccactgg cagcagccac tggtaacagg attagcagag cgaggtatgt aggcggtgct    8640
acagagttct tgaagtggtg gcctaactac ggctacacta agaacagt atttggtatc    8700 tgcgctctgc tgaagccagt taccttcgga aaaagagttg gtagctcttg atccggcaaa    8760
caaaccaccg ctggtagcgg tggttttttt gtttgcaagc agcagattac gcgcagaaaa    8820
aaaggatctc aagaagatcc tttgatcttt tctacgggt ctgacgctca gtggaacgaa    8880
aactcacgtt aagggatttt ggtcatgaga ttatcaaaaa ggatcttcac ctagatcctt    8940
ttaaattaaa aatgaagttt taaatcaatc taaagtatat atgagtaaac ttggtctgac    9000
agttaccaat gcttaatcag tgaggcacct atctcagcga tctgtctatt tcgttcatcc    9060
atagttgcct gactccccgt cgtgtagata actacgatac gggagggctt accatctggc    9120
```

```
cccagtgctg caatgatacc gcgagaccca cgctcaccgg ctccagattt atcagcaata    9180
aaccagccag ccggaagggc cgagcgcaga agtggtcctg caactttatc cgcctccatc    9240
cagtctatta attgttgccg ggaagctaga gtaagtagtt cgccagttaa tagtttgcgc    9300
aacgttgttg ccattgctac aggcatcgtg gtgtcacgct cgtcgtttgg tatggcttca    9360
ttcagctccg gttcccaacg atcaaggcga gttacatgat cccccatgtt gtgcaaaaaa    9420
gcggttagct ccttcggtcc tccgatcgtt gtcagaagta agttggccgc agtgttatca    9480
ctcatggtta tggcagcact gcataattct cttactgtca tgccatccgt aagatgcttt    9540
tctgtgactg gtgagtactc aaccaagtca ttctgagaat agtgtatgcg gcgaccgagt    9600
tgctcttgcc cggcgtcaat acgggataat accgcgccac atagcagaac tttaaaagtg    9660
ctcatcattg gaaaacgttc ttcggggcga aaactctcaa ggatcttacc gctgttgaga    9720
tccagttcga tgtaacccac tcgtgcaccc aactgatctt cagcatcttt tactttcacc    9780
agcgtttctg ggtgagcaaa aacaggaagg caaaatgccg caaaaaaggg aataagggcg    9840
acacggaaat gttgaatact catactcttc cttttcaat attattgaag catttatcag    9900
ggttattgtc tcatgagcgg atacatattt gaatgtattt agaaaaataa acaaataggg    9960
gttccgcgca catttccccg aaaagtgcca cctgac                              9996

<210> SEQ ID NO 9
<211> LENGTH: 11409
<212> TYPE: DNA
<213> ORGANISM: Artificial Sequence
<220> FEATURE:
<223> OTHER INFORMATION: MS2-P65-HS1_GFP sequence. Addgene #61427

<400> SEQUENCE: 9
gtcgacggat cgggagatct cccgatcccc tatggtgcac tctcagtaca atctgctctg      60
atgccgcata gttaagccag tatctgctcc ctgcttgtgt gttggaggtc gctgagtagt     120
gcgcgagcaa aatttaagct acaacaaggc aaggcttgac cgacaattgc atgaagaatc     180
tgcttagggt taggcgtttt cgctgcttc gcgatgtacg ggccagatat acgcgttgac      240
attgattatt gactagttat taatagtaat caattacggg gtcattagtt catagcccat     300
atatggagtt ccgcgttaca taacttacgg taaatggccc gcctggctga ccgcccaacg     360 accccgccc attgacgtca ataatgacgt atgttcccat agtaacgcca atagggactt      420
tccattgacg tcaatgggtg gagtatttac ggtaaactgc ccacttggca gtacatcaag     480
tgtatcatat gccaagtacg ccccctattg acgtcaatga cggtaaatgg cccgcctggc     540
attatgccca gtacatgacc ttatgggact ttcctacttg gcagtacatc tacgtattag     600
tcatcgctat taccatggtg atgcggtttt ggcagtacat caatgggcgt ggatagcggt     660
ttgactcacg gggatttcca agtctccacc ccattgacgt caatgggagt ttgttttggc     720
accaaaatca acgggacttt ccaaaatgtc gtaacaactc cgccccattg acgcaaatgg     780
gcggtaggcg tgtacggtgg gaggtctata taagcagcgc gttttgcctg tactgggtct     840
ctctggttag accagatctg agcctgggag ctctctggct aactagggaa cccactgctt     900
aagcctcaat aaagcttgcc ttgagtgctt caagtagtgt gtgcccgtct gttgtgtgac     960
tctggtaact agagatccct cagacccttt tagtcagtgt ggaaaatctc tagcagtggc    1020
gcccgaacag ggacttgaaa gcgaaaggga accagagga gctctctcga cgcaggactc     1080
ggcttgctga agcgcgcacg gcaagaggcg aggggcggcg actggtgagt acgccaaaaa    1140
```

```
ttttgactag cggaggctag aaggagagag atgggtgcga gagcgtcagt attaagcggg    1200
ggagaattag atcgcgatgg gaaaaaattc ggttaaggcc aggggggaaag aaaaaatata   1260 aattaaaaca tatagtatgg gcaagcaggg agctagaacg attcgcagtt aatcctggcc    1320
tgttagaaac atcagaaggc tgtagacaaa tactgggaca gctacaacca tcccttcaga    1380
caggatcaga agaacttaga tcattatata atacagtagc aaccctctat tgtgtgcatc    1440
aaaggataga gataaaagac accaaggaag ctttagacaa gatagaggaa gagcaaaaca    1500
aaagtaagac caccgcacag caagcggccg ctgatcttca gacctggagg aggagatatg    1560
agggacaatt ggagaagtga attatataaa tataaagtag taaaaattga accattagga    1620
gtagcaccca ccaaggcaaa gagaagagtg gtgcagagag aaaaaagagc agtgggaata    1680
ggagctttgt tccttgggtt cttgggagca gcaggaagca ctatgggcgc agcgtcaatg    1740
acgctgacgg tacaggccag acaattattg tctggtatag tgcagcagca gaacaatttg    1800
ctgagggcta ttgaggcgca acagcatctg ttgcaactca cagtctgggg catcaagcag    1860
ctccaggcaa gaatcctggc tgtggaaaga tacctaaagg atcaacagct cctggggatt    1920
tggggttgct ctggaaaact catttgcacc actgctgtgc cttggaatgc tagttggagt    1980
aataaatctc tggaacagat ttggaatcac acgacctgga tggagtggga cagagaaatt    2040
aacaattaca caagcttaat acactcctta attgaagaat cgcaaaacca gcaagaaaag    2100
aatgaacaag aattattgga attagataaa tgggcaagtt tgtggaattg gtttaacata    2160
acaaattggc tgtggtatat aaaattattc ataatgatag taggaggctt ggtaggttta    2220
agaatagttt ttgctgtact ttctatagtg aatagagtta ggcagggata ttcaccatta    2280
tcgtttcaga cccacctccc aaccccgagg ggacccgaca ggcccgaagg aatagaagaa    2340
gaaggtggag agagagacag agacagatcc attcgattag tgaacggatc ggcactgcgt    2400
gcgccaattc tgcagacaaa tggcagtatt catccacaat tttaaaagaa aaggggggat    2460
tggggggtac agtgcagggg aaagaatagt agacataata gcaacagaca tacaaactaa    2520
agaattacaa aaacaaatta caaaaattca aaattttcgg gtttattaca gggacagcag    2580
agatccagtt tggttaatta atgcaaagat ggataaagtt ttaaacagag aggaatcttt    2640
gcagctaatg gaccttctag gtcttgaaag gagtgggaat tggctccggt gcccgtcagt    2700
gggcagagcg cacatcgccc acagtccccg agaagttggg gggaggggtc ggcaattgaa    2760
ccggtgccta gagaaggtgg cgcggggtaa actgggaaag tgatgtcgtg tactggctcc    2820
gcctttttcc cgagggtggg ggagaaccgt atataagtgc agtagtcgcc gtgaacgttc    2880
tttttcgcaa cgggtttgcc gccagaacac aggtaagtgc cgtgtgtggt tcccgcgggc    2940
ctggcctctt tacgggttat ggcccttgcg tgccttgaat tacttccact ggctgcagta    3000
cgtgattctt gatcccgagc ttcgggttgg aagtgggtgg gagagttcga ggccttgcgc    3060
ttaaggagcc ccttcgcctc gtgcttgagt tgaggcctgg cctgggcgct ggggccgccg    3120
cgtgcgaatc tggtggcacc ttcgcgcctg tctcgctgct ttcgataagt ctctagccat    3180 ttaaatttt tgatgacctg ctgcgacgct ttttttctgg caagatagtc ttgtaaatgc    3240
gggccaagat ctgcacactg gtatttcggt ttttggggcc gcgggcggcg acggggcccg    3300
tgcgtcccag cgcacatgtt cggcgaggcg gggcctgcga gcgcggccac cgagaatcgg    3360 acggggggtag tctcaagctg gccggcctgc tctggtgcct ggcctcgcgc cgccgtgtat    3420
cgccccgccc tgggcggcaa ggctggcccg gtcggcacca gttgcgtgag cggaaagatg    3480
gccgcttccc ggccctgctg cagggagctc aaaatggagg acgcggcgct cgggagagcg    3540
```

```
ggcgggtgag tcacccacac aaaggaaaag ggcctttccg tcctcagccg tcgcttcatg    3600
tgactccacg gagtaccggg cgccgtccag gcacctcgat tagttctcga gcttttggag    3660
tacgtcgtct ttaggttggg gggaggggtt ttatgcgatg gagtttcccc acactgagtg    3720
ggtggagact gaagttaggc cagcttggca cttgatgtaa ttctccttgg aatttgccct    3780
ttttgagttt ggatcttggt tcattctcaa gcctcagaca gtggttcaaa gttttttct    3840 tccatttcag gtgtcgtgac gtacggccac catggcttca aactttactc agttcgtgct    3900
cgtggacaat ggtgggacag gggatgtgac agtggctcct tctaatttcg ctaatggggt    3960
ggcagagtgg atcagctcca actcacggag ccaggcctac aaggtgacat gcagcgtcag    4020
gcagtctagt gcccagaaga gaaagtatac catcaaggtg gaggtcccca agtggctac    4080 ccagacagtg ggcggagtcg aactgcctgt cgccgcttgg aggtcctacc tgaacatgga    4140
gctcactatc ccaattttcg ctaccaattc tgactgtgaa ctcatcgtga aggcaatgca    4200
ggggctcctc aaagacggta atcctatccc ttccgccatc gccgctaact caggtatcta    4260
cagcgctgga ggaggtggaa gcggaggagg aggaagcgga ggaggaggta gcggacctaa    4320
gaaaaagagg aaggtggcgg ccgctggatc cccttcaggg cagatcagca accaggccct    4380
ggctctggcc cctagctccg ctccagtgct ggcccagact atggtgccct ctagtgctat    4440
ggtgcctctg gccagccac ctgctccagc ccctgtgctg accccaggac cacccagtc    4500 actgagcgct ccagtgccca gtctacaca ggccggcgag gggactctga gtgaagctct    4560
gctgcacctg cagttcgacg ctgatgagga cctgggagct ctgctgggga acagcaccga    4620
tcccggagtg ttcacagatc tggcctccgt ggacaactct gagtttcagc agctgctgaa    4680
tcagggcgtg tccatgtctc atagtacagc cgaaccaatg ctgatggagt accccgaagc    4740
cattacccgg ctggtgaccg gcagccagcg gcccccgac cccgctccaa ctcccctggg    4800
aaccagcggc ctgcctaatg ggctgtccgg agatgaagac ttctcaagca tcgctgatat    4860
ggactttagt gccctgctgt cacagatttc ctctagtggg cagggaggag gtggaagcgg    4920
cttcagcgtg gacaccagtg ccctgctgga cctgttcagc cctcggtga ccgtgcccga    4980 catgagcctg cctgaccttg acagcagcct ggccagtatc caagagctcc tgtctcccca    5040 ggagccccc aggcctcccg aggcagagaa cagcagcccg gattcaggga agcagctggt    5100
gcactacaca gcgcagccgc tgttcctgct ggaccccggc tccgtggaca ccgggagcaa    5160
cgacctgccg gtgctgtttg agctgggaga gggctcctac ttctccgaag gggacggctt    5220
cgccgaggac cccaccatct ccctgctgac aggctcggag cctcccaaag ccaaggaccc    5280
cactgtctcc gctagcggca gtggagaggg cagaggaagt ctgctaacat gcggtgacgt    5340
cgaggagaat cctggcccag tgagcaaggg cgaggagctg ttcaccgggg tggtgcccat    5400
cctggtcgag ctggacggcg acgtaaacgg ccacaagttc agcgtgtccg gcgagggcga    5460
gggcgatgcc acctacggca agctgaccct gaagttcatc tgcaccaccg gcaagctgcc    5520
cgtgccctgg cccaccctcg tgaccaccct gacctacggc gtgcagtgct tcagccgcta    5580
ccccgaccac atgaagcagc acgacttctt caagtccgcc atgcccgaag gctacgtcca    5640
ggagcgcacc atcttcttca aggacgacgg caactacaag acccgcgccg aggtgaagtt    5700
cgagggcgac accctggtga accgcatcga gctgaagggc atcgacttca aggaggacgg    5760
caacatcctg gggcacaagc tggagtacaa ctacaacagc cacaacgtct atatcatggc    5820
cgacaagcag aagaacggca tcaaggtgaa cttcaagatc cgccacaaca tcgaggacgg    5880
```

```
cagcgtgcag ctcgccgacc actaccagca gaacaccccc atcggcgacg gccccgtgct    5940
gctgcccgac aaccactacc tgagcaccca gtccgccctg agcaaagacc caacgagaa    6000 gcgcgatcac atggtcctgc tggagttcgt gaccgccgcc gggatcactc tcggcatgga    6060
cgagctgtac aagtaagaat tcgatatcaa gcttatcgat aatcaacctc tggattacaa    6120
aatttgtgaa agattgactg gtattcttaa ctatgttgct ccttttacgc tatgtggata    6180
cgctgcttta atgcctttgt atcatgctat tgcttcccgt atggctttca ttttctcctc    6240
cttgtataaa tcctggttgc tgtctcttta tgaggagttg tggcccgttg tcaggcaacg    6300
tggcgtggtg tgcactgtgt ttgctgacgc aacccccact ggttggggca ttgccaccac    6360
ctgtcagctc ctttccggga ctttcgcttt cccctccct attgccacgg cggaactcat    6420
cgccgcctgc cttgcccgct gctggacagg ggctcggctg ttgggcactg acaattccgt    6480
ggtgttgtcg gggaaatcat cgtccttttc cttggctgct gcctgtgttg ccacctggat    6540
tctgcgcggg acgtccttct gctacgtccc ttcggccctc aatccagcgg accttccttc    6600
ccgcggcctg ctgccggctc tgcggcctct tccgcgtctt cgccttcgcc ctcagacgag    6660
tcggatctcc ctttgggccg cctccccgca tcgataccgt cgacctcgag acctagaaaa    6720
acatggagca atcacaagta gcaatacagc agctaccaat gctgattgtg cctggctaga    6780
agcacaagag gaggaggagg tgggttttcc agtcacacct caggtacctt taagaccaat    6840
gacttacaag gcagctgtag atcttagcca cttttttaaaa gaaaaggggg gactggaagg    6900
gctaattcac tcccaacgaa gacaagatat ccttgatctg tggatctacc acacacaagg    6960
ctacttccct gattggcaga actacacacc agggccaggg atcagatatc cactgacctt    7020
tggatggtgc tacaagctag taccagttga gcaagagaag gtagaagaag ccaatgaagg    7080
agagaacacc cgcttgttac accctgtgag cctgcatggg atggatgacc cggagagaga    7140
agtattagag tggaggtttg acagccgcct agcatttcat cacatggccc gagagctgca    7200
tccggactgt actgggtctc tctgttagac cagatctga gcctgggagc tctctggcta    7260
actagggaac ccactgctta agcctcaata aagcttgcct tgagtgcttc aagtagtgtg    7320
tgcccgtctg ttgtgtgact ctggtaacta gagatccctc agacccttt agtcagtgtg    7380 gaaaatctct agcagggccc gtttaaaccc gctgatcagc ctcgactgtg ccttctagtt    7440
gccagccatc tgttgtttgc ccctcccccg tgccttcctt gaccctggaa ggtgccactc    7500
ccactgtcct ttcctaataa aatgaggaaa ttgcatcgca ttgtctgagt aggtgtcatt    7560
ctattctggg gggtgggtg gggcaggaca gcaaggggga ggattgggaa gacaatagca    7620
ggcatgctgg ggatgcggtg ggctctatgg cttctgaggc ggaaagaacc agctggggct    7680
ctagggggta tccccacgcg ccctgtagcg gcgcattaag cgcggcgggt gtggtggtta    7740
cgcgcagcgt gaccgctaca cttgccagcg ccctagcgcc cgctcctttc gctttcttcc    7800
cttcctttct cgccacgttc gccggctttc cccgtcaagc tctaaatcgg ggctccctt    7860 tagggttccg atttagtgct ttacggcacc tcgaccccaa aaaacttgat tagggtgatg    7920
gttcacgtag tgggccatcg ccctgataga cggttttcg cccttttgacg ttggagtcca    7980 cgttctttaa tagtggactc ttgttccaaa ctggaacaac actcaaccct atctcggtct    8040
attcttttga tttataaggg attttgccga tttcggccta ttggttaaaa atgagctga    8100 tttaacaaaa atttaacgcg aattaattct gtggaatgtg tgtcagttag ggtgtggaaa    8160
gtccccaggc tccccagcag gcagaagtat gcaaagcatg catctcaatt agtcagcaac    8220
caggtgtgga aagtccccag gctccccagc aggcagaagt atgcaaagca tgcatctcaa    8280
```

```
ttagtcagca accatagtcc cgcccctaac tccgcccatc ccgcccctaa ctccgcccag   8340
ttccgcccat tctccgcccc atggctgact aattttttt atttatgcag aggccgaggc    8400
cgcctctgcc tctgagctat tccagaagta gtgaggaggc ttttttggag gcctaggctt   8460
ttgcaaaaag ctcccgggag cttgtatatc cattttcgga tctgatcagc acgtgttgac   8520
aattaatcat cggcatagta tatcggcata gtataatacg acaaggtgag gaactaaacc   8580
atggccaagt tgaccagtgc cgttccggtg ctcaccgcgc gcgacgtcgc cggagcggtc   8640
gagttctgga ccgaccggct cgggttctcc cgggacttcg tggaggacga cttcgccggt   8700
gtggtccggg acgacgtgac cctgttcatc agcgcggtcc aggaccaggt ggtgccggac   8760
aacaccctgg cctgggtgtg ggtgcgcggc ctggacgagc tgtacgccga gtggtcggag   8820
gtcgtgtcca cgaacttccg ggacgcctcc gggccggcca tgaccgagat cggcgagcag   8880
ccgtggggc gggagttcgc cctgcgcgac ccggccggca actgcgtgca cttcgtggcc   8940
gaggagcagg actgacacgt gctacgagat ttcgattcca ccgccgcctt ctatgaaagg   9000
ttgggcttcg gaatcgtttt ccgggacgcc ggctggatga tcctccagcg cggggatctc   9060
atgctggagt tcttcgccca ccccaacttg tttattgcag cttataatgg ttacaaataa   9120
agcaatagca tcacaaattt cacaaataaa gcattttttt cactgcattc tagttgtggt   9180
ttgtccaaac tcatcaatgt atcttatcat gtctgtatac cgtcgacctc tagctagagc   9240
ttggcgtaat catggtcata gctgtttcct gtgtgaaatt gttatccgct cacaattcca   9300
cacaacatac gagccggaag cataaagtgt aaagcctggg gtgcctaatg agtgagctaa   9360
ctcacattaa ttgcgttgcg ctcactgccc gctttccagt cgggaaacct gtcgtgccag   9420
ctgcattaat gaatcggcca acgcgcgggg agaggcggtt tgcgtattgg gcgctcttcc   9480
gcttcctcgc tcactgactc gctgcgctcg gtcgttcggc tgcggcgagc ggtatcagct   9540
cactcaaagg cggtaatacg gttatccaca gaatcagggg ataacgcagg aaagaacatg   9600
tgagcaaaag gccagcaaaa ggccaggaac cgtaaaaagg ccgcgttgct ggcgtttttc   9660
cataggctcc gccccctga cgagcatcac aaaaatcgac gctcaagtca gaggtggcga   9720
aacccgacag gactataaag ataccaggcg tttccccctg gaagctccct cgtgcgctct   9780
cctgttccga ccctgccgct taccggatac ctgtccgcct ttctcccttc gggaagcgtg   9840
gcgctttctc atagctcacg ctgtaggtat ctcagttcgg tgtaggtcgt tcgctccaag   9900
ctgggctgtg tgcacgaacc ccccgttcag cccgaccgct gcgccttatc cggtaactat   9960
cgtcttgagt ccaacccggt aagacacgac ttatcgccac tggcagcagc cactggtaac  10020
aggattagca gagcgaggta tgtaggcggt gctacagagt tcttgaagtg gtggcctaac  10080
tacggctaca ctagaagaac agtatttggt atctgcgctc tgctgaagcc agttaccttc  10140
ggaaaaagag ttggtagctc ttgatccggc aaacaaacca ccgctggtag cggtggtttt  10200
tttgtttgca agcagcagat tacgcgcaga aaaaaaggat ctcaagaaga tcctttgatc  10260
ttttctacgg ggtctgacgc tcagtggaac gaaaactcac gttaagggat tttggtcatg  10320
agattatcaa aaaggatctt cacctagatc cttttaaatt aaaaatgaag ttttaaatca  10380
atctaaagta tatatgagta aacttggtct gacagttacc aatgcttaat cagtgaggca  10440
cctatctcag cgatctgtct atttcgttca tccatagttg cctgactccc cgtcgtgtag  10500
ataactacga tacgggaggg cttaccatct ggccccagtg ctgcaatgat accgcgagac  10560
ccacgctcac cggctccaga tttatcagca ataaaccagc cagccggaag ggccgagcgc  10620
```

```
agaagtggtc ctgcaactttt atccgcctcc atccagtcta ttaattgttg ccgggaagct    10680
agagtaagta gttcgccagt taatagtttg cgcaacgttg ttgccattgc tacaggcatc    10740
gtggtgtcac gctcgtcgtt tggtatggct tcattcagct ccggttccca acgatcaagg    10800
cgagttacat gatcccccat gttgtgcaaa aaagcggtta gctccttcgg tcctccgatc    10860
gttgtcagaa gtaagttggc cgcagtgtta tcactcatgg ttatggcagc actgcataat    10920
tctcttactg tcatgccatc cgtaagatgc ttttctgtga ctggtgagta ctcaaccaag    10980
tcattctgag aatagtgtat gcggcgaccg agttgctctt gcccggcgtc aatacgggat    11040
aataccgcgc cacatagcag aactttaaaa gtgctcatca ttggaaaacg ttcttcgggg    11100
cgaaaactct caaggatctt accgctgttg agatccagtt cgatgtaacc cactcgtgca    11160
cccaactgat cttcagcatc ttttactttc accagcgttt ctgggtgagc aaaaacagga    11220
aggcaaaatg ccgcaaaaaa gggaataagg gcgacacgga aatgttgaat actcatactc    11280
ttcctttttc aatattattg aagcatttat cagggttatt gtctcatgag cggatacata    11340
tttgaatgta tttagaaaaa taaacaaata ggggttccgc gcacatttcc ccgaaaagtg    11400
ccacctgac                                                           11409
```

<210> SEQ ID NO 10
<211> LENGTH: 85
<212> TYPE: RNA
<213> ORGANISM: Artificial Sequence
<220> FEATURE:
<223> OTHER INFORMATION: miRBase Accession No.: MI0000471: human miR126
      (stem-loop)

<400> SEQUENCE: 10

```
cgcuggcgac gggacauuau uacuuuuggu acgcgcugug acacuucaaa cucguaccgu    60
gaguaauaau gcgccgucca cggca                                         85
```

<210> SEQ ID NO 11
<211> LENGTH: 88
<212> TYPE: RNA
<213> ORGANISM: Artificial Sequence
<220> FEATURE:
<223> OTHER INFORMATION: miRBase Accession No.: MI0000461: human miR145
      (stem-loop)

<400> SEQUENCE: 11

```
caccuugucc ucacggucca guuucccag gaaucccuua gaugcuaaga uggggauucc    60
uggaaauacu guucuugagg ucaugguu                                      88
```

<210> SEQ ID NO 12
<211> LENGTH: 106
<212> TYPE: RNA
<213> ORGANISM: Artificial Sequence
<220> FEATURE:
<223> OTHER INFORMATION: miRBase Accession No.: MI0000459: human miR143
      (stem-loop)

<400> SEQUENCE: 12

```
gcgcagcgcc cugucuccca gccugaggug cagugcugca ucucugguca guugggaguc    60
ugagaugaag cacuguagcu caggaagaga gaaguuguuc ugcagc                  106
```

<210> SEQ ID NO 13
<211> LENGTH: 85
<212> TYPE: RNA
<213> ORGANISM: Artificial Sequence
<220> FEATURE:

<223> OTHER INFORMATION: miRBase Accession No.: MI0000442 Human miR-122
(stem-loop)

<400> SEQUENCE: 13
ccuuagcaga gcuguggagu gugacaaugg uguuugusuc uaaacuauca aacgccauua    60
ucacacuaaa uagcuacugc uaggc    85

<210> SEQ ID NO 14
<211> LENGTH: 73
<212> TYPE: RNA
<213> ORGANISM: Artificial Sequence
<220> FEATURE:
<223> OTHER INFORMATION: miRBase Accession No.: MI0017383 Human miR-3591
(stem-loop)

<400> SEQUENCE: 14
caguagcuau uuagugugau aauggcguuu gauaguuuag acacaaacac cauugucaca    60
cuccacagcu cug    73

<210> SEQ ID NO 15
<211> LENGTH: 71
<212> TYPE: RNA
<213> ORGANISM: Artificial Sequence
<220> FEATURE:
<223> OTHER INFORMATION: miRBase Accession No.: MI0000251 Human miR-208a
(stem-loop)

<400> SEQUENCE: 15
ugacgggcga gcuuuuggcc cggguuauac cugaugcuca cguauaagac gagcaaaaag    60
cuuguuggus a    71

<210> SEQ ID NO 16
<211> LENGTH: 77
<212> TYPE: RNA
<213> ORGANISM: Artificial Sequence
<220> FEATURE:
<223> OTHER INFORMATION: miRBase Accession No.: MI0005570 Human miR-208b
(stem-loop)

<400> SEQUENCE: 16
ccucucaggg aagcuuuuug cucgaauuau guuucugauc cgaauauaag acgaacaaaa    60
gguuugucug agggcag    77

<210> SEQ ID NO 17
<211> LENGTH: 88
<212> TYPE: RNA
<213> ORGANISM: Artificial Sequence
<220> FEATURE:
<223> OTHER INFORMATION: miRBase Accession No.: MI0000450Human
miR-133a-1 (stem-loop)

<400> SEQUENCE: 17
acaaugcuuu gcuagagcug guaaaaugga accaaaucgc cucuucaaug gauuuggucc    60
ccuucaacca gcuguagcua ugcauuga    88

<210> SEQ ID NO 18
<211> LENGTH: 102
<212> TYPE: RNA
<213> ORGANISM: Artificial Sequence
<220> FEATURE:
<223> OTHER INFORMATION: miRBase Accession No.: MI0000451 Human
miR-133a-2 (stem-loop)

<400> SEQUENCE: 18
gggagccaaa ugcuuugcua gagcuggùaa aauggaacca aaucgacugu ccaauggauu    60 uggucccccuu caaccagcug uagcugugca uugauggcgc cg    102

<210> SEQ ID NO 19
<211> LENGTH: 119
<212> TYPE: RNA
<213> ORGANISM: Artificial Sequence
<220> FEATURE:
<223> OTHER INFORMATION: miRBase Accession No.: MI0000822 Human miR-133b
      (stem-loop)

<400> SEQUENCE: 19
ccucagaaga aagaugcccc cugcucuggc uggucaaacg gaaccaaguc cgucuuccug    60
agagguuugg uccccuucaa ccagcuacag cagggcuggc aaugcccagu ccuuggaga    119

<210> SEQ ID NO 20
<211> LENGTH: 69
<212> TYPE: RNA
<213> ORGANISM: Artificial Sequence
<220> FEATURE:
<223> OTHER INFORMATION: miRBase Accession No.: MI0000738 Human miR-302a
      (stem-loop)

<400> SEQUENCE: 20
ccaccacuua aacguggaug uacuugcuuu gaaacuaaag aaguaagugc uuccauguuu    60
uggugaugg    69

<210> SEQ ID NO 21
<211> LENGTH: 73
<212> TYPE: RNA
<213> ORGANISM: Artificial Sequence
<220> FEATURE:
<223> OTHER INFORMATION: miRBase Accession No.: MI0000772 Human miR-302b
      (stem-loop)

<400> SEQUENCE: 21
gcucccuuca acuuuaacau ggaagugcuu ucugugacuu uaaaaguaag ugcuuccaug    60
uuuuaguagg agu    73

<210> SEQ ID NO 22
<211> LENGTH: 68
<212> TYPE: RNA
<213> ORGANISM: Artificial Sequence
<220> FEATURE:
<223> OTHER INFORMATION: miRBase Accession No.: MI0000773 Human miR-302c
      (stem-loop)

<400> SEQUENCE: 22
ccuuugcuuu aacauggggg uaccugcugu gugaaacaaa aguaagugcu uccauguuuc    60
aguggagg    68

<210> SEQ ID NO 23
<211> LENGTH: 68
<212> TYPE: RNA
<213> ORGANISM: Artificial Sequence
<220> FEATURE:
<223> OTHER INFORMATION: . miRBase Accession No.: MI0000774 Human
      miR-302d (stem-loop)

<400> SEQUENCE: 23
ccucuacuuu aacauggagg cacuugcugu gacaugacaa aaauaagugc uuccauguuu    60
gagugugg    68

-continued

<210> SEQ ID NO 24
<211> LENGTH: 51
<212> TYPE: RNA
<213> ORGANISM: Artificial Sequence
<220> FEATURE:
<223> OTHER INFORMATION: miRBase Accession No.: MI0006418 Human miR-302f
      (stem-loop)

<400> SEQUENCE: 24
ucuguguaaa ccuggcaauu uucacuuaau ugcuuccaug uuuauaaaag a            51

<210> SEQ ID NO 25
<211> LENGTH: 71
<212> TYPE: RNA
<213> ORGANISM: Artificial Sequence
<220> FEATURE:
<223> OTHER INFORMATION: miRBase Accession No.: MI0006418 Human miR-1-1
      (stem-loop)

<400> SEQUENCE: 25
ugggaaacau acuucuuuau augcccauau ggaccugcua agcuauggaa uguaaagaag   60
uauguaucuc a                                                       71

<210> SEQ ID NO 26
<211> LENGTH: 85
<212> TYPE: RNA
<213> ORGANISM: Artificial Sequence
<220> FEATURE:
<223> OTHER INFORMATION: miRBase Accession No.: MI0000437 Human miR-1-2
      (stem-loop)

<400> SEQUENCE: 26
accuacucag aguacauacu ucuuuaugua cccauaugaa cauacaaugc uauggaaugu   60
aaagaaguau guauuuuugg uaggc                                        85

<210> SEQ ID NO 27
<211> LENGTH: 86
<212> TYPE: RNA
<213> ORGANISM: Artificial Sequence
<220> FEATURE:
<223> OTHER INFORMATION: miRBase Accession No.: MI0000490 Human miR-206
      (stem-loop)

<400> SEQUENCE: 27
ugcuucccga ggccacaugc uucuuuauau ccccauaugg auuacuuugc uauggaaugu   60
aaggaagugu gugguuucgg caagug                                       86

<210> SEQ ID NO 28
<211> LENGTH: 73
<212> TYPE: RNA
<213> ORGANISM: Artificial Sequence
<220> FEATURE:
<223> OTHER INFORMATION: miRBase Accession No.: MI0000474 Human miR-134
      (stem-loop)

<400> SEQUENCE: 28
cagggugugu gacugguuga ccagagggggc augcacugug uucacccugu gggccaccua  60
gucaccaacc cuc                                                     73

<210> SEQ ID NO 29
<211> LENGTH: 88
<212> TYPE: RNA
<213> ORGANISM: Artificial Sequence

```
<220> FEATURE:
<223> OTHER INFORMATION: miRBase Accession No.: MI0000487 Human miR-193a
      (stem-loop)

<400> SEQUENCE: 29
cgaggauggg agcugagggc ugggucuuug cgggcgagau gagggugucg gaucaacugg    60
ccuacaaagu cccaguucuc ggcccccg                                       88

<210> SEQ ID NO 30
<211> LENGTH: 83
<212> TYPE: RNA
<213> ORGANISM: Artificial Sequence
<220> FEATURE:
<223> OTHER INFORMATION: miRBase Accession No.: MI0003137 Human miR-193b
      (stem-loop)

<400> SEQUENCE: 30
guggucucag aaucgggguu uugagggcga gaugaguuua uguuuauccc aacuggcccu    60
caaagucccg cuuuuggggu cau                                            83

<210> SEQ ID NO 31
<211> LENGTH: 82
<212> TYPE: RNA
<213> ORGANISM: Artificial Sequence
<220> FEATURE:
<223> OTHER INFORMATION: miRBase Accession No.: MI0000447 Human
      miR-128-1 (stem-loop)

<400> SEQUENCE: 31
ugagcuguug gauucggggc cguagcacug ucugagaggu uuacauuucu cacagugaac    60
cggucucuuu uucagcugcu uc                                             82

<210> SEQ ID NO 32
<211> LENGTH: 84
<212> TYPE: RNA
<213> ORGANISM: Artificial Sequence
<220> FEATURE:
<223> OTHER INFORMATION: miRBase Accession No.: MI0000727 Human
      miR-128-2 (stem-loop)

<400> SEQUENCE: 32
ugugcagugg aaggggggc cgauacacug uacgagagug aguagcaggu cucacaguga    60
accggucucu uucccuacug uguc                                           84

<210> SEQ ID NO 33
<211> LENGTH: 81
<212> TYPE: RNA
<213> ORGANISM: Artificial Sequence
<220> FEATURE:
<223> OTHER INFORMATION: miRBase Accession No.: MI0000097 Human miR-95
      (stem-loop)

<400> SEQUENCE: 33
aacacagugg gcacucaaua aaugucuguu gaauugaaau gcguuacauu caacggguau    60
uuauugagca cccacucugu g                                              81

<210> SEQ ID NO 34
<211> LENGTH: 84
<212> TYPE: RNA
<213> ORGANISM: Artificial Sequence
<220> FEATURE:
<223> OTHER INFORMATION: miRBase Accession No.: MI0000082 Human miR-25
      (stem-loop)
```

```
<400> SEQUENCE: 34 ggccagguguu gagaggcgga gacuugggca auugcuggac gcugcccugg gcauugcacu    60
ugucucgguc ugacagugcc ggcc                                            84

<210> SEQ ID NO 35
<211> LENGTH: 78
<212> TYPE: RNA
<213> ORGANISM: Artificial Sequence
<220> FEATURE:
<223> OTHER INFORMATION: miRBase Accession No.: MI0000093 Human
      miR-92a-1 (stem-loop)

<400> SEQUENCE: 35
cuuucuacac agguugggau cgguugcaau gcuguguuuc uguauggua ugcacuuguc       60 ccggccuguu gaguuugg                                                   78

<210> SEQ ID NO 36
<211> LENGTH: 75
<212> TYPE: RNA
<213> ORGANISM: Artificial Sequence
<220> FEATURE:
<223> OTHER INFORMATION: miRBase Accession No.: MI0000094 Human
      miR-92a-2 (stem-loop)

<400> SEQUENCE: 36
ucaucccugg gugggauuu guugcauuac uuguguucua uauaaaguau ugcacuuguc       60
ccggccugug gaaga                                                      75

<210> SEQ ID NO 37
<211> LENGTH: 96
<212> TYPE: RNA
<213> ORGANISM: Artificial Sequence
<220> FEATURE:
<223> OTHER INFORMATION: miRBase Accession No.: MI0003560 Human miR-92b
      (stem-loop)

<400> SEQUENCE: 37
cgggccccgg gcgggcggga gggacgggac gcggugcagu guuguuuuuu ccccgccaa       60 uauugcacuc gucccggccu ccggccccccc cggccc                              96

<210> SEQ ID NO 38
<211> LENGTH: 95
<212> TYPE: RNA
<213> ORGANISM: Artificial Sequence
<220> FEATURE:
<223> OTHER INFORMATION: miRBase Accession No.: MI0000457 Human miR-141
      (stem-loop)

<400> SEQUENCE: 38
cggccggccc ugggguccauc uuccaguaca guguuggaug gucuaauugu gaagcuccua    60
acacugucug guaaagaugg cucccgggug gguuc                                95

<210> SEQ ID NO 39
<211> LENGTH: 90
<212> TYPE: RNA
<213> ORGANISM: Artificial Sequence
<220> FEATURE:
<223> OTHER INFORMATION: miRBase Accession No.: MI0000737 Human miR-200a
      (stem-loop)

<400> SEQUENCE: 39 ccgggcccccu gugagcaucu uaccggacag ugcuggauuu cccagcuuga cucuaacacu     60
```

```
gucuggluaac gauguucaaa ggugacccgc                                            90

<210> SEQ ID NO 40
<211> LENGTH: 95
<212> TYPE: RNA
<213> ORGANISM: Artificial Sequence
<220> FEATURE:
<223> OTHER INFORMATION: miRBase Accession No.: MI0000342 Human miR-200b
      (stem-loop)

<400> SEQUENCE: 40
ccagcucggg cagccguggc caucuuacug ggcagcauug gauggaguca ggucucuaau           60
acugccuggu aaugaugacg gcggagcccu gcacg                                      95

<210> SEQ ID NO 41
<211> LENGTH: 68
<212> TYPE: RNA
<213> ORGANISM: Artificial Sequence
<220> FEATURE:
<223> OTHER INFORMATION: miRBase Accession No.: MI0000650 Human miR-200c
      (stem-loop)

<400> SEQUENCE: 41
cccucgucuu acccagcagu guuggguugc gguugggagu cucuaauacu gccggguaau           60
gauggagg                                                                    68

<210> SEQ ID NO 42
<211> LENGTH: 70
<212> TYPE: RNA
<213> ORGANISM: Artificial Sequence
<220> FEATURE:
<223> OTHER INFORMATION: miRBase Accession No.: MI0000238 Human
      miR-196a-1 (stem-loop)

<400> SEQUENCE: 42
gugaauuagg uaguuucaug uuguugggcc ugggluuucug aacacaacaa cauuaaacca         60
cccgauucac                                                                  70

<210> SEQ ID NO 43
<211> LENGTH: 110
<212> TYPE: RNA
<213> ORGANISM: Artificial Sequence
<220> FEATURE:
<223> OTHER INFORMATION: miRBase Accession No.: MI0000279 Human
      miR-196a-2(stem-loop)

<400> SEQUENCE: 43
ugcucgcuca gcugaucugu ggcuuaggua guuucauguu guugggauug aguuugaac           60 ucggcaacaa gaaacugccu gaguuacauc agucgguuuu cgucgagggc                     110

<210> SEQ ID NO 44
<211> LENGTH: 84
<212> TYPE: RNA
<213> ORGANISM: Artificial Sequence
<220> FEATURE:
<223> OTHER INFORMATION: miRBase Accession No.: MI0001150 Human miR-196b
      (stem-loop)

<400> SEQUENCE: 44
acuggucggu gauuuaggua guuccuguu guugggaucc accuuucucu cgacagcacg            60
acacugccuu cauuacuuca guug                                                  84

<210> SEQ ID NO 45
```

<210> SEQ ID NO 45
<211> LENGTH: 110
<212> TYPE: RNA
<213> ORGANISM: Artificial Sequence
<220> FEATURE:
<223> OTHER INFORMATION: miRBase Accession No.: MI0000266 Human miR-10a
      (stem-loop)

<400> SEQUENCE: 45
gaucugucug ucuucuguau auacccugua gauccgaauu uguguaagga auuuuguggu      60
cacaaauucg uaucuagggg aauauguagu ugacauaaac acuccgcucu               110

<210> SEQ ID NO 46
<211> LENGTH: 110
<212> TYPE: RNA
<213> ORGANISM: Artificial Sequence
<220> FEATURE:
<223> OTHER INFORMATION: miRBase Accession No.: MI0000267 Human miR-10b
      (stem-loop)

<400> SEQUENCE: 46
ccagagguug uaacguuguc uauauauacc cuguagaacc gaauugugu gguauccgua      60 uagucacaga uucgauucua ggggaauaua uggucgaugc aaaaacuuca              110

<210> SEQ ID NO 47
<211> LENGTH: 81
<212> TYPE: RNA
<213> ORGANISM: Artificial Sequence
<220> FEATURE:
<223> OTHER INFORMATION: miRBase Accession No.: MI0000101 Human miR-99a
      (stem-loop)

<400> SEQUENCE: 47
cccauuggca uaaacccgua gauccgaucu uguggugaag uggaccgcac aagcucgcuu      60
cuaugggucu gugucagugu g                                               81

<210> SEQ ID NO 48
<211> LENGTH: 70
<212> TYPE: RNA
<213> ORGANISM: Artificial Sequence
<220> FEATURE:
<223> OTHER INFORMATION: miRBase Accession No.: MI0000746 Human miR-99b
      (stem-loop)

<400> SEQUENCE: 48
ggcacccacc cguagaaccg accuugcggg gccuucgccg cacacaagcu cgugucugug      60
gguccguguc                                                            70

<210> SEQ ID NO 49
<211> LENGTH: 80
<212> TYPE: RNA
<213> ORGANISM: Artificial Sequence
<220> FEATURE:
<223> OTHER INFORMATION: miRBase Accession No.: MI0000102 Human miR-100
      (stem-loop)

<400> SEQUENCE: 49
ccuguugcca caaacccgua gauccgaacu uguggauuua guccgcacaa gcuuguaucu      60
auagguaugu gucuguuagg                                                 80

<210> SEQ ID NO 50
<211> LENGTH: 86
<212> TYPE: RNA
<213> ORGANISM: Artificial Sequence
<220> FEATURE:

<223> OTHER INFORMATION: miRBase Accession No.: MI0000469Human miR-125a
    (stem-loop)

<400> SEQUENCE: 50
ugccagucuc uaggucccug agacccuuua accugugagg acauccaggg ucacagguga    60
gguucuuggg agccuggcgu cuggcc                                         86

<210> SEQ ID NO 51
<211> LENGTH: 88
<212> TYPE: RNA
<213> ORGANISM: Artificial Sequence
<220> FEATURE:
<223> OTHER INFORMATION: miRBase Accession No.: MI0000446 Human
    miR-125b-1 (stem-loop)

<400> SEQUENCE: 51
ugcgcuccuc ucagucccug agacccuaac uugugauguu uaccguuuaa auccacgggu    60
uaggcucuug ggagcugcga gucgugcu                                       88

<210> SEQ ID NO 52
<211> LENGTH: 89
<212> TYPE: RNA
<213> ORGANISM: Artificial Sequence
<220> FEATURE:
<223> OTHER INFORMATION: miRBase Accession No.: MI0000470 Human
    miR-125b-2 (stem-loop)

<400> SEQUENCE: 52
accagacuuu uccuaguccc ugagacccua acuugugagg uauuuuagua acaucacaag    60
ucaggcucuu gggaccuagg cggaggggga                                     89

<210> SEQ ID NO 53
<211> LENGTH: 99
<212> TYPE: RNA
<213> ORGANISM: Artificial Sequence
<220> FEATURE:
<223> OTHER INFORMATION: miRBase Accession No.: MI0000477 Human miR-146a
    (stem-loop)

<400> SEQUENCE: 53
ccgaugugua uccucagcuu ugagaacuga auuccauggg uugugucagu gucagaccuc    60
ugaaauucag uucuucagcu gggauaucuc ugucaucgu                           99

<210> SEQ ID NO 54
<211> LENGTH: 73
<212> TYPE: RNA
<213> ORGANISM: Artificial Sequence
<220> FEATURE:
<223> OTHER INFORMATION: miRBase Accession No.: MI0003129 Human miR-146b
    (stem-loop)

<400> SEQUENCE: 54
ccuggcacug agaacugaau uccauaggcu gugagcucua gcaaugcccu guggacucag    60
uucuggugcc cgg                                                       73

<210> SEQ ID NO 55
<211> LENGTH: 71
<212> TYPE: RNA
<213> ORGANISM: Artificial Sequence
<220> FEATURE:
<223> OTHER INFORMATION: miRBase Accession No.: MI0000088 Human miR-30a
    (stem-loop)

<400> SEQUENCE: 55

```
gcgacuguaa acauccucga cuggaagcug ugaagccaca gaugggcuuu cagucggaug    60
uuugcagcug c                                                        71
```

```
<210> SEQ ID NO 56
<211> LENGTH: 88
<212> TYPE: RNA
<213> ORGANISM: Artificial Sequence
<220> FEATURE:
<223> OTHER INFORMATION: miRBase Accession No.: MI0000441 Human miR-30b
      (stem-loop)

<400> SEQUENCE: 56
accaaguuuc aguucaugua aacauccuac acucagcugu aauacaugga uuggcuggga    60
gguggauguu uacuucagcu gacuugga                                      88
```

```
<210> SEQ ID NO 57
<211> LENGTH: 89
<212> TYPE: RNA
<213> ORGANISM: Artificial Sequence
<220> FEATURE:
<223> OTHER INFORMATION: miRBase Accession No.: MI0000736 Human
      miR-30c-1 (stem-loop)

<400> SEQUENCE: 57
accaugcugu agugugugua aacauccuac acucucagcu gugagcucaa gguggcuggg    60 agagdgguugu uuacuccuuc ugccaugga                                    89
```

```
<210> SEQ ID NO 58
<211> LENGTH: 72
<212> TYPE: RNA
<213> ORGANISM: Artificial Sequence
<220> FEATURE:
<223> OTHER INFORMATION: miRBase Accession No.: MI0000254 Human
      miR-30c-2 (stem-loop)

<400> SEQUENCE: 58
agauacugua aacauccuac acucucagcu guggaaagua agaaagcugg gagaaggcug    60
uuuacucuuu cu                                                       72
```

```
<210> SEQ ID NO 59
<211> LENGTH: 70
<212> TYPE: RNA
<213> ORGANISM: Artificial Sequence
<220> FEATURE:
<223> OTHER INFORMATION: miRBase Accession No.: MI0000255 Human miR-30d
      (stem-loop)

<400> SEQUENCE: 59
guuguuguaa acauccccga cuggaagcug uaagacacag cuaagcuuuc agucagaugu    60
uugcugcuac                                                          70
```

```
<210> SEQ ID NO 60
<211> LENGTH: 92
<212> TYPE: RNA
<213> ORGANISM: Artificial Sequence
<220> FEATURE:
<223> OTHER INFORMATION: miRBase Accession No.: MI0000749 Human miR-30e
      (stem-loop)

<400> SEQUENCE: 60
gggcagucuu ugcuacugua aacauccuug acuggaagcu guaagguguu cagaggagcu    60
uucagucgga uguuuacagc ggcaggcugc ca                                 92
```

```
<210> SEQ ID NO 61
<211> LENGTH: 76
<212> TYPE: RNA
<213> ORGANISM: Artificial Sequence
<220> FEATURE:
<223> OTHER INFORMATION: miRBase Accession No.: MI0002467 Human miR-483
      (stem-loop)

<400> SEQUENCE: 61 gaggggggaag acgggaggaa agaagggagu gguuccauca cgccuccuca cuccucuccu      60
cccgucuucu ccucuc                                                       76

<210> SEQ ID NO 62
<211> LENGTH: 110
<212> TYPE: RNA
<213> ORGANISM: Artificial Sequence
<220> FEATURE:
<223> OTHER INFORMATION: miRBase Accession No.: MI0000234 Human miR-192
      (stem-loop)

<400> SEQUENCE: 62
gccgagaccg agugcacagg gcucugaccu augaauugac agccagugcu cucgucuccc      60
cucuggcugc caauuccaua ggucacaggu auguucgccu caaugccagc                 110

<210> SEQ ID NO 63
<211> LENGTH: 110
<212> TYPE: RNA
<213> ORGANISM: Artificial Sequence
<220> FEATURE:
<223> OTHER INFORMATION: miRBase Accession No.: MI0000291 Human miR-215
      (stem-loop)

<400> SEQUENCE: 63
aucauucaga aaugguauac aggaaaauga ccaugaauu gacagacaau auagcugagu       60
uugucuguca uuucuuuagg ccaauauucu guaugacugu gcuacuucaa                 110

<210> SEQ ID NO 64
<211> LENGTH: 71
<212> TYPE: RNA
<213> ORGANISM: Artificial Sequence
<220> FEATURE:
<223> OTHER INFORMATION: miRBase Accession No.: MI0000242 Human
      miR-199a-1 (stem-loop)

<400> SEQUENCE: 64
gccaacccag uguucagacu accuguucag gaggcucuca auguguacag uagucugcac      60
auugguuagg c                                                           71

<210> SEQ ID NO 65
<211> LENGTH: 110
<212> TYPE: RNA
<213> ORGANISM: Artificial Sequence
<220> FEATURE:
<223> OTHER INFORMATION: miRBase Accession No.: MI0000281 Human
      miR-199a-2 (stem-loop)

<400> SEQUENCE: 65
aggaagcuuc uggagauccu gcuccgucgc cccaguguuc agacuaccug uucaggacaa      60
ugccguugua caguagucug cacauugguu agacugggca agggagagca                 110

<210> SEQ ID NO 66
<211> LENGTH: 110
```

<212> TYPE: RNA
<213> ORGANISM: Artificial Sequence
<220> FEATURE:
<223> OTHER INFORMATION: miRBase Accession No.: MI0000282 Human
      miR-199b (stem-loop)

<400> SEQUENCE: 66
ccagaggaca ccuccacucc gucuacccag uguuuagacu aucuguucag gacucccaaa      60
uuguacagua gucugcacau ugguuaggcu gggcuggguu agacccucgg               110

<210> SEQ ID NO 67
<211> LENGTH: 110
<212> TYPE: RNA
<213> ORGANISM: Artificial Sequence
<220> FEATURE:
<223> OTHER INFORMATION: miRBase Accession No.: MI0000290 Human miR-214
      (stem-loop)

<400> SEQUENCE: 67
ggccuggcug acagaguug ucaugugucu gccugucuac acuugcugug cagaacaucc      60
gcucaccugu acagcaggca cagacaggca gucacaugac aacccagccu               110

<210> SEQ ID NO 68
<211> LENGTH: 81
<212> TYPE: RNA
<213> ORGANISM: Artificial Sequence
<220> FEATURE:
<223> OTHER INFORMATION: miRBase Accession No.: MI0014136 Human miR-3120
      (stem-loop)

<400> SEQUENCE: 68
gucaugugac ugccugucug ugccugcugu acaggugagc ggaguuucug cacagcaagu      60
guagacaggc agacacauga c                                                81

<210> SEQ ID NO 69
<211> LENGTH: 110
<212> TYPE: RNA
<213> ORGANISM: Artificial Sequence
<220> FEATURE:
<223> OTHER INFORMATION: miRBase Accession No.: MI0000266 Human miR-10a
      (stem-loop)

<400> SEQUENCE: 69
gaucugucug ucuucuguau auacccugua gauccgaauu uguguaagga auuuuguggu      60
cacaaauucg uaucuagggg aauauguagu ugacauaaac acuccgcucu               110

<210> SEQ ID NO 70
<211> LENGTH: 110
<212> TYPE: RNA
<213> ORGANISM: Artificial Sequence
<220> FEATURE:
<223> OTHER INFORMATION: miRBase Accession No.: MI0000267 Human miR-10b
      (stem-loop)

<400> SEQUENCE: 70
ccagagguug uaacguuguc uauauauacc cuguagaacc gaauuugugu gguauccgua      60
uagucacaga uucgauucua ggggaauaua uggucgaugc aaaaacuuca               110

<210> SEQ ID NO 71
<211> LENGTH: 81
<212> TYPE: RNA
<213> ORGANISM: Artificial Sequence
<220> FEATURE:
<223> OTHER INFORMATION: miRBase Accession No.: MI0000101 Human miR-99a -continued

```
    (stem-loop)

<400> SEQUENCE: 71
cccauuggca uaaacccgua gauccgaucu uguggugaag uggaccgcac aagcucgcuu    60
cuaugggucu gugucagugu g                                              81

<210> SEQ ID NO 72
<211> LENGTH: 70
<212> TYPE: RNA
<213> ORGANISM: Artificial Sequence
<220> FEATURE:
<223> OTHER INFORMATION: miRBase Accession No.: MI0000746 Human miR-99b
      (stem-loop)

<400> SEQUENCE: 72
ggcacccacc cguagaaccg accuugcggg gccuucgccg cacacaagcu cgucucugug    60
gguccguguc                                                           70

<210> SEQ ID NO 73
<211> LENGTH: 80
<212> TYPE: RNA
<213> ORGANISM: Artificial Sequence
<220> FEATURE:
<223> OTHER INFORMATION: miRBase Accession No.: MI0000102 Human miR-100
      (stem-loop)

<400> SEQUENCE: 73
ccuguugcca caaacccgua gauccgaacu ugugguauua guccgcacaa gcuuguaucu    60
auagguaugu gucuguuagg                                                80

<210> SEQ ID NO 74
<211> LENGTH: 86
<212> TYPE: RNA
<213> ORGANISM: Artificial Sequence
<220> FEATURE:
<223> OTHER INFORMATION: miRBase Accession No.: MI0000469 Human miR-125a
      (stem-loop)

<400> SEQUENCE: 74
ugccagucuc uaggucccug agacccuuua accugugagg acauccaggg ucagagguga    60
gguucuuggg agccuggcgu cuggcc                                         86

<210> SEQ ID NO 75
<211> LENGTH: 88
<212> TYPE: RNA
<213> ORGANISM: Artificial Sequence
<220> FEATURE:
<223> OTHER INFORMATION: miRBase Accession No.: MI0000446 Human
      miR-125b-1(stem-loop)

<400> SEQUENCE: 75
ugcgcuccuc ucagucccug agacccuaac uugugauguu uaccguuuaa uccacggu     60 uaggcucuug ggagcugcga gucgugcu                                       88

<210> SEQ ID NO 76
<211> LENGTH: 89
<212> TYPE: RNA
<213> ORGANISM: Artificial Sequence
<220> FEATURE:
<223> OTHER INFORMATION: miRBase Accession No.: MI0000470 Human
      miR-125b-2 (stem-loop)

<400> SEQUENCE: 76
```

```
accagacuuu uccuaguccc ugagacccua acuugugagg uauuuuagua acaucacaag    60
ucaggcucuu gggaccuagg cggagggga                                     89

<210> SEQ ID NO 77
<211> LENGTH: 110
<212> TYPE: RNA
<213> ORGANISM: Artificial Sequence
<220> FEATURE:
<223> OTHER INFORMATION: 78

<400> SEQUENCE: 77
uuggauguug gccuaguucu guguggaaga cuagugauuu uguuguuuuu agauaacuaa    60
aucgacaaca aaucacaguc ugccauaugg cacaggccau gccucuacag              110

<210> SEQ ID NO 78
<211> LENGTH: 110
<212> TYPE: RNA
<213> ORGANISM: Artificial Sequence
<220> FEATURE:
<223> OTHER INFORMATION: miRBase Accession No.: MI0000264 Human miR-7-2
      (stem-loop)

<400> SEQUENCE: 78
cuggauacag aguggaccgg cuggccccau cuggaagacu agugauuuug uuguugucuu    60
acugcgcuca acaacaaauc ccagucuacc uaauggugcc agccaucgca              110

<210> SEQ ID NO 79
<211> LENGTH: 110
<212> TYPE: RNA
<213> ORGANISM: Artificial Sequence
<220> FEATURE:
<223> OTHER INFORMATION: miRBase Accession No.: MI0000265 Human miR-7-3
      (stem-loop)

<400> SEQUENCE: 79
agauuagagu ggcugugguc uagugcugug uggaagacua gugauuuugu uguucugaug    60
uacuacgaca acaagucaca gccggccuca uagcgcagac ucccuucgac              110

<210> SEQ ID NO 80
<211> LENGTH: 71
<212> TYPE: RNA
<213> ORGANISM: Artificial Sequence
<220> FEATURE:
<223> OTHER INFORMATION: miRBase Accession No.: MI0000089 Human miR-31
      (stem-loop)

<400> SEQUENCE: 80
ggagaggagg caagaugcug gcauagcugu ugaacuggga accugcuaug ccaacauauu    60
gccaucuuuc c                                                        71

<210> SEQ ID NO 81
<211> LENGTH: 72
<212> TYPE: RNA
<213> ORGANISM: Artificial Sequence
<220> FEATURE:
<223> OTHER INFORMATION: miRBase Accession No.: MI0000252 Human
      miR-129-1 (stem-loop)

<400> SEQUENCE: 81
ggaucuuuuu gcggucuggg cuugcuguuc cucucaacag uagucaggaa gcccuuaccc    60
caaaaaguau cu                                                       72
```

```
<210> SEQ ID NO 82
<211> LENGTH: 90
<212> TYPE: RNA
<213> ORGANISM: Artificial Sequence
<220> FEATURE:
<223> OTHER INFORMATION: miRBase Accession No.: MI0000473 Human
      miR-129-2 (stem-loop)

<400> SEQUENCE: 82
ugcccuucgc gaaucuuuuu gcggucuggg cuugcuguac auaacucaau agccggaagc    60
ccuuacccca aaaagcauuu gcggagggcg                                    90

<210> SEQ ID NO 83
<211> LENGTH: 110
<212> TYPE: RNA
<213> ORGANISM: Artificial Sequence
<220> FEATURE:
<223> OTHER INFORMATION: miRBase Accession No.: MI0000294 Human
      miR-218-1 (stem-loop)

<400> SEQUENCE: 83
gugauaaugu agcgagauuu ucuguugugc uugaucuaac caugugguug cgaggauga    60 guaaaacaug guuccgucaa gcaccaugga acgucacgca gcuuucuaca             110

<210> SEQ ID NO 84
<211> LENGTH: 110
<212> TYPE: RNA
<213> ORGANISM: Artificial Sequence
<220> FEATURE:
<223> OTHER INFORMATION: miRBase Accession No.: MI0000295 Human
      miR-218-2 (stem-loop)

<400> SEQUENCE: 84
gaccagucgc ugcggggcuu ccuuugugc uugaucuaac caugguggug aacgauggaa    60
acggaacaug guucugucaa gcaccgcgga aagcaccgug cucuccugca             110

<210> SEQ ID NO 85
<211> LENGTH: 89
<212> TYPE: RNA
<213> ORGANISM: Artificial Sequence
<220> FEATURE:
<223> OTHER INFORMATION: miRBase Accession No.: MI0000466 Human miR-9-1
      (stem-loop)

<400> SEQUENCE: 85 cggggiuuggu uguuaucuuu gguuaucuag cuguaugagu ggugggagu cuucauaaag    60 cuagauaacc gaaaguaaaa auaaccca                                      89

<210> SEQ ID NO 86
<211> LENGTH: 87
<212> TYPE: RNA
<213> ORGANISM: Artificial Sequence
<220> FEATURE:
<223> OTHER INFORMATION: miRBase Accession No.: MI0000467 Human miR-9-2
      (stem-loop)

<400> SEQUENCE: 86
ggaagcgagu uguuaucuuu gguuaucuag cuguaugagu guauuggucu ucauaaagcu    60
agauaaccga aaguaaaaac uccuuca                                       87

<210> SEQ ID NO 87
<211> LENGTH: 90
<212> TYPE: RNA
<213> ORGANISM: Artificial Sequence
```

```
<220> FEATURE:
<223> OTHER INFORMATION: miRBase Accession No.: MI0000468 Human miR-9-3
      (stem-loop)

<400> SEQUENCE: 87
ggaggcccgu uucucucuuu gguuaucuag cuguaugagu gccacagagc cgucauaaag    60
cuagauaacc gaaaguagaa augauucuca                                    90

<210> SEQ ID NO 88
<211> LENGTH: 82
<212> TYPE: RNA
<213> ORGANISM: Artificial Sequence
<220> FEATURE:
<223> OTHER INFORMATION: miRBase Accession No.: MI0000447 Human
      miR-128-1 (stem-loop)

<400> SEQUENCE: 88
ugagcuguug gauucggggc cguagcacug ucgagaggu uuacauuucu cacagugaac    60
cggucucuuu uucagcugcu uc                                            82

<210> SEQ ID NO 89
<211> LENGTH: 84
<212> TYPE: RNA
<213> ORGANISM: Artificial Sequence
<220> FEATURE:
<223> OTHER INFORMATION: miRBase Accession No.: MI0000727 Human
      miR-128-2 (stem-loop)

<400> SEQUENCE: 89
ugugcagugg aaggggggc cgauacacug uacgagagug aguagcaggu cucacaguga    60
accggucucu uucccuacug uguc                                          84

<210> SEQ ID NO 90
<211> LENGTH: 86
<212> TYPE: RNA
<213> ORGANISM: Artificial Sequence
<220> FEATURE:
<223> OTHER INFORMATION: miRBase Accession No.: MI0000483 Human miR-186
      (stem-loop)

<400> SEQUENCE: 90
ugcuuguaac uuccaaaga auucuccuuu ugggcuuucu gguuuuauuu uaagcccaaa    60
ggugaauuuu uugggaaguu ugagcu                                        86

<210> SEQ ID NO 91
<211> LENGTH: 110
<212> TYPE: RNA
<213> ORGANISM: Artificial Sequence
<220> FEATURE:
<223> OTHER INFORMATION: miRBase Accession No.: MI0000272 Human miR-182
      (stem-loop)

<400> SEQUENCE: 91
gagcugcuug ccuccccccg uuuuuggcaa ugguagaacu cacacuggug agguaacagg    60 auccggugguu ucuagacuug ccaacuaugg ggcgaggacu cagccggcac            110

<210> SEQ ID NO 92
<211> LENGTH: 110
<212> TYPE: RNA
<213> ORGANISM: Artificial Sequence
<220> FEATURE:
<223> OTHER INFORMATION: miRBase Accession No.: MI0000285 Human miR-205
      (stem-loop)
```

-continued

<400> SEQUENCE: 92
aaagauccuc agacaaucca ugugcuucuc uuguccuuca uuccaccgga gucugucuca    60
uacccaacca gauuucagug gagugaaguu caggaggcau ggagcugaca              110

<210> SEQ ID NO 93
<211> LENGTH: 85
<212> TYPE: RNA
<213> ORGANISM: Artificial Sequence
<220> FEATURE:
<223> OTHER INFORMATION: miRBase Accession No.: MI0003167 Human
      miR-516b-2 (stem-loop)

<400> SEQUENCE: 93
ucucaugaug ugaccaucug gagguaagaa gcacuuugug uuuugugaaa gaaagugcuu    60
ccuuucagag gguuacucuu ugaga                                         85

<210> SEQ ID NO 94
<211> LENGTH: 84
<212> TYPE: RNA
<213> ORGANISM: Artificial Sequence
<220> FEATURE:
<223> OTHER INFORMATION: miRBase Accession No.: MI0003145 Human miR-519e
      (stem-loop)

<400> SEQUENCE: 94
ucucaugcag ucauucucca aagggagca cuuucuguuu gaaagaaaac aaagugccuc     60
cuuuuagagu guuacuguuu gaga                                          84

<210> SEQ ID NO 95
<211> LENGTH: 85
<212> TYPE: RNA
<213> ORGANISM: Artificial Sequence
<220> FEATURE:
<223> OTHER INFORMATION: miRBase Accession No.: MI0003178 Human
      miR-519a-1 (stem-loop)

<400> SEQUENCE: 95
cucaggcugu gacacucuag agggaagcgc uuucuguugu cugaaagaaa ggaaagugca    60
uccuuuuaga guguuacugu uugag                                         85

<210> SEQ ID NO 96
<211> LENGTH: 124
<212> TYPE: RNA
<213> ORGANISM: Artificial Sequence
<220> FEATURE:
<223> OTHER INFORMATION: miRBase Accession No.: MI0003193Human miR-506
      (stem-loop)

<400> SEQUENCE: 96
gccaccacca ucagccauac uauguguagu gccuuauuca ggaagguguu acuuaauaga    60
uuaauauuug uaaggcaccc uucugaguag aguaaugugc aacauggaca acauuugugg   120
uggc                                                                124

<210> SEQ ID NO 97
<211> LENGTH: 115
<212> TYPE: RNA
<213> ORGANISM: Artificial Sequence
<220> FEATURE:
<223> OTHER INFORMATION: miRBase Accession No.: MI0003195 Human miR-508
      (stem-loop)

<400> SEQUENCE: 97

```
ccaccuucag cugaguguag ugcccuacuc cagagggcgu cacucaugua aacuaaaaca      60
ugauuguagc cuuuuggagu agaguaauac acaucacgua acgcauauuu ggugg           115

<210> SEQ ID NO 98
<211> LENGTH: 94
<212> TYPE: RNA
<213> ORGANISM: Artificial Sequence
<220> FEATURE:
<223> OTHER INFORMATION: miRBase Accession No.: MI0003196 Human
      miR-509-1 (stem-loop)

<400> SEQUENCE: 98
caugcugugu gugguacccu acugcagaca guggcaauca uguauaauua aaaaugauug      60
guacgucugu ggguagagua cugcaugaca caug                                 94

<210> SEQ ID NO 99
<211> LENGTH: 91
<212> TYPE: RNA
<213> ORGANISM: Artificial Sequence
<220> FEATURE:
<223> OTHER INFORMATION: miRBase Accession No.: MI0005530 Human
      miR-509-2 (stem-loop)

<400> SEQUENCE: 99
caugcugugu gugguacccu acugcagaca guggcaauca uguauaauua aaaaugauug      60
guacgucugu ggguagagua cugcaugaca c                                    91

<210> SEQ ID NO 100
<211> LENGTH: 75
<212> TYPE: RNA
<213> ORGANISM: Artificial Sequence
<220> FEATURE:
<223> OTHER INFORMATION: miRBase Accession No.: MI0005717 Human
      miR-509-3 (stem-loop)

<400> SEQUENCE: 100
gugguacccu acugcagacg uggcaaucau guauaauuaa aaaugauugg uacgucugug      60
gguagaguac ugcau                                                      75

<210> SEQ ID NO 101
<211> LENGTH: 74
<212> TYPE: RNA
<213> ORGANISM: Artificial Sequence
<220> FEATURE:
<223> OTHER INFORMATION: miRBase Accession No.: MI0003197 Human miR-510
      (stem-loop)

<400> SEQUENCE: 101 guggugu ccu acucaggaga guggcaauca cauguaauua ggugugauug aaaccucuaa     60 gagug gagua acac                                                      74

<210> SEQ ID NO 102
<211> LENGTH: 84
<212> TYPE: RNA
<213> ORGANISM: Artificial Sequence
<220> FEATURE:
<223> OTHER INFORMATION: miRBase Accession No.: MI0006649 Human miR-513c
      (stem-loop)

<400> SEQUENCE: 102
gcguacagug ccuuucucaa ggaggugucg uuuaugugaa cuaaaauaua aauuucaccu      60
uucugagaag aguaauguac agca                                            84
```

-continued

<210> SEQ ID NO 103
<211> LENGTH: 98
<212> TYPE: RNA
<213> ORGANISM: Artificial Sequence
<220> FEATURE:
<223> OTHER INFORMATION: miRBase Accession No.: MI0003198 Human
      miR-514a-1 (stem-loop)

<400> SEQUENCE: 103
aacauguugu cugugguacc cuacucugga gagugacaau cauguauaau uaaauuugau    60
ugacacuucu gugaguagag uaacgcauga cacguacg                           98

<210> SEQ ID NO 104
<211> LENGTH: 88
<212> TYPE: RNA
<213> ORGANISM: Artificial Sequence
<220> FEATURE:
<223> OTHER INFORMATION: miRBase Accession No.: MI0003199 Human
      miR-514a-2 (stem-loop)

<400> SEQUENCE: 104
guugucugug guacccuacu cuggagagug acaaucaugu auaacuaaau uugauugaca    60
cuucugugag uagaguaacg caugacac                                      88

<210> SEQ ID NO 105
<211> LENGTH: 88
<212> TYPE: RNA
<213> ORGANISM: Artificial Sequence
<220> FEATURE:
<223> OTHER INFORMATION: miRBase Accession No.: MI0003200 Human
      miR-514a-3 (stem-loop)

<400> SEQUENCE: 105
guugucugug guacccuacu cuggagagug acaaucaugu auaacuaaau uugauugaca    60
cuucugugag uagaguaacg caugacac                                      88

<210> SEQ ID NO 106
<211> LENGTH: 80
<212> TYPE: RNA
<213> ORGANISM: Artificial Sequence
<220> FEATURE:
<223> OTHER INFORMATION: miRBase Accession No.: MI0014251 Human miR-514b
      (stem-loop)

<400> SEQUENCE: 106 cauggguac ucuucucaag agggaggcaa ucauguguaa uuagauauga uugacaccuc     60
ugugagugga guaacacaug                                               80

<210> SEQ ID NO 107
<211> LENGTH: 83
<212> TYPE: RNA
<213> ORGANISM: Artificial Sequence
<220> FEATURE:
<223> OTHER INFORMATION: miRBase Accession No.: MI0000069 Human miR-15a
      (stem-loop)

<400> SEQUENCE: 107
ccuuggagua aaguagcagc acauaauggu uuguggauuu ugaaaaggug caggccauau    60
ugugcugccu caaaaauaca agg                                           83

<210> SEQ ID NO 108
<211> LENGTH: 98
<212> TYPE: RNA

<213> ORGANISM: Artificial Sequence
<220> FEATURE:
<223> OTHER INFORMATION: miRBase Accession No.: MI0000438Human miR-15b
      (stem-loop)

<400> SEQUENCE: 108
uugaggccuu aaaguacugu agcagcacau cauggyuuac augcuacagu caagaugcga    60
aucauuauuu gcugcucuag aaauuuaagg aaauucau                           98

<210> SEQ ID NO 109
<211> LENGTH: 89
<212> TYPE: RNA
<213> ORGANISM: Artificial Sequence
<220> FEATURE:
<223> OTHER INFORMATION: miRBase Accession No.: MI0000070 Human miR-16-1
      (stem-loop)

<400> SEQUENCE: 109
gucagcagug ccuuagcagc acguaaauau uggcguuaag auucuaaaau uaucuccagu    60
auuaacugug cugcugaagu aagguugac                                     89

<210> SEQ ID NO 110
<211> LENGTH: 81
<212> TYPE: RNA
<213> ORGANISM: Artificial Sequence
<220> FEATURE:
<223> OTHER INFORMATION: miRBase Accession No.: MI0000115 Human miR-16-2
      (stem-loop)

<400> SEQUENCE: 110
guuccacucu agcagcacgu aaauauuggc guagugaaau auauauuaaa caccaauauu    60
acugugcugc uuuaguguga c                                             81

<210> SEQ ID NO 111
<211> LENGTH: 87
<212> TYPE: RNA
<213> ORGANISM: Artificial Sequence
<220> FEATURE:
<223> OTHER INFORMATION: miRBase Accession No.: MI0000489 Human miR-195
      (stem-loop)

<400> SEQUENCE: 111
agcuucccug gcucuagcag cacagaaaua uuggcacagg gaagcgaguc ugccaauauu    60
ggcugugcug cuccaggcag gguggug                                       87

<210> SEQ ID NO 112
<211> LENGTH: 119
<212> TYPE: RNA
<213> ORGANISM: Artificial Sequence
<220> FEATURE:
<223> OTHER INFORMATION: miRBase Accession No.: MI0000100 Human miR-98
      (stem-loop)

<400> SEQUENCE: 112
aggauucugc ucaugccagg gugagguagu aaguuguauu guugggggu agggauauua    60 ggccccaauu agaagauaac uauacaacuu acuacuuucc cuggugugug gcauauuca    119

<210> SEQ ID NO 113
<211> LENGTH: 80
<212> TYPE: RNA
<213> ORGANISM: Artificial Sequence
<220> FEATURE:
<223> OTHER INFORMATION: miRBase Accession No.: MI0000060 Human let-7a-1
      (stem-loop)

<400> SEQUENCE: 113 uggaugagg uaguagguug uauaguuuua gggucacacc caccacuggg agauaacuau    60
acaaucuacu gucuuuccua                                              80

<210> SEQ ID NO 114
<211> LENGTH: 72
<212> TYPE: RNA
<213> ORGANISM: Artificial Sequence
<220> FEATURE:
<223> OTHER INFORMATION: miRBase Accession No.: MI0000061 Human let-7a-2
      (stem-loop)

<400> SEQUENCE: 114
agguugaggu aguagguugu auaguuuaga auuacaucaa gggagauaac uguacagccu    60
ccuagcuuuc cu                                                       72

<210> SEQ ID NO 115
<211> LENGTH: 74
<212> TYPE: RNA
<213> ORGANISM: Artificial Sequence
<220> FEATURE:
<223> OTHER INFORMATION: miRBase Accession No.: MI0000062 Human let-7a-3
      (stem-loop)

<400> SEQUENCE: 115
gggugaggua guagguugua uaguuugggg cucugcccug cuaugggaua acauacaau    60 cuacugucuu uccu                                                     74

<210> SEQ ID NO 116
<211> LENGTH: 83
<212> TYPE: RNA
<213> ORGANISM: Artificial Sequence
<220> FEATURE:
<223> OTHER INFORMATION: miRBase Accession No.: MI0000063 Human let-7b
      (stem-loop)

<400> SEQUENCE: 116
cggggugagg uaguagguug uguggguuuca gggcagugau guugcccuc ggaagauaac    60 uauacaaccu acugccuucc cug                                           83

<210> SEQ ID NO 117
<211> LENGTH: 84
<212> TYPE: RNA
<213> ORGANISM: Artificial Sequence
<220> FEATURE:
<223> OTHER INFORMATION: miRBase Accession No.: MI0000064 Human let-7c
      (stem-loop)

<400> SEQUENCE: 117
gcauccgggu ugagguagua gguuguaugg uuuagaguua cacccuggga guuaacugua    60
caaccuucua gcuuuccuug gagc                                          84

<210> SEQ ID NO 118
<211> LENGTH: 87
<212> TYPE: RNA
<213> ORGANISM: Artificial Sequence
<220> FEATURE:
<223> OTHER INFORMATION: miRBase Accession No.: MI0000065 Human let-7d
      (stem-loop)

<400> SEQUENCE: 118
ccuaggaaga gguaguaggu ugcauaguuu uagggcaggg auuuugccca caaggaggua    60

```
acuauacgac cugcugccuu ucuuagg                                               87
```

<210> SEQ ID NO 119
<211> LENGTH: 79
<212> TYPE: RNA
<213> ORGANISM: Artificial Sequence
<220> FEATURE:
<223> OTHER INFORMATION: miRBase Accession No.: MI0000066 Human let-7e
      (stem-loop)

<400> SEQUENCE: 119

```
cccgggcuga gguaggaggu uguauaguug aggaggacac ccaaggagau cacuauacgg        60
ccuccuagcu uuccccagg                                                     79
```

<210> SEQ ID NO 120
<211> LENGTH: 87
<212> TYPE: RNA
<213> ORGANISM: Artificial Sequence
<220> FEATURE:
<223> OTHER INFORMATION: miRBase Accession No.: MI0000067 Human let-7f-1
      (stem-loop)

<400> SEQUENCE: 120

```
ucagagugag guaguagauu guauaguugu gggguaguga uuuuacccug uucaggagau        60
aacuauacaa ucuauugccu ucccuga                                            87
```

<210> SEQ ID NO 121
<211> LENGTH: 83
<212> TYPE: RNA
<213> ORGANISM: Artificial Sequence
<220> FEATURE:
<223> OTHER INFORMATION: miRBase Accession No.: MI0000068 Human let-7f-2
      (stem-loop)

<400> SEQUENCE: 121

```
ugugggauga gguaguagau uguauaguuu uagggucaua ccccaucuug gagauaacua        60
uacagucuac ugucuuuccc acg                                                83
```

<210> SEQ ID NO 122
<211> LENGTH: 84
<212> TYPE: RNA
<213> ORGANISM: Artificial Sequence
<220> FEATURE:
<223> OTHER INFORMATION: miRBase Accession No.: MI0000433 Human let-7g
      (stem-loop)

<400> SEQUENCE: 122

```
aggcugaggu aguaguuugu acaguuugag ggucuaugau accacccggu acaggagaua        60
acuguacagg ccacugccuu gcca                                               84
```

<210> SEQ ID NO 123
<211> LENGTH: 84
<212> TYPE: RNA
<213> ORGANISM: Artificial Sequence
<220> FEATURE:
<223> OTHER INFORMATION: miRBase Accession No.: MI0000434 Human let-7i
      (stem-loop)

<400> SEQUENCE: 123

```
cuggcugagg uaguaguuug ugcuguuggu cggguuguga cauugcccgc uguggagaua        60
acugcgcaag cuacugccuu gcua                                               84
```

```
<210> SEQ ID NO 124
<211> LENGTH: 110
<212> TYPE: RNA
<213> ORGANISM: Artificial Sequence
<220> FEATURE:
<223> OTHER INFORMATION: miRBase Accession No.: MI0000289 Human
      miR-181a-1 (stem-loop)

<400> SEQUENCE: 124
ugaguuuuga gguugcuuca gugaacauuc aacgcugucg gugaguuugg aauuaaaauc    60
aaaaccaucg accguugauu guacccuaug gcuaaccauc aucuacucca             110

<210> SEQ ID NO 125
<211> LENGTH: 110
<212> TYPE: RNA
<213> ORGANISM: Artificial Sequence
<220> FEATURE:
<223> OTHER INFORMATION: miRBase Accession No.: MI0000269 Human
      miR-181a-2 (stem-loop)

<400> SEQUENCE: 125
agaagggcua ucaggccagc cuucagagga cuccaaggaa cauucaacgc ugucggugag    60
uuugggauuu gaaaaaacca cugaccguug acuguaccuu ggggguccuua            110

<210> SEQ ID NO 126
<211> LENGTH: 110
<212> TYPE: RNA
<213> ORGANISM: Artificial Sequence
<220> FEATURE:
<223> OTHER INFORMATION: miRBase Accession No.: MI0000270 Human
      miR-181b-1 (stem-loop)

<400> SEQUENCE: 126
ccugugcaga gauuauuuuu uaaaagguca caaucaacau ucauugcugu cgguggguug    60
aacugugugg acaagcucac ugaacaauga augcaacugu ggccccgcuu             110

<210> SEQ ID NO 127
<211> LENGTH: 89
<212> TYPE: RNA
<213> ORGANISM: Artificial Sequence
<220> FEATURE:
<223> OTHER INFORMATION: miRBase Accession No.: MI0000683 Human
      miR-181b-2 (stem-loop)

<400> SEQUENCE: 127
cugauggcug cacucaacau ucauugcugu cgguggguuu gagucugaau caacucacug    60
aucaaugaau gcaaacugcg gaccaaaca                                     89

<210> SEQ ID NO 128
<211> LENGTH: 110
<212> TYPE: RNA
<213> ORGANISM: Artificial Sequence
<220> FEATURE:
<223> OTHER INFORMATION: miRBase Accession No.: MI0000271 Human miR-181c
      (stem-loop)

<400> SEQUENCE: 128
cggaaaauuu gccaaggguu uggggggaaca uucaaccugu cggugaguuu gggcagcuca    60
ggcaaaccau cgaccguuga guggacccug aggccuggaa uugccauccu              110

<210> SEQ ID NO 129
<211> LENGTH: 137
<212> TYPE: RNA
<213> ORGANISM: Artificial Sequence
```

```
<220> FEATURE:
<223> OTHER INFORMATION: miRBase Accession No.: MI0003139 Human miR-181d
      (stem-loop)

<400> SEQUENCE: 129
gucccucccc cuaggccaca gccgagguca caaucaacau ucauuguugu cgguggguug      60
ugaggacuga ggccagaccc accggggau gaaugucacu guggcugggc cagacacggc     120
uuaaggggaa ugggac                                                     137

<210> SEQ ID NO 130
<211> LENGTH: 110
<212> TYPE: RNA
<213> ORGANISM: Artificial Sequence
<220> FEATURE:
<223> OTHER INFORMATION: miRBase Accession No.: MI0000284 Human miR-204
      (stem-loop)

<400> SEQUENCE: 130
ggcuacaguc uuucuucaug ugacucgugg acuucccuuu gucauccuau gccugagaau      60
auaugaagga ggcugggaag gcaaagggac guucaauugu caucacuggc                110

<210> SEQ ID NO 131
<211> LENGTH: 110
<212> TYPE: RNA
<213> ORGANISM: Artificial Sequence
<220> FEATURE:
<223> OTHER INFORMATION: miRBase Accession No.: MI0000287 Human miR-211
      (stem-loop)

<400> SEQUENCE: 131
ucaccuggcc augugacuug ugggcuuccc uuugucaucc uucgccuagg gcucugagca      60
gggcagggac agcaaagggg ugcucaguug ucacuuccca cagcacggag                110

<210> SEQ ID NO 132
<211> LENGTH: 85
<212> TYPE: RNA
<213> ORGANISM: Artificial Sequence
<220> FEATURE:
<223> OTHER INFORMATION: miRBase Accession No.: MI0000078 Human miR-22
      (stem-loop)

<400> SEQUENCE: 132
ggcugagccg caguaguucu ucagugggcaa gcuuuauguc cugacccagc uaaagcugcc     60
aguugaagaa cuguugcccu cugcc                                            85

<210> SEQ ID NO 133
<211> LENGTH: 110
<212> TYPE: RNA
<213> ORGANISM: Artificial Sequence
<220> FEATURE:
<223> OTHER INFORMATION: miRBase Accession No.: MI0000268 Human miR-34a
      (stem-loop)

<400> SEQUENCE: 133
ggccagcugu gaguguuucu uuggcagugu cuuagcuggu uguugugagc aauaguaagg      60
aagcaaucag caaguauacu gcccagaag ugcugcacgu ugggggccc                  110

<210> SEQ ID NO 134
<211> LENGTH: 84
<212> TYPE: RNA
<213> ORGANISM: Artificial Sequence
<220> FEATURE:
<223> OTHER INFORMATION: miRBase Accession No.: MI0000742 Human miR-34b
```

-continued

```
       (stem-loop)

<400> SEQUENCE: 134
gugcucgguu uguaggcagu gucauuagcu gauuguacug uggugguuac aaucacuaac    60
uccacugcca ucaaaacaag gcac                                          84

<210> SEQ ID NO 135
<211> LENGTH: 77
<212> TYPE: RNA
<213> ORGANISM: Artificial Sequence
<220> FEATURE:
<223> OTHER INFORMATION: miRBase Accession No.: MI0000743 Human miR-34c
       (stem-loop)

<400> SEQUENCE: 135
agucuaguua cuaggcagug uaguuagcug auugcuaaua guaccaauca cuaaccacac    60
ggccagguaa aaagauu                                                  77
```